US008916745B2

(12) United States Patent
Schroeder et al.

(10) Patent No.: US 8,916,745 B2
(45) Date of Patent: Dec. 23, 2014

(54) PLANT $CO_2$ SENSORS, NUCLEIC ACIDS ENCODING THEM, AND METHODS FOR MAKING AND USING THEM

(75) Inventors: Julian Schroeder, La Jolla, CA (US); Maria Israelsson-Nordstrom, Taby (SE); Josef M. Kuhn, Ludwigshafen (DE); Yingzhen Yang, Geneva, NY (US); Honghong Hu, San Diego, CA (US); Aurelien Boisson-Dernier, Paris (FR)

(73) Assignee: The Regents of the University of California, Oakland, CA (US)

( * ) Notice: Subject to any disclaimer, the term of this patent is extended or adjusted under 35 U.S.C. 154(b) by 1181 days.

(21) Appl. No.: 12/597,880

(22) PCT Filed: Apr. 25, 2008

(86) PCT No.: PCT/US2008/061654
§ 371 (c)(1),
(2), (4) Date: Jul. 12, 2010

(87) PCT Pub. No.: WO2008/134571
PCT Pub. Date: Nov. 6, 2008

(65) Prior Publication Data
US 2010/0299782 A1    Nov. 25, 2010

Related U.S. Application Data

(60) Provisional application No. 60/914,640, filed on Apr. 27, 2007.

(51) Int. Cl.
*C12N 15/82* (2006.01)
*A01H 5/00* (2006.01)
*C07K 14/415* (2006.01)

(52) U.S. Cl.
CPC .......... *C07K 14/415* (2013.01); *C12N 15/8261* (2013.01)
USPC .......................................... 800/278; 435/468

(58) Field of Classification Search
None
See application file for complete search history.

(56) References Cited

U.S. PATENT DOCUMENTS 8,183,436 B2 * 5/2012 Alexandrov et al. ......... 800/295
2006/0143729 A1   6/2006 Alexandrov et al.
2006/0143739 A1   6/2006 Medrano et al.
2008/0028489 A1   1/2008 Sze et al.

FOREIGN PATENT DOCUMENTS

WO        2005085449 A2    9/2005

OTHER PUBLICATIONS

Fett and Coleman Plant Physiology (1994) vol. 105, pp. 707-713.*
Majeau, 1994, Plant Mol. Bio., 25:377-385.*
Bailey, "Coordinate Regulation of Phosphoenolpyruvate Carboxylase and Phosphoenolpyruvate Carboxykinase by Light and CO2 During C4 Photosynthesis," Plant Physiology, May 2007, vol. 144, pp. 479-486.
Fabre et al., "Characterization and expression analysis of genes encoding α and β carbonic anhydrases in *Arabidopsis*," Plant, Cell and Environment (2007) 30, 617-629.
Furbank et al., "Regulation of Photosynthesis in C3 and C4 Plants: A Molecular Approach," The Plant Cell, vol. 7, 797-807, Jul. 1995.
Jenneau et al., "Manipulating PEPC levels in plants,"Journal of Experimental Botany, vol. 53, No. 376, pp. 1837-1845, Sep. 2002.
Jiao et al., "Physiological characteristics of the primitive CO2 concentrating mechanism in PEPC transgenic rice," Science in China (Series C), vol. 46, No. 4, Aug. 2003, pp. 438-446.
Keller, First Office Action issued in 08754936.6, European Patent Office, Apr. 13, 2012.
Kim, Written Opinion issued in PCT/US2008/061654, Korean Patent Office, Sep. 30, 2008.
Kuwahara, International Preliminary Report on Patentability, International Bureau of WIPO, Oct. 27, 2009.
Majeau et al., "Modification of carbonic anhydrase activity by antisense and over-expression constructs in transgenic tobacco," Plant Molecular Biology, 25: 377-385, 1994.
Nikita, First Office Action issued in Eurasian Application No. 200901457, Dec. 12, 2011, with translation.
Nikita, Second Office Action issued in Eurasian Application No. 200901457, Apr. 25, 2012, with translation.
Nikita, Third Office Action issued in Eurasian Application No. 200901457, Oct. 3, 2012, with translation.
Raines et al., "*Arabidopsis thaliana* carbonic anhydrase: cDNA sequence and effect of CO2 on mRNA levels," Plant Molecular Biology 20: 1143-1148, 1992.
Rogues, Response to First Office Action, 08754936.6, European Patent Office, Sep. 20, 2012.
Rogues, Response to ESSR, 08754936.6, European Patent Office, Mar. 15, 2011.

(Continued)

*Primary Examiner* — Ashwin Mehta
*Assistant Examiner* — Jason Deveau Rosen
(74) *Attorney, Agent, or Firm* — Gregory P. Einhorn; Gavrilovich, Dodd & Lindsey LLP

(57) ABSTRACT

The invention provides compositions and methods for manipulating the exchange of water and/or carbon dioxide ($CO_2$) through plant stomata by controlling $CO_2$ sensor genes. The invention provides compositions and methods for enhancing or optimizing biomass accumulation in a plant. The invention provides compositions and methods for for opening or closing a stomatal pore on a guard cell in the epidermis of a plant. The invention provides compositions and methods for increasing or decreasing oxygenation efficiency and/or carbon fixation in a guard cell in the epidermis of a plant by manipulating expression of a ribulose-1,5-bisphosphate carboxylase/oxygenase. The invention provides promoters for regulating expression of a nucleic acid in a plant guard cell.

21 Claims, 32 Drawing Sheets

(56) References Cited

OTHER PUBLICATIONS

Sharma et al., "Zinc Requirement for Stomatal Opening in Cauliflower," Plant Physiol., 1995, 107:751-756.
Steffan, Extended European Search Report, 08754936.6, European Patent Office, Aug. 9, 2010.
Zhang, First Office Action issued in 200880022556.3, Chinese Patent Office, Jun. 2, 2011.
Zhang, Second Office Action issued in 200880022556.3, Chinese Patent Office, Feb. 15, 2012.
Zhang, Third Office Action issued in 200880022556.3, Chinese Patent Office, Aug. 17, 2012.

* cited by examiner

Fig. 3A-H
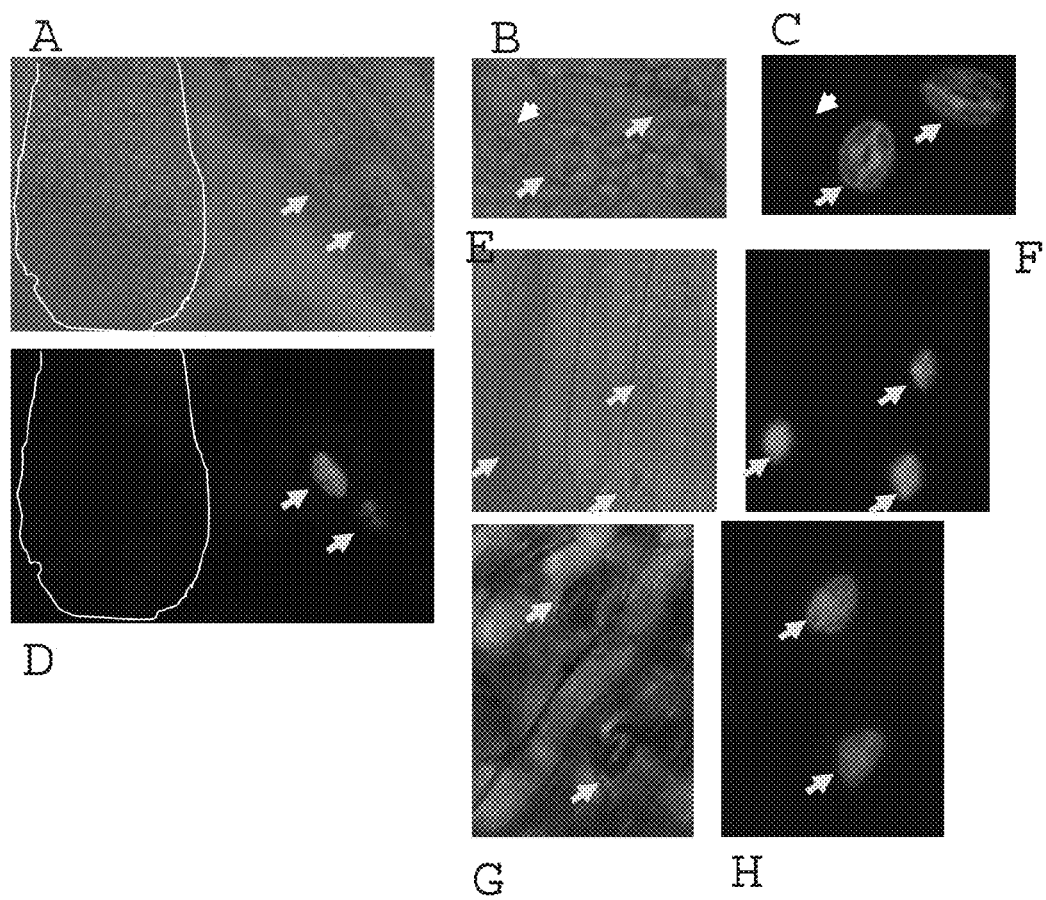

Col plants transformed with CA1 cDNA ca1/4 mutants transformed with CA1 cDNA ca1/4/6 mutants transformed with CA1 cDNA

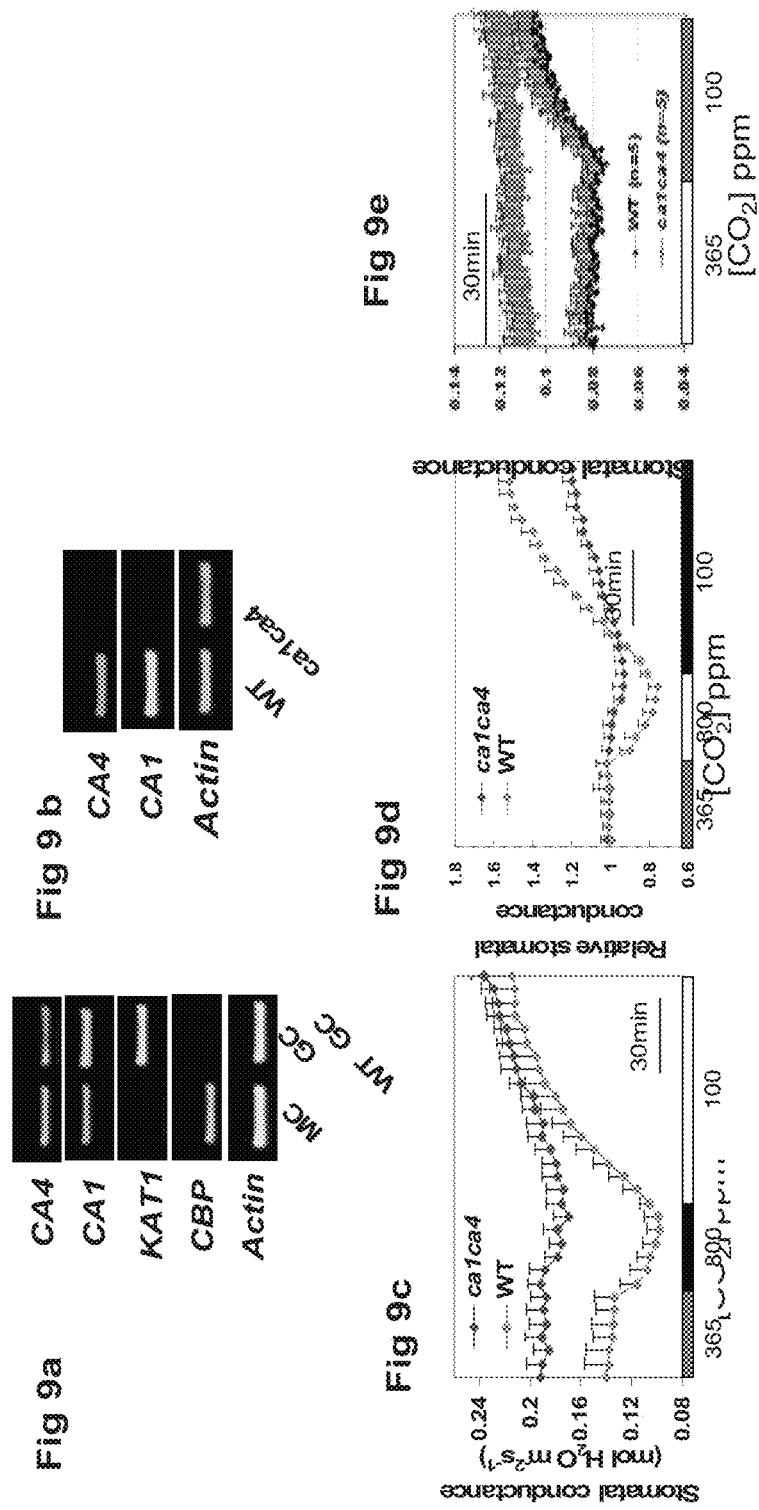

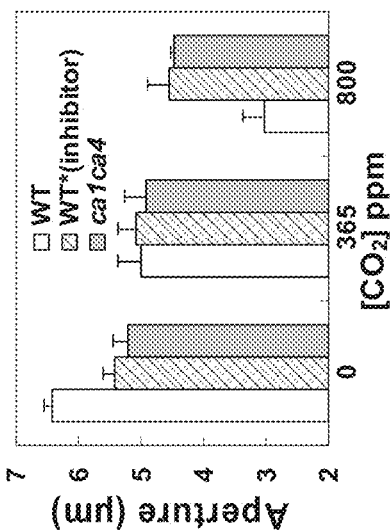
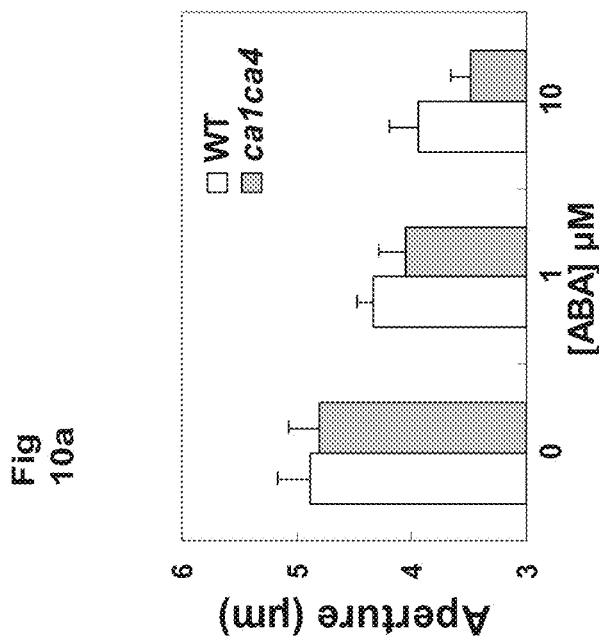
Figure 10

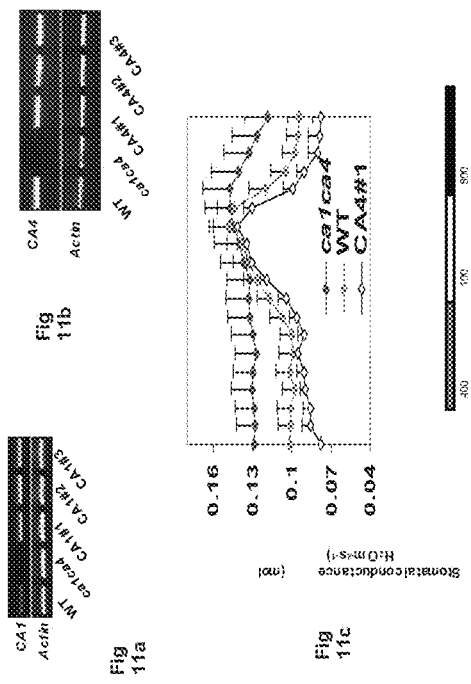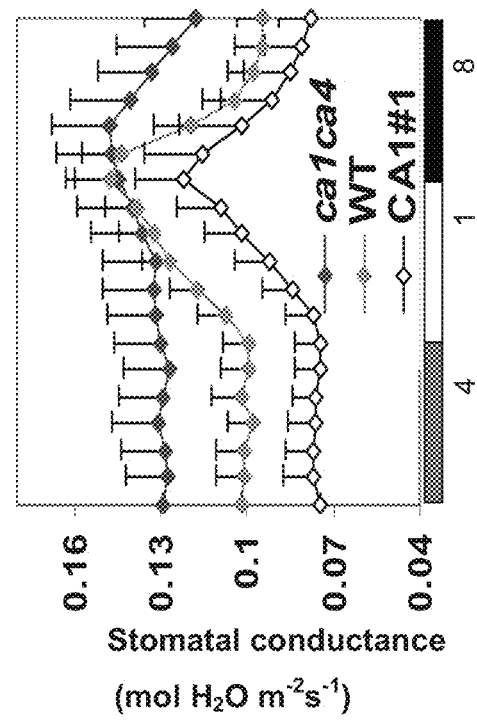
Fig. 11a
Fig. 11b
Fig. 11c
Fig. 11D

Fig. 14
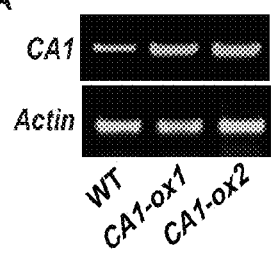
Fig 14A
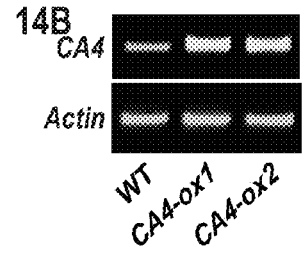
Fig 14B
Fig. 14C
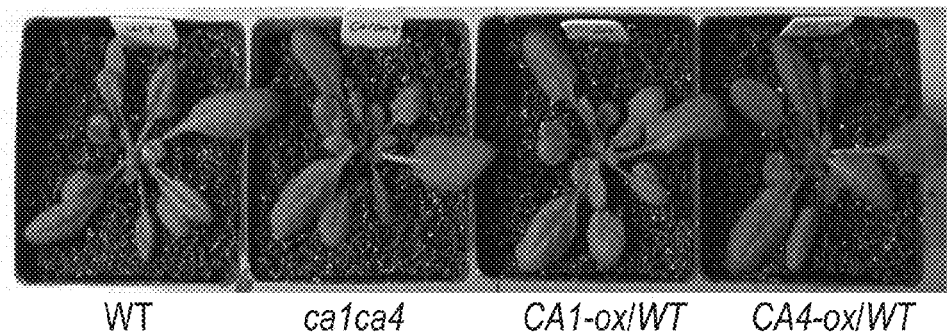

Fig. 16

Fig. 17G to 17N
Fig. 17G
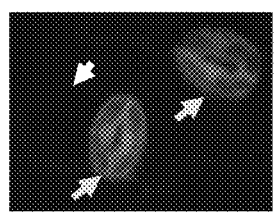
Fig. 17H
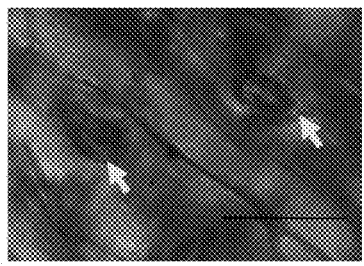
Fig. 17I
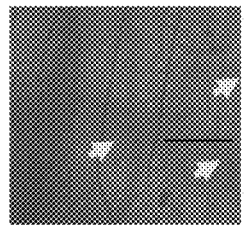
Fig. 17J
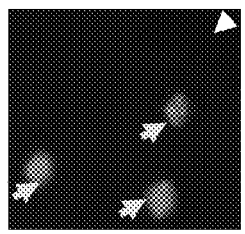
Fig. 17K
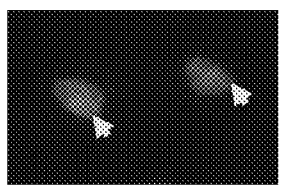
Fig. 17L
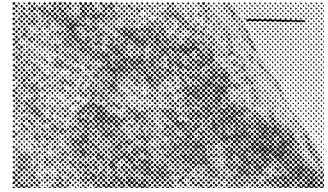
Fig. 17N
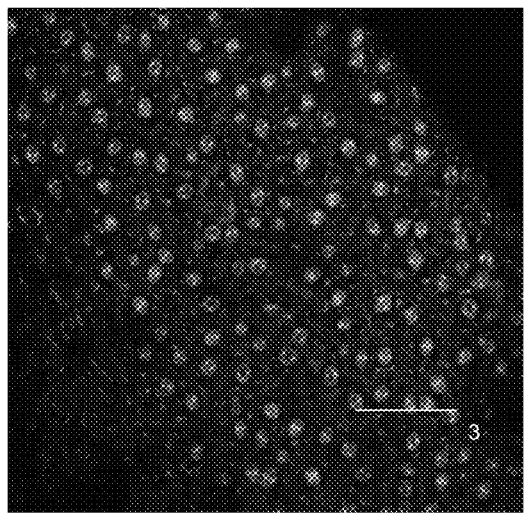
Fig. 17M
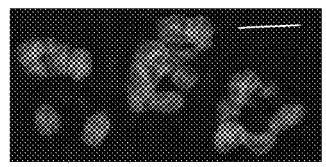

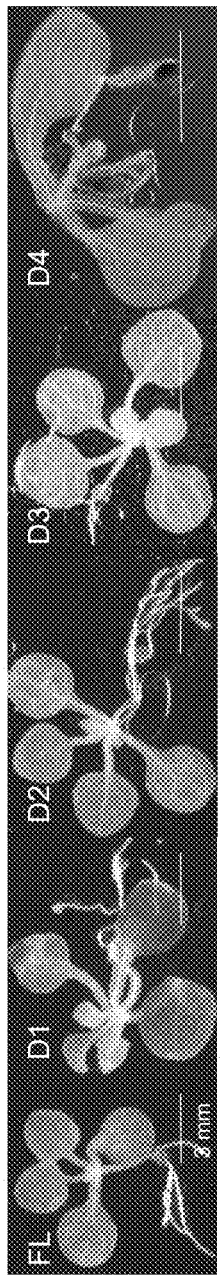
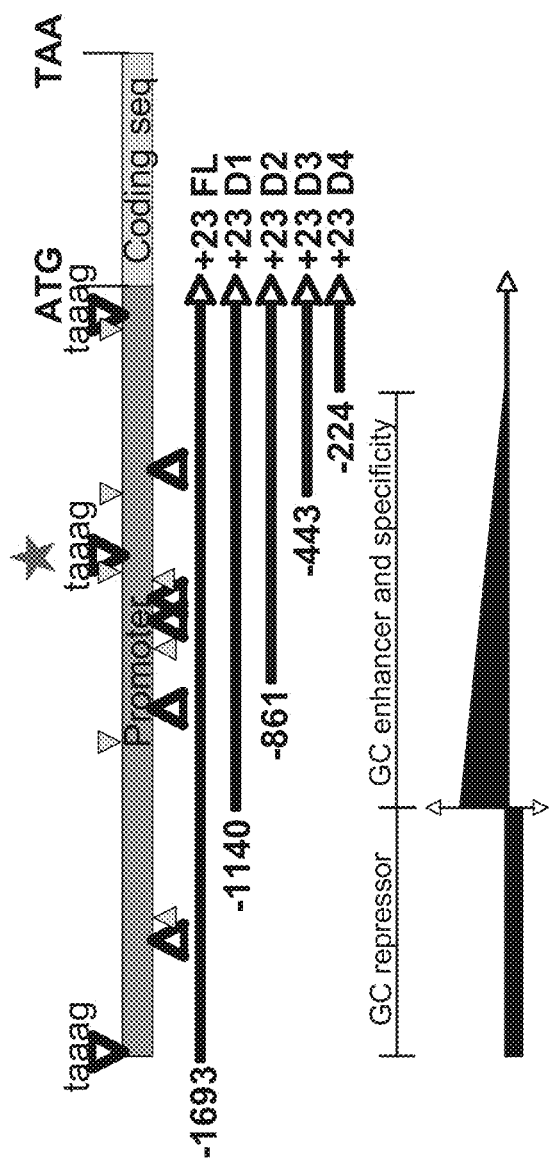
Fig. 18A
Fig. 18B

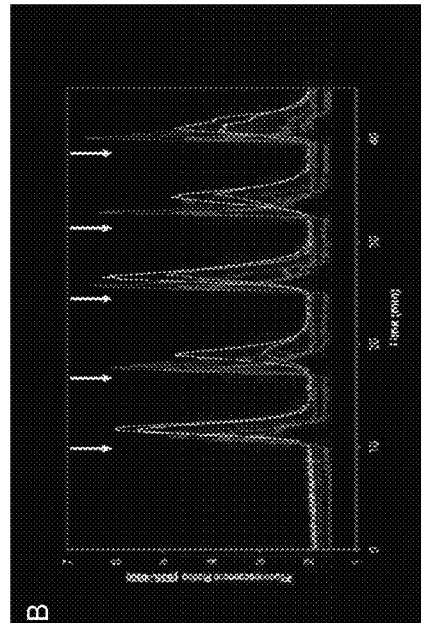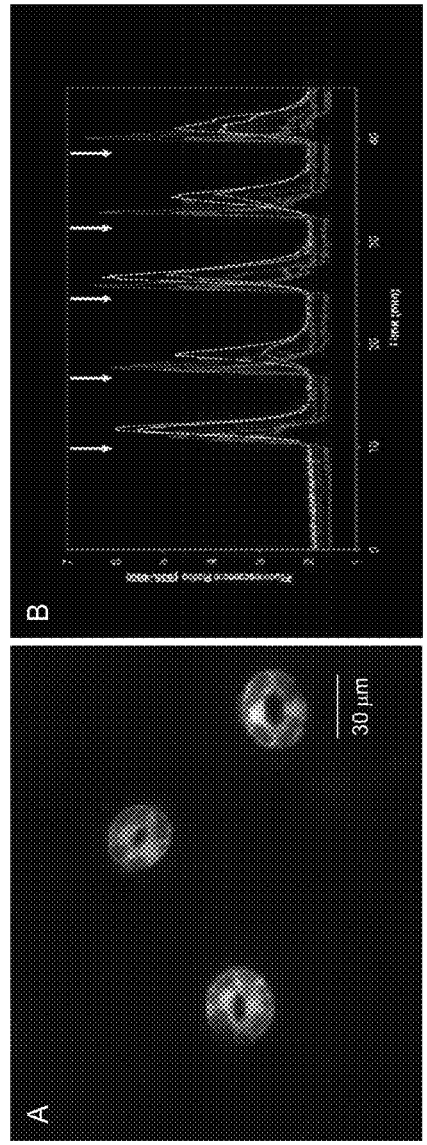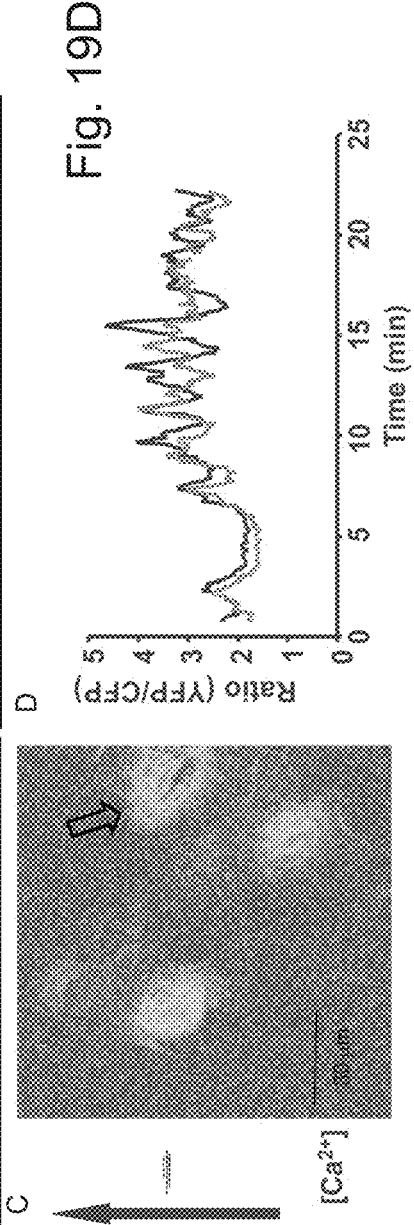
Fig. 19A  Fig. 19B  Fig. 19C  Fig. 19D

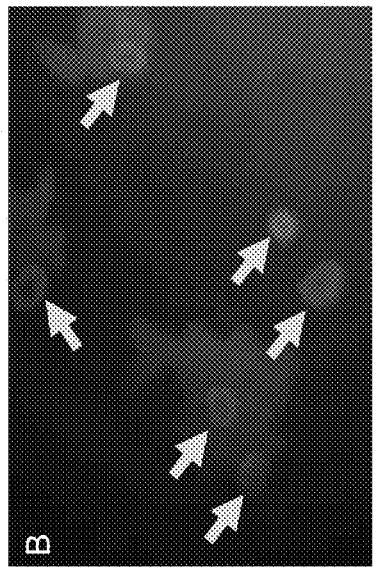
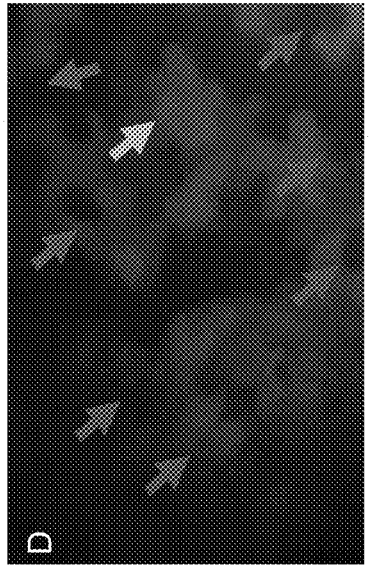
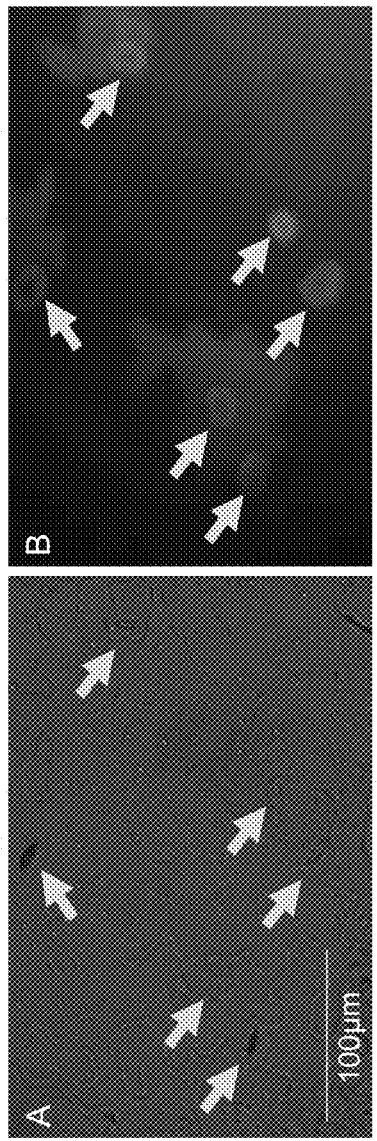
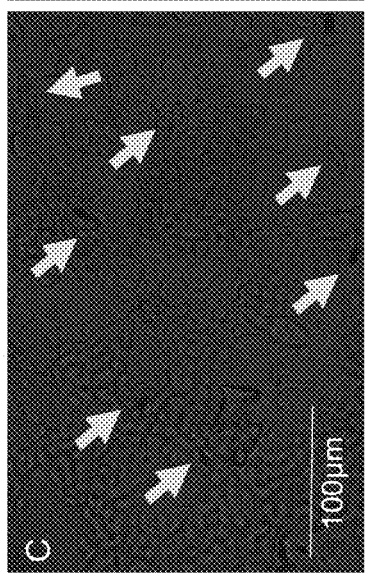

PLANT $CO_2$ SENSORS, NUCLEIC ACIDS ENCODING THEM, AND METHODS FOR MAKING AND USING THEM

RELATED APPLICATIONS

This U.S. utility patent application is a national phase under 35 USC 371 of international patent application PCT/US2008/061654, filed Apr. 25, 2008, which has as a priority document (claims the benefit of priority of) U.S. Provisional Application No. 60/914,640, filed Apr. 27, 2007. The aforementioned applications are explicitly incorporated herein by reference in their entirety and for all purposes.

STATEMENT AS TO FEDERALLY SPONSORED RESEARCH

This invention was made with United States government support under grant number GM60396, awarded by the National Institutes of Health, and NSF contract # MCB-0417118; and NSF MCB0417118 and NIH R01GM060396. The government has certain rights in this invention.

TECHNICAL FIELD

This invention generally relates to plant molecular and cellular biology. In particular, the invention provides compositions and methods for manipulating the exchange of water and/or carbon dioxide ($CO_2$) through plant stomata by expressing and controlling $CO_2$ sensor genes, including the novel $CO_2$ sensor genes of this invention. The invention also provides drought-resistant plants; and methods for engineering plants with increased water use efficiency and drought-resistant plants.

BACKGROUND

Stomatal pores in the epidermis of plant leaves enable the control of plant water loss and the influx of $CO_2$ into plants from the atmosphere. Carbon dioxide is taken up for photosynthetic carbon fixation and water is lost through the process of transpiration through the stomatal pores. Each stomate is made up of a specialized pair of cells named guard cells, which can modify the size of the stomatal pore by controlling guard cell turgor status. An important trait in agriculture, in biotechnological applications and the production of biofuels is the water use efficiency of plants. The water use efficiency defines how well a plant can balance the loss of water through stomata with the net $CO_2$ uptake into leaves for photosynthesis and hence its biomass accumulation. Several biotic and abiotic factors influence the state of stomatal opening thereby optimizing the water use efficiency of a plant in a given condition. The concentration of $CO_2$ regulates stomatal movements, where high levels of $CO_2$ will lead to stomatal closing and low levels of $CO_2$ will induce stomatal opening. Thus $CO_2$ regulates $CO_2$ influx into plants and plant water loss on a global scale. However, at present no $CO_2$ sensors have been identified. Knowledge on the $CO_2$ receptors that regulate $CO_2$ responses could be used to manipulate the $CO_2$ response so that the water use efficiency during plant growth could be enhanced through engineering.

How plants sense the level of carbon dioxide ($CO_2$) has remained unknown. Knowledge of how $CO_2$ is perceived by a plant could be used to manipulate the $CO_2$ response so that the carbon and water use efficiency during plant growth could be enhanced.

Phosphoenolpyruvate (PEP) Carboxylase (PEPC; EC 4.1.1.31) is a key enzyme of photosynthesis in those plant species exhibiting the C4 or CAM pathway for $CO_2$ fixation. The principal substrate of PEPC is the free form of PEP. PEPC catalyzes the conversion of PEP and bicarbonate to oxalacetic acid inorganic phosphate (Pi). This reaction is the first step of a metabolic route known as the C4 dicarboxylic acid pathway, which minimizes losses of energy produced by photorespiration. PEPC is present in plants, algae, cyanobacteria, and bacteria.

Carbon fixation, or the conversion of $CO_2$ to reduced forms amenable to cellular biochemistry, occurs by several metabolic pathways in diverse organisms. The most familiar of these is the Calvin Cycle (or "Calvin-Benson" cycle), which is present in cyanobacteria and their plastid derivatives, such as chloroplasts, and proteobacteria. The Calvin cycle utilizes the enzyme "rubisco", or "ribulose-1,5-bisphosphate carboxylase/oxygenase". Rubisco exists in at least two forms: form I rubisco is found in proteobacteria, cyanobacteria, and plastids, e.g., as an octo-dimer composed of eight large subunits, and eight small subunits; form II rubisco is a dimeric form of the enzyme, e.g., as found in proteobacteria. Rubisco contains two competing enzymatic activities: an oxygenase and a carboxylase activity. The oxygenation reaction catalyzed by Rubisco is a "wasteful" process since it competes with and significantly reduces the net amount of carbon fixed. The Rubisco enzyme species encoded in various photosynthetic organisms have been selected by natural evolution to provide higher plants with a Rubisco enzyme that is substantially more efficient at carboxylation in the presence of atmospheric oxygen.

SUMMARY

The invention provides compositions and methods for manipulating the exchange of water and/or carbon dioxide ($CO_2$) through plant stomata by controlling $CO_2$ sensor genes, including the novel $CO_2$ sensor genes of this invention, designated "$CO_2$Sen genes". The invention's methods, by controlling how $CO_2$ is perceived by a plant, can be used to manipulate the $CO_2$ response so that the carbon and water are used more (or less) efficiently during plant growth. Thus, the methods of the invention can be used to modify net $CO_2$ uptake and water use efficiency in plants by manipulating the expression and/or activity of $CO_2$ sensor genes, including any of the novel $CO_2$ sensor genes of this invention, or any combination thereof. These findings demonstrate a potentially vital role of $CO_2$ sensor genes, including any of the novel $CO_2$ sensor genes of this invention, in the sensing and/or signaling of $CO_2$ perception in plants.

The invention provides compositions and methods for manipulating the exchange of water and $CO_2$ through stomata by controlling $CO_2$ sensor genes, including any of the novel $CO_2$ sensor genes of this invention, including upregulating or down-regulating expression, which can be accomplished by upregulating or downregulating or inhibiting $CO_2$ sensor genes and/or transcripts, including the sequence of this invention. The invention provides compositions and methods to modify net $CO_2$ uptake and water use efficiency in plants. The invention provides plants, e.g., transgenic plants, that show improved growth under limiting water conditions; thus, the invention provides drought-tolerant plants (e.g., crops). The invention provides methods for engineering enhanced water use efficiency in plants or drought-tolerance in plants (e.g., crops). The invention provides compositions and methods for manipulating biomass accumulation and/or biofuel production in a plant by controlling any one, two or three newly discovered $CO_2$ sensor genes and/or transcripts of this invention.

The invention provides compositions and methods for manipulating the opening or closing of stomatal pores on guard cells in the epidermis of plant leaves, thereby enabling the control of plant water loss and the influx of $CO_2$ into plants from the atmosphere. The invention provides compositions and methods for manipulating carbon dioxide uptake, photosynthetic carbon fixation and/or water loss through the process of transpiration through the stomatal pores; each stomate is made up of a specialized pair of cells named guard cells, which can modify the size of the stomatal pore by controlling guard cell turgor status. The invention provides compositions and methods for manipulating guard cell turgor status.

The invention provides compositions and methods for enhancing the production of biomass for biofuel production by manipulating water use efficiency of plants; the water use efficiency defines how well a plant can balance the loss of water through stomata with the net $CO_2$ uptake for photosynthesis, and hence its biomass accumulation.

The inventors have identified a double mutant and a triple mutant in *Arabidopsis thaliana* that lacks the full-length expression of homologous genes that are highly expressed in wild-type guard cells, according to cell-specific microarray analyses. The $CO_2$Sen double mutant and triple mutant show an impaired stomatal response as measured by real-time gas exchange analysis to changes in carbon dioxide concentration ($[CO_2]$); both with regards to changes from ambient 365 ppm $CO_2$ to elevated 800 ppm $CO_2$ and from 800 ppm $CO_2$ to reduced 100 ppm $CO_2$. The $CO_2$Sens-encoded proteins are known to bind $CO_2$. These findings demonstrate a role of the nucleic acids of this invention, the so-called "CO2Sen genes", in the sensing/signaling of $CO_2$ perception. The invention provides means to control how plants can sense $CO_2$, thus also providing means to produce crops with altered carbon and water use efficiency. Thus, the invention provides compositions (e.g., transgenic plants) and methods to ameliorate the effects of rising atmospheric $[CO_2]$ on different plant species.

The invention provides compositions and methods for manipulating how $CO_2$ is sensed in plants, and compositions and methods for controlling the production of crops with altered water use efficiency (WUE). Many plants exhibit a weak stomatal movement response to different $CO_2$ concentrations. Data from the double mutant of this invention (of the CA1/CA4 genes) shows an impaired stomatal response to altered $[CO_2]$, and over-expression of either gene in guard cells dramatically increases the water use efficiency of plants. These data demonstrate that over-expression of all or one of these genes (e.g., $CO_2$Sens of the invention) evokes an improved $CO_2$ response. Thus, overexpression of the nucleic acids of this invention (resulting in overexpression of $CO_2$Sens-encoded proteins) enhances WUE in light of the continuously rising atmospheric $CO_2$ concentrations. Transgenic or manipulated plants (e.g., crops) of this invention would close their stomata to a greater extent than wild-type plants, thereby preserving their water usage; the invention provides methods for overexpressing $CO_2$Sens-encoded proteins by, e.g., inserting or infecting plants with $CO_2$Sens-encoding nucleic acids, e.g., as plasmids, viruses, and the like. As a consequence, plants (e.g., crops) of this invention will have higher water use efficiency and will have increased drought resistance.

The invention also provides compositions and methods for inhibiting the expression of $CO_2$Sens genes, transcripts and $CO_2$Sens proteins by, e.g., antisense and/or RNAi repression of $CO_2$ sensors in guard cells. Crops can show a strong response to elevated atmospheric $CO_2$ such that they close their stomata relatively strongly, which has several disadvantages for agricultural production and yields, e.g., a strong $CO_2$-induced stomatal closing response will limit the ability of these crops to fix carbon for maximal growth. The $CO_2$Sens under-expressing transgenic plants or $CO_2$Sens-under-expressing plants of this invention address this issue by opening their stomata to a greater extent than wild-type plants, preventing limited yields when sufficient water is available.

The invention also provides compositions and methods that address the major problem when crops cannot withstand increased temperatures leading to "breakdown" of metabolism, photosynthesis and growth: elevated $CO_2$ causes stomata to close; and this increases leaf temperature because of reduced water evaporation (transpiration) from leaves. Thus, compositions and methods of this invention, by inhibiting the expression of $CO_2$Sens nucleic acids and/or $CO_2$Sens proteins, help crops that otherwise would be sensitive to elevated temperatures to cope with the increased atmospheric $CO_2$ concentrations, also reducing or ameliorating an accelerated increase in leaf temperatures. The invention provides compositions and methods comprising antisense and RNAi for repression of $CO_2$ sensors in guard cells. In one aspect, a guard cell promoter provides a means to reduce leaf temperature through enhancing transpiration in these crops and also to maximize crop yields.

The compositions and methods of the invention can be used to manipulate how plants sense $CO_2$, thus practicing this invention can aid in the production of crops with altered and improved carbon and water use efficiency. Practicing this invention also improves our predictions of the effects of rising atmospheric $CO_2$ concentrations on different plant species. This invention also demonstrates a vital role of the identified $CO_2$Sen genes in the sensing/signaling of $CO_2$ perception. The compositions and methods of the invention can be used to manipulate plant growth, e.g., by manipulating how $CO_2$ is perceived in a plant, the compositions and methods of the invention can be used to manipulate the plant $CO_2$ response such that the carbon and water use efficiency during plant growth is enhanced.

Also provided herein are kits comprising nucleic acids and/or proteins of this invention, and instructions for making and/or using them, and instructions for practicing the methods provided herein.

The invention provides isolated, synthetic or recombinant nucleic acids (polynucleotide) comprising (a) a nucleic acid (polynucleotide) sequence encoding SEQ ID NO:3, SEQ ID NO:6 or SEQ ID NO:9, or functional fragments thereof, wherein the functional fragment has a $CO_2$Sen ($CO_2$ sensor) protein activity, a carbonic anhydrase (carbonate dehydratase) activity, or a β-carbonic anhydrase activity;

(b) a nucleic acid (polynucleotide) sequence having at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or complete sequence identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over a region of at least about 50, 75, 100, 150, 200, 250, 300, 350, 400, 450, 500, 550, 600, 650, 700, 750, 800, 850, 900, 950, 1000, 1050, 1100, 1150 or more residues, or over the full length of a protein coding sequence (transcript) or gene,
  wherein the nucleic acid encodes:
  (i) a $CO_2$Sen ($CO_2$ sensor) protein that has a $CO_2$Sen ($CO_2$ sensor) protein activity,
  (ii) a polypeptide having a carbonic anhydrase (carbonate dehydratase) activity, or a β-carbonic anhydrase activity; or
  (iii) a polypeptide or peptide capable of generating an antibody that binds specifically to a polypeptide having a sequence SEQ ID NO:3, SEQ ID NO:6 and/or SEQ ID NO:9;
(c) a nucleic acid (polynucleotide) encoding a functional fragment of the protein encoded by the nucleic acid of (b), wherein the functional fragment has a $CO_2$Sen ($CO_2$ sensor) protein activity or a carbonic anhydrase (carbonate dehydratase) activity, or a β-carbonic anhydrase activity;
(d) a nucleic acid (polynucleotide) sequence having at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or complete sequence identity to SEQ ID NO:10 and/or SEQ ID NO:11, over a region of at least about 50, 75, 100, 150, 200, 250, 300, 350, 400, 450, 500, 550, 600, 650, 700, 750, 800 or more residues, or over the full length of a promoter having guard-cell specific activity, or a transcriptional regulatory region having guard-cell specific activity,
  wherein the nucleic acid comprises or consists of a guard cell-specific promoter, or a guard cell-specific transcriptional regulatory region;
(e) the nucleic acid (polynucleotide) of (b) or (d), wherein the sequence identity is calculated using a sequence comparison algorithm consisting of a BLAST version 2.2.2 algorithm where a filtering setting is set to blastall -p blastp -d "nr pataa" -F F, and all other options are set to default;
(f) a nucleic acid (polynucleotide) sequence that hybridizes under stringent conditions to a nucleic acid comprising:
  (i) SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, wherein the nucleic acid encodes
    (A) a $CO_2$Sen ($CO_2$ sensor) protein that has a $CO_2$Sen ($CO_2$ sensor) protein activity, or
    (B) a polypeptide having a carbonic anhydrase (carbonate dehydratase) activity, or a β-carbonic anhydrase activity;
  (ii) SEQ ID NO:10 and/or SEQ ID NO:11, wherein the nucleic acid has a guard-cell specific promoter activity, or a guard-cell specific transcriptional regulatory activity;
  and the stringent conditions include a wash step comprising a wash in 0.2×SSC at a temperature of about 65° C. for about 15 minutes;
(g) the nucleic acid of (f), wherein the nucleic acid is at least about 20, 30, 40, 50, 60, 75, 100, 150, 200, 300, 400, 500, 600, 700, 800, 900, 1000 or more residues in length or the full length of the protein coding region or gene, or promoter or transcriptional regulatory region; or
(h) a nucleic acid (polynucleotide) fully (completely) complementary to any of (a) to (g).

The invention provides antisense oligonucleotides comprising
(a) a nucleic acid sequence complementary to or capable of hybridizing under stringent conditions to a sequence of the invention, or a subsequence thereof; or,
(b) the antisense oligonucleotide of (a), wherein the antisense oligonucleotide is between about 10 to 50, about 20 to 60, about 30 to 70, about 40 to 80, or about 60 to 100 bases in length.

The invention provides methods of inhibiting or decreasing the translation of a $CO_2$Sen ($CO_2$ sensor) protein-encoding message in a cell or plant, or a plant or plant part, comprising administering to the cell, or a plant or plant part, or expressing in the cell, or a plant or plant part, an antisense oligonucleotide comprising (a) a nucleic acid of the invention; or, (b) a nucleic acid sequence complementary to or capable of hybridizing under stringent conditions to a nucleic acid sequence of the invention.

The invention provides double-stranded inhibitory RNA (RNAi) molecules comprising
(a) a subsequence of a nucleic acid sequence of the invention;
(b) the double-stranded inhibitory RNA (RNAi) molecule of (a), wherein the double-stranded inhibitory RNA is an siRNA or an miRNA molecule, or
(c) the double-stranded inhibitory RNA (RNAi) molecule of (a) or (b) having a length of about 15, 16, 17, 18, 19, 20, 21, 22, 23, 24, 25 or more duplex nucleotides in length.

The invention provides methods of inhibiting or decreasing the expression of $CO_2$Sen ($CO_2$ sensor) protein and/or $CO_2$Sen message in a cell, or a plant or plant part, comprising administering to the cell, or a plant or plant part, or expressing in the cell, or a plant or plant part: (a) the double-stranded inhibitory RNA (RNAi) molecule of claim 4; or, (b) a double-stranded inhibitory RNA (iRNA), wherein the RNA comprises a subsequence of a nucleic acid sequence of the invention, wherein in one aspect the RNAi is an siRNA or an miRNA molecule.

The invention provides an expression cassette, plasmid, recombinant virus, vector, cosmid or artificial chromosome comprising:
(a) a nucleic acid (sequence) of the invention;
(b) the expression cassette, plasmid, virus, vector, cosmid or artificial chromosome of (a), wherein the nucleic acid of the invention comprises or consists of a $CO_2$Sen ($CO_2$ sensor) protein coding sequence, and the protein coding sequence is operably linked to a promoter or a transcriptional regulatory region;
(c) the expression cassette, plasmid, recombinant virus, vector, cosmid or artificial chromosome of (b), wherein the promoter is a guard-cell specific promoter, or a guard-cell specific transcriptional regulatory region;
(d) the expression cassette, plasmid, recombinant virus, vector, cosmid or artificial chromosome of (c), wherein the nucleic acid of the invention comprises or consists of a guard-cell specific promoter, or a guard-cell specific transcriptional regulatory region, and the promoter is operably linked to a protein coding sequence;
(e) the expression cassette, plasmid, recombinant virus, vector, cosmid or artificial chromosome of (d), wherein the protein coding sequence encodes a polypeptide having carbonic anhydrase (carbonate dehydratase) activity, or a β-carbonic anhydrase activity;
(f) the expression cassette, plasmid, recombinant virus, vector, cosmid or artificial chromosome of (b), wherein the promoter or a transcriptional regulatory region comprises a constitutive promoter or a transcriptional regulatory region, a tissue specific promoter or a transcriptional regulatory region, an inducible promoter or a transcriptional regulatory region, a silencing promoter, a $CO_2$ sensing promoter;

(g) the expression cassette, plasmid, recombinant virus, vector, cosmid or artificial chromosome of any of (a) to (f), wherein the recombinant virus is a plant virus or the vector is a plant vector; or (h) the expression cassette, plasmid, recombinant virus, vector, cosmid or artificial chromosome of any of (a) to (g), wherein the promoter comprises the promoter sequence or a transcriptional regulatory region of SEQ ID NO:10 or SEQ ID NO:11, or functional (transcriptional regulatory) subsequences thereof.

The invention provides a transduced or transformed cell comprising (a) the expression cassette, plasmid, recombinant virus, vector, cosmid or artificial chromosome of the invention, or a nucleic acid (sequence) of the invention;

(b) the transduced or transformed cell of (a), wherein the cell is a bacterial cell, a mammalian cell, a fungal cell, a yeast cell, an insect cell or a plant cell;

(c) the transduced or transformed cell of (a), wherein the cell is a plant guard cell.

The invention provides a plant, plant cell, plant organ, plant leaf, plant fruit or seed comprising (a) the expression cassette, plasmid, recombinant virus, vector, cosmid or artificial chromosome of the invention, or a nucleic acid (sequence) of the invention;

(b) the plant, plant cell, plant organ, plant leaf, plant fruit or seed of (a), wherein the plant is, or the plant cell, plant organ, plant leaf, plant fruit or seed is derived from: (i) a dicotyledonous or monocotyledonous plant; (ii) wheat, oat, rye, barley, rice, sorghum, maize (corn), tobacco, a legume, a lupins, potato, sugar beet, pea, bean, soybean (soy), a cruciferous plant, a cauliflower, rape (or rapa or canola), cane (sugarcane), flax, cotton, palm, sugar beet, peanut, a tree, a poplar, a lupin, a silk cotton tree, desert willow, creosote bush, winterfat, balsa, ramie, kenaf, hemp, roselle, jute, or sisal abaca; or, (c) a specie from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea*.

The invention provides a transgenic plant, plant cell, plant part, plant leaf, plant organ, plant fruit or seed comprising (a) a heterologous nucleic acid, wherein the heterologous nucleic acid comprises a nucleic acid (sequence) of the invention, or the expression cassette, plasmid, virus, vector, cosmid or artificial chromosome of the invention, (b) the transgenic plant, plant cell, plant part, plant leaf, plant organ, plant fruit or seed of (a), wherein the plant cell is a plant guard cell; or (c) the transgenic plant, plant cell, plant part, plant leaf, plant organ, plant fruit or seed of (a), wherein the plant is, or the plant cell, plant organ, plant fruit or seed is derived from: (i) a dicotyledonous or monocotyledonous plant; (ii) wheat, oat, rye, barley, rice, sorghum, maize (corn), tobacco, a legume, a lupins, potato, sugar beet, pea, bean, soybean (soy), a cruciferous plant, a cauliflower, rape (or rapa or canola), cane (sugarcane), flax, cotton, palm, sugar beet, peanut, a tree, a poplar, a lupin, a silk cotton tree, desert willow, creosote bush, winterfat, balsa, ramie, kenaf, hemp, roselle, jute, or sisal abaca; or, (c) a specie from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea*.

The invention provides isolated, synthetic or recombinant polypeptides comprising:

(a) an amino acid sequence comprising the sequence of SEQ ID NO:3, SEQ ID NO:6 or SEQ ID NO:9, or functional fragments thereof, wherein the functional fragment has a $CO_2Sen$ ($CO_2$ sensor) protein activity or a carbonic anhydrase (carbonate dehydratase) activity, or a β-carbonic anhydrase activity;

(b) an amino acid sequence having at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or complete (amino acid) sequence identity to SEQ ID NO:3, SEQ ID NO:6 and/or SEQ ID NO:9, over a region of at least about 20, 30, 40, 50, 75, 100, 150, 200, 250, 300, 350, 400, 450, 500, 550, 600, 650, 700 or more residues, or over the full length of the polypeptide, wherein the polypeptide has a $CO_2Sen$ ($CO_2$ sensor) protein activity, or a carbonic anhydrase (carbonate dehydratase) activity, or a β-carbonic anhydrase activity, or the polypeptide is capable of generating an antibody that binds specifically to a polypeptide having a sequence SEQ ID NO:3, SEQ ID NO:6 and/or SEQ ID NO:9;

(c) a functional fragment of the polypeptide of (b), wherein the functional fragment has a $CO_2Sen$ ($CO_2$ sensor) protein activity or a carbonic anhydrase (carbonate dehydratase) activity, or a β-carbonic anhydrase activity;

(d) the polypeptide of (b), wherein the sequence identity is calculated using a sequence comparison algorithm consisting of a BLAST version 2.2.2 algorithm where a filtering setting is set to blastall -p blastp -d "nr pataa" -F F, and all other options are set to default;

(e) the polypeptide of any of (a) to (d) having at least one conservative amino acid substitution and retaining its $CO_2Sen$ ($CO_2$ sensor) protein activity or a carbonic anhydrase (carbonate dehydratase) activity, or a β-carbonic anhydrase activity;

(f) the polypeptide of (e), wherein the at least one conservative amino acid substitution comprises substituting an amino acid with another amino acid of like characteristics; or, a conservative substitution comprises: replacement of an aliphatic amino acid with another aliphatic amino acid; replacement of a serine with a threonine or vice versa; replacement of an acidic residue with another acidic residue; replacement of a residue bearing an amide group with another residue bearing an amide group; exchange of a basic residue with another basic residue; or replacement of an aromatic residue with another aromatic residue;

(g) the polypeptide of any of (a) to (f), further comprising a heterologous amino acid sequence.

The invention provides a transgenic plant, plant cell, plant part, plant leaf, plant organ, plant fruit or seed comprising (a) a heterologous or synthetic polypeptide comprising the polypeptide of the invention;

(b) the transgenic plant, plant cell, plant part, plant leaf, plant organ, plant fruit or seed of (a), wherein the plant cell is a plant guard cell; or (c) the transgenic plant, plant cell, plant part, plant leaf, plant organ, plant fruit or seed of (a), wherein the plant is, or the plant cell, plant organ, plant fruit or seed is isolated and/or derived from: (i) a dicotyledonous or monocotyledonous plant; (ii) wheat, oat, rye, barley, rice, sorghum, maize (corn), tobacco, a legume, a lupins, potato, sugar beet, pea, bean, soybean (soy), a cruciferous plant, a cauliflower, rape (or rapa or canola), cane (sugarcane), flax, cotton, palm, sugar beet, peanut, a tree, a poplar, a lupin, a silk cotton tree, desert willow, creosote bush, winterfat, balsa, ramie, kenaf, hemp, roselle, jute, or sisal abaca; or, (c) a specie from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea*.

The invention provides a protein preparation comprising the polypeptide of the invention, wherein the protein preparation comprises a liquid, a solid or a gel.

The invention provides an immobilized protein or an immobilized polynucleotide, wherein the protein comprises the polypeptide of the invention, and the polynucleotide comprises the nucleic acid of the invention, wherein in one aspect the protein or polynucleotide is immobilized on a wood chip, a paper, a cell, a metal, a resin, a polymer, a ceramic, a glass, a microelectrode, a graphitic particle, a bead, a gel, a plate, an array or a capillary tube.

The invention provides an isolated, synthetic or recombinant antibody that specifically binds to the polypeptide of the invention, wherein in one aspect the antibody is a monoclonal or a polyclonal antibody, or is a single chained antibody.

The invention provides a hybridoma comprising an antibody of the invention.

The invention provides an array comprising immobilized protein or an immobilized polynucleotide of the invention; or the antibody of the invention; or, a combination thereof.

The invention provides a method of producing a recombinant polypeptide comprising the steps of: (a) providing a nucleic acid operably linked to a promoter, wherein the nucleic acid comprises a nucleic acid sequence of the invention; and (b) expressing the nucleic acid of step (a) under conditions that allow expression of the polypeptide, thereby producing a recombinant polypeptide, and in one aspect the method further comprises transforming a host cell with the nucleic acid of step (a) followed by expressing the nucleic acid of step (a), thereby producing a recombinant polypeptide in a transformed cell.

The invention provides a method for enzymatically catalyzing the conversion of carbon dioxide to bicarbonate and protons comprising contacting the polypeptide of the invention, or a polypeptide encoded by the nucleic acid of the invention, with a carbon dioxide to under conditions allowing the enzymatic catalysis of the conversion of carbon dioxide to bicarbonate and protons.

The invention provides methods for down-regulating or decreasing carbon dioxide ($CO_2$) and/or water exchange in a guard cell of a plant, plant cell, plant leaf, plant organ or plant part comprising (A) (a) providing:
  (i) a $CO_2$Sen ($CO_2$ sensor) protein-expressing nucleic acid and/or a $CO_2$Sen gene or transcript (message);
  (ii) the $CO_2$Sen nucleic acid or gene of (i), wherein the protein-expressing nucleic acid or the $CO_2$Sen gene or transcript (message) comprises a sequence of the invention, and/or the protein-expressing nucleic acid or $CO_2$Sen protein comprises an amino acid sequence of the invention;
  (iii) a polypeptide having a carbonic anhydrase (CA) activity, or a β-carbonic anhydrase activity, or a nucleic acid encoding the CA polypeptide;
  (iv) a nucleic acid encoding a CA polypeptide, wherein the nucleic acid comprises SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35;
  (v) an antisense nucleic acid or a nucleic acid inhibitory to the expression of a PEPC polypeptide-encoding nucleic acid; and/or
  (vi) the method of (v), wherein the antisense or inhibitory nucleic acid target a Phosphoenolpyruvate (PEP) Carboxylase (or PEP carboxylase, or PEPC) polypeptide-encoding nucleic acid comprising SEQ ID NO:12, SEQ ID NO:13, SEQ ID NO:14 and/or SEQ ID NO:15; and (b) (i) expressing, or overexpressing, the nucleic acid or gene of (a), or a $CO_2$Sen ($CO_2$ sensor) protein-expressing nucleic acid and/or a $CO_2$Sen gene or transcript (message), and/or a carbonic anhydrase or a β-carbonic anhydrase or carbonic anhydrase-expressing nucleic acid, in the guard cell, or (ii) expressing the antisense nucleic acid or nucleic acid inhibitory to the expression of a PEPC polypeptide-encoding nucleic acid, in the guard cell, or (iii) contacting the guard cell with the polypeptide having carbonic anhydrase activity, thereby up-regulating or increasing carbon dioxide ($CO_2$) and/or water exchange in a guard cell;

(B) the method of (A), wherein the plant is a transgenic plant of the invention, or a plant transduced, transformed or infected with the expression cassette, plasmid, virus or vector of the invention, or the plant cell is the transduced cell of the invention;

(C) the method of (A) or (B), wherein the plant is characterized by controlled $CO_2$ exchange under ambient 365 ppm $CO_2$, elevated ppm $CO_2$ or reduced ppm $CO_2$, or the plant is characterized by controlled water exchange under ambient 365 ppm $CO_2$, elevated ppm $CO_2$ or reduced ppm $CO_2$; or (D) the method of any of (A) to (C), wherein the antisense nucleic acid or nucleic acid inhibitory to the expression of a PEPC polypeptide-encoding nucleic acid comprises miRNA or siRNA, or an antisense oligonucleotide.

The invention provides methods for up-regulating or increasing carbon dioxide ($CO_2$) and/or water exchange in a guard cell of a plant, plant cell, plant leaf, plant organ or plant part comprising (A) (a) providing:
  (i) a nucleic acid antisense to or otherwise inhibitory to the expression of a $CO_2$Sen gene or transcript (message), wherein the $CO_2$Sen gene or transcript (message) comprises a sequence of the invention, and/or a sequence encoding the $CO_2$Sen protein of the invention;
  (ii) a nucleic acid antisense to or otherwise inhibitory to a nucleic acid encoding a plant carbonic anhydrase (CA), or a plant β-carbonic anhydrase;
  (iii) a Phosphoenolpyruvate (PEP) Carboxylase (or PEP carboxylase, or PEPC) protein-expressing nucleic acid and/or a PEPC gene or transcript (message); and/or
  (iv) a Phosphoenolpyruvate (PEP) Carboxylase (or PEP carboxylase, or PEPC) polypeptide; and (b) (i) expressing the antisense or inhibitory nucleic acid in the guard cell, or (ii) expressing the PEPC) protein-expressing nucleic acid and/or a PEPC gene or transcript (message) in the guard cell, or (iii) contacting the guard cell with the polypeptide having PEPC activity, thereby up-regulating or increasing carbon dioxide ($CO_2$) and/or water exchange in a guard cell;

(B) the method of (A), wherein the plant is a transgenic plant of the invention, or a plant transduced, transformed or infected with the expression cassette, plasmid, virus or vector of the invention, or the plant cell is the transduced cell of the invention;

(C) the method of (A) or (B), wherein the plant is characterized by controlled $CO_2$ exchange under ambient 365 ppm $CO_2$, elevated ppm $CO_2$ or reduced ppm $CO_2$, or the plant is characterized by controlled water exchange under ambient 365 ppm $CO_2$, elevated ppm $CO_2$ or reduced ppm $CO_2$; or (D) the method of (A), (B) or (C), wherein the nucleic acid antisense to or otherwise inhibitory to the expression of the $CO_2$Sen gene or transcript (message), or antisense to or otherwise inhibitory to the expression of the carbonic anhydrase (CA) or β-carbonic anhydrase, comprises the antisense oligonucleotide of claim 2, or the double-stranded inhibitory RNA (RNAi) molecule of claim 4, or an miRNA or an siRNA.

The invention provides methods for regulating water exchange in a cell of a plant, plant cell, plant leaf, plant organ or plant part comprising:

(A) over-expressing or under-expressing in the plant, plant cell, plant leaf, plant organ or plant part:
(i) a $CO_2$Sen ($CO_2$ sensor) protein and/or a $CO_2$Sen gene or transcript (message), wherein the $CO_2$Sen gene or transcript (message) comprises a sequence of the invention, and/or the $CO_2$Sen protein comprises an amino acid sequence of the invention, or
(ii) a polypeptide having a carbonic anhydrase (CA) activity, or a β-carbonic anhydrase activity, or a nucleic acid encoding the carbonic anhydrase polypeptide; or
(iii) a polypeptide having a Phosphoenolpyruvate (PEP) Carboxylase (or PEP carboxylase, or PEPC) activity, or a nucleic acid encoding the PEPC polypeptide; or
(iv) a polypeptide having a ribulose-1,5-bisphosphate carboxylase/oxygenase, or "Rubisco" activity, or a nucleic acid encoding the Rubisco polypeptide, thereby regulating water exchange (down-regulating or decreasing water exchange by overexpression of the $CO_2$Sen or CA protein, or up-regulating or increasing water exchange by under-expression of the $CO_2$Sen or CA protein) in the plant, plant cell, plant leaf, plant organ or plant part;

(B) the method of (A), wherein the plant is a transgenic plant of the invention, or a plant transduced, transformed or infected with the expression cassette, plasmid, virus or vector of the invention, or the plant cell is the transduced cell of the invention; or (C) the method of (A) or (B), wherein the plant is characterized by controlled $CO_2$ exchange under ambient 365 ppm $CO_2$, elevated ppm $CO_2$ or reduced ppm $CO_2$, or the plant is characterized by controlled water exchange under ambient 365 ppm $CO_2$, elevated ppm $CO_2$ or reduced ppm $CO_2$; or (D) the method of any of (A) to (C), wherein the overexpression or increased expression, or under-expressing or inhibition, is in a plant guard cell; or (E) the method of any of (A) to (D), wherein overexpressing a $CO_2$Sen ($CO_2$ sensor) or carbonic anhydrase protein and/or a $CO_2$Sen or carbonic anhydrase gene or transcript (message) decreases water exchange, and under-expressing or inhibiting expression of a $CO_2$Sen ($CO_2$ sensor) or carbonic anhydrase protein and/or a $CO_2$Sen or carbonic anhydrase gene or transcript (message) increases water exchange; or (F) the method of any of (A) to (D), wherein under-expressing or inhibiting expression of a PEPC protein and/or a PEPC gene or transcript (message) decreases water exchange, or overexpressing a PEPC protein and/or a PEPC gene or transcript (message) increases water exchange.

The invention provides methods for regulating water uptake or water loss in a plant, plant cell, plant leaf, plant organ or plant part comprising over-expressing or under-expressing in the plant, plant cell, plant leaf, plant organ or plant part:

(A) (i) a $CO_2$Sen ($CO_2$ sensor) protein and/or a $CO_2$Sen gene or transcript (message), wherein the $CO_2$Sen gene or transcript (message) comprises a sequence of the invention, and/or the $CO_2$Sen protein comprises an amino acid sequence of the invention, or
(ii) a polypeptide having a carbonic anhydrase (CA) activity, or a β-carbonic anhydrase activity, or a nucleic acid encoding the polypeptide; or
(iii) a polypeptide having a Phosphoenolpyruvate (PEP) Carboxylase (or PEP carboxylase, or PEPC) activity, or a nucleic acid encoding the PEPC polypeptide; or
(iv) a polypeptide having a ribulose-1,5-bisphosphate carboxylase/oxygenase, or "Rubisco" activity, or a nucleic acid encoding the Rubisco polypeptide, thereby regulating water uptake or water loss (down-regulating water uptake, or causing water conservation, by overexpression of the $CO_2$Sen or CA protein, or up-regulating water exchange or increasing water loss by under-expression of the $CO_2$Sen or CA protein) in the plant, plant cell, plant leaf, plant organ or plant part;

(B) the method of (A), wherein the plant is a transgenic plant of the invention, or a plant transduced, transformed or infected with the expression cassette, plasmid, virus or vector of the invention, or the plant cell is the transduced cell of the invention;

(C) the method of (A) or (B), wherein the plant is characterized by controlled $CO_2$ exchange under ambient 365 ppm $CO_2$, elevated ppm $CO_2$ or reduced ppm $CO_2$, or the plant is characterized by controlled water exchange under ambient 365 ppm $CO_2$, elevated ppm $CO_2$ or reduced ppm $CO_2$; or (D) the method of any of (A) to (C), wherein the overexpression or increased expression is in a plant guard cell; or (E) the method of any of (A) to (D), wherein overexpressing a $CO_2$Sen ($CO_2$ sensor) or carbonic anhydrase protein and/or a $CO_2$Sen or carbonic anhydrase gene or transcript (message) decreases water loss, and under-expressing or inhibiting expression of a $CO_2$Sen ($CO_2$ sensor) or carbonic anhydrase protein and/or a $CO_2$Sen or carbonic anhydrase gene or transcript (message) increases water loss; or (F) the method of any of (A) to (D), wherein under-expressing or inhibiting expression of a PEPC protein and/or a PEPC gene or transcript (message) decreases water loss, or overexpressing a PEPC protein and/or a PEPC gene or transcript (message) increases water loss.

The invention provides methods for making an enhanced water use efficiency (WUE), or drought-resistant, plant comprising:

(A) over-expressing or increasing expression of:
(i) a $CO_2$Sen ($CO_2$ sensor) protein and/or a $CO_2$Sen gene or transcript (message), wherein the $CO_2$Sen gene or transcript (message) comprises a sequence of the invention, and/or the $CO_2$Sen protein comprises an amino acid sequence of the invention, or (ii) a polypeptide having a carbonic anhydrase (CA) activity, or a β-carbonic anhydrase activity, or a nucleic acid encoding the polypeptide; or (iii) a polypeptide having a Phosphoenolpyruvate (PEP) Carboxylase (or PEP carboxylase, or PEPC) activity, or a nucleic acid encoding the PEPC polypeptide; or (iv) a polypeptide having a ribulose-1,5-bisphosphate carboxylase/oxygenase, or "Rubisco" activity, or a nucleic acid encoding the Rubisco polypeptide, thereby making an enhanced water use efficiency (WUE), or drought-resistant, plant;

(B) the method of (A), wherein the plant is a transgenic plant of the invention, or a plant transduced, transformed or infected with the expression cassette, plasmid, virus or vector of the invention, or the plant cell is the transduced cell of the invention; or (C) the method of (A) or (B), wherein the overexpression or increased expression is in a plant guard cell; or (D) the method of any of (A) to (C), wherein overexpressing a $CO_2$Sen ($CO_2$ sensor) or carbonic anhydrase protein and/or a $CO_2$Sen or carbonic anhydrase gene or transcript (message) enhances water use efficiency (WUE), or enhances drought-resistance, and under-expressing or inhibiting expression of a $CO_2$Sen ($CO_2$ sensor) or carbonic anhydrase protein and/or a $CO_2$Sen or carbonic anhydrase gene or transcript (message) increases water loss or decreases WUE; or (E) the method of any of (A) to (C), wherein under-expressing or inhibiting expression of a PEPC protein and/or a PEPC gene or transcript (message) enhances water use efficiency (WUE), or enhances drought-resistance, or overexpressing a PEPC protein and/or a PEPC gene or transcript (message) increases water loss or decreases WUE.

The invention provides a plant, plant part, plant organ, leaf or seed: (a) made by a process comprising the method of the invention; or (b) made by a process comprising the method of the invention, or modified by the method of the invention, wherein the plant is isolated and/or derived from: (i) a dicotyledonous or monocotyledonous plant; (ii) wheat, oat, rye, barley, rice, sorghum, maize (corn), tobacco, a legume, a lupins, potato, sugar beet, pea, bean, soybean (soy), a cruciferous plant, a cauliflower, rape (or rapa or canola), cane (sugarcane), flax, cotton, palm, sugar beet, peanut, a tree, a poplar, a lupin, a silk cotton tree, desert willow, creosote bush, winterfat, balsa, ramie, kenaf, hemp, roselle, jute, or sisal abaca; or, (c) a specie from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea*.

The invention provides methods for making a heat-resistant plant comprising under-expressing a $CO_2$Sen protein and/or a $CO_2$Sen gene or transcript (message), or a carbonic anhydrase (CA), in a cell or cells of a plant, the method comprising:

(A) (a) providing:
(i) a nucleic acid antisense to or otherwise inhibitory to the expression of a $CO_2$Sen gene or transcript (message), wherein the $CO_2$Sen gene or transcript (message) comprises a sequence of the invention, and/or a sequence encoding the $CO_2$Sen protein of the invention;

(ii) a nucleic acid antisense to or otherwise inhibitory to a nucleic acid encoding a plant carbonic anhydrase (CA), or a plant β-carbonic anhydrase; and/or (iii) a nucleic acid encoding a Phosphoenolpyruvate (PEP) Carboxylase (or PEP carboxylase, or PEPC), and (b) expressing the $CO_2$Sen or CA antisense or inhibitory nucleic acid in the guard cell, and/or expressing the PEPC-encoding nucleic acid, thereby making a heat-resistant plant by up-regulating or increasing carbon dioxide ($CO_2$) and/or water exchange in the plant cell or cells;

(B) the method of (A), wherein the cell is a plant guard cell;

(C) the method of (A) or (B), wherein the plant is a transgenic plant of the invention, or a plant transduced, transformed or infected with the expression cassette, plasmid, virus or vector of the invention, or the plant cell is the transduced cell of the invention;

(D) the method of any of (A) to (C), wherein the plant is characterized by controlled $CO_2$ exchange under ambient 365 ppm $CO_2$, elevated ppm $CO_2$ or reduced ppm $CO_2$, or the plant is characterized by controlled water exchange under ambient 365 ppm $CO_2$, elevated ppm $CO_2$ or reduced ppm $CO_2$; or (E) the method of any of (A) to (D), wherein the nucleic acid antisense to or otherwise inhibitory to the expression of the $CO_2$Sen gene or transcript (message), or antisense to or otherwise inhibitory to the expression of the carbonic anhydrase (CA) or β-carbonic anhydrase, comprises the antisense oligonucleotide of claim 2, or the double-stranded inhibitory RNA (RNAi) molecule of claim 4, or an miRNA or an siRNA.

The invention provides a plant, plant part, plant organ, leaf or seed: (a) made by a process comprising the method of the invention; or (b) made by a process comprising the method of the invention, or modified by the method of the invention, wherein the plant is isolated and/or derived from: (i) a dicotyledonous or monocotyledonous plant; (ii) wheat, oat, rye, barley, rice, sorghum, maize (corn), tobacco, a legume, a lupins, potato, sugar beet, pea, bean, soybean (soy), a cruciferous plant, a cauliflower, rape (or rapa or canola), cane (sugarcane), flax, cotton, palm, sugar beet, peanut, a tree, a poplar, a lupin, a silk cotton tree, desert willow, creosote bush, winterfat, balsa, ramie, kenaf, hemp, roselle, jute, or sisal abaca; or, (c) a specie from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea*.

The invention provides methods for opening a stomatal pore in a plant, plant part, a plant organ, a plant leaf, or a plant cell, comprising under-expressing or inhibiting expression of a $CO_2$Sen protein and/or a $CO_2$Sen gene or transcript (message), or a carbonic anhydrase (CA), in a cell or cells of the plant, plant part, plant organ, plant leaf or plant cell the method comprising:

(A) (a) providing:
(i) a nucleic acid antisense to or otherwise inhibitory to the expression of a $CO_2$Sen gene or transcript (message), wherein the $CO_2$Sen gene or transcript (message) comprises a sequence of the invention, and/or a sequence encoding the $CO_2$Sen protein of the invention;

(ii) a nucleic acid antisense to or otherwise inhibitory to a nucleic acid encoding a plant carbonic anhydrase (CA), or a plant β-carbonic anhydrase; and/or (iii) a nucleic acid encoding a Phosphoenolpyruvate (PEP) Carboxylase (or PEP carboxylase, or PEPC); and (b) expressing the $CO_2$Sen and/or CA antisense or inhibitory nucleic acid in the cell or cells of the plant, plant part, plant organ, plant leaf or plant cell, or expressing the PEPC-encoding nucleic acid in the plant, plant part, plant organ, plant leaf or plant cell, thereby causing under-expression and/or inhibition of expression of the $CO_2$Sen protein and/or the $CO_2$Sen gene or transcript (message), and/or the carbonic anhydrase (CA), and/or expressing the PEPC, and causing the stomatal pore to open;

(B) the method of (A), wherein the cell is a plant guard cell;

(C) the method of (A) or (B), wherein the plant is a transgenic plant of the invention, or a plant transduced, transformed or infected with the expression cassette, plasmid, virus or vector of the invention, or the plant cell is the transduced cell of the invention;

(D) the method of any of (A) to (C), wherein the plant is characterized by controlled $CO_2$ exchange under ambient 365 ppm $CO_2$, elevated ppm $CO_2$ or reduced ppm $CO_2$, or the plant is characterized by controlled water exchange under ambient 365 ppm $CO_2$, elevated ppm $CO_2$ or reduced ppm $CO_2$; or (E) the method of any of (A) to (D), wherein the nucleic acid antisense to or otherwise inhibitory to the expression of the $CO_2$Sen gene or transcript (message), or antisense to or otherwise inhibitory to the expression of the carbonic anhydrase (CA) or β-carbonic anhydrase, comprises the antisense oligonucleotide of claim 2, or the double-stranded inhibitory RNA (RNAi) molecule of claim 4, or an miRNA or an siRNA.

The invention provides methods for closing a stomatal pore on a guard cell in the epidermis of a plant, a plant leaf, plant organ, or a plant cell, comprising over-expressing a $CO_2$Sen protein and/or a $CO_2$Sen gene or transcript (message) in a cell or cells of the plant, comprising:

(A) (a) over-expressing or increasing expression of:

(i) a $CO_2$Sen ($CO_2$ sensor) protein and/or a $CO_2$Sen gene or transcript (message), wherein the $CO_2$Sen gene or transcript (message) comprises a sequence of the invention, and/or the $CO_2$Sen protein comprises an amino acid sequence of the invention, or (ii) a polypeptide having a carbonic anhydrase (CA) activity, or a β-carbonic anhydrase activity, or a nucleic acid encoding the polypeptide, thereby causing over-expression and/or increase in expression of the $CO_2$Sen protein and/or the $CO_2$Sen gene or transcript (message), and/or the carbonic anhydrase (CA), and causing the stomatal pore to close, or (b) inhibiting or decreasing expression of a Phosphoenolpyruvate (PEP) Carboxylase (or PEP carboxylase, or PEPC) gene or message (transcript);

(B) the method of (A), wherein the cell is a plant guard cell; or (C) the method of (A) or (B), wherein the plant is a transgenic plant of the invention, or a plant transduced, transformed or infected with the expression cassette, plasmid, virus or vector of the invention, or the plant cell is the transduced cell of the invention.

The invention provides methods for enhancing or optimizing biomass accumulation in a plant, a plant leaf, a plant organ, a plant part, a plant cell or seed by balancing the loss of water through stomata with the net $CO_2$ uptake for photosynthesis, and hence enhancing or optimizing biomass accumulation in the plant, plant leaf, plant part, plant organ, plant cell or seed, comprising opening or closing stomatal pores using a composition and/or method of the invention.

The invention provides methods for reducing leaf temperature and enhancing transpiration in a plant, a plant leave, or a plant cell, comprising opening a stomatal pore a cell or cells of the plant using a composition and/or method of the invention.

In alternative embodiments of any of the methods of the invention, the plant or plant cell is isolated and/or derived from: (i) a dicotyledonous or monocotyledonous plant; (ii) wheat, oat, rye, barley, rice, sorghum, maize (corn), tobacco, a legume, a lupins, potato, sugar beet, pea, bean, soybean (soy), a cruciferous plant, a cauliflower, rape (or rapa or canola), cane (sugarcane), flax, cotton, palm, sugar beet, peanut, a tree, a poplar, a lupin, a silk cotton tree, desert willow, creosote bush, winterfat, balsa, ramie, kenaf, hemp, roselle, jute, or sisal abaca; or, (c) a specie from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea.*

The invention provides transcriptional activators, e.g., acting as promoters or enhancers, for regulating expression of a nucleic acid in a plant cell, wherein the transcriptional activator (e.g., promoter) comprises a sequence as set forth in SEQ ID NO:10 or SEQ ID NO:11, or functional (transcriptional regulatory) subsequences thereof, wherein in one aspect the transcriptional activator (e.g., promoter) up-regulates transcription, and in one aspect the transcriptional activator (e.g., promoter) up-regulates transcription in a plant guard cell-specific manner, and in one aspect the guard cell is a leaf guard cell or a stem guard cell.

The invention provides methods for decreasing oxygenation efficiency and increasing carbon fixation in a guard cell in the epidermis of a plant, a plant leaf, plant organ, or a plant cell, comprising inhibiting or decreasing a ribulose-1,5-bisphosphate carboxylase/oxygenase, or "Rubisco" activity enzyme and/or a Rubisco gene or transcript (message) in a cell or cells of the plant, comprising:

(A) (a) providing a nucleic acid antisense to or otherwise inhibitory to a nucleic acid encoding a plant Rubisco; and (b) inhibiting or decreasing expression of a Rubisco gene or message (transcript) in the plant guard cell;

(B) the method of (A), wherein the cell is a plant guard cell;

(C) the method of (A) or (B), wherein the plant is a transgenic plant of the invention, or a plant transduced, transformed or infected with the expression cassette, plasmid, virus or vector of the invention, or the plant cell is the transduced cell of the invention; or (D) the method of any of (A) to (C), wherein the Rubisco-encoding nucleic acid is a Rubisco gene or message (transcript), or a Rubisco-encoding nucleic acid comprising all or a subsequence of SEQ ID NO:16, SEQ ID NO:17, SEQ ID NO:18 or SEQ ID NO:19.

The invention provides methods for increasing oxygenation efficiency and decreasing carbon fixation in a guard cell in the epidermis of a plant, a plant leaf, plant organ, or a plant cell, comprising increasing expression of a ribulose-1,5-bisphosphate carboxylase/oxygenase, or "Rubisco" activity enzyme and/or a Rubisco gene or transcript (message) in a cell or cells of the plant, comprising:

(A) (a) providing a nucleic acid encoding a plant Rubisco; and (b) expressing the Rubisco-encoding nucleic acid in the guard cell;

(B) the method of (A), wherein the cell is a plant guard cell;

(C) the method of (A) or (B), wherein the plant is a transgenic plant of the invention, or a plant transduced, transformed or infected with the expression cassette, plasmid, virus or vector of the invention, or the plant cell is the transduced cell of the invention; or (D) the method of any of (A) to (C), wherein the Rubisco-encoding nucleic acid is a Rubisco gene or message (transcript), or a Rubisco-encoding nucleic acid comprising all or a subsequence of SEQ ID NO:16, SEQ ID NO:17, SEQ ID NO:18 or SEQ ID NO:19.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

The patent or application file contains at least one drawing executed in color. Copies of this patent or patent application publication with color drawing(s) will be provided by the Office upon request and payment of the necessary fee.

FIG. 2 illustrates pictures showing various expression levels in different stages of guard cell (GC) development.

FIGS. 3A-H are pictures showing expression of 27-YC3.6 (SEQ ID NO:10) in GC on the stem of adjacent leaf but not in the very young leaf (outlined) (A & A'). 27-YC3.6 is mainly expressed in mature GC, very weak in young or immature GC (white arrow in B & B'). 27-YC3.60 (SEQ ID NO:11) is also expressed in GCs on hypocotyle (C & C'). 27-YC3.6 (SEQ ID NO:10) is also expressed in GCs on sepals (D & D'); as described in detail in Example 1, below.

FIG. 4a and FIG. 4b, illustrate (a) the relative stomatal conductances of double mutant (corp1 corp2), WT (wild-type) and (b) a transgenic complemented line (CORP1/corp1 corp2) expressing CORP1 in response to changes in $CO_2$ concentrations (X-axis: ppm $[CO_2]$)

FIG. 6 illustrates data showing the relative stomatal conductance, which reflect gas exchange and water use efficiency (WUE), of the CA1 (SEQ ID NO:7) and CA4 (SEQ ID NO:1) complementation plants; these results are summarized and graphically illustrated in FIG. 7, FIG. 7A graphically illustrating the water use efficiency (WUE) data, and FIG. 7A graphically illustrating the relative stomatal conductance data; as described in detail in Example 2, below.

FIGS. 9A and 9B illustrate photomicrographs of Northern blots showing the expression level of CA1 (SEQ ID NO:7) and CA4 (SEQ ID NO:1) in double knockouts (of CA1 (SEQ ID NO:7) and CA4 (SEQ ID NO:1)). FIGS. 9C, 9D and 9E illustrate data from a $CO_2$ sensor showing deficient $CO_2$ regulation of gas exchange; note: Light condition=red light (50 $\mu mol \cdot m^{-2} \cdot s^{-1}$), blue light (6 $\mu mol \cdot m^{-2} \cdot s^{-1}$); as described in detail in Example 2 and Example 4, below.

FIG. 10A graphically illustrates a summary of data showing intact abscisic acid response in the ca1ca4 (CA1 (SEQ ID NO:7) and CA4 (SEQ ID NO:1)) double mutant. FIG. 10B graphically illustrates a summary of data showing that an inhibitor of CA1 (SEQ ID NO:7) and/or CA4 (SEQ ID NO:1) mimics $CO_2$ Insensitivity in wild-type (WT) plants; as described in detail in Example 2 and Example 4, below.

FIGS. 11A and 11B illustrate photomicrographs of Northern blots showing the expression level of CA1 (SEQ ID NO:7) and CA4 (SEQ ID NO:1) in double knockouts (of CA1 (SEQ ID NO:7) and CA4 (SEQ ID NO:1)), and FIGS. 11C and 11D graphically illustrate data showing that genomic DNA of CA1 (SEQ ID NO:7) (FIG. 11C) or CA4 (SEQ ID NO:1) (FIG. 11D) genes can complement $CO_2$ response; light condition: red light (50 $\mu mol \cdot m^{-2} \cdot s^{-1}$), blue light (6 $\mu mol \cdot m^{-2} \cdot s^{-1}$); as described in detail in Example 2 and Example 4, below.

FIGS. 14A and 14B illustrate photomicrographs of Northern blots showing the expression level of CA1 (SEQ ID NO:7) and CA4 (SEQ ID NO:1) in double knockouts (of CA1 (SEQ ID NO:7) and CA4 (SEQ ID NO:1)); and FIG. 14C, graphically and pictorially illustrate that $CO_2$ sensor over-expression plants where the CA1 (SEQ ID NO:7) and CA4 (SEQ ID NO:1) are operatively linked to guard cell targeted promoters of this invention show enhanced water use efficiency (WUE); in FIG. 14C, the data shows no effect observed on flowering time; as described in detail in Example 2 and Example 4, below.

FIG. 16 is the nucleic acid sequence of GC1 (SEQ ID NO:10); as described in detail in Example 3, below.

FIG. 17A to L illustrate photomicrographs of a GC1 (At1g22690) gene expression analysis in response to different treatments: FIG. 17A illustrates a picture showing that the GC1 promoter mediates strong reporter expression in guard cells of wild-type Arabidopsis seedlings, the picture showing a two-week-old pGC1::GUS transgenic seedling; FIG. 17B illustrating that the pGC1::GUS delivered strong GUS expression in guard cells in leaves, and also in guard cells in petioles and hypocotyls as illustrated in FIG. 17C, D, E; younger or immature guard cells showed no or much less GFP expression, as illustrated in FIG. 17F, G; and guard cells in sepals and hypocotyls also showed GFP expression, as illustrated in FIG. 17H, I, J, K; and GUS staining showed reporter gene expression in clustered stomata, as illustrated in FIG. 17L; GFP expression was observed in clustered stomata in tmm plants transformed with pGC1::YC3.60, as illustrated in FIG. 17M; and, strong guard cell GFP expression was observed in tobacco leaves, as illustrated in FIG. 17N, as described in detail in Example 3, below.

FIG. 18A illustrates photographs that are representative T1 plants from different promoter::GUS transgenic lines; and, FIG. 18B graphically illustrates serial (structural, or sequence) deletion of the pGC1 promoter to define regions for guard cell expression, as described in detail in Example 3, below.

FIG. 19 illustrates imposed intracellular calcium transients in pGC1::YC3.60 expressing guard cells and spontaneous calcium transients occur in guard cells of intact pGC1::YC3.60 transgenic plants: FIG. 19A illustrates fluorescence image of leaf epidermis of pGC1::YC3.60 transgenic plant; FIG. 19B illustrates data showing that the 6 guard cells in panel A all produced intracellular calcium transients in response to imposed calcium oscillations; FIG. 19C illustrates a pseudo-colored ratiometric image of a leaf from an intact Col plants transformed with pGC1::YC3.60; FIG. 19D illustrates a time course of the emission ratios of the two guard cells marked by an arrow in C shows that spontaneous calcium transients occur in intact Arabidopsis plants, as described in detail in Example 3, below.

FIG. 20 illustrates micrographs of pGC1 (D1)::anti-GFP caused reduction of GFP expression in guard cells of 35S::GFP plants: FIG. 20A illustrates leaf epidermis of a 35S::GFP transgenic plant (bright field with GFP filter); FIG. 20B illustrates the fluorescence imaging of same leaf epidermis shown in 20A; FIG. 20C illustrates leaf epidermis of a T1 transgenic plant expressing pGC1(D1)::anti-GFP in the 35S::GFP background; FIG. 20D illustrates the fluorescence imaging of the same leaf epidermis shown in 20C, as described in detail in Example 3, below.

FIG. 24B, FIG. 24C, FIG. 24D and FIG. 24E graphically illustrate stomatal conductance in mol water $m^{-2}$ $sec^{-1}$, as described in detail in Example 4, below.

FIG. 27A and FIG. 27B graphically illustrate a RT-PCR analysis of CA1 and CA4 expression in guard cell protoplasts and mesophyll cells of complementation plants with CA1 or CA4 driven by the guard cell-targeted promoter of this invention; FIG. 27C and FIG. 27D graphically illustrate $CO_2$-induced stomatal conductance change of guard cell-targeted lines, ca1ca4 double mutant and wild-type (WT) plants in response to the indicated [$CO_2$] shifts: CA1 or CA4 expression in guard cells is sufficient for restoration of the $CO_2$ response; FIG. 27E graphically illustrates stomatal conductance of ca1ca4, wild-type, ht1-2 and triple ca1ca4ht1-2 mutant leaves in response to the indicated [$CO_2$] changes; FIG. 27F and FIG. 27G graphically illustrate stomatal conductance of CA over-expressing lines and wild-type (WT) plants in response to the indicated [$CO_2$] changes, as described in detail in Example 4, below.

FIGS. 28C to F graphically illustrate relative stomatal conductance values were normalized to the last data point prior to the 365-800 ppm $CO_2$ switch, as described in detail in Example 4, below.

FIG. 29C and FIG. 29D graphically illustrate RT-PCR analysis of CA1 or CA4 in leaves of over-expressing lines driven by the preferential guard cell promoter pGC1; stomatal conductance measurements of an additional line over-expressing the CA1 gene, as illustrated in FIG. 29A, and additional line over-expressing the CA4 gene, as illustrated in FIG. 29B. Relative stomatal conductance values, as illustrated in FIG. 29C, FIG. 29D, FIG. 29E, and FIG. 29F, were normalized to the last data point prior to the 365-800 ppm $CO_2$ switch, as described in detail in Example 4, below.

Like reference symbols in the various drawings indicate like elements.

DETAILED DESCRIPTION

Figure 1:
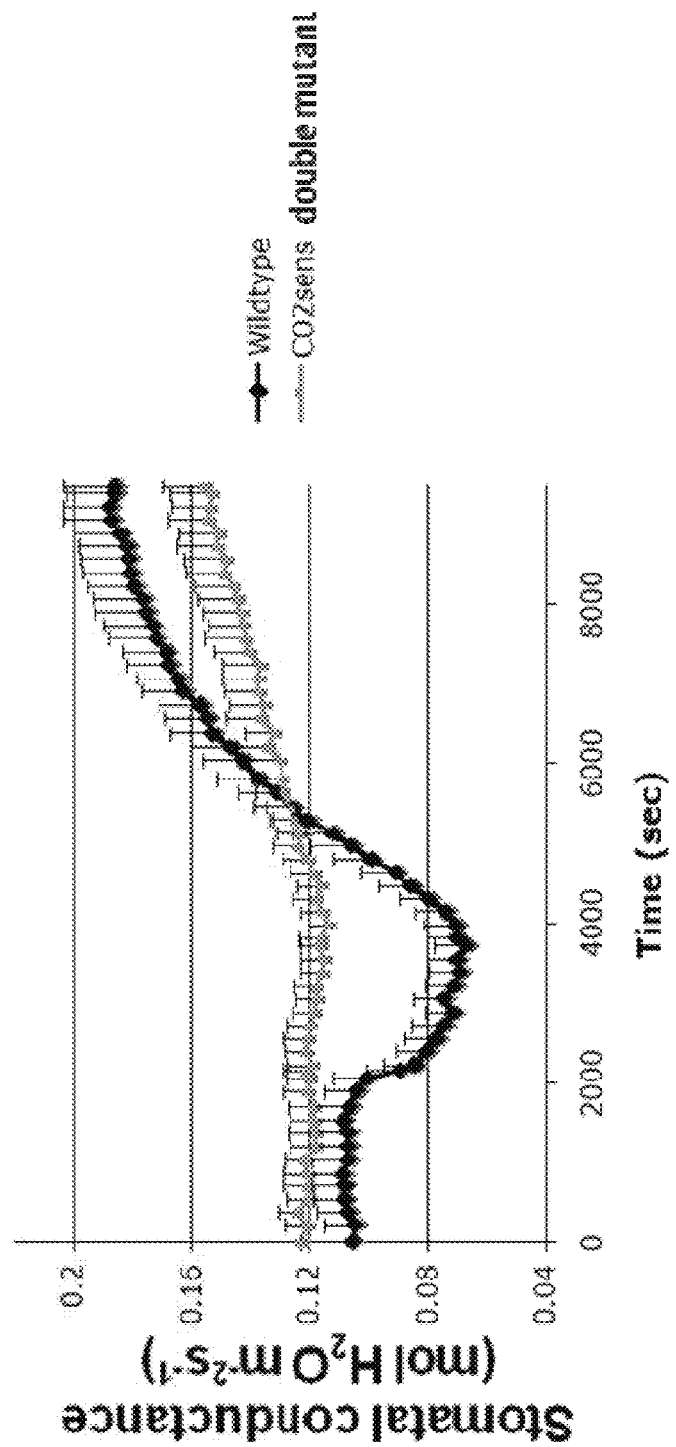
FIG. 1 graphically illustrates data showing stomatal conductance in wild-type *Arabidopsis thaliana* and the $CO_2$ sense double mutant of this invention; as described in detail in Example 1, below.

The invention provides compositions and methods for manipulating the exchange of water and carbon dioxide ($CO_2$) through plant stomata by controlling $CO_2$ sensor genes, designated "$CO_2$Sen genes", including the $CO_2$ sensor nucleic acids (e.g., as genes or messages or transcripts) and polypeptides of this invention. The invention provides compositions and methods for over or under-expressing $CO_2$ sensor nucleic acids and $CO_2$ sensor polypeptides, including the $CO_2$ sensor nucleic acids and polypeptides of this invention. The invention provides compositions and methods for over-expressing $CO_2$ sensor nucleic acids and $CO_2$ sensor polypeptides, including the $CO_2$ sensor nucleic acids and polypeptides of this invention, to engineer an improved $CO_2$ response in a plant, plant part, plant organ, a leaf, and the like.

Over-expression of one or several $CO_2$ sensor genes, designated "$CO_2$Sen genes", including the $CO_2$ sensor nucleic acids (e.g., as genes or messages or transcripts), or $CO_2$ sensor polypeptides, including the $CO_2$ sensor polypeptides of this invention, evokes an improved $CO_2$ response. Thus, overexpression of all or one of the nucleic acids of this invention (to overexpress the $CO_2$Sen proteins) enhances WUE and produces a more efficient and drought resistant plant, particularly in light of the continuously rising atmospheric $CO_2$ concentrations. Transgenic plants (e.g., crops) of this invention (by overexpressing of all or one of the $CO_2$Sen proteins of this invention) close their stomata to a greater extent than wild-type plants, thereby preserving their water usage. Because water use efficiency defines how well a plant can balance the loss of water through stomata with the net $CO_2$ uptake for photosynthesis, and hence its biomass accumulation, the invention can be used in increase a plant's biomass, and thus the methods of the invention have applications in the biofuels/alternative energy area.

The invention also provides compositions and methods for inhibiting the expression of $CO_2$Sens genes, transcripts and $CO_2$Sens proteins by, e.g., antisense and/or RNAi repression of $CO_2$ sensors in guard cells in any plant or plant cell, e.g., an agricultural crops. The $CO_2$Sens underexpressing transgenic plants or $CO_2$Sens-under-expressing plants of this invention can open their stomata to a greater extent than wild-type plants.

The invention also provides plants, e.g., agricultural crops, that can withstand increased temperatures—thus preventing a "breakdown" of metabolism, photosynthesis and growth. Thus, compositions and methods of this invention, by inhibiting the expression of $CO_2$Sens nucleic acids and/or $CO_2$Sens proteins, help crops that otherwise would be sensitive to elevated temperatures to cope with the increased atmospheric $CO_2$ concentrations, also reducing or ameliorating an accelerated increase in leaf temperatures. The invention provides compositions and methods comprising antisense and RNAi for repression of $CO_2$ sensors in guard cells. In one aspect, a guard cell promoter provides a means to reduce leaf temperature through enhancing transpiration in these crops and also to maximize crop yields.

The invention provides compositions and methods for down-regulating/decreasing or alternatively increasing carbon dioxide ($CO_2$) and/or water exchange in a plant, e.g., through the guard cell of a plant, plant cell, plant leaf, plant organ or plant part comprising inter alia use of a polypeptide having carbonic anhydrase, "Phosphoenolpyruvate (PEP) Carboxylase" (or PEP carboxylase, or PEPC) and/or a ribulose-1,5-bisphosphate carboxylase/oxygenase, or "Rubisco" enzyme activity.

The invention provides compositions and methods for manipulating PEP carboxylase, which is a key enzyme in photosynthesis in C4 plants. Since PEP carboxylase, or PEPC, cannot use $CO_2$ directly as a substrate PEPC relies on carbonic anhydrase (CA) to provide $HCO_3^-$. The reaction catalyzed by PEP carboxylase (PEPC) is (note: Pi is inorganic phosphate):

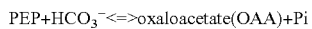

$$PEP+HCO_3^- <=> \text{oxaloacetate(OAA)} + Pi$$

OAA can be subsequently reduced into malate. In some plant cells, $CO_2$ is released for Rubisco and C3 photosynthesis.

In C4 plants (using the C4 carbon fixation pathway, also called the Hatch-Slack pathway) the malate can be transported into bundle sheath cells (in C4 plants, bundle sheath cells are photosynthetic cells arranged into tightly packed sheaths around the veins of a leaf; the Calvin cycle is confined to the chloroplasts of bundle sheath cells) where $CO_2$ is released for Rubisco and C3 photosynthesis; and the invention also provides compositions and methods for manipulating Rubisco enzymes. In one aspect of the invention, expression of Rubisco enzymes, e.g., a Rubisco small subunit, is inhibited or repressed (decreased), e.g., in a guard cell of a plant. By inhibiting or repressing (decreasing) Rubisco expression, oxygenation efficiency decreases and carbon fixation may increase, and $CO_2$ levels in guard cells goes down. This could reduce $CO_2$ regulation of stomatal closing.

In one aspect of the invention, high or reduced levels of PEP carboxylase, or PEPC, are engineered in guard cells of plants to manipulate $CO_2$ control of stomatal movements and the amount of intracellular organic anion malate$^{2-}$. An increase in PEPC levels will induce stomatal opening; a decrease in PEPC will result in stomatal closing; so, while the invention is not limited by any particular mechanism of action, increase in PEPC levels will induce an increase in malate, which balances the positive potassium ion ($K^+$) accumulation during stomatal opening; and because an increase in the intracellular potassium ($K^+$) salt concentration this will induce stomatal opening. Thus, the invention provides compositions and methods for opening and closing plant stomata, or increasing or decreasing the amount of stomata, by over- or under-expressing PEPC, respectively.

The invention provides compositions and methods for regulating carbon dioxide ($CO_2$) exchange and $CO_2$ use and uptake in a plant or plant part, e.g., a leaf, by manipulating expression of a $CO_2$ binding protein "Phosphoenolpyruvate (PEP) Carboxylase" (or PEP carboxylase, or PEPC) and/or a ribulose-1,5-bisphosphate carboxylase/oxygenase, or "Rubisco" enzyme; thus, the invention also provides compositions and methods for manipulating $CO_2$ signal transduction and regulation of gas exchange in a plant or plant part. For example, in one aspect, the invention provides compositions and methods for engineering an increased amount of PEPC (to facilitate stomatal opening) and/or engineering the amount of "Rubisco" enzyme.

In alternative aspects of this invention, PEPCs and Rubisco nucleic acids are expressed in plant cells, e.g., in plant guard cells and mesophyll cells; and in one aspect, they are expressed at high levels (higher than wild type levels); or, PEPCs and Rubisco nucleic acids expression is inhibited, decreased or repressed in plant cells, e.g., in plant guard cells and mesophyll cells; and in one aspect, they are expressed at lower levels (lower than wild type levels). Plant cells engineered in these alternative embodiments include isolated, cultured or transgenic plants and plant cells of this invention.

Transcriptional Regulatory Elements

The invention also provides promoters for regulating expression of a nucleic acid in a plant cell, wherein the promoter comprises a sequence as set forth in SEQ ID NO:10 or SEQ ID NO:11, or functional (transcriptional regulatory) subsequences thereof, wherein in one aspect the promoter upregulates transcription, and in one aspect the promoter upregulates transcription in a plant guard cell specific manner, and in one aspect the guard cell is a leaf guard cell or a stem guard cell. The invention also provides expression cassettes, plasmids, viruses and vectors comprising the promoter of invention. In one aspect, the invention also provides expression cassettes, plasmids, viruses and vectors comprising a promoter of invention operably linked to a nucleic acid of the invention, e.g., any genus of polynucleotides based on the exemplary SEQ ID NO:1, SEQ ID NO:2, SEQ ID NO:4, SEQ ID NO:5, SEQ ID NO:7 or SEQ ID NO:8.

This promoter of the invention is a strong promoter, particularly in plant guard cells, and in some embodiments is guard cell specific, e.g., the exemplary SEQ ID NO:10 and SEQ ID NO:11 (its expression can be weak in other cells, e.g., epidermal cells, or mesophyll cells, and still be considered "guard cell specific").

Based on multiple microarray data, the promoters of the invention are about 20 times stronger than the known guard cell KAT1 promoter, and is also stronger in guard cells than the known cauliflower mosaic virus 35S promoter. See Figures of this invention, and Examples, below.

While a nucleic acid of the invention can be operably linked to a promoter of this invention, in alternative embodiments, it also can be operatively linked to any constitutive and/or plant specific, or plant cell specific promoter, e.g., a cauliflower mosaic virus (CaMV) 35S promoter, a mannopine synthase (MAS) promoter, a 1' or 2' promoter derived from T-DNA of *Agrobacterium tumefaciens*, a figwort mosaic virus 34S promoter, an actin promoter, a rice actin promoter, a ubiquitin promoter, e.g., a maize ubiquitin-1 promoter, and the like.

Examples of constitutive plant promoters which can be useful for expressing the TF sequence include: the cauliflower mosaic virus (CaMV) 35S promoter, which confers constitutive, high-level expression in most plant tissues (see, e.g., Odell et al. (1985) Nature 313: 810-812); the nopaline synthase promoter (An et al. (1988) Plant Physiol. 88: 547-552); and the octopine synthase promoter (Fromm et al. (1989) Plant Cell 1: 977-984).

The transcription factors (e.g., the promoters) of the invention, or other transcription factors, may be operably linked to a coding sequence of the invention, e.g., a $CO_2$ regulatory protein of the invention. $CO_2$ regulatory proteins of the invention may be operably linked with a specific promoter or enhancer that causes the transcription factor, and thus the coding sequence, to be expressed in response to environmental, tissue-specific or temporal signals. A variety of plant gene promoters that regulate gene expression in response to environmental, hormonal, chemical, developmental signals, and in a tissue-active manner can be used for expression of a TF sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like.

Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening (such as the dm 1 promoter (U.S. Pat. No. 5,783,393), or the 2A11 promoter (e.g., see U.S. Pat. No. 4,943,674) and the tomato polygalacturonase promoter (e.g., see Bird et al. (1988) Plant Mol. Biol. 11: 651-662), root-specific promoters, such as those disclosed in U.S. Pat. Nos. 5,618,988, 5,837,848 and 5,905,186, pollen-active promoters such as PTA29, PTA26 and PTA13 (e.g., see U.S. Pat. No. 5,792,929), promoters active in vascular tissue (e.g., see Ringli and Keller (1998) Plant Mol. Biol. 37: 977-988), flower-specific (e.g., see Kaiser et al. (1995) Plant Mol. Biol. 28: 231-243), pollen (e.g., see Baerson et al. (1994) Plant Mol. Biol. 26: 1947-1959), carpels (e.g., see Ohl et al. (1990) Plant Cell 2: 837-848), pollen and ovules (e.g., see Baerson et al. (1993) Plant Mol. Biol. 22: 255-267), auxin-inducible promoters (such as that described in van der Kop et al. (1999) Plant Mol. Biol. 39: 979-990 or Baumann et al., (1999) Plant Cell 11: 323-334), cytokinin-inducible promoter (e.g., see Guevara-Garcia (1998) Plant Mol. Biol. 38: 743-753), promoters responsive to gibberellin (e.g., see Shi et al. (1998) Plant Mol. Biol. 38: 1053-1060, Willmott et al. (1998) Plant Molec. Biol. 38: 817-825) and the like.

Additional promoters that can be used to practice this invention are those that elicit expression in response to heat (e.g., see Ainley et al. (1993) Plant Mol. Biol. 22: 13-23), light (e.g., the pea rbcS-3A promoter, Kuhlemeier et al. (1989) Plant Cell 1: 471-478, and the maize rbcS promoter, Schaffner and Sheen (1991) Plant Cell 3: 997-1012); wounding (e.g., wunI, Siebertz et al. (1989) Plant Cell 1: 961-968); pathogens (such as the PR-1 promoter described in Buchel et al. (1999) Plant Mol. Biol. 40: 387-396, and the PDF1.2 promoter described in Manners et al. (1998) Plant Mol. Biol. 38: 1071-1080), and chemicals such as methyl jasmonate or salicylic acid (e.g., see Gatz (1997) Annu. Rev. Plant Physiol. Plant Mol. Biol. 48: 89-108). In addition, the timing of the expression can be controlled by using promoters such as those acting at senescence (e.g., see Gan and Amasino (1995) Science 270: 1986-1988); or late seed development (e.g., see Odell et al. (1994) Plant Physiol. 106: 447-458).

Tissue-specific promoters can promote transcription only within a certain time frame of developmental stage within that tissue. See, e.g., Blazquez (1998) Plant Cell 10:791-800, characterizing the *Arabidopsis* LEAFY gene promoter. See also Cardon (1997) *Plant J* 12:367-77, describing the transcription factor SPL3, which recognizes a conserved sequence motif in the promoter region of the *A. thaliana* floral meristem identity gene AP1; and Mandel (1995) Plant Molecular Biology, Vol. 29, pp 995-1004, describing the meristem promoter eIF4. Tissue specific promoters which are active throughout the life cycle of a particular tissue can be used. In one aspect, the nucleic acids of the invention are operably linked to a promoter active primarily only in cotton fiber cells. In one aspect, the nucleic acids of the invention are operably linked to a promoter active primarily during the stages of cotton fiber cell elongation, e.g., as described by Rinehart (1996) supra. The nucleic acids can be operably linked to the Fb12A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids of the invention. Examples of root-specific promoters include the promoter from the alcohol dehydrogenase gene (DeLisle (1990) Int. Rev. Cytol. 123:39-60). Other promoters that can be used to express the nucleic acids of the invention include, e.g., ovule-specific, embryo-specific, endosperm-specific, integument-specific, seed coat-specific promoters, or some combination thereof; a leaf-specific promoter (see, e.g., Busk (1997) Plant J 11:1285 1295, describing a leaf-specific promoter in maize); the ORF13 promoter from *Agrobacterium rhizogenes* (which exhibits high activity in roots, see, e.g., Hansen (1997) supra); a maize pollen specific promoter (see, e.g., Guerrero (1990) Mol. Gen. Genet. 224:161 168); a tomato promoter active during fruit ripening, senescence and abscission of leaves and, to a lesser extent, of flowers can be used (see, e.g., Blume (1997) Plant J 12:731 746); a pistil-specific promoter from the potato SK2 gene (see, e.g., Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see, e.g., Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells.

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (Sheen (1996) Science 274:1900-1902).

The nucleic acids of the invention can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324). Using chemically- (e.g., hormone- or pesticide-) induced promoters, i.e., promoter responsive to a chemical which can be applied to the transgenic plant in the field, expression of a polypeptide of the invention can be induced at a particular stage of development of the plant. Thus, the invention also provides for transgenic plants containing an inducible gene encoding for polypeptides of the invention whose host range is limited to target plant species, such as corn, rice, barley, wheat, potato or other crops, inducible at any stage of development of the crop.

One of skill will recognize that a tissue-specific plant promoter may drive expression of operably linked sequences in tissues other than the target tissue. Thus, a tissue-specific promoter is one that drives expression preferentially in the target tissue or cell type, but may also lead to some expression in other tissues as well.

The nucleic acids of the invention can also be operably linked to plant promoters which are inducible upon exposure to chemicals reagents. These reagents include, e.g., herbicides, synthetic auxins, or antibiotics which can be applied, e.g., sprayed, onto transgenic plants. Inducible expression of the nucleic acids of the invention will allow the grower to select plants with the optimal protein expression and/or activity. The development of plant parts can thus controlled. In this way the invention provides the means to facilitate the harvesting of plants and plant parts. For example, in various embodiments, the maize In2-2 promoter, activated by benzenesulfonamide herbicide safeners, is used (De Veylder (1997) Plant Cell Physiol. 38:568-577); application of different herbicide safeners induces distinct gene expression patterns, including expression in the root, hydathodes, and the shoot apical meristem. Coding sequences of the invention are also under the control of a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324).

In some aspects, proper polypeptide expression may require polyadenylation region at the 3'-end of the coding region. The polyadenylation region can be derived from the natural gene, from a variety of other plant (or animal or other) genes, or from genes in the Agrobacterial T-DNA.

Plants Comprising a Nucleic Acid of this Invention

The invention provides transgenic plants and seeds comprising a nucleic acid, a polypeptide (e.g., a $CO_2$Sen protein), an expression cassette or vector or a transfected or transformed cell of the invention. The invention also provides plant products, e.g., seeds, leaves, extracts and the like, comprising a nucleic acid and/or a polypeptide (e.g., a $CO_2$Sen protein of the invention. The transgenic plant can be dicotyledonous (a dicot) or monocotyledonous (a monocot). The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's a $CO_2$Sen protein production is regulated by endogenous transcriptional or translational control elements, or by a heterologous promoter, e.g., a promoter of this invention. The invention also provides "knockout plants" where insertion of gene sequence by, e.g., homologous recombination, has disrupted the expression of the endogenous gene. Means to generate "knockout" plants are well-known in the art.

The nucleic acids and polypeptides of the invention can be expressed in or inserted in any plant, plant part, plant cell or seed. Transgenic plants of the invention, or a plant or plant cell comprising a nucleic acid of this invention (e.g., a transfected, infected or transformed cell) can be dicotyledonous or monocotyledonous. Examples of monocots comprising a nucleic acid of this invention, e.g., as monocot transgenic plants of the invention, are grasses, such as meadow grass (blue grass, *Poa*), forage grass such as *festuca, lolium*, temperate grass, such as *Agrostis*, and cereals, e.g., wheat, oats, rye, barley, rice, sorghum, and maize (corn). Examples of dicots comprising a nucleic acid of this invention, e.g., as dicot transgenic plants of the invention, are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, plant or plant cell comprising a nucleic acid of this invention, including the transgenic plants and seeds of the invention, include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

The nucleic acids and polypeptides of the invention can be expressed in or inserted in any plant cell, organ, seed or tissue, including differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. The plant tissue may be in plants or in organ, tissue or cell culture.

Transgenic Plants

The invention provides transgenic plants comprising and expressing the $CO_2$Sen genes and proteins of this invention; for example, the invention provides plants, e.g., transgenic plants, that show improved growth under limiting water conditions; thus, the invention provides drought-tolerant plants (e.g., crops).

A transgenic plant of this invention can also include the machinery necessary for expressing or altering the activity of a polypeptide encoded by an endogenous gene, for example, by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homolog, of the invention, standard techniques can be used to introduce the polynucleotide into a plant, a plant cell, a plant explant or a plant tissue of interest. In one aspect the plant cell, explant or tissue can be regenerated to produce a transgenic plant.

The plant can be any higher plant, including gymnosperms, monocotyledonous and dicotyledonous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al., eds., (1984) Handbook of Plant Cell Culture—Crop Species, Macmillan Publ. Co., New York, N.Y.; Shimamoto et al. (1989) Nature 338: 274-276; Fromm et al. (1990) Bio/Technol. 8: 833-839; and Vasil et al. (1990) Bio/Technol. 8: 429-434.

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and include for example: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,619,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's $CO_2$ sensor production is regulated by endogenous transcriptional or translational control elements.

The invention also provides "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

In one aspect, making transgenic plants or seeds comprises incorporating sequences of the invention and, in one aspect (optionally), marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides, e.g., a $CO_2$ sensor of the invention. The desired effects can be passed to future plant generations by standard propagation means.

Antisense Inhibitory Molecules

In one aspect, the invention provides an antisense inhibitory molecules comprising a sequence of this invention (which include both sense and antisense strands). Naturally occurring or synthetic nucleic acids can be used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl)glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, as described above.

RNA interference (RNAi)

In one aspect, the invention provides an RNA inhibitory molecule, a so-called "RNAi" molecule, comprising a sequence of this invention. In one aspect, the RNAi molecule comprises a double-stranded RNA (dsRNA) molecule. The RNAi molecule can comprise a double-stranded RNA (dsRNA) molecule, e.g., siRNA, miRNA (microRNA) and/or short hairpin RNA (shRNA) molecules. The RNAi molecule, e.g., siRNA (small inhibitory RNA) can inhibit expression of a $CO_2Sen$ genes, and/or miRNA (micro RNA) to inhibit translation of a $CO_2Sen$ gene, or any related $CO_2$ sensor genes.

In alternative aspects, the RNAi is about 11, 12, 13, 14, 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi, e.g., siRNA for inhibiting transcription and/or miRNA to inhibit translation, is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an plant tissue or organ or seed, or a plant.

In one aspect, intracellular introduction of the RNAi (e.g., miRNA or siRNA) is by internalization of a target cell specific ligand bonded to an RNA binding protein comprising an RNAi (e.g., microRNA) is adsorbed. The ligand is specific to a unique target cell surface antigen. The ligand can be spontaneously internalized after binding to the cell surface antigen. If the unique cell surface antigen is not naturally internalized after binding to its ligand, internalization can be promoted by the incorporation of an arginine-rich peptide, or other membrane permeable peptide, into the structure of the ligand or RNA binding protein or attachment of such a peptide to the ligand or RNA binding protein. See, e.g., U.S. Patent App. Pub. Nos. 20060030003; 20060025361; 20060019286; 20060019258. In one aspect, the invention provides lipid-based formulations for delivering, e.g., introducing nucleic acids of the invention as nucleic acid-lipid particles comprising an RNAi molecule to a cell, see e.g., U.S. Patent App. Pub. No. 20060008910.

Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Methods for making expression constructs, e.g., vectors or plasmids, from which a $CO_2$Sen gene inhibitory polynucleotide (e.g., a duplex siRNA of the invention) is transcribed are well known and routine. A regulatory region (e.g., promoter, enhancer, silencer, splice donor, acceptor, etc.) can be used to transcribe an RNA strand or RNA strands of a $CO_2$Sen gene inhibitory polynucleotide from an expression construct. When making a duplex siRNA $CO_2$Sen gene inhibitory molecule, the sense and antisense strands of the targeted portion of the targeted IRES can be transcribed as two separate RNA strands that will anneal together, or as a single RNA strand that will form a hairpin loop and anneal with itself. For example, a construct targeting a portion of a $CO_2$Sen gene is inserted between two promoters (e.g., two plant, viral, bacteriophage T7 or other promoters) such that transcription occurs bidirectionally and will result in complementary RNA strands that may subsequently anneal to form an inhibitory siRNA of the invention. Alternatively, a targeted portion of a $CO_2$Sen gene can be designed as a first and second coding region together on a single expression vector, wherein the first coding region of the targeted $CO_2$Sen gene is in sense orientation relative to its controlling promoter, and wherein the second coding region of the $CO_2$Sen gene is in antisense orientation relative to its controlling promoter. If transcription of the sense and antisense coding regions of the targeted portion of the targeted $CO_2$Sen gene occurs from two separate promoters, the result may be two separate RNA strands that may subsequently anneal to form a $CO_2$Sen gene inhibitory siRNA, e.g., a $CO_2$Sen gene-inhibitory siRNA of the invention.

In another aspect, transcription of the sense and antisense targeted portion of the targeted $CO_2$Sen gene is controlled by a single promoter, and the resulting transcript will be a single hairpin RNA strand that is self-complementary, i.e., forms a duplex by folding back on itself to create a $CO_2$Sen gene-inhibitory siRNA molecule. In this configuration, a spacer, e.g., of nucleotides, between the sense and antisense coding regions of the targeted portion of the targeted $CO_2$Sen gene can improve the ability of the single strand RNA to form a hairpin loop, wherein the hairpin loop comprises the spacer. In ones embodiment, the spacer comprises a length of nucleotides of between about 5 to 50 nucleotides. In one aspect, the sense and antisense coding regions of the siRNA can each be on a separate expression vector and under the control of its own promoter.

Inhibitory Ribozymes

The invention provides ribozymes capable of binding $CO_2$ sensor gene message. These ribozymes can inhibit $CO_2$ sensor gene activity by, e.g., targeting mRNA. Strategies for designing ribozymes and selecting the $CO_2$ sensor gene-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

Carbonic Anhydrase (Carbonate Dehydratase)

The invention provides methods for down-regulating or decreasing carbon dioxide ($CO_2$) and/or water exchange in a guard cell of a plant, plant cell, plant leaf, plant organ or plant part comprising expressing in a cell a polypeptide having a carbonic anhydrase (carbonate dehydratase) activity, or a β-carbonic anhydrase activity. In alternative aspects, any carbonic anhydrase (carbonate dehydratase) can be used, e.g., including plant or bacterial carbonic anhydrase (carbonate dehydratase) enzymes. Exemplary carbonic anhydrase (carbonate dehydratase) enzymes that can be used to practice this invention include carbonic anhydrase (carbonate dehydratase) enzymes isolated or derived from:

| Rice (*Oryza sativa*) |
|---|
| NM_001072713 (= Genbank accession number)<br>*Oryza sativa* (*japonica* cultivar-group) Os12g0153500 (Os12g0153500) mRNA, complete cds<br>gi\|115487387\|ref\|NM_001072713.1\|[115487387]<br>NM_001072308 (= Genbank accession number)<br>*Oryza sativa* (*japonica* cultivar-group) Os11g0153200 (Os11g0153200) mRNA, complete cds<br>gi\|115484228\|ref\|NM_001072308.1\|[115484228]<br>NM_001069944 (= Genbank accession number)<br>*Oryza sativa* (*japonica* cultivar-group) Os09g0464000 (Os09g0464000) mRNA, complete cds<br>gi\|115479630\|ref\|NM_001069944.1\|[115479630]<br>NM_001069887 (= Genbank accession number)<br>*Oryza sativa* (*japonica* cultivar-group) Os09g0454500 (Os09g0454500) mRNA, complete cds<br>gi\|115479516\|ref\|NM_001069887.1\|[115479516]<br>NM_001068550 (= Genbank accession number)<br>*Oryza sativa* (*japonica* cultivar-group) Os08g0470200 (Os08g0470200) mRNA, complete cds<br>gi\|115476837\|ref\|NM_001068550.1\|[115476837]<br>NM_001068366 (= Genbank accession number)<br>*Oryza sativa* (*japonica* cultivar-group) Os08g0423500 (Os08g0423500) mRNA, complete cds<br>gi\|115476469\|ref\|NM_001068366.1\|[115476469]<br>NM_001064586 (= Genbank accession number)<br>*Oryza sativa* (*japonica* cultivar-group) Os06g0610100 (Os06g0610100) mRNA, complete cds<br>gi\|115468903\|ref\|NM_001064586.1\|[115468903]:<br>NM_001053565 (= Genbank accession number)<br>*Oryza sativa* (*japonica* cultivar-group) Os02g0533300 (Os02g0533300) mRNA, complete cds<br>gi\|115446500\|ref\|NM_001053565.1\|[115446500]<br>NM_001050212 (= Genbank accession number)<br>*Oryza sativa* (*japonica* cultivar-group) Os01g0640000 (Os01g0640000) mRNA, complete cds | gi|115438794|ref|NM_001050212.1|[115438794]
NM_001050211 (= Genbank accession number)
*Oryza sativa* (*japonica* cultivar-group) Os01g0639900 (Os01g0639900) mRNA, partial cds
gi|115438792|ref|NM_001050211.1|[115438792]
EF576561
*Oryza sativa* (*indica* cultivar-group) clone OSS-385-480-G10 carbonic anhydrase mRNA, partial cds
gi|149392692|gb|EF576561.1|[149392692]
AF182806
*Oryza sativa* carbonic anhydrase 3 mRNA, complete cds
gi|5917782|gb|AF182806.1|AF182806[5917782]
U08404
*Oryza sativa* chloroplast carbonic anhydrase mRNA, complete cds
gi|606816|gb|U08404.1|OSU08404[606816]
Corn: (*zea may*)

NM_001111889
*Zea mays* carbonic anhydrase (LOC542302), mRNA
gi|162459146|ref|NM_001111889.1|[162459146]
U08403
*Zea mays* Golden Bantam carbonic anhydrase mRNA, complete cds
gi|606814|gb|U08403.1|ZMU08403[606814]
U08401
*Zea mays* carbonic anhydrase mRNA, complete cds
gi|606810|gb|U08401.1|ZMU08401[606810]
M95073
*Zea mays* putative carbonic anhydrase homolog mRNA, partial cds
gi|168561|gb|M95073.1|MZEORFN[168561]
Soybean: (*Glycine*)

AJ239132
*Glycine max* mRNA for carbonic anhydrase
gi|4902524|emb|AJ239132.1|[4902524]
Tomato (*Lycopersicon*)

AJ849376
*Lycopersicon esculentum* mRNA for chloroplast carbonic anhydrase (ca2 gene)
gi|56562176|emb|AJ849376.1|[56562176]
AJ849375
*Lycopersicon esculentum* mRNA for carbonic anhydrase (ca1 gene)
gi|56562174|emb|AJ849375.1|[56562174]
Tobacco *Nicotiana*

AF492468
*Nicotiana langsdorffii* x *Nicotiana sanderae* nectarin III (NEC3) mRNA, complete cds
gi|29468279|gb|AF492468.1|[29468279]
AF454759
*Nicotiana tabacum* beta-carbonic anhydrase (CA) mRNA, complete cds; nuclear gene for chloroplast product
gi|22550385|gb|AF454759.2|[22550385]
AB009887
*Nicotiana tabacum* mRNA for carbonic anhydrase, partial cds
gi|8096276|dbj|AB009887.1|[8096276]
AB012863
*Nicotiana paniculata* mRNA for NPCA1, complete cds
gi|3061270|dbj|AB012863.1|[3061270]
L19255
*Nicotiana tabacum* chloroplastic carbonic anhydrase mRNA, 3' end
gi|310920|gb|L19255.1|TOBCARANHY[310920]
M94135
*Nicotiana tabacum* chloroplast carbonic anhydrase gene, complete cds
gi|170218|gb|M94135.1|TOBCLCAA[170218]
AY974608
*Nicotiana benthamiana* clone 30F62 chloroplast carbonic anhydrase mRNA, partial cds; nuclear gene for chloroplast product
gi|62865756|gb|AY974608.1|[62865756]
AY974607
*Nicotiana benthamiana* clone 30C84 chloroplast carbonic anhydrase mRNA, partial cds; nuclear gene for chloroplast product
gi|62865754|gb|AY974607.1|[62865754]
AY974606
*Nicotiana benthamiana* clone 30B10 chloroplast carbonic anhydrase mRNA, partial cds; nuclear gene for chloroplast product
gi|62865752|gb|AY974606.1|[62865752]

Barley (*Hordeum*)

L36959
*Hordeum vulgare* carbonic anhydrase mRNA, complete cds
gi|558498|gb|L36959.1|BLYCA[558498]
Cotton (*Gossypium*)

AF132855
*Gossypium hirsutum* carbonic anhydrase isoform 2 (CA2) mRNA, partial cds; nuclear gene for plastid product
gi|4754914|gb|AF132855.1|AF132855[4754914]
AF132854
*Gossypium hirsutum* carbonic anhydrase isoform 1 (CA1) mRNA, partial cds; nuclear gene for plastid product
gi|4754912|gb|AF132854.1|AF132854[4754912]
Poplar U55837
*Populus tremula* x *Populus tremuloides* carbonic anhydrase (CA1a) mRNA, nuclear gene encoding chloroplast protein, complete cds
gi|1354514|gb|U55837.1|PTU55837[1354514]:
U55838
*Populus tremula* x *Populus tremuloides* carbonic anhydrase (CA1b) mRNA, nuclear gene encoding chloroplast protein, complete cds
gi|1354516|gb|U55838.1|PTU55838[1354516]
*Cucumis*

DQ641132
*Cucumis sativus* clone CU8F3 carbonic anhydrase mRNA, partial cds
gi|117663159|gb|DQ641132.1|[117663159]
*Lycopersicon*

AJ849376
*Lycopersicon esculentum* mRNA for chloroplast carbonic anhydrase (ca2 gene)
gi|56562176|emb|AJ849376.1|[56562176]
AJ849375
*Lycopersicon esculentum* mRNA for carbonic anhydrase (ca1 gene)
gi|56562174|emb|AJ849375.1|[56562174]
*Medicago*

X93312
*M. sativa* mRNA for carbonic anhydrase
gi|1938226|emb|X93312.1|[1938226]
*Phaseolus*

AJ547634
*Phaseolus vulgaris* partial mRNA for carbonic anhydrase (ca gene)
gi|28556429|emb|AJ547634.1|[28556429]
*Pisum*

X52558
Pea cap mRNA for carbonic anhydrase (EC 4.2.1.1)
gi|20672|emb|X52558.1|[20672]
M63627
*P. sativum* carbonic anhydrase mRNA, complete cds
gi|169056|gb|M63627.1|PEACAMRA[169056]
*Pyrus*

AF195204
*Pyrus pyrifolia* strain Whangkeumbae carbonic anhydrase isoform 1 (CA1) mRNA, complete cds
gi|8698882|gb|AF195204.1|AF195204[8698882]
*Prunus*

EF640698
*Prunus dulcis* clone Pdbcs-E45 putative carbonic anhydrase mRNA, partial cds
gi|148807206|gb|EF640698.1|[148807206]
*Vigna*

AF139464
*Vigna radiata* carbonic anhydrase (CipCa1) mRNA, complete cds; nuclear gene for chloroplast product
gi|8954288|gb|AF139464.2|AF139464[8954288]

Carbonic anhydrase encoding nucleic acids from any carbonic anhydrase gene, e.g., including plant and bacterial genes, can be used to practice this invention; for example, a nucleic acid from any carbonic anhydrase gene of any plant can be used, including any carbonic anhydrase-encoding nucleic acid sequence from any gene family of *Arabidopsis*, e.g., any carbonic anhydrase-encoding nucleic acid sequence from an *Arabidopsis* family, e.g., from *Arabidopsis thaliana*, can be used to practice the compositions and methods of this invention, such as the exemplary carbonic anhydrase-encoding nucleic acid sequences (see Example 6, below):

Carbonic Anhydrase Encoding Nucleic Acids:

| Gene family | AGI number[a] | Official Nomenclature[b] | designation |
|---|---|---|---|
| alpha (α) | At3g52720 | AtαCA1 | SEQ ID NO: 21 |
| | At2g28210 | AtαCA2 | SEQ ID NO: 22 |
| | At5g04180 | AtαCA3 | SEQ ID NO: 23 |
| | At4g20990 | AtαCA4 | SEQ ID NO: 24 |
| | At1g08065 | AtαCA5 | SEQ ID NO: 25 |
| | At4g21000 | AtαCA6 | SEQ ID NO: 26 |
| | At1g08080 | AtαCA7 | SEQ ID NO: 27 |
| | At5g56330 | AtαCA8 | SEQ ID NO: 28 |
| beta (β) | At3g01500 | AtβCA1 | CA1 (SEQ ID NO: 7) |
| | At5g14740 | AtβCA2 | CA2 (SEQ ID NO: 20) |
| | At1g23730 | AtβCA3 | SEQ ID NO: 29 |
| | At1g70410 | AtβCA4 | CA4 (SEQ ID NO: 1) |
| | At4g33580 | AtβCA5 | SEQ ID NO: 30 |
| | At1g58180 | AtβCA6 | CA6 (SEQ ID NO: 4) |
| gamma (γ) | At1g19580 | AtγCA1 | SEQ ID NO: 31 |
| | At1g47260 | AtγCA2 | SEQ ID NO: 32 |
| | At5g66510 | AtγCA3 | SEQ ID NO: 33 |
| | At5g63510 | AtγCAL1 | SEQ ID NO: 34 |
| | At3g48680 | AtγCAL2 | SEQ ID NO: 35 |

[a] *Arabidopsis thaliana* Genome Initiative locus numbers
[b] according to Fabre N. et al. (2007) Plant, Cell Environment 30: 617-629; or from The *Arabidopsis* Information Resource web site (Carnegie Institution for Science, Department of Plant Biology, Stanford, CA, funded by the National Science Foundation).

Accordingly, in alternative aspects, any carbonic anhydrase (carbonate dehydratase) can be used to practice this invention.

Generating and Manipulating Nucleic Acids

In alternative aspects, the invention provides, e.g., isolated, synthetic and/or recombinant nucleic acids encoding novel $CO_2$ sensor genes and coding sequences of this invention, nucleic acids (e.g., siRNA, microRNA, antisense) that can inhibit the expression of $CO_2$ sensor genes or messages, and guard cell specific transcriptional regulatory elements, such as promoters. The nucleic acids of the invention can be made, isolated and/or manipulated by, e.g., cloning and expression of cDNA libraries, amplification of message or genomic DNA by PCR, and the like.

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides (e.g., glycosyl hydrolases of the invention) generated from these nucleic acids can be individually isolated or cloned and tested for a desired activity. Any recombinant expression system can be used, including bacterial, fungal, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The invention provides fusion proteins and nucleic acids encoding them. A polypeptide of the invention can be fused to a heterologous peptide or polypeptide, such as N-terminal identification peptides which impart desired characteristics, such as fluorescent detection, increased stability and/or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Nucleic acids or nucleic acid sequences of the invention can be an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. The phrases "nucleic acid" or "nucleic acid sequence" includes oligonucleotide, nucleotide, polynucleotide, or to a fragment of any of these, to DNA or RNA (e.g., mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., e.g., double stranded iRNAs, e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. "Oligonucleotide" includes either a single stranded polydeoxynucleotide or two complementary polydeoxynucleotide strands that may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

In alternative aspects, the term gene means the segment of DNA involved in producing a polypeptide chain; it can include regions preceding and following the coding region (leader and trailer) as well as, where applicable, intervening sequences (introns) between individual coding segments (exons). "Operably linked" can refer to a functional relationship between two or more nucleic acid (e.g., DNA) segments. In alternative aspects, it can refer to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. In alternative aspects, promoter transcriptional regulatory sequences can be operably linked to a transcribed sequence where they can be physically contiguous to the transcribed sequence, i.e., they can be cis-acting. In alternative aspects, transcriptional regulatory sequences, such as enhancers, need not be physically contiguous or located in close proximity to the coding sequences whose transcription they enhance.

In alternative aspects, the invention provides "expression cassette" comprising a nucleotide sequence of this invention, which can be capable of affecting expression of the nucleic acid, e.g., a structural gene (i.e., a protein coding sequence of the invention) in a host compatible with such sequences. Expression cassettes can include at least a promoter operably linked with the polypeptide coding sequence; and, in one aspect, with other sequences, e.g., transcription termination signals. Additional factors necessary or helpful in effecting expression may also be used, e.g., enhancers. In alternative aspects, expression cassettes also include plasmids, expression vectors, recombinant viruses, any form of recombinant "naked DNA" vector, and the like. In alternative aspects, a "vector" of the invention can comprise a nucleic acid that can infect, transfect, transiently or permanently transduce a cell. In alternative aspects, a vector can be a naked nucleic acid, or a nucleic acid complexed with protein or lipid. In alternative aspects, vectors comprise viral or bacterial nucleic acids and/or proteins, and/or membranes (e.g., a cell membrane, a viral lipid envelope, etc.). In alternative aspects, vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In alternative aspects, the vector may either be stably replicated by the cells during mitosis as an autonomous structure, or is incorporated within the host's genome.

In alternative aspects, "promoter" used to practice this invention include all sequences capable of driving transcription of a coding sequence in a cell, e.g., a plant cell. Thus, promoters used in the constructs of the invention include cis-acting transcriptional control elements and regulatory sequences that are involved in regulating or modulating the timing and/or rate of transcription of a gene. For example, a promoter used to practice this invention can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters used to practice this invention can be those that drive expression continuously under most environmental conditions and states of development or cell differentiation. "Inducible" or "regulatable" promoters used to practice this invention can direct expression of the nucleic acid of the invention under the influence of environmental conditions or developmental conditions. Examples of environmental conditions that may affect transcription by inducible promoters used to practice this invention include anaerobic conditions, elevated temperature, drought, or the presence of light. "Tissue-specific" promoters used to practice this invention can be transcriptional control elements that are only active in particular cells or tissues or organs, e.g., in plants or animals. Tissue-specific regulation may be achieved by certain intrinsic factors that ensure that genes encoding proteins specific to a given tissue are expressed.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature and are well known in the art. In particular, stringency can be increased by reducing the concentration of salt, increasing the concentration of formamide, or raising the hybridization temperature. In alternative aspects, nucleic acids of the invention are defined by their ability to hybridize under various stringency conditions (e.g., high, medium, and low), as set forth herein.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS and 200 ug/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature as desired. Variations on the above ranges and conditions are well known in the art.

Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA and CLUSTALW (Pearson and Lipman, Proc. Natl. Acad. Sci. USA 85(8): 2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

One example of a useful algorithm is BLAST and BLAST 2.0 algorithms, which are described in Altschul et al., Nuc. Acids Res. 25:3389-3402, 1977 and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3 and expectations (E) of 10 and the BLOSUM62 scoring matrix (see Henikoff & Henikoff, Proc. Natl. Acad. Sci. USA 89:10915, 1989) alignments (B) of 50, expectation (E) of 10, M=5, N=−4 and a comparison of both strands.

In one aspect, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

Polypeptides and Peptides

In one aspect, the invention provides isolated, synthetic or recombinant polypeptides and peptides having $CO_2$ sensor activity, or polypeptides and peptides capable of generating an antibody that specifically binds to a $CO_2$ sensor, including a $CO_2$ sensor of this invention, including the amino acid sequences of the invention, which include those having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more, or 100% (complete) sequence identity to an exemplary $CO_2$ sensor polypeptide of the invention.

For example, exemplary sequences of this invention include:

```
CA4 At1g70410 CO₂Sen protein-encoding gene (CO₂Sen), coding nucleic acid sequence (SEQ ID NO: 1):
Encodes: CO₂-Response Protein 2 (CORP2) (SEQ ID NO: 3).
Also designated "CA4", or At1g70410 or SEQ ID NO: 1.
(SEQ ID NO: 1) Full-length CO₂Sen cDNA
CGAACGGTCGTCATAATTCCTTGAAACCTCGAAAATCCAAAAACCCATATCCAATCTTCTTCCCATATAAATTAAGATTTTTAT TTATTTATTTGTTTACTTATTTCAATTCCCAAAATCCTCTGCCTCATCATCTTCAAACTGTTACCACGTCCATAGGGTTGTCGAA GAGCTAGGAAGAGCCTTACCAAGAGCTTCTTCTTCCCCTAACATTTAGGTTGGTAGGAGAAGCAAAGGAAGAGATCATTTAT AATGGCTCCTGCATTCGGAAAATGTTTCATGTTCTGCTGCGCTAAAACCTCCCCGGAAAAAGACGAAATGGCAACGGAATCG TACGAAGCCGCCATTAAAGGACTCAATGATCTTCTCAGTACGAAAGCGGATCTCGGAAACGTCGCCGCCGCGAAGATCAAAG CGTTGACGGCGGAGCTAAAGGAGCTTGACTCAAGCAATTCAGACGCAATTGAACGAATCAAGACCGGTTTTACTCAATTCAA AACCGAGAAATATTTGAAGAATAGTACTTTGTTCAATCATCTTGCCAAGACTCAGACCCCAAAGTTTCTGGTGTTTGCTTGCT CTGATTCTCGAGTTTGTCCATCTCACATCTTGAATTTCCAACCTGGTGAGGCTTTTGTTGTCAGAAACATAGCCAATATGGTTC CACCTTTTGACCAGAAGAGACACTCTGGAGTTGGCGCCGCCGTTGAATACGCAGTTGTACATCTCAAGGTGGAGAACATTTTG
```

GTGATAGGCCATAGCTGCTGTGGTGGTATTAAGGGACTCATGTCCATTGAAGATGATGCTGCCCCAACTCAAAGTGACTTCAT

TGAAAATTGGGTGAAGATAGGCGCATCAGCGAGGAACAAGATCAAGGAGGAACATAAAGACTTGAGCTACGATGATCAATG

CAACAAGTGTGAGAAGGAAGCTGTGAACGTATCGCTTGGAAACTTGCTTTCGTACCCATTCGTGAGAGCTGAGGTGGTGAAG

AACACACTTGCAATAAGAGGAGGTCACTACAATTTCGTCAAAGGAACGTTTGATCTCTGGGAGCTCGATTTCAAGACCACTCC

TGCTTTTGCCTTCTCTTAAGAAAGAAAGCTACCGGAACATATAAAACTCTTTTGAGATAAAAAAAGACACTTTGACTCATCTT

TCTTCATTCTCTCATGTTGATGATTCCTCTCCAACTTCTTTGATTTCTTTTTGTTAATTCAAAACTTCAACTTTGCTGCTTCTATT

TCAAAAGCTCAAACAATAAAGCTGTAACCAACGTTTGAAACTTCTATATTTGTCTAATTGATGTTTGAACGAAGATTTGAACT

TTCCTTCT (SEQ ID NO: 2) Full-length CO$_2$Sen CDS
ATGGCTCCTGCATTCGGAAAATGTTTCATGTTCTGCTGCGCTAAAACCTCCCCGGAAAAAGACGAAATGGCAACGGAATCGT ACGAAGCCGCCATTAAAGGACTCAATGATCTTCTCAGTACGAAAGCGGATCTCGGAAACGTCGCCGCCGCGAAGATCAAAGC GTTGACGGCGGAGCTAAAGGAGCTTGACTCAAGCAATTCAGACGCAATTGAACGAATCAAGACCGGTTTTACTCAATTCAAA ACCGAGAAATATTTGAAGAATAGTACTTTGTTCAATCATCTTGCCAAGACTCAGACCCCAAAGTTTCTGGTGTTTGCTTGCTCT GATTCTCGAGTTTGTCCATCTCACATCTTGAATTTCCAACCTGGTGAGGCTTTTGTTGTCAGAAACATAGCCAATATGGTTCCA CCTTTTGACCAGAAGAGACACTCTGGAGTTGGCGCCGCCGTTGAATACGCAGTTGTACATCTCAAGGTGGAGAACATTTTGGT GATAGGCCATAGCTGCTGTGGTGGTATTAAGGGACTCATGTCCATTGAAGATGATGCTGCCCCAACTCAAAGTGACTTCATTG AAAATTGGGTGAAGATAGGCGCATCAGCGAGGAACAAGATCAAGGAGGAACATAAAGACTTGAGCTACGATGATCAATGCA ACAAGTGTGAGAAGGAAGCTGTGAACGTATCGCTTGGAAACTTGCTTTCGTACCCATTCGTGAGAGCTGAGGTGGTGAAGAA CACACTTGCAATAAGAGGAGGTCACTACAATTTCGTCAAAGGAACGTTTGATCTCTGGGAGCTCGATTTCAAGACCACTCCTG

CTTTTGCCTTCTCTTAA (SEQ ID NO: 3) CO$_2$Sen Protein sequence: CO$_2$-Response Protein 2 (CORP2)
Encoded by, e.g., "CA4", or At1g70410 or SEQ ID NO: 1.
MAPAFGKCFMFCCAKTSPEKDEMATESYEAAIKGLNDLLSTKADLGNVAAAKIKALTAELKELDSSNSDAIERIKTGFTQFKTEKY LKNSTLFNHLAKTQTPKFLVFACSDSRVCPSHILNFQPGEAFVVRNIANMVPPFDQKRHSGVGAAVEYAVVHLKVENILVIGHSCC GGIKGLMSIEDDAAPTQSDFIENWVKIGASARNKIKEEHKDLSYDDQCNKCEKEAVNVSLGNLLSYPFVRAEVVKNTLAIRGGHYN

FVKGTFDLWELDFKTTPAFAFS

CA6 At1g58180 CO$_2$Sen protein-encoding gene (CO$_2$Sen), coding nucleic acid sequence:
Encodes SEQ ID NO: 6, a CO$_2$-response protein.
(SEQ ID NO: 4) Full-length CO$_2$Sen cDNA
CAAAATTCATGTGTTAGTTCTTCTTCTTTACAAAATTGAGTTTAAACTGTTTTATTACTAATCCAAATGAGGAATCACTTTGCA

CTATTAATAGAAATAATACACAACCAAACATCTAAAAGATACTATAATAGTAGAGATCAAAGACCTGAGCAAAACTGAA

AGAAAAAAAAAAAAAAAAAAAAAGACTTCTCCTCAAAAATGGCGTTTACACTAGGTGGAAGAGCTCGTCGTCTAGTCTCTGC

AACATCAGTTCATCAAAATGGTTGCTTACACAAACTGCAACAAATTGGATCGGATCGGTTTCAGCTTGGTGAAGCAAAAGCA

ATAAGATTACTACCCAGGAGAACAAACATGGTTCAAGAATTAGGAATCAGGGAAGAATTTATGGATCTAAACAGAGAAACA

GAGACAAGTTATGATTTTCTGGATGAAATGAGACACAGATTTCTGAAATTCAAGAGACAAAAGTATCTACCGGAGATAGAAA

AGTTTAAAGCTTTGGCCATAGCTCAATCACCAAAGGTAATGGTGATAGGATGTGCAGATTCAAGGGTATGTCCATCTTATGTA

CTAGGATTTCAACCTGGTGAAGCTTTTACTATCCGAAATGTCGCCAATCTCGTTACCCCGGTTCAGAATGGACCAACAGAAAC

CAACTCGGCTCTTGAGTTTGCGGTCACCACTCTTCAGGTTGAGAACATTATAGTTATGGGTCATAGCAATTGTGGAGGAATTG

CAGCACTTATGAGTCATCAAAACCACCAAGGGCAACACTCTAGTTTAGTAGAAAGGTGGGTTATGAATGGGAAGCCGCTAA

GTTAAGAACACAATTAGCTTCATCACATTTATCCTTTGATGAACAATGCAGAAACTGTGAGAAGGAATCTATAAAGGATTCTG

TGATGAATTTGATAACTTATTCATGGATAAGAGATAGAGTAAAGAGAGGTGAAGTCAAGATTCATGGATGTTATTACAATTT

GTCAGATTGTAGTCTTGAGAAGTGGAGATTAAGTTCAGACAAGACTAACTATGGATTCTATATTTCAGACAGAGAGATATGG

AGTTGAGTAAATATTGAACAATCCTCAGTTCTAATATTCAGATGTATCTTTGTACATACGAAATGATATTTACACAATTGG (SEQ ID NO: 5) Full-length $CO_2$Sen CDS
ATGGCGTTTACACTAGGTGGAAGAGCTCGTCGTCTAGTCTCTGCAACATCAGTTCATCAAAATGGTTGCTTACACAAACTGCA ACAAATTGGATCGGATCGGTTTCAGCTTGGTGAAGCAAAAGCAATAAGATTACTACCCAGGAGAACAAACATGGTTCAAGAA TTAGGAATCAGGGAAGAATTTATGGATCTAAACAGAGAAACAGAGACAAGTTATGATTTTCTGGATGAAATGAGACACAGAT TTCTGAAATTCAAGAGACAAAAGTATCTACCGGAGATAGAAAAGTTTAAAGCTTTGGCCATAGCTCAATCACCAAAGGTAAT GGTGATAGGATGTGCAGATTCAAGGGTATGTCCATCTTATGTACTAGGATTTCAACCTGGTGAAGCTTTTACTATCCGAAATG TCGCCAATCTCGTTACCCCGGTTCAGAATGGACCAACAGAAACCAACTCGGCTCTTGAGTTTGCGGTCACCACTCTTCAGGTT GAGAACATTATAGTTATGGGTCATAGCAATTGTGGAGGAATTGCAGCACTTATGAGTCATCAAAACCACCAAGGGCAACACT CTAGTTTAGTAGAAAGGTGGGTTATGAATGGGAAAGCCGCTAAGTTAAGAACACAATTAGCTTCATCACATTTATCCTTTGAT GAACAATGCAGAAACTGTGAGAAGGAATCTATAAAGGATTCTGTGATGAATTTGATAACTTATTCATGGATAAGAGATAGAG TAAAGAGAGGTGAAGTCAAGATTCATGGATGTTATTACAATTTGTCAGATTGTAGTCTTGAGAAGTGGAGATTAAGTTCAGA

CAAGACTAACTATGGATTCTATATTTCAGACAGAGAGATATGGAGTTGA (SEQ ID NO: 6) $CO_2$Sen Protein sequence, a $CO_2$-Response Protein
Encoded by, e.g., SEQ ID NO: 4, or "CA6", or At1g58180, a $CO_2$Sen protein-encoding gene ($CO_2$Sen)
MAFTLGGRARRLVSATSVHQNGCLHKLQQIGSDRFQLGEAKAIRLLPRRTNMVQELGIREEFMDLNRETETSYDFLDEMRHRFLKF KRQKYLPEIEKFKALAIAQSPKVMVIGCADSRVCPSYVLGFQPGEAFTIRNVANLVTPVQNGPTETNSALEFAVTTLQVENIIVMGH SNCGGIAALMSHQNHQGQHSSLVERWVMNGKAAKLRTQLASSHLSFDEQCRNCEKESIKDSVMNLITYSWIRDRVKRGEVKIHGC

YYNLSDCSLEKWRLSSDKTNYGFYISDREIWS

CA1: $CO_2$Sen protein-encoding gene ($CO_2$Sen) (SEQ ID NO: 7)
Encodes: $CO_2$-Response Protein 1 (CORP1) (SEQ ID NO: 9).
Also designated "CA1", or At3g01500 or SEQ ID NO: 7.
CA1 At3g01500: $CO_2$Sen protein-encoding gene ($CO_2$Sen), coding nucleic acid sequence:
(SEQ ID NO: 7) Full-length $CO_2$Sen cDNA
ATGAGACTCCGTTCTTTTAAACTCCCAAATCTTTCAACCAATCCCATTATTCACTTAAGTATATAGTAGCTTCCATAAGAGTCT TAGTTCTAACTATAAATACACATATCTCACTCTCTCTGATCTCCGCTTCTCTTCGCCAACAAATGTCGACCGCTCCTCTCTCCG GCTTCTTTCTCACTTCACTTTCTCCTTCTCAATCTTCTCTCCAGAAACTCTCTCTTCGTACTTCTTCCACCGTCGCTTGCCTCCCA CCCGCCTCTTCTTCTTCCTCATCTTCCTCCTCCTCGTCTTCCCGTTCCGTTCCAACGCTTATCCGTAACGAGCCAGTTTTTGCCG CTCCTGCTCCTATCATTGCCCCTTATTGGAGTGAAGAGATGGGAACCGAAGCATACGACGAGGCTATTGAAGCTCTCAAGAA GCTTCTCATCGAGAAGGAAGAGCTAAAGACGGTTGCAGCGGCAAAGGTGGAGCAGATCACAGCGGCTCTTCAGACAGGTAC TTCATCCGACAAGAAAGCTTTCGACCCCGTCGAAACCATTAAGCAGGGCTTCATCAAATTCAAGAAGGAGAAATACGAAACC AACCCTGCTTTGTACGGTGAGCTCGCAAAGGGTCAAAGTCCTAAGTACATGGTGTTTGCTTGTTCAGACTCACGTGTGTGTCC ATCACACGTTCTGGACTTTCAGCCAGGAGATGCCTTCGTGGTCCGTAACATAGCCAACATGGTTCCTCCTTTCGACAAGGTCA AATACGGTGGCGTTGGAGCAGCCATTGAATACGCGGTCTTACACCTTAAGGTGGAGAACATTGTGGTGATAGGACACAGTGC ATGTGGTGGGATCAAAGGGCTTATGTCTTTCCCCTTAGATGGAAACAACTCCACTGACTTCATAGAGGACTGGGTCAAAATCT GTTTACCAGCCAAGTCAAAGGTTATATCAGAACTTGGAGATTCAGCCTTTGAAGATCAATGTGGCCGATGTGAAAGGGAGGC GGTGAATGTTTCACTAGCAAACCTATTGACATATCCATTTGTGAGAGAAGGACTTGTGAAGGGAACACTTGCTTTGAAGGGA GGCTACTATGACTTCGTCAAGGGTGCTTTTGAGCTTTGGGGACTTGAATTTGGCCTCTCCGAAACTAGCTCTGTTAAAGATGT GGCTACCATACTACATTGGAAGCTGTAGGAAACTCTTTGAAGCCTTACCCGATTTCACATTGTCAATTCAATAACACCAAGTT

GTTGTTTACATGCAGATCTTGATGAAACTGGTTTTTGATTTTACAGAATTAAAATCTTGGGGACAGAAATTTG (SEQ ID NO: 8) Full-length CDS
ATGTCGACCGCTCCTCTCTCCGGCTTCTTTCTCACTTCACTTTCTCCTTCTCAATCTTCTCTCCAGAAACTCTCTCTTCGTACTTC TTCCACCGTCGCTTGCCTCCCACCCGCCTCTTCTTCTTCCTCATCTTCCTCCTCCTCGTCTTCCCGTTCCGTTCCAACGCTTATCC GTAACGAGCCAGTTTTTGCCGCTCCTGCTCCTATCATTGCCCCTTATTGGAGTGAAGAGATGGGAACCGAAGCATACGACGAG GCTATTGAAGCTCTCAAGAAGCTTCTCATCGAGAAGGAAGAGCTAAAGACGGTTGCAGCGGCAAAGGTGGAGCAGATCACA GCGGCTCTTCAGACAGGTACTTCATCCGACAAGAAAGCTTTCGACCCCGTCGAAACCATTAAGCAGGGCTTCATCAAATTCAA -continued

```
GAAGGAGAAATACGAAACCAACCCTGCTTTGTACGGTGAGCTCGCAAAGGGTCAAAGTCCTAAGTACATGGTGTTTGCTTGT

TCAGACTCACGTGTGTGTCCATCACACGTTCTGGACTTTCAGCCAGGAGATGCCTTCGTGGTCCGTAACATAGCCAACATGGT

TCCTCCTTTCGACAAGGTCAAATACGGTGGCGTTGGAGCAGCCATTGAATACGCGGTCTTACACCTTAAGGTGGAGAACATTG

TGGTGATAGGACACAGTGCATGTGGTGGGATCAAAGGGCTTATGTCTTTCCCCTTAGATGGAAACAACTCCACTGACTTCATA

GAGGACTGGGTCAAAATCTGTTTACCAGCCAAGTCAAAGGTTATATCAGAACTTGGAGATTCAGCCTTTGAAGATCAATGTG

GCCGATGTGAAAGGGAGGCGGTGAATGTTTCACTAGCAAACCTATTGACATATCCATTTGTGAGAGAAGGACTTGTGAAGGG

AACACTTGCTTTGAAGGGAGGCTACTATGACTTCGTCAAGGGTGCTTTTGAGCTTTGGGGACTTGAATTTGGCCTCTCCGAAA

CTAGCTCTGTTAAAGATGTGGCTACCATACTACATTGGAAGCTGTAG
```

(SEQ ID NO: 9) Protein Sequence for CO$_2$-Response Protein 1 (CORP1)
Encoded by, e.g., the gene (coding sequence) designated "CA1", or At3g01500 or SEQ ID NO: 7.
MSTAPLSGFFLTSLSPSQSSLQKLSLRTSSTVACLPPASSSSSSSSSSSSRSVPTLIRNEPVFAAPAPIIAPYWSEEMGTEAYDEAIEALK KLLIEKEELKTVAAAKVEQITAALQTGTSSDKKAFDPVETIKQGFIKFKKEKYETNPALYGELAKGQSPKYMVFACSDSRVCPSHVL DFQPGDAFVVRNIANMVPPFDKVKYGGVGAAIEYAVLHLKVENIVVIGHSACGGIKGLMSFPLDGNNSTDFIEDWVKICLPAKSKV ISELGDSAFEDQCGRCEREAVNVSLANLLTYPFVREGLVKGTLALKGGYYDFVKGAFELWGLEFGLSETSSVKDVATILHWKL Guard cell promoter of this invention (SEQ ID NO: 10):

```
GAGTAAAGATTCAGTAACCCGATGCTCCTGCTCTTCCTCAAGACCTTCCTTGATTCGCCGCCGGTATGTTCTCCGTCTGTGGTAGCGCCTTTGGAACACT

CTACCAACGCCGCCATGAAAGGATCTCTCATGGCCGCAGGGGACGTGTTCTTCTTACATCTGGTGTTAGGGCTATGGTTACTCCAGTGAGGAGGGAGAGG

CAAGAGGTTGCTTAATGATTCGTTTTTCCGGTGATACGAGAACTCTTTAGGTTTACCGGGAAGCTTTTCCCATGAAAATGGGATGCCAAGTGGATGGAGA

GGAGTTGCCGGAGAGTTGCCGGAGAATAGGAGGGAATTGGAGGAGGAGGAAGAGAGTGATCGCCGGGTTGAAATGTTAACCGTCGAGGAGAATTTGACCG

AGTTGGATCGTCTAGTAGGTACAATTCGGGTCCTTGGCGAAGTATCCATcaaaatagtgtttagttttggacttgagaacttgttgtctctttgatctc ttttatataaaactttggacgtgtaggacaaacttgtcaacataagaaacaaaatggttgcaacagagaggatgaatttataagttttcaacaccgcttt tcttattagacggacaacaatctatagtggagtaaattttatttttggtaaaatggttagtgaattcaaatatctaaattttgtgactcactaacatta acaaatatgcataagacataaaaaaagaaagaataattcttatgaaacaagaaaaaaaacctatacaatcaatctttaggaattgacgatgtagaattg tagatgataaattttctcaaatatagatgggcctaatgaagggtgccgcttattggatctgacccattttgaggacattaatattttcattggttataag ccttttaatcaaaattgtcattaaattgatgtctccctctcgggtcattttcctttctccctcacaattaatgtagactttagcaatttgcacgctgtgc tttgtctttatatttagtaacacaaacattttgacttgtcttgtagagttttctcttttattttctatccaatatgaaaactaaaagtgttctcgtat acatatattaaaattaaagaaacctatgaaaacaccaatacaaatgcgatattgttttcagttcgacgtttcatgtttgttagaaaatttctaatgacgt ttgtataaaatagacaattaaacgccaaacactacatctgtgttttcgaacaatattgcgtctgcgtttccttcatctatctctctcagtgtcacaatgt ctgaactaagagacagctgtaaactatcattaagacataaactaccaaagtatcaagctaatgtaaaaattactctcatttccacgtaacaaattgagtt agcttaagatattgtgaaactaggtttgaattttcttcttcttcttccatgcatcctccgaaaaaagggaaccaatcaaaactgtttgcatatcaaact ccaacactttacagcaaatgcaatctataatctgtgatttatccaataaaaacctgtgatttatgtttggctccagcgatgaaagtctatgcatgtgatc tctatccaacatgagtaattgttcagaaaataaaaagtagctgaaatgtatctatataaagaatcatccacaagtactattttcacacactacttcaaaa tcactactcaagaaat (SEQ ID NO: 10)
```

Alternative guard cell promoter of this invention (SEQ ID NO: 11), a truncated, but "stronger",
promoter than the SEQ ID NO: 10 promoter:

```
atggttgcaacagagaggatgaatttataagttttcaacaccgcttttcttattagacggacaacaatctatagtggagtaaattttatttttggtaaaatg gttagtgaattcaaatatctaaattttgtgactcactaacattaacaaatatgcataagacataaaaaaagaaagaataattcttatgaaacaaga aaaaaacctatacaatcaatctttaggaattgacgatgtagaattgtagatgataaattttctcaaatatagatgggcctaatgaagggtgccgctta ttggatctgacccattttgaggacattaatattttcattggttataagccttttaatcaaaattgtcattaaattgatgtctccctctcgggtcatttcc tttctccctcacaattaatgtagactttagcaatttgcacgctgtgctttgtctttatatttagtaacacaaacattttgacttgtcttgtagagttttt ctcttttattttctatccaatatgaaaactaaaagtgttctcgtatacatatattaaaattaaagaaacctatgaaaacaccaatacaaat gcgatattgttttcagttcgacgtttcatgtttgttagaaaatttctaatgacgtttgtataaaatagacaattaaacgccaaacactacatct gtgttttcgaacaatattgcgtctgcgtttccttcatctatctctctcagtgtcacaatgtctgaactaagagacagctgtaaactatcattaa
```

-continued

```
gacataaactaccaaagtatcaagctaatgtaaaaattactctcatttccacgtaacaaattgagttagcttaagatattagtgaaacta ggtttgaattttcttcttcttcttccatgcatcctccgaaaaagggaaccaatcaaaactgtttgcatatcaaactccaacactttacagc aaatgcaatctataatctgtgatttatccaataaaaacctgtgatttatgtttggctccagcgatgaaagtctatgcatgtgatctctatcca acatgagtaattgttcagaaaataaaaagtagctgaaatgtatctatataaagaatcatccacaagtactattttcacacactactt caaaatcactactcaagaaat (SEQ ID NO: 11)
```

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

In alternative aspects, amino acids and/or amino acid sequences of this invention include an oligopeptide, peptide, polypeptide, or protein sequence, or to a fragment, portion, or subunit of any of these and to naturally occurring or synthetic molecules. In alternative aspects, polypeptides of the invention are amino acids joined to each other by peptide bonds or modified peptide bonds and may contain modified amino acids other than the 20 gene-encoded amino acids. The polypeptides may be modified by either natural processes, such as post-translational processing, or by chemical modification techniques that are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, phosphorylation, prenylation, racemization, selenoylation, sulfation and transfer-RNA mediated addition of amino acids to protein such as arginylation. See for example, Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983)).

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a $CO_2$ sensor activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

The invention includes polypeptides of the invention with and without signal sequences, i.e., leader sequences. The polypeptide comprising a signal sequence of the invention can be a $CO_2$ sensor of the invention or another $CO_2$ sensor or another enzyme or other polypeptide.

Antibodies and Antibody-Based Screening Methods

The invention provides isolated, synthetic or recombinant antibodies that specifically bind to a $CO_2$ sensor of the invention. These antibodies can be used to isolate, identify or quantify the $CO_2$ sensor polypeptides of the invention or related polypeptides. These antibodies can be used to isolate other polypeptides within the scope the invention or other related $CO_2$ sensors. The antibodies can be designed to bind to an active site of a $CO_2$ sensor. Thus, the invention provides methods of inhibiting $CO_2$ sensor using the antibodies of the invention.

The invention provides fragments of the enzymes of the invention, including immunogenic fragments of a polypeptide of the invention. The invention provides compositions comprising a polypeptide or peptide of the invention and adjuvants or carriers and the like.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

In alternative aspects, an antibody of the invention includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) an Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

Arrays, or "Biochips"

Nucleic acids and/or polypeptides of the invention can be immobilized to or applied to an array, e.g., a "biochip". Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a $CO_2$ sensor gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Kits and Libraries

The invention provides kits comprising compositions and methods of the invention, including cells and/or fish of the invention, target sequences, transfecting agents, transducing agents, instructions (regarding the methods of the invention), or any combination thereof. As such, kits, cells, vectors and the like are provided herein.

The invention provides compositions and methods for modulation of a plant's size and/or stature, e.g., including selection modulation of, for example, an entire plant, or a particular portion of a plant, or growth rate, or seedling vigor allows production of plants better suited for a particular industry. For example, reductions in the height of specific crops and tree species can be beneficial by allowing easier harvesting. Alternatively, increasing height, thickness or organ size, organ number may be beneficial by providing more biomass useful for processing into food, feed, fuels and/or chemicals. Other examples of commercially desirable traits include increasing the length of the floral stems of cut flowers, increasing or altering leaf size and shape or enhancing the size of seeds and/or fruits. Changes in organ size, organ number and biomass also result in changes in the mass of constituent molecules such as secondary products and convert the plants into factories for these compounds. Thus, the compositions and methods of the invention can be used to modulate plant size, vegetative growth, plant growth rate, organ number, plant architecture and/or biomass.

The invention will be further described with reference to the following examples; however, it is to be understood that the invention is not limited to such examples.

EXAMPLES

Example 1

Manipulating the Exchange of Water and Carbon Dioxide ($CO_2$) Through Plant Stomata by Controlling $CO_2$ Sensor Genes of the Invention The invention provides methods for manipulating the exchange of water and carbon dioxide ($CO_2$) through plant stomata by controlling $CO_2$ sensor genes of this invention.

A double mutant of *Arabidopsis thaliana* was constructed: this double mutant lacks the full-length expression of two homologous genes that are highly expressed in wildtype guard cells, according to cell-specific microarray analyses was constructed.

The double mutant of *Arabidopsis thaliana* lacks the full-length expression of homologous genes highly expressed in wildtype guard cells, according to cell-specific microarray analyses. The CO2Sen double mutant shows an impaired stomatal response as measured by real-time gas exchange analysis to changes in [$CO_2$]; both with regards to changes from ambient 365 ppm $CO_2$ to elevated 800 ppm $CO_2$ and from 800 ppm $CO_2$ to reduced 100 ppm $CO_2$. The $CO_2$sens-type encoded proteins bind $CO_2$.

FIG. 1 graphically illustrates data showing stomatal conductance in wild-type *Arabidopsis thaliana* ecotype Columbia and the $CO_2$ sense double mutant. Ambient 365 ppm CO2 0-1800 seconds, 800 ppm CO2 1800-3600 seconds, 100 ppm CO2 3600-9000.

Figure 2A:
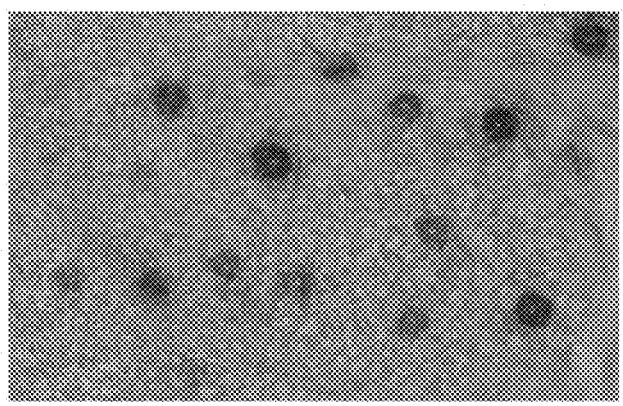
FIG. 2A: various expression levels in different stages of guard cell development.

FIG. 2 illustrates various expression levels in different stages of guard cell (GC) development:

FIG. 2A: various expression levels in different stages of GCs

Figure 2B:
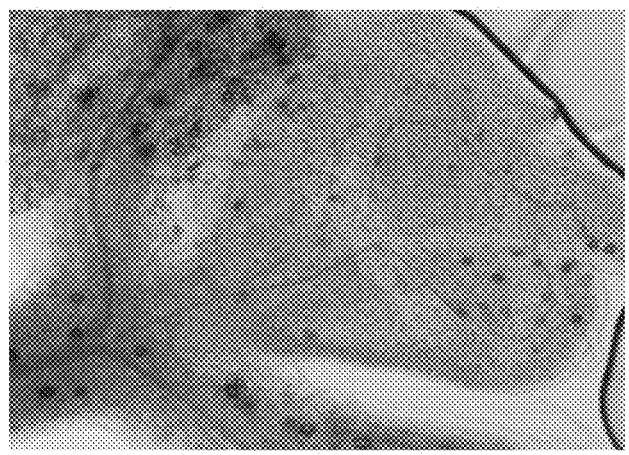
FIG. 2B: Expression of 27-GUS in young leaf and leaf stems.

FIG. 2B: Expression of 27-GUS in young leaf and leaf stems.

Figure 2C:
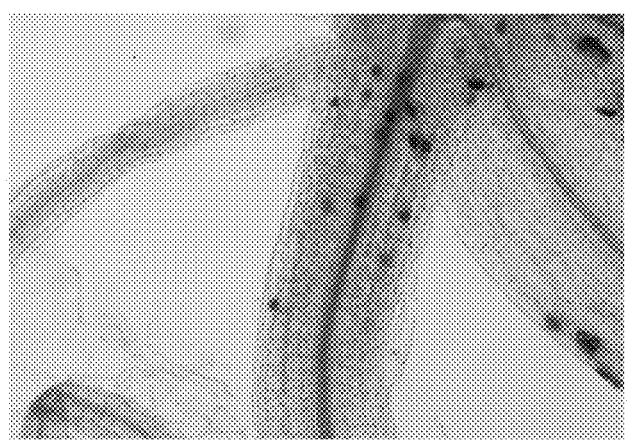
FIG. 2C: Expression of 27-GUS in upper level of hypocotyl.

FIG. 2C: Expression of 27-GUS in upper level of hypocotyl.

Figure 2D:
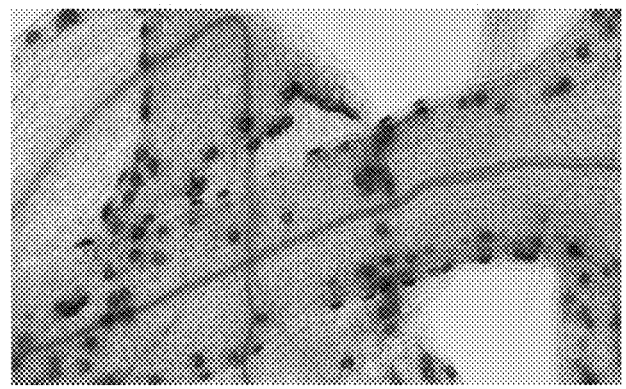
FIG. 2D: Expression of 27-GUS in leaf stem and edge.

FIG. 2D: Expression of 27-GUS in leaf stem and edge.

Figure 2E:
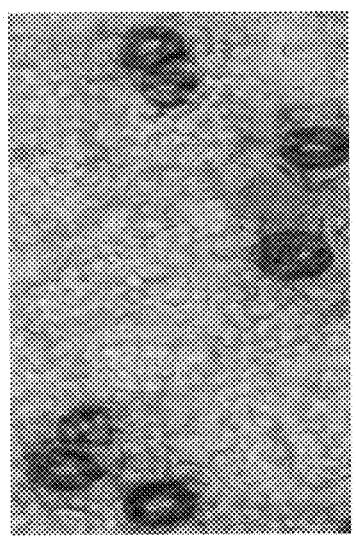
FIG. 2E and FIG. 2F: Four lips in wild type (wt); as described in detail in Example 1, below.
Figure 2F:
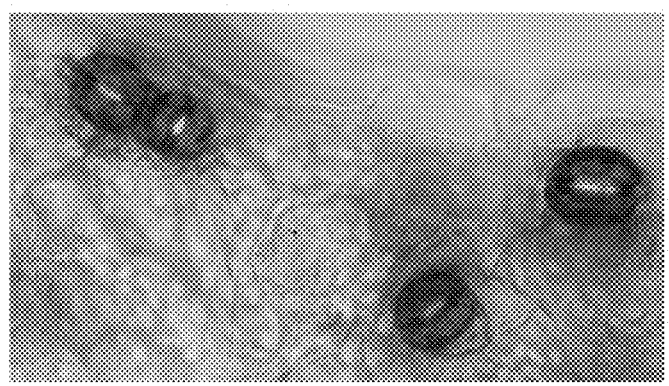

FIG. 2E & FIG. 2F: Four lips in wt.

FIG. 3 illustrates expression of 27-YC3.6 (SEQ ID NO:10) in GC on the stem of adjacent leaf but not in the very young leaf (outlined) (A & A'). 27-YC3.6 is mainly expressed in mature GC, very weak in young or immature GC (white arrow in B & B'). 27-YC3.60 (SEQ ID NO:11) is also expressed in GCs on hypocotyle (C & C'). 27-YC3.6 (SEQ ID NO:10) is also expressed in GCs on sepals (D & D').

Example 2

Characterization of $CO_2$ Receptors that Control Plant $CO_2$ Uptake and Water Use Efficiency The invention provides compositions and methods for controlling the opening and/or closing of plant stomatal pores. Stomatal pores are formed by guard cells pairs in the epidermis of leaves and enable the control of plant water loss and influx of carbon dioxide ($CO_2$) into plants. The invention provides compositions and methods for controlling the amount of $CO_2$ taken up for photosynthetic carbon fixation, and amount of water lost through the process of transpiration through these "controlled" stomatal pores.

The invention provides compositions and methods for providing signal transduction mechanisms in guard cells to sense $CO_2$ levels, water status, light and other environmental stimuli to regulate stomatal apertures for optimization of $CO_2$ influx, water loss and plant growth under diverse conditions.

The invention provides compositions and methods for sensitizing plants to high levels of $CO_2$ to trigger stomatal closing, and to sensitize plants to low $CO_2$ levels to induce stomatal opening. In one aspect, the compositions and methods of the invention are used to aid in sequestering(?) atmospheric [$CO_2$] (which in one aspect is accomplished by inhibiting the expression of $CO_2$-Response proteins in vivo or in situ), for example, to ameliorate increasing levels of atmospheric [$CO_2$], which is predicted to double within the present century. In one aspect, the compositions and methods of the invention will ameliorate the "stomatal closing" effect of increasing levels of atmospheric [$CO_2$] (which in one aspect is accomplished by enhancing the expression of $CO_2$-Response proteins in vivo or in situ), noting that ambient $CO_2$ increases will reduce stomatal apertures of different plant species by up to 40%. In one aspect, the compositions and methods of the invention can be used to ameliorate the profound effects on gas exchange, carbon fixation, leaf temperature and/or water use efficiency of plants caused, e.g., on a global scale, by the increasing levels of atmospheric [$CO_2$].

Figure 4C:
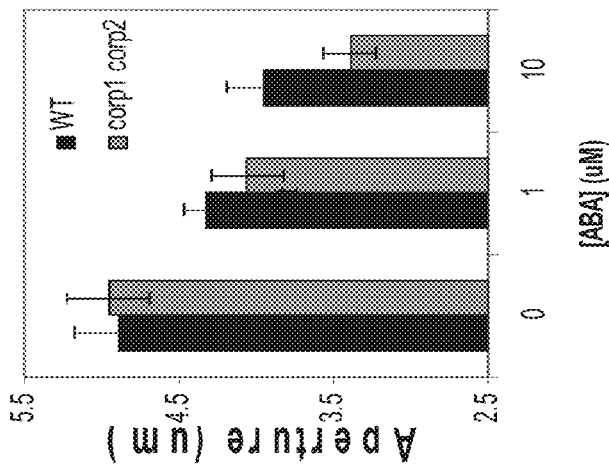
FIG. 4C graphically illustrates data showing that double mutant corp1/corp2 plants did not show disruption of other important signaling pathways in guard cells, including stomatal closing induced by the drought-induced hormone abscisic acid (ABA), FIG. 4(c) graphically illustrates data demonstrating the intact response of the SEQ ID NO:7/SEQ ID NO:1, or corp1/corp2, double mutant and WT plants to abscisic acid (ABA); as described in detail in Example 2, below.
Figure 4B:
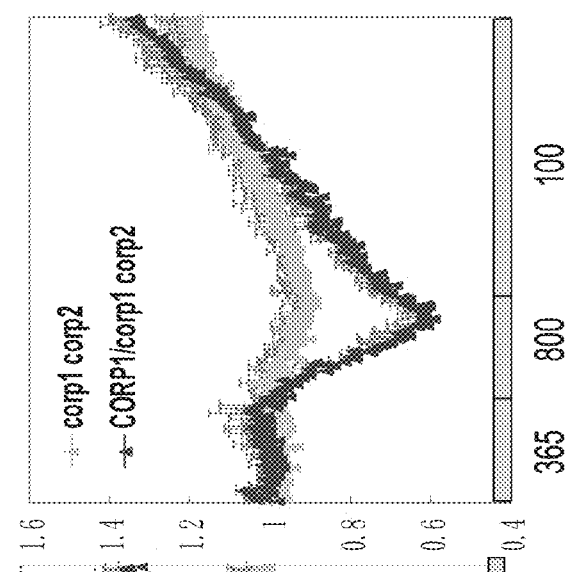
FIG. 4B graphically illustrates studies showing complementation of the double mutant SEQ ID NO:1/SEQ ID NO:7 $CO_2$ phenotype by transgenic expression of the CORP1 cDNA (SEQ ID NO:7)
Figure 4A:
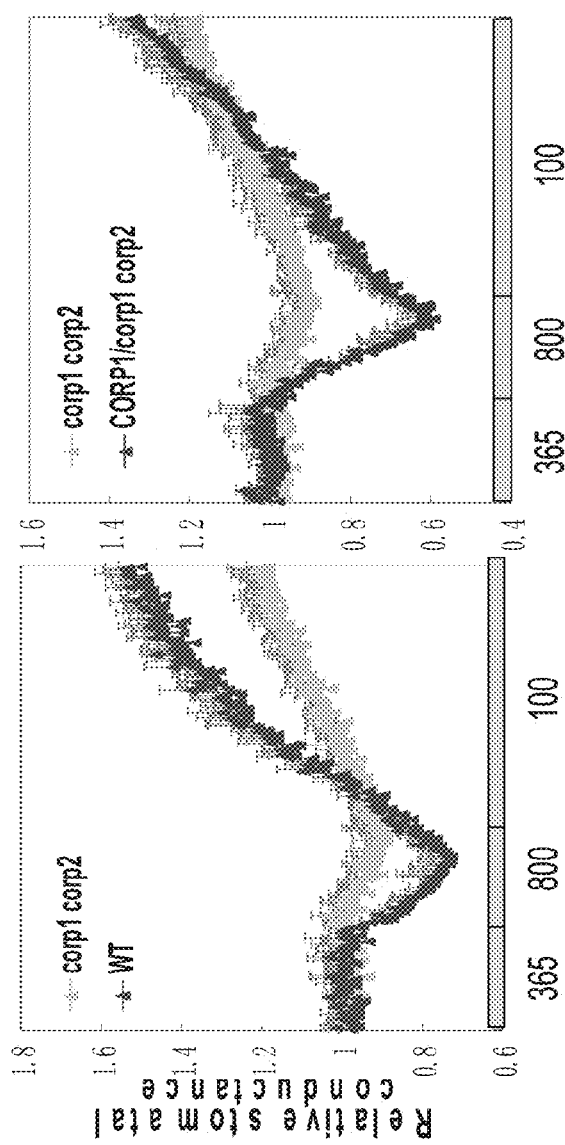
FIG. 4A graphically illustrates data showing that in double mutant SEQ ID NO:1/SEQ ID NO:7 plants loss of ability to express these two genes resulted in a strong impairment in $CO_2$-induced stomatal closing compared to wild-type (wt) plants.

For the first time mutants that show $CO_2$ insensitivity in stomatal $CO_2$ responses, but do not impair the abscisic responses, have been made and characterized by the inventors. Using guard cell specific microarray analysis, this invention identified a double mutant in two homologous genes named: $CO_2$-Response Protein 1 (CORP1), also designated "CA 1", or At3g01500 or SEQ ID NO:7; and, $CO_2$-Response Protein 2 (CORP2), also designated "CA4", or At1g70410 or SEQ ID NO:1; both of which are highly expressed in guard cells of *Arabidopsis* plants. Whereas single knock-out mutants showed no phenotype, double mutant plants in these two genes showed a strong impairment in $CO_2$-induced stomatal closing compared to wild-type (wt) plants, as illustrated in FIG. 4a. Studies show complementation of this $CO_2$ phenotype by transgenic expression of the CORP1 cDNA (SEQ ID NO:7), as illustrated in FIG. 4b. FIG. 4a and FIG. 4b, illustrate the relative stomatal conductances of double mutant (corp1 corp2), WT (wild-type) and (b) a transgenic complemented line (CORP1/corp1 corp2) expressing CORP1 in response to changes in $CO_2$ concentrations (X-axis: ppm [$CO_2$]).

CORP proteins bind $CO_2$. corp1 (encoded by, e.g., SEQ ID NO:7) and corp2 (encoded by, e.g., SEQ ID NO:1) are also expressed in other plant cells. Double mutant corp1/corp2 plants did not show disruption of other important signaling pathways in guard cells, including stomatal closing induced by the drought-induced hormone abscisic acid (ABA), as illustrated in FIG. 4c. FIG. 4(c) graphically illustrates data demonstrating the intact response of the SEQ ID NO:7/SEQ ID NO:1, or corp1/corp2, double mutant and WT plants to abscisic acid (ABA).

These data demonstrate that CORP1 (encoded by, e.g., SEQ ID NO:7) and CORP2 (SEQ ID NO:1) function as $CO_2$ receptors in guard cells that control global plant gas exchange and to achieve an understanding of the molecular mechanisms that mediate CO₂ signal transduction via CORP1 (encoded by, e.g., SEQ ID NO:7) and CORP2 (encoded by, e.g., SEQ ID NO:1) in guard cells.

In another aspect, to facilitate analyses of subcellular localization(s) of CORP proteins, including the CORP proteins of this invention, e.g., CORP1 and CORP2 proteins, the invention also provides N- and C-terminal tags (e.g., YFP fusions) with CORP proteins, including the CORP proteins of this invention, e.g., CORP1 and CORP2. These tagged CORP proteins are introduced into wild-type and corp1 corp2 double mutant plants. Cellular localization and simultaneous complementation are analyzed.

In another aspect, CORP-encoding genes, such as the nucleic acids of this invention encoding CORP proteins, e.g., corp 1 and corp 2, are operatively linked to various transcriptional regulatory sequences, e.g., promoters, such as the guard cell specific transcriptional regulatory sequences, e.g., guard cell specific promoters of this invention. These nucleic acids are used to determine whether CORP1 and/or CORP2 can be expressed in guard cells for functional stomatal CO₂ signaling; e.g., whether CORP1 and/or CORP2 alone or together are sufficient for functional stomatal CO₂ signaling in a plant cell, tissue or organ.

In one aspect, the invention introduces these two genes under the control of a guard cell specific promoter, e.g., guard cell specific transcriptional regulatory sequences of this invention, e.g., guard cell specific promoters of this invention, mesophyll cell specific promoter and/or the ecotopic 35S promoter, into corp1 corp2 double mutant plants to determine the cell specific requirement for complementation of the impaired CO₂ response. Gas exchange and stomatal signaling transduction analysis are conducted for this goal. Data has shown that these receptors function in stomatal CO₂ signaling in guard cells.

In one aspect, the invention characterizes the CO₂ signaling mechanisms mediated by CORP proteins, e.g., using CORP-encoding nucleic acids of this invention, and in one exemplary methods, CORP-interacting proteins are isolated from plant, bacteria or other cells. In one aspect, methods comprise use of yeast two-hybrid screening systems, split ubiquitin system screening and/or co-immunoprecipitation systems using, e.g., YFP-tagged (or equivalently tagged) CORP proteins. The functions of CORP interactors in CO₂ signal transduction are identified and analyzed.

In one aspect, the invention provides cell type-specific CORP over-expression cells, tissues, organs and/or cells lines to, e.g., analyze water use efficiency of plants at different CO₂ concentrations and engineer improved water use efficiency in *Arabidopsis* and selected important economical crops, e.g., important economically for fixing carbon. Data shows a greater than fifty percent (>50%) increase in water use efficiency in *Arabidopsis* by CORP over-expression (using corp-encoding nucleic acids of this invention).

Figure 5A:
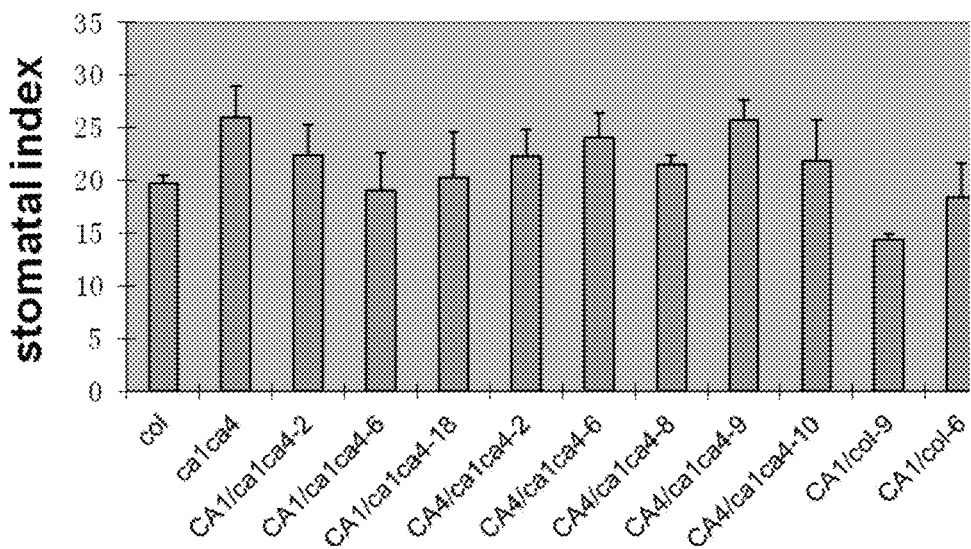
FIG. 5A and FIG. 5B, graphically illustrates data showing that both CA1 (SEQ ID NO:7) and CA4 (SEQ ID NO:1) can complement ca1ca4 (mutants are designated by lower case italics) double mutants to varying degrees; as described in detail in Example 2, below.
Figure 5B:
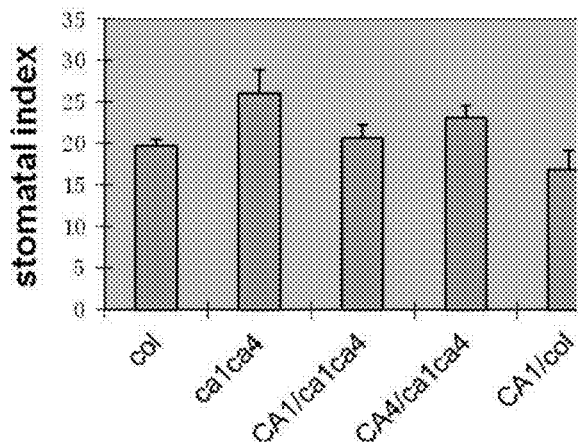

Complementation of the double mutant of the two homologous genes CO₂-Response Protein 1 (CORP1), also designated "CA1", or At3g01500 or SEQ ID NO:7; and, CO₂-Response Protein 2 (CORP2), also designated "CA4", or At1g70410 or SEQ ID NO:1, was made. We measured the stomatal index of complementation plants and overexpression plants. As illustrated in FIG. 5A and FIG. 5B, both CA1 (SEQ ID NO:7) and CA4 (SEQ ID NO:1) can complement this double mutants to varying degrees. Overexpression of CA1 decreases the "stomatal index". A "stomatal index" is defined as: (number of stomata per mm²×100)/(number of stomata per mm²+number of epidermal cells per mm²; or alternatively phrased: Stomatal Index (I)=[S/(E+S)]*100, where S is the number of stomata per unit area, and E is the number of epidermal cells per same unit area. This "stomatal index" value can be useful in comparing leaves of different sizes; relative humidity and light intensity during leaf development affect the value of stomata index.

Figure 6:
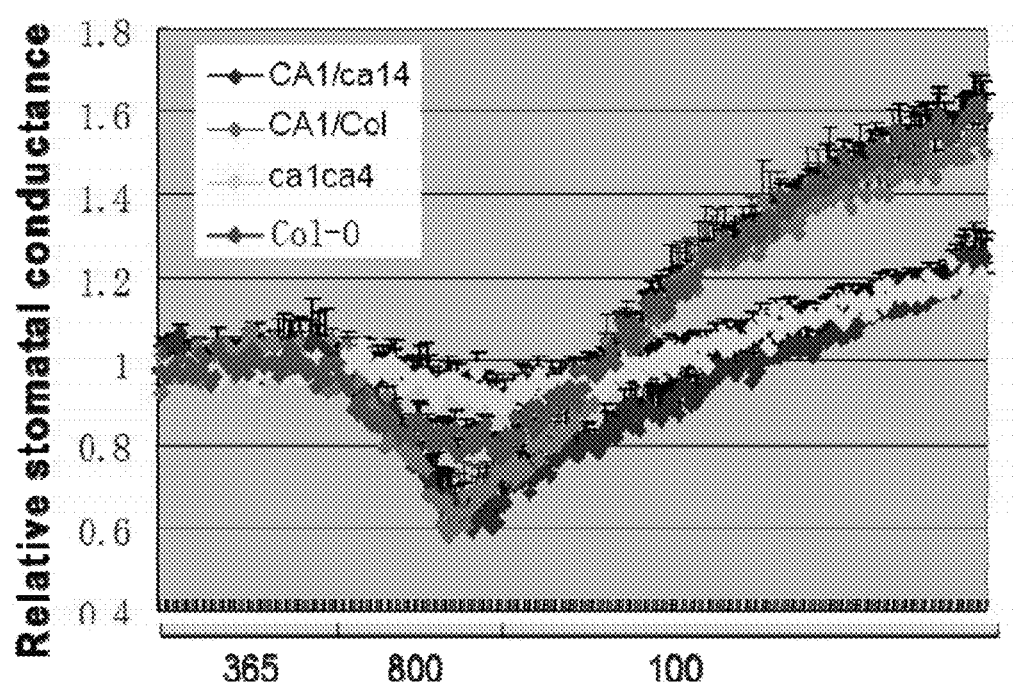
FIGS. 6 and 7.
Figure 7A:
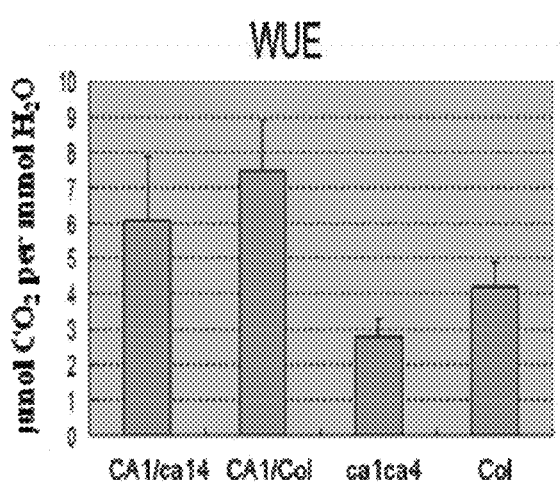
Figure 7B:
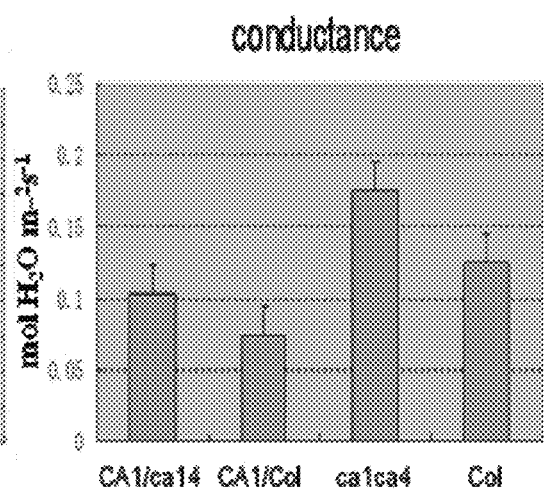

The gas exchange and water use efficiency (WUE) of the CA1 (SEQ ID NO:7) and CA4 (SEQ ID NO:1) complementation plants were also measured. Plant gas exchange and WUE are measured in the morning. Exemplary results are analyzed and shown in FIG. 6, showing the relative stomatal conductance; where these results are summarized and graphically illustrated in FIG. 7, FIG. 7A graphically illustrating the water use efficiency (WUE) data, and FIG. 7A graphically illustrating the relative stomatal conductance data.

Figure 8A:
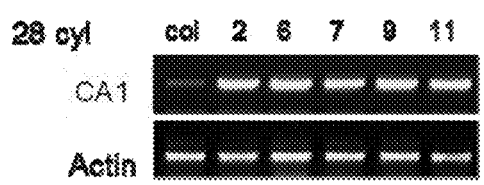
FIG. 8 illustrates photomicrographs of Northern blots showing the expression level of CA1 (SEQ ID NO:7) and CA4 (SEQ ID NO:1) in complementation plants, in particular, in leaves, and in guard cells and in mesophyll cells, as indicated in the Figures, FIG. 8A illustrating Col plants transformed with CA1 cDNA.
FIG. 8B illustrating CA1/4 mutants transformed with CA1 cDNA; and, FIG. 8C illustrating CA1/4/6 mutants transformed with CA1 cDNA; as described in detail in Example 2, below.
Figure 8B:
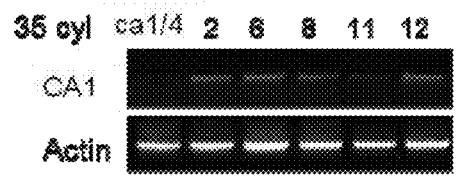
Figure 8C:
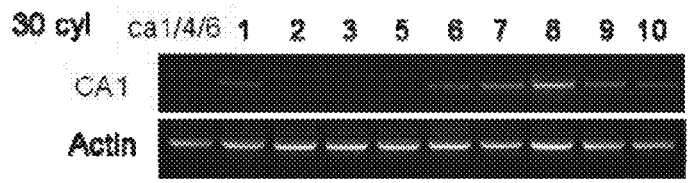

FIG. 8 illustrates photomicrographs of Northern blots showing the expression level of CA1 (SEQ ID NO:7) and CA4 (SEQ ID NO:1) in complementation plants, in particular, in leaves, and in guard cells and in mesophyll cells; FIG. 8A illustrating Col plants transformed with CA1 cDNA; FIG. 8B illustrating CA1/4 mutants transformed with CA1 cDNA; and, FIG. 8C FIG. 8B illustrating CA1/4/6 mutants transformed with CA1 cDNA.

FIGS. 9A and 9B illustrate photomicrographs of Northern blots showing the expression level of CA1 (SEQ ID NO:7) and CA4 (SEQ ID NO:1) in double knockouts (of CA1 (SEQ ID NO:7) and CA4 (SEQ ID NO:1)). FIGS. 9C, 9D and 9E illustrate data from a CO₂ sensor showing deficient CO₂ regulation of gas exchange; note: Light condition=red light (50 $\mu mol \cdot m^{-2} \cdot s^{-1}$), blue light (6 $\mu mol \cdot m^{-2} \cdot s^{-1}$).

FIG. 10A graphically illustrates a summary of data showing intact abscisic acid response in the ca1ca4 (CA1 (SEQ ID NO:7) and CA4 (SEQ ID NO:1)) double mutant. FIG. 10B graphically illustrates a summary of data showing that an inhibitor of CA1 (SEQ ID NO:7) and/or CA4 (SEQ ID NO:1) mimics CO₂ Insensitivity in wild-type (WT) plants.

FIGS. 11A and 11B illustrate photomicrographs of Northern blots showing the expression level of CA1 (SEQ ID NO:7) and CA4 (SEQ ID NO:1) in double knockouts (of CA1 (SEQ ID NO:7) and CA4 (SEQ ID NO:1)), and FIG. 11C illustrates data showing that genomic DNA of CA1 (SEQ ID NO:7) or CA4 (SEQ ID NO:1) genes can complement CO₂ response under different light conditions: red light (50 $\mu mol \cdot m^{-2} \cdot s^{-1}$), blue light (6 $\mu mol \cdot m^{-2} \cdot s^{-1}$).

FIGS. 12A, 12B and 12C, graphically illustrate a summary of data showing that photosynthesis is not impaired in ca1ca4 triple CO₂ sensor knockout mutant plants: Light during pre-adaptation time, prior to PS fluorescence measurements: 50 umol/m2/s: 88% red light, 12% blue light; 2000 umol/m2/s: 90% red light, 10% blue light. FIG. 12D illustrates the CO₂ assimilation rate in dark and in red light (where the red light: 300 $\mu mol \cdot m^{-2} \cdot s^{-1}$).

FIGS. 13A, 13B and 13C, graphically and pictorially illustrate that photosynthesis-impaired bleached leaves show intact CO₂ regulation of gas exchange.

FIGS. 14A and 14B illustrate photomicrographs of Northern blots showing the expression level of CA1 (SEQ ID NO:7) and CA4 (SEQ ID NO:1) in double knockouts (of CA1 (SEQ ID NO:7) and CA4 (SEQ ID NO:1)); and FIG. 14C, graphically and pictorially illustrate that CO₂ sensor overexpression plants where the CA1 (SEQ ID NO:7) and CA4 (SEQ ID NO:1) are operatively linked to guard cell targeted promoters of this invention show enhanced water use efficiency (WUE). In FIG. 14C, the data shows no effect observed on flowering time.

Example 3

Isolation and Characterization of a Strong *Arabidopsis* Guard Cell Promoter and its Use as a Guard Cell Transcriptional Activator The invention provides transcriptional activators that are very active in plant guard cell; including guard cell-specific transcriptional activators, such as promoters. For example, the invention provides nucleic acids (polynucleotides) having a sequence at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or complete sequence identity to SEQ ID NO:10 and/or SEQ ID NO:11, over a region of at least about 50, 75, 100, 150, 200, 250, 300, 350, 400, 450, 500, 550, 600, 650, 700, 750, 800 or more residues, or over the full length of a promoter having guard-cell specific activity, or a transcriptional regulatory region having guard-cell specific activity, wherein the nucleic acid comprises or consists of a guard cell-specific promoter, or a guard cell-specific transcriptional regulatory region.

In one aspect, the invention provides guard-cell transcriptional regulatory regions that consistently give high expression of heterologous sequences in a plant cell, e.g., consistently give high expression of transgenes of interest. In one aspect, the transcriptional regulatory regions of this invention are used to improve available methods for targeted gene expression in guard cells.

Strong guard cell promoter candidates were isolated based on new guard cell-specific microarray analyses of 23,000 genes. A guard cell specific microarray-based approach was used to analyze putative strong guard cell specific promoters. A promoter pGC1 (At1g22690) drove very strong expression of reporter genes (GUS and GFP-based calcium reporter) in guard cells of both *Arabidopsis* and tobacco. Specific gene suppression in guard cells was also achieved by pGC1 driving antisense repression.

Results:

A promoter, pGC1(At1 g22690), drove strong and relatively specific reporter gene expression in guard cells including GUS (beta-glucuronidase) and yellow cameleon YC3.60 (GFP-based calcium FRET reporter). Reporter gene expression was weaker in immature guard cells. The expression of YC3.60 was sufficiently strong to image intracellular $Ca^{2+}$ dynamics in guard cells of intact plants and resolved spontaneous calcium transients in guard cells. The GC1 promoter also mediated strong reporter expression in clustered stomata in the stomatal development mutant too-many-mouths (tmm).

Furthermore, the same promoter::reporter constructs also drove guard cell specific reporter expression in tobacco, illustrating the potential of this promoter as a method for high level expression in guard cells. A serial deletion of the promoter defined a guard cell expression promoter region. In addition, anti-sense repression using pGC1 was powerful for reducing specific GFP gene expression in guard cells while expression in leaf epidermal cells was not repressed, demonstrating strong cell-type preferential gene repression.

Conclusion

The pGC1 promoter of this invention drives strong reporter expression in guard cells of *Arabidopsis* and tobacco plants. The promoters of this invention can provide a potent tool for targeted guard cell expression or gene silencing. Promoters of this invention can be used to reduce specific gene expression in guard cells, providing a method for circumvention of limitations arising from genetic redundancy and lethality. Promoters of this invention can be used for manipulating signaling pathways in guard cells and modifying plant performance under stress conditions.

Results

Isolation of pGC1, a Strong Guard Cell Promoter

Guard cell-specific microarray data were analyzed side by side with mesophyll cell-specific microarray data [see reference 26, cited below] to search for strong guard cell promoter candidates with low expression levels in mesophyll cells. Additional guard cell and mesophyll cell microarray experiments were conducted covering 234,000 genes (source: ATH1 Affymetrix, Santa Clara, Calif.). Furthermore, candidate genes were analyzed using GENEVESTIGATOR™ to select genes with low expression levels in non-leaf tissues across more than 2000 microarray experiments [see reference 27, cited below]. Guard cells and mesophyll cells exposed to ABA were also analyzed, as ABA synthesis is induced under several stress conditions. The following criteria were used for selection of strong guard cell promoter candidates. The raw signal in guard cells was set above 10000, the raw signal in mesophyll cells was set below 1000, and the reduction or induction fold by ABA was set to be less than two. Transcriptional profiles of several genes passed these criteria, see FIG. 15, which graphically summarizes data showing the transcriptional profiles of guard cell expressed genes in both guard cells and mesophyll cells.

Figure 15:
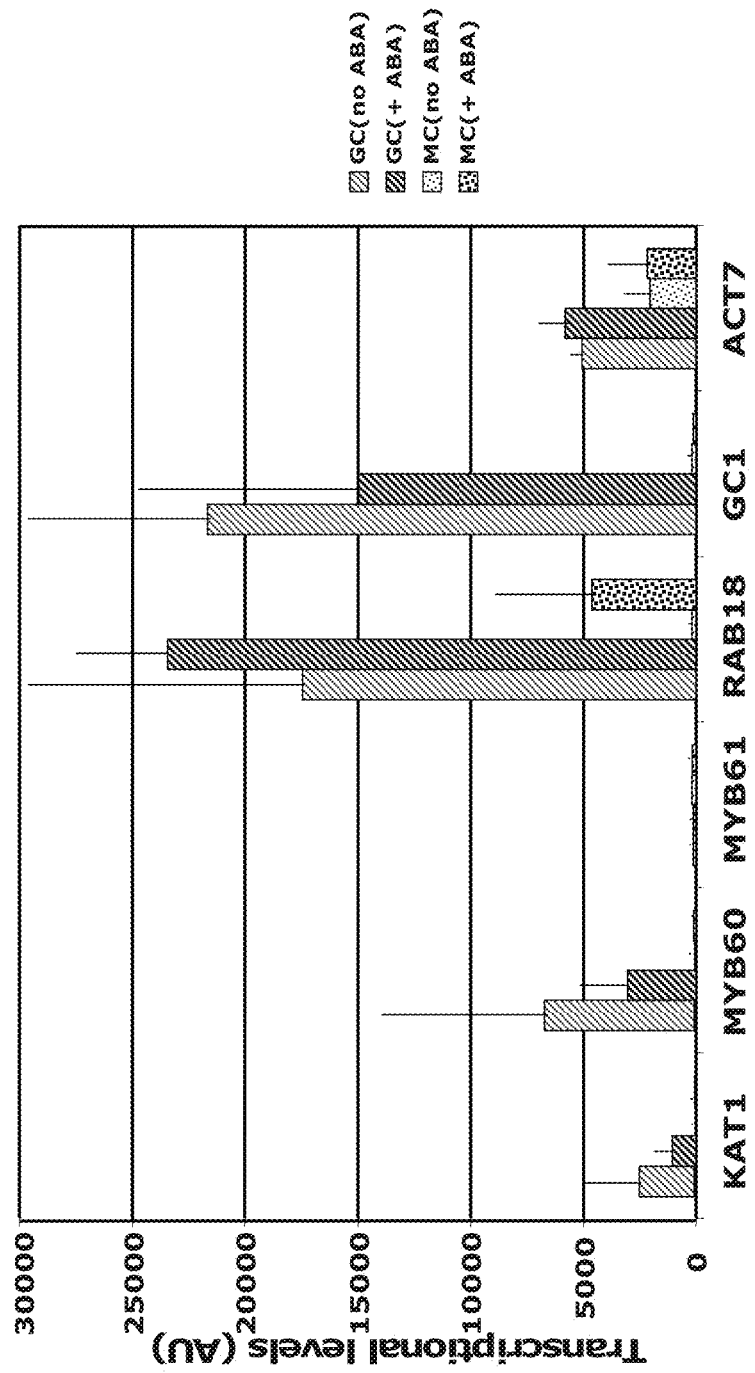
FIG. 15 graphically summarizes data showing the transcriptional profiles of guard cell expressed genes in both guard cells and mesophyll cells; as described in detail in Example 3, below.

In FIG. 15, average transcript levels of KATI (At5g46240), AtMYB60 (At1g08810), AtMYB61 (At1g09540), RAB18 (At5g66400), GC1 (At1g22690) (SEQ ID NO:10), and AtACT7 (At5g09810) from two independent microarrays are displayed. While KAT1, AtMYB60 and GC1 all exhibited guard cell-specific expression, the transcript level of GC1 was the highest among the three genes. RAB18 also exhibited very strong guard cell expression, but its expression level in mesophyll cells was strongly induced by ABA treatment.

The putative promoters (1 to 2 kb upstream of the annotated ATG start codon, see FIG. 16) were amplified by PCR and cloned into a GUS reporter vector. GUS staining of the T1 transgenic plants showed guard cell specific staining for one particular promoter candidate (At1g22690), designated as pGC1. At1g22690 is among the most highly expressed genes in guard cells. It showed relatively high expression in guard cells and low expression in mesophyll cells. At1g22690 encodes a small cysteine rich protein (119 amino acids). It belongs to the GASA family (GA-stimulated transcript (GAST1) protein homolog). A study by Wigoda et al. [28] suggested that GIP2 (a GASA protein from *Petunia hybrida*) exhibited in planta antioxidant activity. T-DNA insertional line in At1g22690 did not yield any noticeable stomatal phenotypes under our typical laboratory conditions (unpublished data). Furthermore, our guard cell microarray data showed that two other GASA genes also showed high expression level in guard cells (GASA 1 (At1g75750) and GASA 4 (At5g15230).

Figure 16:
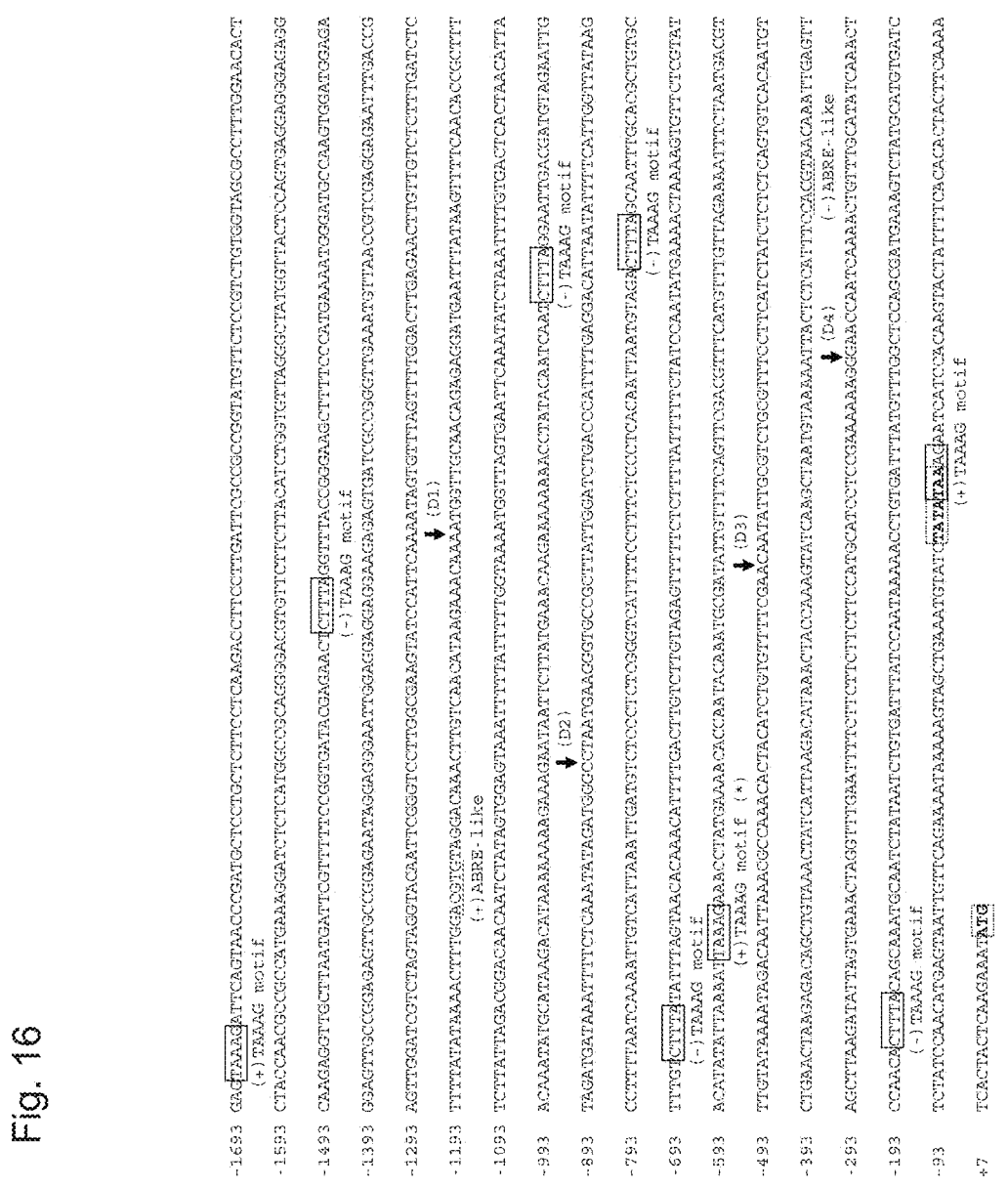

FIG. 16 is the promoter sequence of GC1 (SEQ ID NO:10, but the sequence of FIG. 16 also having an ATG added at the 3' end): in GC1 the transcriptional start site is denoted as +1, and the putative start codon (ATG) is located at +23/+25 bp. The D of target sites, 5'-TAAAG-3' (+) or 5'-CTTTA-3'(−), which have been shown to contribute to guard-cell specific gene expression [24], are boxed. The ABRE, abscisic acid-response element, 5'-ACGTG-3' (+) or 5'-CACGT-3' (−), are underscored and labeled. The TATA box (5'-TATATAA-3') and the start codon (ATG) are shown in bold with dotted boxes. The arrowheads mark the positions for promoter deletion analyses in FIG. 18.

We analyzed GC1 (At1g22690) gene expression in response to different treatments in the microarrays data compiled by GENEVESTIGATOR™ [27, 29]. Among 96 treatments, 8 treatments affected At1g22690 expression more than two fold. Salt and osmotic stress dramatically deceased At1g22690 gene expression (more than 10 fold) [30]. Meanwhile, light, ABA, GA, cold or drought did not induce more than a two-fold change in gene expression of At1g22690. This suggests that GC1 (At1g22690) has a relatively constant expression under most common situations.

Figure 17A:
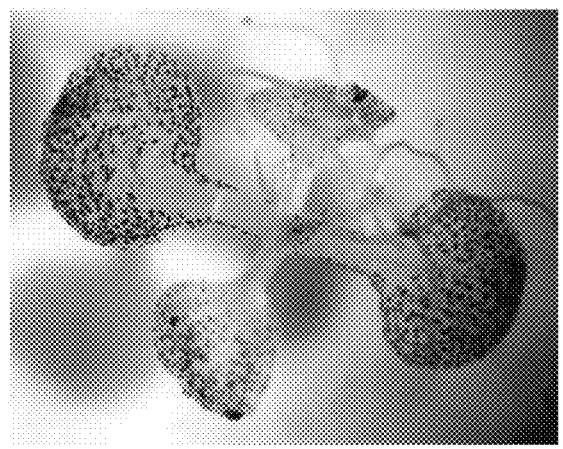
Figure 17B:
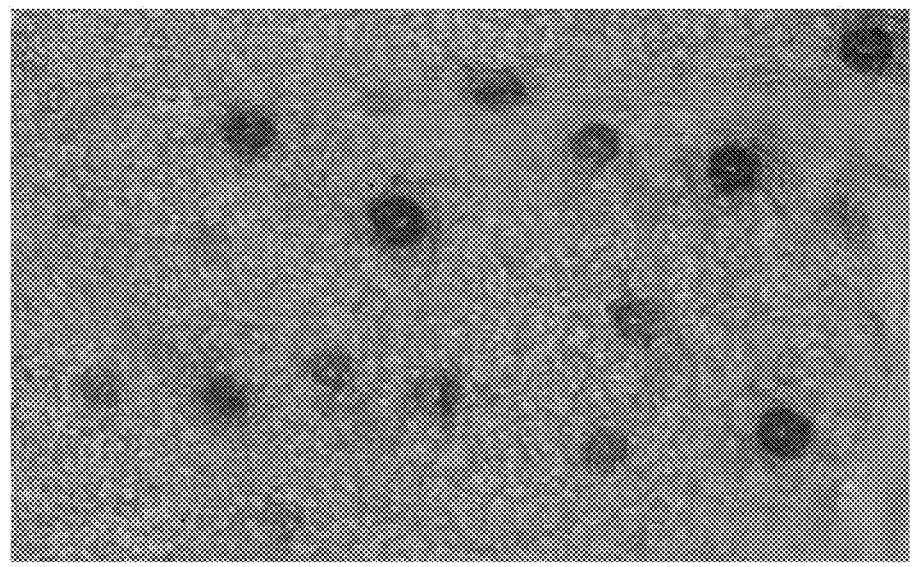
Figure 17C:
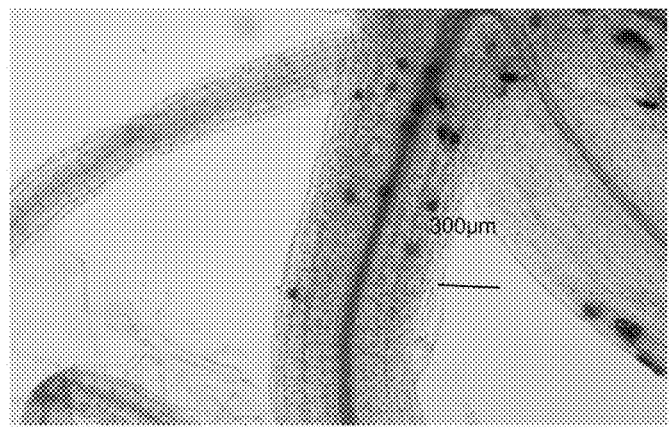

Interestingly, the pGC1::GUS not only delivered strong GUS expression in guard cells in leaves (FIG. 17A, B), but also in guard cells in petioles and hypocotyls (FIG. 17C, D, E). GUS staining from other candidate promoter-GUS fusions was either not very strong in guard cells and/or showed reporter expression in other tissues. We therefore focused on pGC1 for the rest of this study. The GC1 promoter was also fused to a second reporter, a GFP-based calcium reporter, yellow cameleon 3.60 (YC3.60) [31]. Most T1 transgenic plants (approximately 75%) transformed with pGC1::YC3.60 exhibited strong guard cell specific fluorescence, indicating a high degree of guard cell expression efficiency per transform ant. Some plants also showed fluorescence in some leaf epidermal cells (data not shown). However, younger or immature guard cells showed no or much less GFP expression (FIG. 17F, G). Furthermore, guard cells in sepals and hypocotyls also showed GFP expression (FIG. 17H, I, J, K).

We further examined whether the GC1 (SEQ ID NO:10) promoter could drive guard cell specific reporter expression in a guard cell development mutant, too many mouths (tmm) [32]. The tmm mutant was transformed with either the pGC1::GUS or the pGC1::YC3.60 construct. GUS staining showed reporter gene expression in clustered stomata (FIG. 17L). Similarly, GFP expression was observed in clustered stomata in tmm plants transformed with pGC1::YC3.60 (FIG. 17M).

To test if the GC1 promoter can drive guard cell specific reporter gene expression in plants besides *Arabidopsis*, we also transformed pGC1::YC3.60 into tobacco plants. Interestingly, strong guard cell GFP expression was observed in tobacco leaves, see FIG. 17N.

In summary, for FIG. 17: the GC1 promoter mediates strong reporter expression in guard cells of wild-type *Arabidopsis* seedlings, too many mouths mutant and also in tobacco:

FIG. 17A: A two-week-old pGC1::GUS transgenic seedling.

FIG. 17B. Different stages of guard cells exhibited different levels of GUS expression.

FIG. 17C. Upper part of the hypocotyl.

Figure 17D:
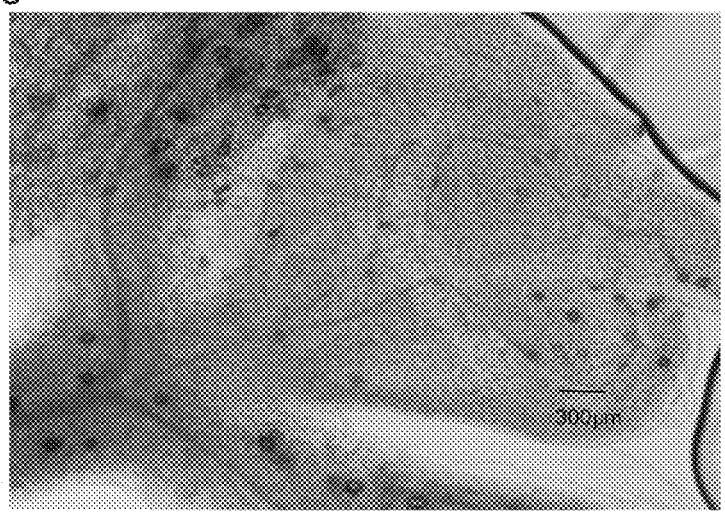

FIG. 17D: Young leaf and petiole.

Figure 17E:
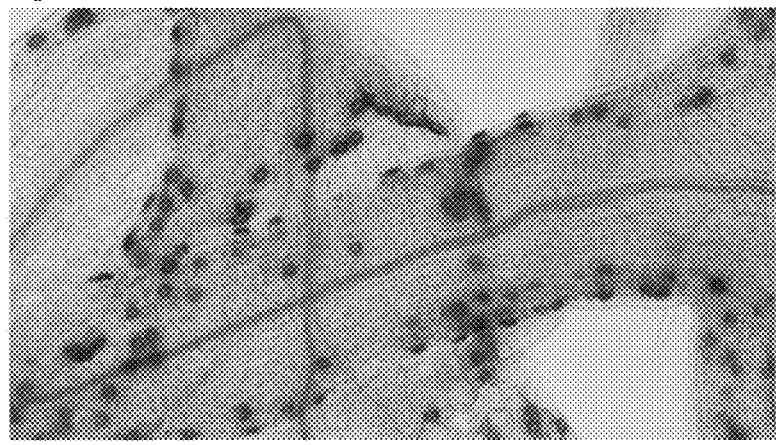
Figure 17F:
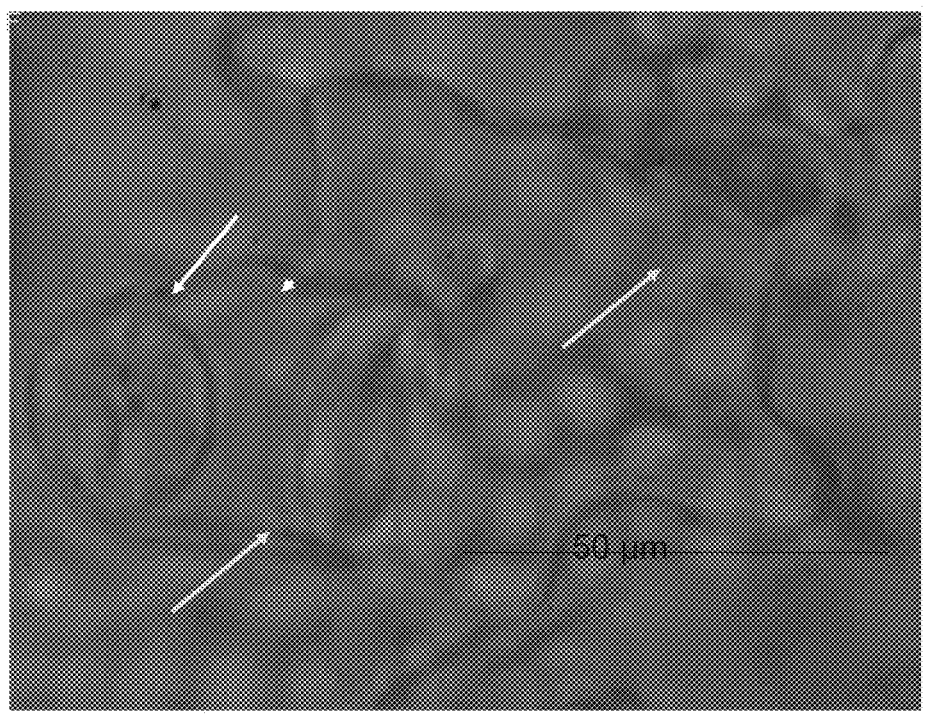
Figure 21A:
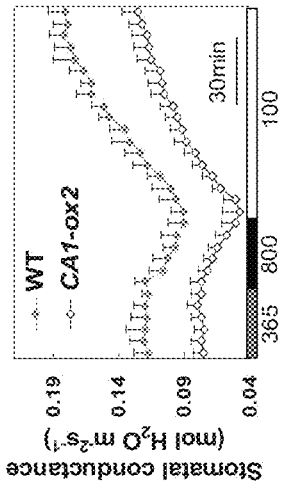
FIG. 21A, FIG. 21B, FIG. 21C, and FIG. 21D illustrate that $CO_2$ sensor, guard cell-targeted, over-expression in plants show enhanced $CO_2$ responses in gas exchange regulation, as described in detail in Example 3, below.
Figure 21B:
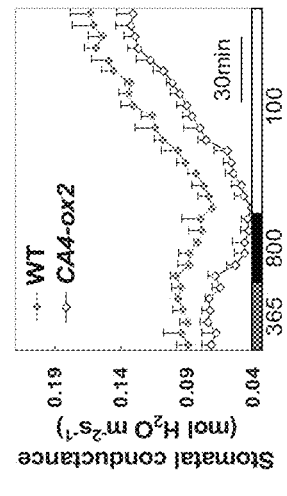
Figure 21C:
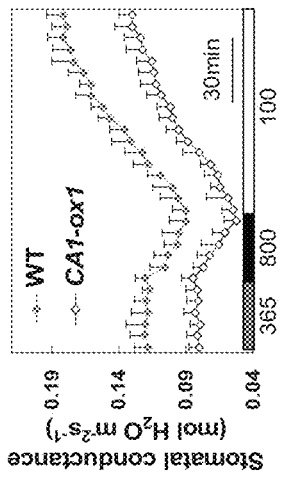
Figure 21D:
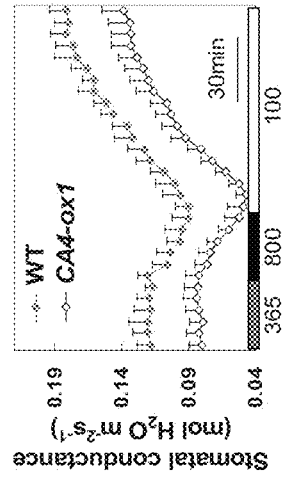

FIG. 17E: Leaf edge and petiole.

FIG. 17F and FIG. G: pGC1::YC3.60 was mainly expressed in mature guard cells, very weak in young or immature guard cells (white arrows in (f) & (g)).

FIGS. 17H and 17I: pGC1::YC3.60 was expressed in guard cells on the hypocotyl.

FIGS. 17J and 17K: pGC1::YC3.60 was expressed in guard cells on the sepal.

FIGS. 17L and 17M: pGC1 mediated GUS (L) and GFP (M) reporter expression in clustered stomata in too many mouths.

FIG. 17N: pGC1 mediated strong reporter gene expression in tobacco guard cells.

Serial Promoter Deletions Define a Region for Guard Cell Specificity and Strength A promoter region may contain both enhancer and repressor elements. To probe which part of the original 1716 base pair (bp) promoter (full length, FL, −1693 bp/+23 bp) is required for strong guard cell specific reporter expression, four 5' truncated versions of the GC1 (SEQ ID NO:10) promoter were generated as D1 (−1140 bp/+23 bp), D2 (−861 bp/+23 bp), D3 (−443 bp/+23 bp), and D4 (−224 bp/+23 bp), see FIG. 18. These truncated promoters were fused to the GUS reporter to generate the following constructs: pGC1(D1)::GUS, pGC1(D2)::GUS, pGC1(D3)::GUS and pGC1(D4)::GUS. These GUS reporter constructs were transformed into Columbia wild type plants side-by-side with the original pGC1(FL)::GUS construct. T1 seedlings (n=50-100) from each transformation event were pooled and stained. The truncated pGC1(D1) drove similar or stronger GUS expression in seedlings than the original full-length promoter (FIG. 4A), suggesting that elements in the region from −1693 bp to −1140 bp might repress promoter activity in guard cells. Promoters pGC1(D2) and pGC1(D3) led to weaker reporter gene expression in guard cells than pGC1(FL), suggesting elements in the region from −1140 bp to −443 bp might enhance the promoter activity in guard cells. The shortest promoter, pGC1(D4), drove reporter gene expression in tissues other than guard cells, such as roots and seed coats, suggesting the region from −861 by to −224 by was required for guard cell specific activity. This region contains 8 (T/A) AAAG elements that have been shown to be required for guard cell specific activity of the KST1 promoter in potato [24]. The truncated promoter, pGC1(D1), showed strong guard cell expression, suggesting that it contains elements for both guard cell specificity and promoter strength. Accordingly, the invention provides transcriptional activators (such as promoters) that are guard cell specific that comprise or consist essentially of the region from −861 bp to −224 bp; and provides transcriptional activators (such as promoters) that are guard cell specific that comprise or consist essentially of the region from −1140 bp to −443 bp.

In summary, FIG. 18 illustrates serial deletions of the pGC1 promoter to define regions for guard cell expression, where FIG. 18A illustrates photographs that are representative T1 plants from different promoter::GUS transgenic lines. The pGC1(D1) (−1140/+23) promoter mediated stronger GUS expression in guard cells than the original full-length promoter (FL) (−1693/+23). GUS expression of pGC1(D2):: GUS and pGC1(D3)::GUS was weaker than that of the pGC1 (FL)::GUS and pGC1 (D1)::GUS. The shortest promoter pGC1(D4) (−224/+23) drives reporter expression in tissues and cells besides guard cells.

FIG. 18B graphically illustrates serial (structural, or sequence) deletion of the pGC1 promoter to define regions for guard cell expression. The black arrowheads stand for TAAAG elements while the smaller gray arrowheads stand for AAAAG elements. Arrowheads on the top of the promoter line are on the sense strand while arrowheads below the promoter line are on the antisense strand. The central TAAAG on the sense strand was also marked by a star and was chosen for block mutagenesis. The region from −1693 to −1140 contains repressor elements for guard cell expression and the region from −1140 to −224 contains elements for guard cell specificity and also enhancer elements for guard cells expression.

Calcium Imaging in Guard Cells of Intact Plants

Many physiological stimuli in plant cells induce changes in the intracellular calcium concentration. Calcium acts as a secondary messenger in many signal transduction cascades

[33]. Cytosolic calcium concentrations can be monitored either by chemical reporters such as the ratiometric $Ca^{2+}$-sensitive fluorescent dye fura-2 [34, 35], the genetically encoded calcium sensitive luminescent protein aequorin [14] or the fluorescent ratiometric calcium reporter yellow cameleon [12, 15, 36]. Stomatal closing signals, such as ABA and $CO_2$, have been shown to induce calcium elevations in guard cells [16, 18, 19, 37-42]. Spontaneous calcium transients in leaf epidermal samples have also been observed without any ABA treatment [15, 43, 44]. It is not clear whether spontaneous calcium transients occur in guard cells in intact plants as fura-2 injected *Vicia faba* guard cells did not show such transients [45].

A new generation calcium indicator, yellow cameleon, YC3.60, shows an enhanced calcium-dependent change in the ratio of YFP/CFP by nearly 600% compared with yellow cameleon 2.1 [31]. By combining the GC1 promoter (SEQ ID NO:10) with YC3.60, pGC1::YC3.60, as described before, we observed strong guard cell expression of the YC3.60 in intact leaves, hypocotyls, and sepals, as illustrated in FIG. 19.

In brief, FIG. 19 illustrates imposed intracellular calcium transients in pGC1::YC3.60 expressing guard cells and spontaneous calcium transients occur in guard cells of intact pGC1::YC3.60 transgenic plants:

FIG. 19A illustrates fluorescence image of leaf epidermis of pGC1::YC3.60 transgenic plant. Note the surrounding epidermal cells were not fluorescent.

FIG. 19B illustrates that the six guard cells in panel A all produced intracellular calcium transients in response to imposed calcium oscillations. The arrows mark the switch point from the depolarizing buffer to the $Ca^{2+}$-containing hyperpolarizing buffer (see Methods section).

FIG. 19C illustrates a pseudo-colored ratiometric image of a leaf from an intact Col plants transformed with pGC1::YC3.60. The orange-yellow color indicates higher $[Ca^{2+}]$ and the blue color indicates lower $[Ca^{2+}]$. Spontaneous calcium transients occurred in leaves of intact *Arabidopsis* plants.

FIG. 19D illustrates a time course (25 minutes) of the emission ratios of the two guard cells marked by an arrow in C shows that spontaneous calcium transients occur in intact *Arabidopsis* plants. The ratio was calculated for individual cells by dividing the YFP emission intensity by the CFP emission intensity.

We first measured calcium transients in intact leaf epidermis from plants transformed with pGC1::YC3.60 by imposing calcium oscillations as described previously [11, 46]. Robust calcium transients with ratiometric changes of up to a factor of 4 relative to the baseline ratio could be observed in guard cells, see FIG. 19B. Ratiometric changes of approximately 0.5 were observed using 35S::YC2.1 in response to imposed calcium transients [15, 43, 44, 46]. This further confirmed the robust ratiometric signal to noise efficiency of YC3.60.

Next, we performed calcium imaging in intact *Arabidopsis* seedlings by mounting leaves to a microscope cover glass. Two different methods were tested: the first one was to submerge only the root with water and leave the shoot in air, and the second one was to submerge the entire plant in water. Spontaneous calcium transients were detected under both conditions, see Table 1, below.

A representative calcium transients/time course is shown in FIG. 19D. Interestingly, the spontaneous calcium transients of two guard cells from the same stomate were often not synchronized, see FIG. 19C, D. These experiments clearly demonstrate that spontaneous calcium transients occurred in guard cells of intact plants and were not an artifact of imaging excised epidermis and illustrate the potential of the pGC1 (SEQ ID NO:10) promoter of this invention as a method for driving transgene and reporter expression in guard cells.

The Use of pGC1 to Manipulate Specific Gene Expression in Guard Cells

Manipulation of specific gene expression in guard cells, either by highly expressing the wild-type gene or a dominant mutant form, or reducing its expression in guard cells, would be very powerful to probe a specific gene function in guard cells. To further explore the application of the GC1 (SEQ ID NO:10) promoter, we took the antisense approach to analyze reduction of gene expression in guard cells. For this purpose, a 35S::GFP transgenic line with stable GFP expression in both guard cells and epidermal cells, see FIG. 20A, B, was transformed with a pGC1(D1)::anti-GFP construct (anti-GFP fused to the truncated GC1 promoter pGC1(D1)). 34 out of 40 T1 plants of 35S::GFP plants transformed with pGC1(D1)::anti-GFP showed greatly reduced GFP expression in guard cells while the GFP expression level in epidermal cells was unchanged, as illustrated in FIG. 20C, D.

In summary, FIG. 20 illustrates micrographs of pGC1(D1)::anti-GFP caused reduction of GFP expression in guard cells of 35S::GFP plants:

FIG. 20A illustrates leaf epidermis of a 35S::GFP transgenic plant (bright field with GFP filter). The arrows mark stomata.

FIG. 20B illustrates the fluorescence imaging of same leaf epidermis shown in A. Stomata are marked by lighter (yellow) arrows. Note that both the guard cells and surrounding epidermal cells are fluorescent.

FIG. 20C illustrates leaf epidermis of a T1 transgenic plant expressing pGC1(D1)::anti-GFP in the 35S::GFP background. All stomata are marked by lighter (yellow) arrows.

FIG. 20D illustrates the fluorescence imaging of the same leaf epidermis shown in 20C. Note that 7 (marked by relatively darker (blue) arrows) out of 8 stomata showed reduced GFP expression compared with the surrounding epidermal cells. One pair of guard cells (marked by the lighter (yellow) arrow) still exhibited moderate GFP expression. This stomate was relatively immature compared with the other 7 stomata.

These observations demonstrate a remarkable antisense repression efficiency using the sequence of this invention pGC1 (D1) (SEQ ID NO:10). Interestingly, less suppression of GFP expression was observed in immature guard cells (see lighter (yellow) arrow in FIG. 20D, versus the relatively darker (blue) arrows). This is consistent with the observation that pGC1 drove less reporter gene expression in immature guard cells, see e.g., FIG. 17G, discussed above. This experiment demonstrates that an antisense approach using sequences of this invention can be used to reduce expression of selected genes in guard cells without affecting its expression in other cell types.

Discussion

This invention for the first time identifies the strong *Arabidopsis* guard cell promoter, pGC1 (SEQ ID NO:10). Promoter::reporter fusion analyses showed pGC1 (SEQ ID NO:10) has strong guard cell specific reporter gene expression in e.g. wild-type *Arabidopsis* plants and the guard cell development mutant, too many mouths [32] and also tobacco plants. Serial deletions of the GC1 (SEQ ID NO:10) promoter defined regions for guard cell expression. Calcium imaging in guard cells in intact plants was made possible via the combination of the GC1 (SEQ ID NO:10) promoter and a new generation of calcium reporter, YC3.60 [31]. The GC1 (SEQ ID NO:10) promoter of the invention was also powerful for knocking down specific gene expression in guard cells using an antisense approach.

Comparison Between the GC1 Promoter and Other Known Guard Cell Promoters

As the central regulator of water transpiration and $CO_2$ uptake, guard cells have been developed as an integrative model system to investigate interplay among ion channel/transporter activities, light, plant hormones, secondary messengers, the cytoskeleton and membrane trafficking in regulating the physiological output: the stomatal aperture [2, 4, 5, 47, 48]. Several guard cell promoters have been reported. The KAT1 (At5g46240) promoter delivered specific reporter expression in guard cells even though it sometimes induced reporter expression in other cells and tissues such as roots and inflorescences [25]. AtMYB60 (At1g08810) also showed specific expression in guard cells based on promoter::GUS and promoter::GFP study [49]. AtMYB61(At1 g09540) has also been shown to be mainly expressed in guard cells [50].

Based on our guard cell-specific microarray data, we estimated the average transcription levels in FIG. 15, discussed above. The AtMYB61 gene expression signal was the lowest among these genes. In the case of KAT1, its expression in guard cells was much higher than that in mesophyll cells. But its raw signal was approximately 5 to 10 fold lower than that of GC1. AtMYB60 also exhibited highly guard cell specific expression compared with its expression in mesophyll cells. However, the raw signal of AtMYB60 was only approximately one third of that of the promoter of this invention GC1 (SEQ ID NO:10). Furthermore, AtMYB60 is also highly expressed in seeds based on GENEVESTIGATOR™ microarray analyses [27, 29, 51-54]. Similarly, RAB18 (At5g66400) is also highly expressed in seeds besides its strong expression in guard cells. pGC1 drove very strong and specific reporter gene expression in guard cells (expression is very low in non-leaf tissues/organs), although reporter gene expression was observed in epidermal cells in some plants transformed with the pGC1::YC3.60. In summary, the GC1 promoter is a very strong guard cell promoter among those analyzed.

Spontaneous Calcium Transients in Guard Cells

Studies with intact *Arabidopsis* plants using the genetically encoded calcium reporter YC3.60 driven by the GC1 promoter showed that spontaneous calcium transients occurred in guard cells in intact *Arabidopsis* plants. This is consistent with previous observations of spontaneous calcium transients in *Arabidopsis* guard cells [15, 43, 44]. However, the mechanisms causing spontaneous calcium transients are not yet characterized in depth. Several lines of evidence suggest a connection between hyperpolarization of the guard cell plasma membrane and spontaneous calcium transients in guard cells.

In experiments where membrane potential and $[Ca^{2+}]_{cyt}$ were measured simultaneously, hyperpolarization caused ABA-induced $[Ca^{2+}]_{cyt}$ increases. Maintaining guard cells in a more hyperpolarized state produced spontaneous $[Ca^{2+}]_{cyt}$ oscillations in *Vicia faba* guard cells [38], in a sub-population of *Commelina* guard cells [39] and in *Arabidopsis* guard cells [43]. Calcium imaging analyses in intact *Arabidopsis* plants using pGC1::YC3.60 show that spontaneous calcium transients also occur in intact plants.

These spontaneous $Ca^{2+}$ transients may also be the result of integrated signaling by multiple stimuli converging in guard cells, such as light conditions, $CO_2$ and water balance. In *Vicia faba* no spontaneous calcium transients were observed in guard cells in intact plants [45]. In this case fura-2 (ca. 100 μM) was injected into guard cells. High concentrations of fura-2 may inhibit spontaneous calcium elevations, as loading the close fura-2 analogue, BAPTA, into *Arabidopsis* guard cells effectively inhibits these calcium transients [44].

By contrast, the estimated yellow cameleon concentration in guard cells of pGC1 (SEQ ID NO:10)::YC3.60 transgenic plants was approximately 1 μM (see Methods, discussed herein). The lower concentration of yellow cameleon should interfere less with guard cell calcium homeostasis and could monitor more faithfully calcium concentration dynamics. Note that low concentrations of injected fura-2 also allowed resolution of repetitive calcium transients in guard cells [38, 39]. Note that BAPTA-derived fluorescent dyes such as fura-2 and indo-1 have certain complementary advantages to cameleon, as they can be loaded into cells that are not easily transformed [55] and these dyes can report rapid millisecond scale $Ca^{2+}$ transients that occur in neurons [56], but have presently not yet been reported in plants using fura-2 or indo-1.

Circadian calcium oscillations at the whole plant leaf level with a daily rhythm have been demonstrated by several groups using aequorin as the calcium reporter [57-59]. Most likely this circadian calcium oscillation results from synchronous changes in baseline cytosolic calcium in a cell population [60]. As the circadian calcium oscillation is related to the baseline of intracellular calcium, the rapid spontaneous calcium transients in individual guard cells likely would be filtered from circadian calcium measurements [60]. Repetitive calcium transients may reflect functions that include continuous calcium homeostasis between extracellular calcium, cytoplasmic calcium, and intracellular calcium stores. Spontaneous calcium transients in guard cells also correlate with the recent proposed calcium sensor priming hypothesis for calcium specificity in signaling, in which the stomatal closing signals ABA and $CO_2$ are proposed to prime (de-inactivate) calcium sensitive steps that mediate stomatal closing [44, 61].

(T/A)AAAG Cis Elements and Guard Cell Specific Expression (T/A)AAAG, a binding motif for Dof zinc finger transcription factors, has been suggested to play a critical role for guard-cell specific expression of KST1 promoter activity in potato based on block mutagenesis [24]. However, the putative promoter regions (1800 by before ATG start codon) for AtACT7 (At5g09810), KAT1 (At5g46240), RAB18 (At5g66400), AtMYB60 (At1g08810), AtMYB61 (At1g09540) and GC1 (At1g22690) all contain a similar number of D of factor binding motifs, the (T/A)AAAG elements, even though some of them do not show guard cell expression preference. AtMYB61, which showed low expression in guard cells (FIG. 15), contains 29 (T/A)AAAG elements in its putative promoter region, while the AtACT7 promoter contains 23 (T/A)AAAG elements. Promoter truncation suggests that the region from −861 by to −224 by in the GC1 (SEQ ID NO:10) promoter contains elements for guard cell specific promoter activity; see FIG. 18, discussed above. This region contains 8 (T/A)AAAG elements. However, block mutagenesis of the central TAAAG motif on the sense strand (marked by a star in FIG. 18B) in this region did not affect reporter expression in guard cells. Thus the (T/A)AAAG element alone may not explain why GC1 and other guard cell-specific genes exhibited guard cell-specific expression.

Conclusions

Microarray (ATH1) analyses of guard cell expressed genes was used to isolate and characterize a novel strong guard cell promoter of this invention, pGC1 (SEQ ID NO:10). We analyzed the potential of pGC1 (SEQ ID NO:10) as a tool for manipulating gene expression in guard cells. The GC1 (SEQ ID NO:10) promoter was used to test several experimental manipulations. The GC1 (SEQ ID NO:10) promoter was used to express the calcium reporter YC3.60 in guard cells. This enabled us to perform calcium imaging experiments in guard cells of intact *Arabidopsis* plants.

For T-DNA insertional mutants hundreds of transformants are often needed to be generated to obtain at best a few lines expressing a reporter gene in guard cells when using the 35S promoter. In contrast, use of the GC1 (SEQ ID NO:10) promoter of this invention provides a method to dramatically increase the success rate of reporter gene expression. Furthermore, guard cell-specific antisense GFP expression using the GC1 promoter efficiently silenced GFP expression in guard cells of 35S::GFP transgenic plants.

These data and the high transformation efficiency together demonstrate that promoters of this invention, including the GC1 (SEQ ID NO:10) promoter of this invention, provide a powerful tool for manipulating the expression of guard cell signaling components and for expressing reporters of diverse secondary messengers. Thus, promoters of this invention, including the GC1 (SEQ ID NO:10) promoter, provide compositions and methods to selectively enhance expression in guard cells, to monitor signaling events in guard cells in response to different treatments, and to study whole plant responses in guard cell specific transgenic mutants.

Material and Methods

Plant Material

*Arabidopsis thaliana* (Columbia ecotype) plants were used for transformation experiments unless otherwise specified. The 35S::GFP transgenic line was generated for a previous study [62]. The guard cell development mutant, too many mouths, was a kind gift from Dr. Fred Sack at the University of British Columbia, Vancouver.

GeneChip Microarray Experiments

Plant growth, ABA treatment, guard cell protoplast isolation, and RNA extraction were performed as previously described [26]. Affymetrix *Arabidopsis* ATH1 genome arrays (Affymetrix, Santa Clara, Calif.) were used, representing approximately 24,000 genes. Transcripts were amplified, labeled, and hybridized at the University of California, San Diego Gene Chip Core facility. For each condition (with or without ABA treatment, guard cell or mesophyll cell), two independent hybridizations were performed. Transcriptional inhibitors (33 mg/L actinomycin D and 100 mg/L cordycepin) were added during protoplast isolation for RNA samples for four chip hybridizations as described [26]. ATH1 microarray data were deposited at MIAMEXPRESS™ [63] with an accession number E-MEXP-1443.

Construction of Recombinant Plasmids

To amplify the GC1 (At1g22690) promoter from the Col genomic DNA by PCR, primers YZ27 (5'-CATG CCATGGatttcttgagtagtgattttgaag-3', (SEQ ID NO:37), right before the ATG start codon with NcoI site) and YZ28 (5'-ACGCGTCGACgagtaaagattcagtaacccg-3', (SEQ ID NO:38), 1693 bp upstream of the transcriptional start (FIG. 16) with SalI site) were utilized. The PCR product was cloned into pGEM-Teasy vector (Invitrogen, Carlsbad, Calif.) to create pGEM-T-pGC1.

To clone the GC1 promoter into the pBI101 vector, pGEM-T-pGC1 was first cut by NcoI. The sticky end was then filled-in by T4 DNA polymerase (New England BioLabs) to create a blunt end. The pGC1 fragment was then released by SalI digestion. Meanwhile, the destination vector, pBI101, was cut sequentially by SmaI and SalI. The pGC1 fragment was then inserted upstream of the GUS reporter gene in the pBI101 vector to create pBI101-pGC1::GUS construct (simplified as pGC1::GUS).

To create the 5'-deletion series of the pGC1 promoter, primer YZ27 was used with primers YZ159 (5'-GC GTCGACatggttgcaacagagaggatga-3', (SEQ ID NO:39), 1141 bp upstream of the transcriptional start, D1), YZ160 (5'-GCGTCGACctaatgaagggtgccgcttattg-3', (SEQ ID NO:40), 861 bp upstream of the transcriptional start, D2), YZ161 (5'-GCGTCGACcaatattgcgtctgcgtttcct-3', (SEQ ID NO:41), 466 bp upstream of the transcriptional start, D3) and YZ162 (5'-GCGTCGACgaaccaatcaaaactgtttgcata-3', (SEQ ID NO:42), 224 bp upstream of the transcriptional start, D4) respectively for genomic PCR to amplify pGC1(D1), pGC1 (D2), pGC1(D3) and pGC1(D4) respectively (FIG. 4). The PCR fragments were then cloned into pGEM-T-easy vector and then subcloned into pBI101 vector to create pBI101-pGC1(D1)::GUS, pBI101-pGC1(D2)::GUS, pBI101-pGC1 (D3)::GUS, and pBI101-pGC1(D4)::GUS.

To create pBI101-pGC1::YC3.60 construct, YC3.60 was first released from pcDNA3-YC3.60 [31] by EcoRI/BamHI double digestion. Then the BamHI-5'-YC3.60-3'-EcoRI fragment was cloned into pSK vector (prepared by EcoRI and BamHI digestion) to create pSK-YC3.60 construct. The pSK-YC3.60 was then digested with NotI and NcoI to receive NotI-5'-pGC1-3'-NcoI fragment from pGEM-T-pGC1. This ligation resulted in the pSK-pGC1::YC3.60. The pGC1:: YC3.60 fragment was released by SalI/SacI double digestion, meanwhile the pBI101 vector was digested with SalI/SacI to remove the GUS reporter gene. The pBI101/(SalI/SacI) was ligated with SalI-5'-pGC1::YC3.60-3'-SacI to create pBI101-pGC1::YC3.60 construct.

To create pGreenII 0179-pGC1(D1)::anti-GFP binary vector with hygromycin selective marker in plant, the 35S terminator was amplified with YZ439 (5'-AAGAGATCTA TCTAGAGTCCGCAA-3', (SEQ ID NO:43), with XbaI) and YZ440 (5'-GCACGCTCGAGCTCgtcactggattttggttttagg-3', (SEQ ID NO:44), with SacI site) from vector pAVA319 [64]. The PCR product was then subsequently digested with XbaI and SacI. The 5'-XbaI-35S terminator-SacI-3' was ligated into pGreenII 0179-XabI . . . . SacI to create pGreenII 0179-terminator. The pGC1 (D1) was released from pGEM-T-pGC1 (D1) by NotI digestion, then filled-in, then cut by SalI to create 5'-SalI-pGC1(D1)-NotI(filled-in blunt end). Meanwhile, the pGreenII 0179-terminator was doubled digested with SalI and EcoRV. These two fragments were ligated to generate pGreenII 0179-pGCP(D1)-terminator vector. The antisense GFP was amplified with primers YZ449 (5'-ACATGCCATGGttacttgtacagctcgtccatgcc-3', (SEQ ID NO:45), reverse end of GFP with NcoI) and YZ513 (5'-ctag TCTAGAatggtgagcaagggcgagg-3', (SEQ ID NO:46), start of GFP with XbaI). The PCR fragment was double digested with NcoI and XbaI. The pGreenII 0179-pGC1(D1)-Terminator was also double digested with NcoI and XbaI. The pGreenII 0179-pGC1(D1)-Terminator fragment was ligated with 5'-NcoI-anti-GFP-XbaI-3' to produce pGreenII 0179-pGC1 (D1)::anti-GFP binary construct.

The central TAAAG motif (-579->-575) on the sense stand was changed to CGGGA by block mutagenesis using the QUICKCHANGE™ site-directed mutagenesis kit from Stratagene (La Jolla, Calif.).

*Arabidopsis* Transformation and Selection

The binary constructs, pBI101-pGC1::YC3.60, pBI101-pGC1::GUS, pBI101-pGC1(D1)::GUS, pBI101-pGC1 (D2)::GUS, pBI101-pGC1(D3)::GUS and pBI101-pGC1 (D4)::GUS were transformed into the *Agrobacterium tumefaciens* strain GV3101 by electroporation. The transformants were selected on LB plates with both kanamycin (selective marker for the construct) and gentamycin (selective marker for the *Agrobacterium*). *Arabidopsis* plants were then transformed by *Agrobacterium* GV3101 hosting respective constructs following the dipping method as described by Clough and Bent [65]. The T0 seeds were selected on ½ MS plates with 50 μg/ml kanamycin.

In the case of pGreenII 0179-pGC1(D1)::anti-GFP, the GV3101 with the helper plasmid pSOUP was used as the host strain, and the selection for *Agrobacterium* transformants was carried on LB plates with Kanamycin, gentamycin, and tetracycline. This was used to transform 35S::GFP transgenic plants (kanamycin resistant). The T0 seeds were selected on ½ MS plates with 25 μg/ml hygromycin (Roche).

GUS Staining

Seedlings were stained following a previously described protocol [62].

Epi-Fluorescence Image Acquisition

Transgenic *Arabidopsis* seedlings or sepals of pBI101-pGC1::YC3.60 were simply placed between a microscope slide and a cover glass. A NIKON™ digital camera was attached to the microscope. Exposure time for the bright image is 5 seconds and 15-25 seconds for fluorescence image (excitation wavelength is 440 nm). For 35S::GFP plants and 35S::GFP plants transformed with pGREENII™ 0179-pGC1(D1)::anti-GFP, intact leaf epidermis were used for epi-fluorescence image acquisition.

Tobacco Plant Transformation

In vitro sterile shoot cultures of *Nicotiana tabacum* cv. SR1 were maintained on ½MS agar medium containing 15 g/l sucrose. The pH was adjusted to 5.5 before autoclaving. The tobacco culture was grown at 25° C., with a light/dark cycle of 16/8 h (light intensity was approximately 70 μmol $M^{-2}$ $s^{-1}$). Stable transformation of *Nicotiana tabacum* SR1 with pBI101-pGC1-YC3.60 was performed as described previously [66]. Transgenic regenerated tobacco shoots were selected by kanamycin (100 μg/ml) resistance and were then transferred on ½MS agar medium containing 15 g/l sucrose supplemented with kanamycin (100 μg/ml) and cefotaxime (200 μg/ml). T1 regenerated plants, which were able to set up root organogenesis in presence of kanamycin, were then analyzed for cameleon expression.

Confocal Analysis of Transgenic Tobacco

The tobacco leaves of plant transformed with pBI101-pGC1-YC3.60 were observed with a Leica TCS SP2™ laser confocal microscope (Leica Microsystems). For cameleon detection, excitation was at 514 nm and emission between 525 and 540 nm. The images acquired from the confocal microscope were processed using IMAGE J™ [67].

Calcium Imaging and Imposed $Ca^{2+}$ Transients

All calcium imaging in this work was performed with a TE300™ inverted microscope using a TE-FM™ epi-fluorescence attachment (Nikon Inc. Melville, N.Y.). Excitation from a 75 W xenon lamp (Osram, Germany) was always attenuated 97% by using both 4× and 8× neutral density filters (3% transmission) to reduce bleaching of reporters during time-resolved imaging. Wavelength specificity was obtained with a cameleon filter set (440/20 excitation, 485/40 emission1, 535/30 emission2, 455DCLP™ dichroic; filter set 71007a™ Chroma Technology, Rockingham, Vt.). Filter wheel, shutter and COOLSNAP™ CCD camera from Photomerics (Roper Scientific, Germany) were controlled with METAFLUOR™ software (MDS, Inc., Toronto, Canada).

Intact leaf epidermes of pGC1::YC3.60 transgenic plants were prepared for microscopy as described in Mori et al. (2006)[11]. On the microscope, intact epidermis was perfused with depolarization buffer (10 mM MES-Tris buffer, pH 6.1 containing 25 mM dipotassium imminodiacetate, and 100 μM BAPTA) for 10 minutes to obtain a background. Subsequently hyperpolarizing buffer containing $Ca^{2+}$ (10 mM MES-Tris buffer, pH 6.1, 1 mM dipotassium imminodi- acetate, and 1 mM $CaCl_2$) was applied for 2 minutes intervals, followed by 5 minutes of depolarizing buffer.

Calcium Imaging in Guard Cells of Intact Plants

Both intact leaves and intact plants were used in this study. Medical adhesive (Hollister Inc., Libertyville, Ill.) was used to attach leaves to microscope cover glasses. A paintbrush was used to gently press the leaf to the coverslip. In the case of intact plants two different methods were followed. The first method was to submerge only the root with water while the shoot was left in air. The second method was to completely submerge entire seedlings in water. Sometimes submerging only the root but not the shoot caused the leaf attached to the cover slip to show wilting in less than 10 minutes with subsequent closure of the stomata. Most of the intact plant imaging experiments were therefore carried out by submerging both the shoot (leaves) and the root in water. The submersion of the entire plant prevented the leaf from drying out and no stomatal closure was observed for more than 50 minutes. The imaging protocol was the same as in Mori et al., 2006 [11].

Estimation of Yellow Cameleon Concentration in Guard Cells

Recombinant yellow cameleon protein was isolated after expression in *E coli*. Recombinant cameleon protein was then added at defined concentrations to a glass cover slip for fluorescence imaging. Then two additional cover slips were used to create a slanted gradient of cameleon solution thicknesses. This enabled analysis of various solution thicknesses in the range of stomatal guard cell thicknesses. Diluted yellow cameleon protein solutions at different concentrations were analyzed and the florescence intensity was measured for each concentration at various thicknesses. Calibration curves were generated for protein concentrations and florescent intensities at different thicknesses. This was utilized to estimate the yellow cameleon protein concentration in guard cells of pGC1::YC3.6 transgenic plants.

REFERENCES

1. MacRobbie EAC: Signal transduction and ion channels in guard cells. *Phil Trans Roy Soc London* 1998, 1374:1475-1488.
2. Hetherington AM, Woodward FI: The role of stomata in sensing and driving environmental change. *Nature* 2003, 21:901-908.
3. Assmann SM, Shimazaki K: The multisensory guard cell. Stomatal responses to blue light and abscisic acid. *Plant Physiol* 1999, 119:809-816.
4. Schroeder JI, Allen GJ, Hugouvieux V, Kwak JM, Waner D: Guard cell signal transduction. *Ann Rev Pl Physiol & Pl Mol Biol* 2001, 52:627-658.
5. Shimazaki K, Doi M, Assmann SM, Kinoshita T: Light regulation of stomatal movement. *Annu Rev Plant Biol* 2007, 58:219-247.
6. Pei Z-M, Murata Y, Benning G, Thomine S, Klusener B, Allen GJ, Grill E, Schroeder JI: Calcium channels activated by hydrogen peroxide mediate abscisic acid signalling in guard cells. *Nature* 2000, 406:731-734.
7. Lemtiri-Chlieh F, MacRobbie EA, Webb AA, Manison NF, Brownlee C, Skepper JN, Chen J, Prestwich GD, Brearley CA: Inositol hexakisphosphate mobilizes an endomembrane store of calcium in guard cells. *Proc Natl Acad Sci USA* 2003, 100:10091-10095.
8. Coursol S, Fan LM, Le Stunff H, Spiegel S, Gilroy S, Assmann SM: Sphingolipid signalling in *Arabidopsis* guard cells involves heterotrimeric G proteins. *Nature* 2003, 423:651-654.

9. Webb AA, Larman MG, Montgomery LT, Taylor JE, Hetherington AM: The role of calcium in ABA-induced gene expression and stomatal movements. *Plant J* 2001, 26:351-362.
10. Ng C, Carr K, McAinsh M, Powell B, Hetherington A: Drought-induced guard cell signal transduction involves sphingosine-1-phosphate. *Nature* 2001, 410:596-599.
11. Mori IC, Murata Y, Yang Y, Munemasa S, Wang YF, Andreoli S, Tiriac H, Alonso JM, Harper JF, Ecker JR et al: CDPKs CPK6 and CPK3 function in ABA regulation of guard cell S-type anion- and $Ca^{2+}$- permeable channels and stomatal closure. *PLoS Biol* 2006, 4:1749-1762.
12. Miyawaki A, Griesbeck O, Heim R, Tsien RY: Dynamic and quantitative $Ca^{2+}$ measurements using improved cameleons. *Proc Natl Acad Sci USA* 1999, 96:2135-2140.
13. Belousov VV, Fradkov AF, Lukyanov KA, Staroverov DB, Shakhbazov KS, Terskikh AV, Lukyanov S: Genetically encoded fluorescent indicator for intracellular hydrogen peroxide. *Nat Methods* 2006, 3:281-286.
14. Knight MR, Campbell AK, Smith SM, Trewavas AJ: Transgenic plant aequorin reports the effects of touch and cold-shock and elicitors on cytoplasmic calcium. *Nature* 1991, 8:524-526.
15. Allen GJ, Kwak JM, Chu SP, Llopis J, Tsien RY, Harper FJ, Schroeder JI: Cameleon calcium indicator reports cytoplasmic calcium dynamics in *Arabidopsis* guard cells. *Plant Journal* 1999b, 19:735-738.
16. Gilroy S, Fricker MD, Read ND, Trewavas AJ: Role of calcium in signal transduction of *Commelina* guard cells. *Plant Cell* 1991, 3:333-344.
17. Allen GJ, Kuchitsu K, Chu SP, Murata Y, Schroeder JI: *Arabidopsis abi*1-1-1 and *abi*2-1 *phosphatase* mutations reduce abscisic acid-induced cytoplasmic calcium rises in guard cells. *Plant Cell* 1999a, 11:1780-1798.
18. McAinsh MR, Brownlee C, Hetherington AM: Abscisic acid-induced elevation of guard cell cytosolic $Ca^{2+}$ precedes stomatal closure. *Nature* 1990, 343:186-188.
19. Schroeder JI, Hagiwara S: Repetitive increases in cytosolic $Ca^{2+}$ of guard cells by abscisic acid activation of non-selective $Ca^{2+}$-permeable channels. *Proc Natl Acad Sci USA* 1990, 87:9305-9309.
20. Benfey PN, Ren L, Chua NH: The CaMV 35S enhancer contains at least two domains which can confer different developmental and tissue-specific expression patterns. *EMBO J* 1989, 8:2195-2202.
21. Kwak JM, Murata Y, Baizabal-Aguirre VM, Merrill J, Wang J, Kemper A, Hawke D, Tallman G, Schroeder JI: Dominant negative guard cell $K^+$ channel mutants reduce inward rectifying $K^+$ currents and light-induced stomatal opening in *Arabidopsis*. *Plant Physiol* 2001, 127:1-13.
22. Ichida AM, Pei Z-M, Baizabal-Aguirre V, Turner KJ, Schroeder JI: Expression of a $Cs^+$ resistant guard cell $K^+$ channel confers $Cs^+$ -resistant light-induced stomatal opening in transgenic *Arabidopsis*. *Plant Cell* 1997, 9:1843-1857.
23. Li J, Want X, Watson MB, Assmann SM: Regulation of abscisic acid-induced stomatal closure and anion channels by guard cell AAPK kinase. *Science* 2000, 287:300-303.
24. Plesch G, Ehrhardt T, Mueller-Roeber B: Involvement of TAAAG elements suggests a role for Dof transcription factors in guard cell-specific gene expression. *Plant J* 2001, 28:455-464.
25. Nakamura RL, McKendree WL, Hirsch RE, Sedbrook JC, Gaber RF, Sussman MR: Expression of an Arabidopsis potassium channel gene in guard cells. *Plant Physiol* 1995, 109:371-374.
26. Leonhardt N, Kwak JM, Robert N, Waner D, Leonhardt N, Schroeder JI: Microarray expression analyses of *Arabidopsis* guard cells and isolation of a recessive ABA hypersensitive PP2C mutant. *Plant Cell* 2004, 16:596-615.
27. *Arabidopsis thaliana* microarray database and analysis toolbox
28. Wigoda N, Ben-Nissan G, Granot D, Schwartz A, Weiss D: The gibberellin- induced, cysteine-rich protein GIP2 from *Petunia hybrida* exhibits in planta antioxidant activity. *Plant J* 2006, 48:796-805.
29. Zimmermann P, Hirsch-Hoffmann M, Hennig L, Gruissem W: GENEVESTIGATOR. *Arabidopsis* microarray database and analysis toolbox. *Plant Physiol* 2004, 136: 2621-2632.
30. Kilian J, Whitehead D, Horak J, Wanke D, Weinl S, Batistic O, D'Angelo C, Bornberg-Bauer E, Kudla J, Harter K: The AtGenExpress global stress expression data set: protocols, evaluation and model data analysis of UV-B light, drought and cold stress responses. *Plant J* 2007, 50:347-363.
31. Nagai T, Yamada S, Tominaga T, Ichikawa M, Miyawaki A: Expanded dynamic range of fluorescent indicators for Ca2+by circularly permuted yellow fluorescent proteins. *Proc Natl Acad Sci USA* 2004, 101:10554-10559.
32. Yang M, Sack FD: The too many mouths and four lips mutations affect stomatal production in *Arabidopsis*. *Plant Cell* 1995, 7:2227-2239.
33. Hetherington AM, Brownlee C: The generation of $Ca^{2+}$ signals in plants. *Annu Rev Plant Biol* 2004, 55:401-427.
34. Ehrhardt DW, Wais R, Long SR: Calcium spiking in plant root hairs responding to Rhizobium nodulation signals. *Cell* 1996, 85:673-681.
35. Pierson ES, Miller DD, Callaham DA, van Aken J, Hackett G, Hepler PK: Tip-localized calcium entry fluctuates during pollen tube growth. *Dev Biol* 1996, 174:160-173.
36. Miyawaki A, Llopis J, Heim R, McCaffery JM, Adams JM, Ikura JA, Tsien M: Fluorescent indicators for $Ca^{2+}$ based on green fluorescent proteins and calmodulin. *Nature* 1997, 388:882-887.
37. Allen GJ, Chu SP, Schumacher K, Shimazaki CT, Vafeados D, Kemper A, Hawke SD, Tallman G, Tsien RY, Harper JF et al: Alteration of stimulus- specific guard cell calcium oscillations and stomatal closing in *Arabidopsis det3* mutant. *Science* 2000, 289:2338-2342.
38. Grabov A, Blatt MR: Membrane voltage initiates $Ca^{2+}$ waves and potentiates $Ca^{2+}$ increases with abscisic acid in stomatal guard cells. *Proc Natl Acad Sci USA* 1998, 95:4778-4783.
39. Staxen I, Pical C, Montgomery LT, Gray JE, Hetherington AM, McAinsh MR: Abscisic acid induces oscillations in guard-cell cytosolic free calcium that involve phosphoinositide-specific phospholipase C. *Proc Natl Acad Sci USA* 1999, 96:1779-1784.
40. Allan AC, Fricker MD, Ward JL, Beale MH, Trewavas AJ: Two transduction pathways mediate rapid effects of abscisic acid in *Commelina* guard cells. *Plant Cell* 1994, 6:1319-1328.
41. Irving HR, Gehring CA, Parish RW: Changes in cytosolic pH and calcium of guard cells precede stomatal movements. *Proc Natl Acad Sci USA* 1992, 89:1790-1794.
42. Marten H, Konrad KR, Dietrich P, Roelfsema MR, Hedrich R: $Ca^{2+}$ -dependent and -independent abscisic acid activation of plasma membrane anion channels in guard cells of *Nicotiana tabacum*. *Plant Physiol* 2007, 143:28-37.
43. Klüsener B, Young J, Murata Y, Allen G, Mori I, Hugouvieux V, Schroeder JI: Convergence of calcium signaling pathways of pathogenic elicitors and ABA in *Arabidopsis* guard cells. *Plant Physiol* 2002, 130:2152-2163.
44. Young JJ, Mehta S, Israelsson M, Godoski J, Grill E, Schroeder JI: $CO_2$ signaling in guard cells: calcium sensitivity response modulation, a $Ca^{2+}$-independent phase, and $CO_2$ insensitivity of the gca2mutant. *Proc Natl Acad Sci USA* 2006, 103:7506-7511.
45. Levchenko V, Konrad KR, Dietrich P, Roelfsema MR, Hedrich R: Cytosolic abscisic acid activates guard cell anion channels without preceding $Ca^{2+}$ signals. *Proc Natl Acad Sci USA* 2005, 102:4203-4208.
46. Allen GJ, Chu SP, Harrington CL, Schumacher K, Hoffmann T, Tang YY, Grill E, Schroeder JI: A defined range of guard cell calcium oscillation parameters encodes stomatal movements. *Nature* 2001, 411:1053-1057.
47. Pandey S, Zhang W, Assmann SM: Roles of ion channels and transporters in guard cell signal transduction. *FEBS Lett* 2007, 581:2325-2336.
48. Sutter JU, Sieben C, Hartel A, Eisenach C, Thiel G, Blatt MR: Abscisic acid triggers the endocytosis of *Arabidopsis* KAT1 $K^+$ channel and its recycling to the plasma membrane. *Curr Biol* 2007, 17:1396-1402.
49. Cominelli E, Galbiati M, Vavasseur A, Conti L, Sala T, Vuylsteke M, Leonhardt N, Dellaporta SL, Tonelli C: A guard-cell-specific MYB transcription factor regulates stomatal movements and plant drought tolerance. *Curr Biol* 2005, 15:1196-1200.
50. Liang YK, Dubos C, Dodd IC, Holroyd GH, Hetherington AM, Campbell MM: AtMYB61, an R2R3-MYB transcription factor controlling stomatal aperture in *Arabidopsis thaliana*. *Curr Biol* 2005, 15:1201-1206.
51. Fait A, Angelovici R, Less H, Ohad I, Urbanczyk-Wochniak E, Fernie AR, Galili G: *Arabidopsis* seed development and germination is associated with temporally distinct metabolic switches. *Plant Physiol* 2006, 142:839-854.
52. Nakabayashi K, Okamoto M, Koshiba T, Kamiya Y, Nambara E: Genome-wide profiling of stored mRNA in *Arabidopsis thaliana* seed germination: epigenetic and genetic regulation of transcription in seed. *Plant J* 2005, 41:697-709.
53. Schmid M, Davison TS, Henz SR, Pape UJ, Demar M, Vingron M, Scholkopf B, Weigel D, Lohmann JU: A gene expression map of *Arabidopsis thaliana* development. *Nat Genet* 2005, 37:501-506.
54. Yamauchi Y, Ogawa M, Kuwahara A, Hanada A, Kamiya Y, Yamaguchi S: Activation of gibberellin biosynthesis and response pathways by low temperature during imbibition of *Arabidopsis thaliana* seeds. *Plant Cell* 2004, 16:367-378.
55. Kuchitsu K, Ward JM, Allen GJ, Schelle I, Schroeder JI: Loading acetoxymethyl ester fluorescent dyes into the cytoplasm of *Arabidopsis* and *Commelina* guard cells. *New Phytologist* 2002, 153:527-533.
56. Grynkiewicz G, Poenie M, Tsien RY: A new generation of $Ca^{2+}$ indicators with greatly improved fluorescence properties. *J Biol Chem* 1985, 260:3440-3450.
57. Tang RH, Han S, Zheng H, Cook CW, Choi CS, Woerner TE, Jackson RB, Pei ZM: Coupling diurnal cytosolic $Ca^{2+}$ oscillations to the CAS-IP3 pathway in *Arabidopsis*. *Science* 2007, 315:1423-1426.
58. Johnson CH, Knight MR, Kondo T, Masson P, Sedbrook J, Haley A, Trewavas A: Circadian oscillations of cytosolic and chloroplastic free calcium in plants. *Science* 1995, 269:1863-1865.
59. Dodd AN, Jakobsen MK, Baker AJ, Telzerow A, Hou SW, Laplaze L, Barrot L, Poethig RS, Haseloff J, Webb AA: Time of day modulates low-temperature Ca signals in *Arabidopsis*. *Plant J* 2006, 48:962-973.
60. Imaizumi T, Schroeder JI, Kay SA: In SYNC: the ins and outs of circadian oscillations in calcium. *Sci STKE* 2007, 2007(390):pe32.
61. Israelsson M, Siegel RS, Young J, Hashimoto M, Iba K, Schroeder JI: Guard cell ABA and $CO_2$ signaling network updates and $Ca^{2+}$ sensor priming hypothesis. *Curr Opin Plant Biol* 2006, 9:654-663.
62. Hugouvieux V, Murata Y, Young JJ, Kwak M, Mackesy DZ, Schroeder JI: Localization, ion channel regulation and genetic interactions during abscisic acid signaling of the nuclear mRNA cap-binding protein, ABH1. *Plant Physiol* 2002, 130:1276-1287.
63. MIAMExpress, from the European Bioinformatics Institute (EBI), a non-profit academic organization that forms part of the European Molecular Biology Laboratory, Cambridge, Great Britain.
64. von Arnim AG, Deng XW, Stacey MG: Cloning vectors for the expression of green fluorescent protein fusion proteins in transgenic plants. *Gene* 1998, 221:35-43.
65. Clough SJ, Bent AF: Floral dip: a simplified method for Agrobacterium-mediated transformation of *Arabidopsis thaliana*. *Plant J* 1998, 16:735-743.
66. Horsch RB, Fry JE, Hoffmann NL, Eichholtz D, Rogers SG, Fraley RT: A simple and general method for transferring genes into plants. *Science* 1985, 227:1229-1231.
67. Image J, Centre de Recherche Public Henri Tudor, Luxembourg.

TABLE I

Summary of calcium imaging in guard cells of intact pGC1::YC3.60 transgenic *Arabidopsis* plants.

| Experiments | plants | GCs analyzed | GCs with Spontaneous Ca2+ transients | Percentage % |
|---|---|---|---|---|
| I | 5 | 24 | 18 | 75 |
| II | 11 | 52 | 36 | 62.23 |
| III | 11 | 55 | 36 | 65.45 |
| IV | 9 | 54 | 24 | 44.44 |
| Total | 36 | 185 | 114 | 61.78% |

Only roots were submerged in water in experiment I. Both leaves and roots were submerged in water in experiments II, III, and IV.

Example 4

Characterization of $CO_2$ Receptors that Control Plant $CO_2$ Uptake and Water use Efficiency The invention provides compositions and methods for down-regulating or decreasing carbon dioxide ($CO_2$) and/or water exchange in a guard cell of a plant, plant cell, plant leaf, plant organ or plant part comprising inter alia use of a polypeptide having a carbonic anhydrase (carbonate dehydratase) activity, or a β-carbonic anhydrase activity, or a nucleic acid encoding the carbonic anhydrase polypeptide; and, expressing, or overexpressing, a $CO_2$Sen ($CO_2$ sensor) protein-expressing nucleic acid and/or a $CO_2$Sen gene or transcript (message), and/or a carbonic anhydrase or a β-carbonic anhydrase, in the guard cell. The invention provides compositions and methods for up-regulating or increasing carbon dioxide ($CO_2$) and/or water exchange in a guard cell of a plant, plant cell, plant leaf, plant organ or plant part comprising inter alia use of a nucleic acid antisense to or otherwise inhibitory to a nucleic acid encoding a plant carbonic anhydrase (carbonate dehydratase), or a plant β-carbonic anhydrase; and expressing the antisense or inhibitory nucleic acid in the guard cell.

The invention provides compositions and methods for controlling guard cells in vivo, including their ability to form adjustable stomatal pores in the plant epidermis; thus, the invention provides compositions and methods for controlling $CO_2$ influx for photosynthesis and transpirational water loss from plants to the atmosphere.

The invention provides compositions and methods for controlling the diurnal rise in leaf $CO_2$ concentration during the night phase, as well as the continuing rise in atmospheric $[CO_2]$ causes closing of the stomatal gas exchange pores; and thus the invention can affects carbon fixation and water use efficiency of plants. The invention provides compositions and methods for controlling signal transduction mechanisms that control $CO_2$-induced stomatal movements, including $CO_2$ sensors that control this response.

Using guard cell and leaf mesophyll cell specific microarrays, we identified highly expressed β-carbonic anhydrase genes, e.g., as designated CA1 and CA4 herein, also called in this application SEQ ID NO:3 (encoded, e.g., by SEQ ID NO:1, or "CA4" or "CORP2"), or SEQ ID NO:9 (encoded, e.g., by SEQ ID NO:7, or "CA1", or "CORP1"); and also including SEQ ID NO:6 (encoded, e.g., by SEQ ID NO:4, or "CA6").

This invention demonstrates that double knock-out mutant plants (for the nucleic acids of the invention CA1 and CA4) show a dramatic reduction in $CO_2$ regulation of plant gas exchange and stomatal movements. ca1ca4 double mutant plants exhibit functional responses to other physiological stimuli including blue light, light-dark transitions and the phytohormone abscisic acid. Short-term addition of a carbonic anhydrase enzyme (CA) inhibitor to wild-type leaf epidermi mimics the $CO_2$ insensitivity of ca1 ca4, consistent with this invention's demonstrated role for carbonic anhydrases in $CO_2$ signaling.

Guard cell-targeted expression of either CA gene of this invention complements $CO_2$ perception and signaling in ca1ca4 mutant plants, demonstrating that this $CO_2$ response originates from guard cells. Analyses of photosynthesis of intact mutant leaves show that ca1ca4 mutation does not affect chlorophyll fluorescence or the $CO_2$ assimilation rate. Moreover, norflurazon-bleached wild-type leaves show intact $CO_2$-induced stomatal movements, together suggesting that the CA-mediated signaling pathway that controls gas exchange is not, in first order, linked to photosynthesis.

Epistasis analyses with the ht1 kinase mutant (e.g., see Hashimoto et al., 2006) further provide genetic evidence that CA1 and CA4 function upstream in the guard cell $CO_2$ signaling pathway.

Targeted over-expression of either CA1 or CA4 in guard cells greatly enhances the water use efficiency of *Arabidopsis* plants, consistent with a vital role for these CAs in $CO_2$ regulation of plant gas exchange. Together these findings demonstrate for the first time an essential function of these guard cell-expressed carbonic anhydrases, including polypeptides of this invention, in $CO_2$ regulation of $CO_2$ influx and water use efficiency of plants, and also demonstrate that CA1 and CA4 function within the $CO_2$ sensory machinery of $CO_2$ signaling.

The invention compositions and methods of this invention can be used to ameliorate the continuing rise in atmospheric $[CO_2]$ that is predicted to affect natural and agricultural ecosystems on a global level.

Results:

The invention provides compositions and methods for over- and under-expressing) β-carbonic anhydrase genes, e.g., genes of the invention as designated CA1 and CA4 herein, also called in this application SEQ ID NO:3 (encoded, e.g., by SEQ ID NO:1, or "CA4" or "CORP2", or At1g70410), or SEQ ID NO:9 (encoded, e.g., by SEQ ID NO:7, or "CA1", or "CORP1", or At3g01500); and also including SEQ ID NO:6 (encoded, e.g., by SEQ ID NO:4, or "CA6", or At1g58180).

Figure 22:
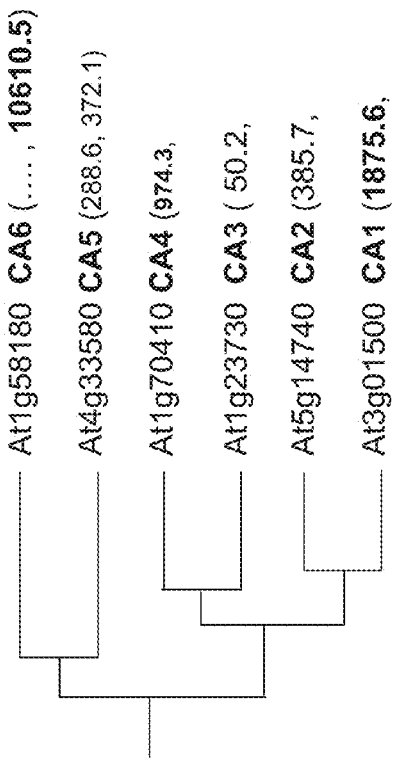
FIG. 22 illustrates a phylogenetic tree of Arabidopsis carbonic anhydrases, as described in detail in Example 4, below.

Among the different carbonic anhydrase (CAs) classes that catalyze the reversible hydration of $CO_2$, the β-class CA members CA1 (At3g01500), CA4 (At1g70410) and CA6 (At1g58180) showed high expression levels in guard cells according to cell-specific microarray analyses, see FIG. 22, as described e.g., by Leonhardt et al., 2004; Yang et al., 2008. FIG. 22 illustrates a phylogenetic tree of *Arabidopsis* carbonic anhydrases (CAs), see e.g., Fabre et al., 2007, and corresponding guard cell specific microarray expression data in brackets; Left, 8K microarray data from Leonhardt et al., 2004; Right, 23K microarray data from Yang et al., 2008. As noted in FIG. 22, CA1, CA4 and CA6 (in bold) show the highest expression values among CAs in guard cells.

FIG. 9 illustrates that disruption of the guard cell-expressed carbonic anhydrases CA1 and CA4 impair $CO_2$-induced stomatal movements. For example, guard-cell expression of CA1, CA4 and CA6 was confirmed by RT-PCR along with the highly guard cell-specific KAT1 (At5g46240) and mesophyll-specific CBP (At4g33050) marker genes (Mori et al., 2006), as illustrated in FIG. 9A.

RT-PCR was used to confirm CA1 and CA4 expression in guard cells and mesophyll cells compared to the highly guard cell marker KAT1 (At5g46240) and mesophyll cell marker CBP (At4g33050); see e.g., Nakamura et al., 1995; Mori et al., 2006. FIGS. 9B and 9C illustrate RT-PCR analysis of ca1ca4 double mutant leaves, the data shows lack of CA1 and CA4 transcripts.

Figure 23:
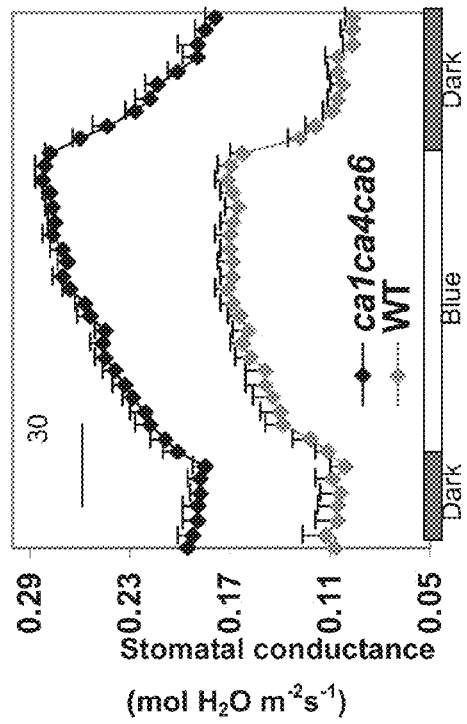
FIG. 23 graphically illustrates data showing carbonic anhydrase mutant plants showed robust stomatal responses to blue light and light-dark transition, as described in detail in Example 4, below.

FIG. 9C, FIG. 9D, FIG. 9E, and FIG. 23 illustrate stomatal conductance responses to $CO_2$, blue-light and light-dark transitions in WT, ca1 ca4 or ca1ca4ca6 mutant plants (d, e, n=7; n=5). The ca1ca4 double mutant leaves show strong insensitivity to high $CO_2$-induced closing (FIG. 9C, FIG. 9C, FIG. 9C) and consistent with this phenotype show elevated stomatal conductance at ambient (365-400 ppm) $[CO_2]$ (FIG. 9C, FIG. 9E); while ca mutant plants showed robust stomatal responses to blue light and light-dark transition (FIG. 23). Values in d were normalized to the last data point prior to the 365-800 ppm $CO_2$ transition.

FIG. 10A illustrates stomata in ca1ca4 double mutant leaves close in response to abscisic acid; n=3 experiments, 30 stomata/experiment and condition. Error bars depict means±s.e.m. FIG. 10B illustrates $CO_2$-induced stomatal movements are impaired in ca1ca4 double mutant leaves and in wild-type leaf epidermis treated with the carbonic anhydrase inhibitor 6-ethoxy-2-benzothiazolesulphonamide (EZA) (n=6, 30 stomata/sample); see e.g., Becker et al., 2007.

Figures 24A, 24C, 24E:
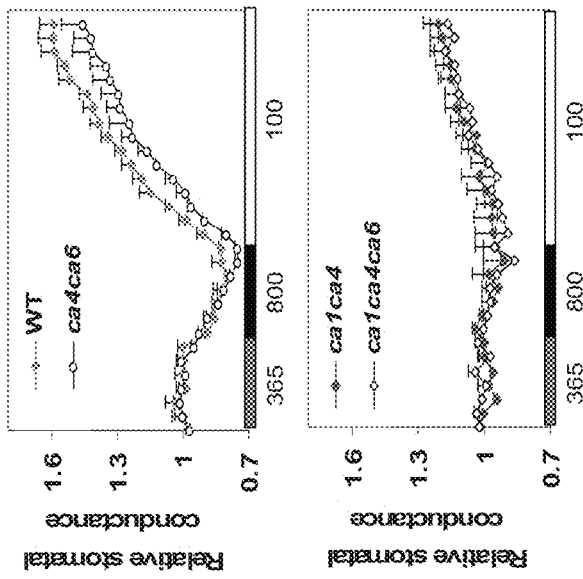
FIG. 24A illustrates data showing that the ca1ca4ca6 triple mutant does not express CA6, where a positive control is a wild type (WT) expressing CA6.
FIG. 24B, FIG. 24C, FIG. 24D and FIG. 24E graphically illustrate data showing that the ca4ca6 double mutants exhibit intact $CO_2$ responses while ca1ca4 and ca1ca4ca6 display the same impairment of $CO_2$ perception.
Figures 24B, 24D:
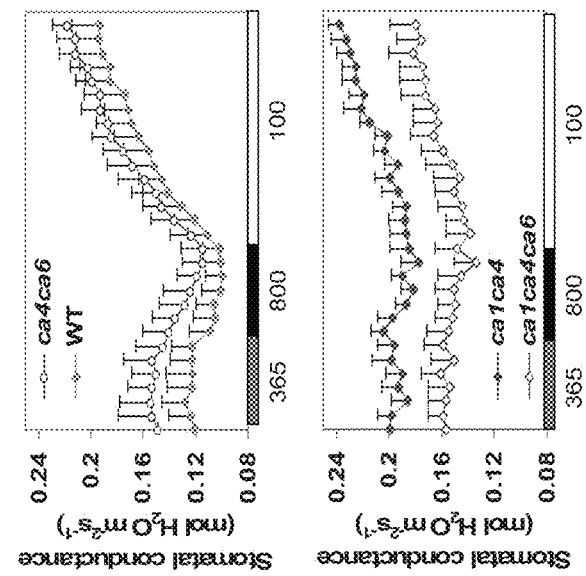
Figure 25A:
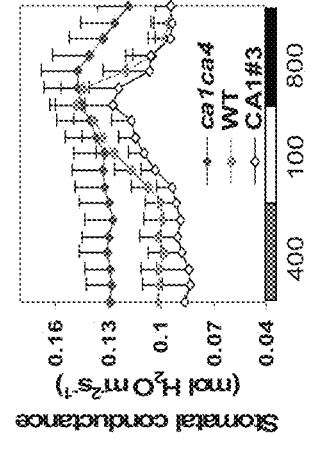
FIG. 25 illustrates data demonstrating that several independent transgenic lines of ca1ca4 transformed with wild-type copy of either CA1 or CA4 exhibit recovery of [$CO_2$] changes-induced responses: Two additional complemented lines with CA1, CA1#2 (FIG. 25A) and CA1#3 (FIG. 25B) or CA4, CA4#2 (FIG. 25C) and CA4#3 (FIG. 25D) show normal stomatal conductance increase and decrease in response to [$CO_2$] changes, as described in detail in Example 4, below.
Figure 25B:
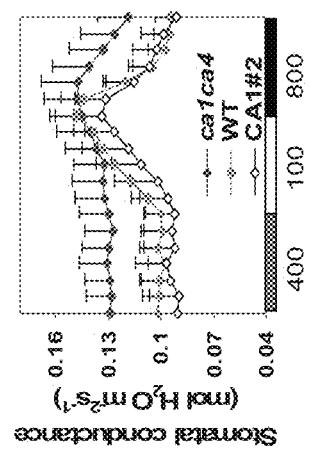
Figure 25C:
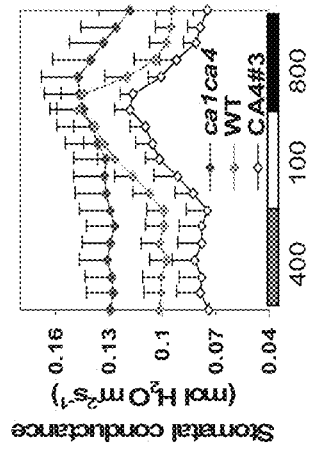
Figure 25D:
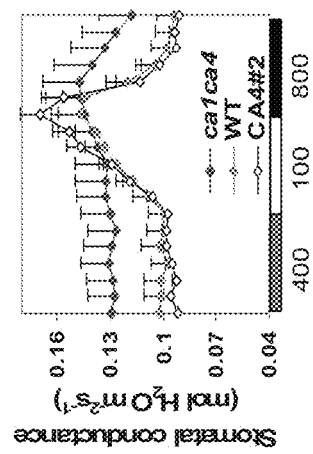

One sequence-indexed T-DNA (transfer DNA) insertion mutant were obtained through The *Arabidopsis* Information Resource (TAIR) center for each of the three CAs genes and referred to as ca1 (SALK_106570), ca4 (WiscDsLox508D11) and ca6 (SALK_044658). Because initial data indicated that all single mutants retained normal $CO_2$ sensitivity, the ca1ca4, ca4ca6, ca1ca6 double mutants as well as the ca1ca4ca6 triple mutant were subsequently generated for assessment of $CO_2$ sensitivity. CA1 and CA4 expression was not detected in ca1ca4 double mutant leaves, as illustrated in FIG. 9B, and the additional lack of CA6 transcript in ca1ca4ca6 was also confirmed, as illustrated in FIG. 24A. FIG. 24B, FIG. 24C, FIG. 24D and FIG. 24E graphically illustrate data showing that ca4ca6 double mutants exhibit intact $CO_2$ responses while ca1ca4 and ca1ca4ca6 display the same impairment of $CO_2$ perception. FIG. 24B, FIG. 24C, FIG. 24D and FIG. 24E graphically illustrate stomatal conductance in mol water $m^{-2}$ $sec^{-1}$.

Stomatal conductance analyses in response to $[CO_2]$ changes showed a strong $CO_2$ insensitivity in ca1ca4 double mutant, as illustrated in FIG. 9C, FIG. 9D, FIG. 9E; and ca1ca4ca6 triple mutant, as illustrated in FIG. 24B, FIG. 24C, FIG. 24D and FIG. 24E, plants while ca1ca6 and ca4ca6 plants were behaving like wild-type.

FIG. 9C illustrates that the ca mutant plants showed a higher stomatal conductance at ambient $[CO_2]$ (365-400 ppm). In contrast to the impairment in $CO_2$ responses, as illustrated in FIG. 9C, FIG. 9D, FIG. 9E and FIG. 24D, FIG. 24E and FIG. 24F, ca1ca4ca6 plants showed robust blue light and light-dark transitions induced responses despite the higher starting stomatal conductance of the ca mutant plants, as illustrated in FIG. 23.

To determine whether the impaired $CO_2$ responses in intact leaves (see FIG. 9C, FIG. 9D, FIG. 9E) are linked to stomatal movements, $CO_2$ responses were analyzed in leaf epidermis. $CO_2$-induced stomatal movements were impaired in ca1ca4 as compared to wild-type, as illustrated in FIG. 10B. Furthermore, when wild-type leaf epidermis were treated for 30 min with the membrane-permeable CA inhibitor EZA (see, e.g., Becker et al., 2007), $CO_2$-induced stomatal opening and closing were inhibited, which correlates with a role for carbonic anhydrases in $CO_2$ sensing, rather than a long-term developmental effect of CA gene disruption on the rapid $CO_2$ response, as illustrated in FIG. 10B. In contrast, abscisic acid (ABA)-induced stomatal closing was completely functional in ca1ca4 leaf epidermis, as illustrated in FIG. 10A.

When genomic constructs (approximately 4.5 Kb) containing only the wild-type CA1 or CA4 gene and flanking sequences were introduced in the ca1ca4 mutant, CA1 or CA4 expression was restored in leaves of several independent transgenic lines, as illustrated in FIG. 11A and FIG. 11B. In contrast to ca1ca4, all transgenic lines exhibited wild-type-like response to $[CO_2]$ changes, as illustrated in FIG. 11C and FIG. 11D, and FIG. 25. These data therefore demonstrate that disruption of CA1 and CA4 is indeed responsible for the phenotypes observed in ca1ca4 plants and that expression of either gene is sufficient for complementation.

In summary, FIG. 11 illustrates that introduction of wild-type genomic copies of CA1 or CA4 complements the ca1ca4 $CO_2$-insensitive phenotypes. FIG. 11A and FIG. 11B: illustrates data of RT-PCR analyses (29 cycles) confirming restoration of CA1 (FIG. 11A) and CA4 (FIG. 11B) expression in ca1ca4 double mutant leaves transformed with genomic CA1 (FIG. 11A) or CA4 (FIG. 11B) constructs. Three independent transgenic lines per genomic construct were analyzed. Actin (At2g37620) was used as a control. FIG. 11C and FIG. 11D in contrast to ca1ca4, both complemented CA/#1 (FIG. 11C) and CA4#1 (FIG. 11D) lines exhibit recovery of $[CO_2]$-regulated stomatal conductance changes (n=8 leaves for ca1ca4, n=10 for WT and n=4 for any of the complemented lines). Error bars depict means±s.e.m. See also FIG. 25 for data from other independent transgenic lines.

In summary, FIG. 25 illustrates data demonstrating that several independent transgenic lines of ca1ca4 transformed with wild-type copy of either CA1 or CA4 exhibit recovery of $[CO_2]$ changes-induced responses. Two additional complemented lines with CA1, CA1#2 (FIG. 25A) and CA1#3 (FIG. 25B) or CA4, CA4#2 (FIG. 25C) and CA4#3 (FIG. 25D) show normal stomatal conductance increase and decrease in response to $[CO_2]$ changes. n=4 leaves for each of the complemented lines. Wild-type (n=10) and ca1ca4 (n=8) shown here are the same as the ones depicted in FIG. 11, discussed above. Error bars depict means±s.e.m.

Figure 26:
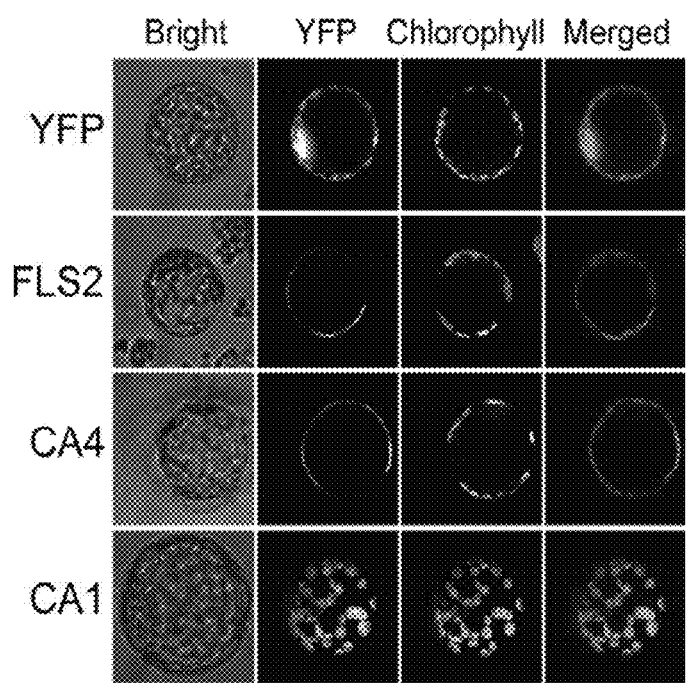
FIG. 26 illustrates fluorescent pictures (confocal imaging) of cells with different localization patterns of CA1-YFP and CA4-YFP in tobacco protoplasts: plasmids encoding YFP, FLS2-YFP, CA1-YFP and CA4-YFP were transiently expressed in tobacco protoplasts; filters are indicated on the top of the figure, while the fusions are indicated on the left of the figure; pictures on the far right of FIG. 26 show an overlay of YFP and chlorophyll images, as described in detail in Example 4, below.

To examine the subcellular localization of CA1 and CA4, the yellow fluorescent protein (YFP) fused to the C-terminus of CA1 or CA4 was transiently expressed in tobacco protoplasts, as illustrated in FIG. 26; which illustrates fluorescent pictures (confocal imaging) of cells with different localization patterns of CA1-YFP and CA4-YFP in tobacco protoplasts. As noted in FIG. 26, plasmids encoding YFP, FLS2-YFP, CA1-YFP and CA4-YFP were transiently expressed in tobacco protoplasts; filters are indicated on the top of the figure, while the fusions are indicated on the left of the figure; pictures on the far right of FIG. 26 show an overlay of YFP and chlorophyll images. Similar to the plasma membrane-localized FLS2-YFP fusion, this data demonstrates that CA4-YFP localizes to the cell periphery, while CA1-YFP fluorescence appears to co-localize with the chloroplasts.

Confocal imaging of the CA4-YFP showed a cell-peripheral expression pattern identical to the Leu-rich repeat transmembrane receptor kinase FLS2-YFP (FLAGELLIN SENSITIVE2) (see e.g., Robatzek et al, 2006) fusion pattern, as illustrated in FIG. 26. In contrast, fluorescence from the CA1-YFP fusion seemed to surround the autofluorescence of the chlorophyll suggesting that CA1 may be localized to the chloroplasts, as illustrated in FIG. 26. This differential expression pattern of CA1-YFP and CA4-YFP fusions is in accordance with another CA localization study (see, e.g., Fabre et al., 2007.

Since CA4 appeared to be localized to chloroplasts, we then assessed whether the role of CAs in $CO_2$ perception is dependent on photosynthesis by comparing the chlorophyll fluorescence of wild-type and the ca1ca4ca6 mutant in which the three major guard cells-expressed CA genes (see FIG. 22) are knocked-out. The maximum efficiency of photosystem II (Fv/Fm) in dark-adapted leaves was unaffected by CA misexpression, as illustrated in FIG. 12A. Similarly, no difference between quantum yield of photosystem II (PSII, $\Phi_{PSII}$) in wild-type and ca1ca4ca6 leaves pre-adapted at low (50 µmol $m^{-2}s^{-1}$) or high (2000 µmol $m^{-2}s^{-1}$) photosynthetically active radiation was detected, as illustrated in FIG. 12B and FIG. 12C. If the role of CAs in $CO_2$ perception is mediated through photosynthetic activities, the onset of photosynthesis at the transition from darkness to illumination with photosynthetically active red light should be affected. Analysis of the $CO_2$ assimilation rate in ca1ca4ca6 and wild-type showed that both genotypes reached their steady-state photosynthetic activity in the same time frame upon 300 µmol $m^{-2}s^{-1}$ red light irradiation, as illustrated in FIG. 12D.

Figure 12:
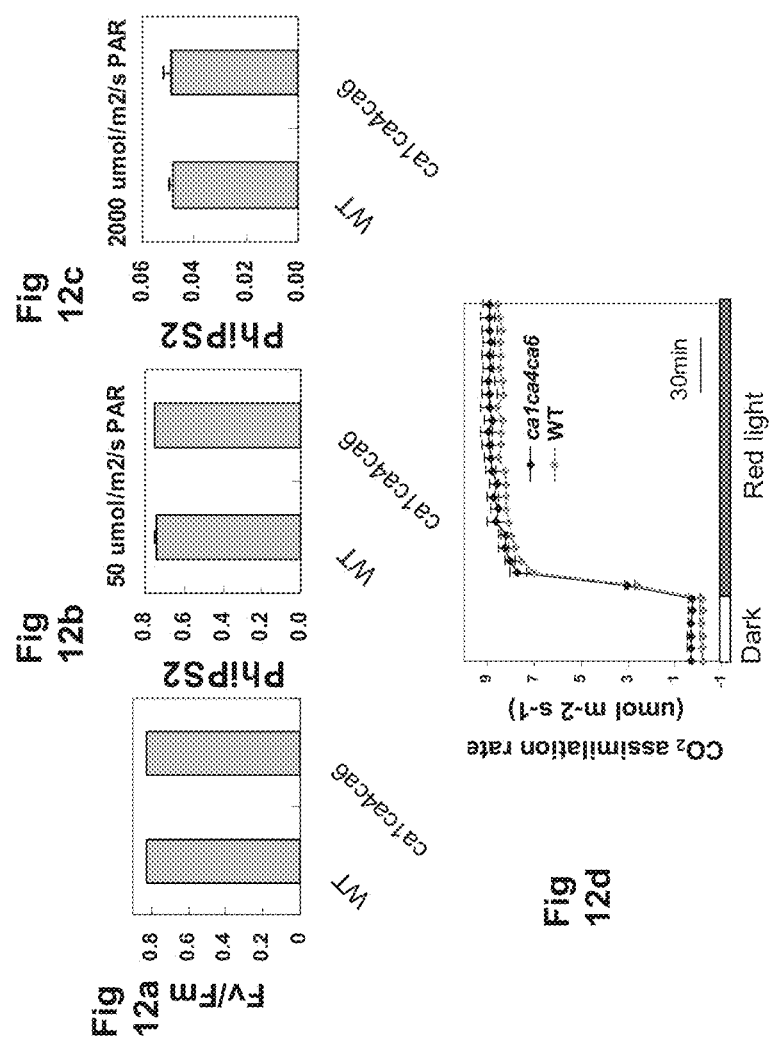
FIGS. 12A, 12B and 12C, graphically illustrate a summary of data showing that photosynthesis is not impaired in triple $CO_2$ sensor knockout mutant: Light during pre-adaptation time, prior to PS fluorescence measurements: 50 umol/m2/s: 88% red light, 12% blue light; 2000 umol/m2/s: 90% red light, 10% blue light.
FIG. 12D illustrates the $CO_2$ assimilation rate in dark and in red light (where the red light: 300 $\mu mol \cdot m^{-2} \cdot s^{-1}$); as described in detail in Example 2 and Example 4, below.
Figure 13:
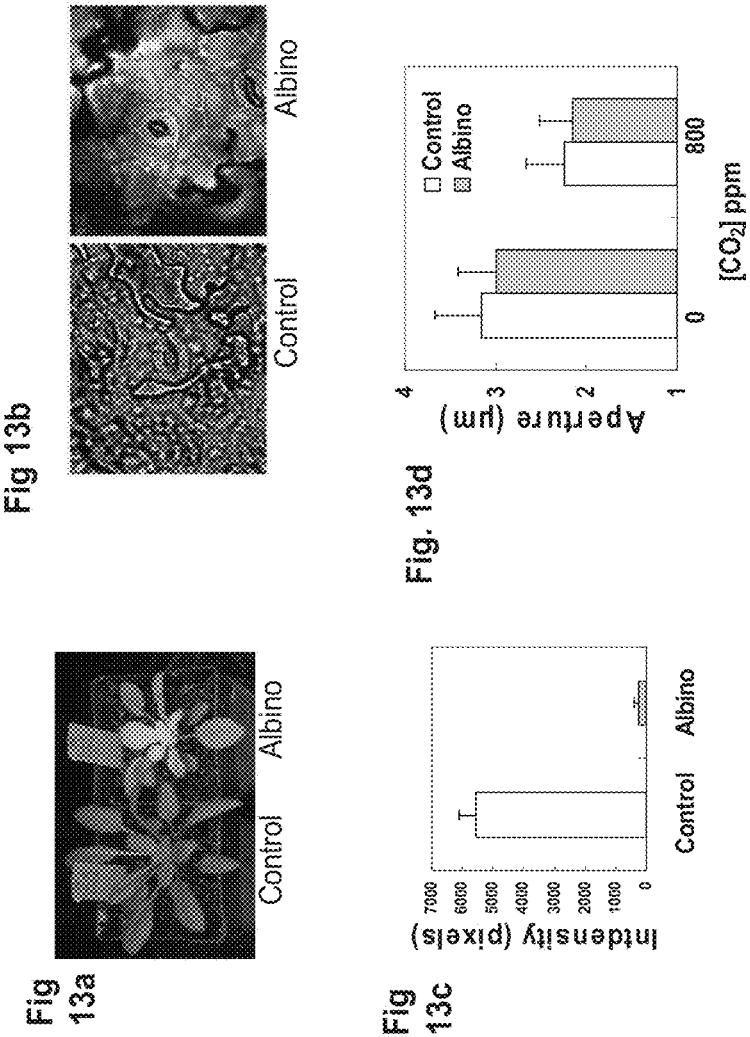
FIGS. 13A, 13B, 13C and 13D, graphically and pictorially illustrate that photosynthesis-impaired bleached leaves show intact $CO_2$ regulation of gas exchange; as described in detail in Example 2 and Example 4, below.

To further analyze whether intact photosynthesis is required for $CO_2$ regulation of stomatal movements, another approach was carried out. Photosynthetic activities were blocked in newly emerging leaves by watering 3 to 4 week-old wild-type *Arabidopsis thaliana* plants with the carotenoid biosynthesis inhibitor Norflurazon (Nf) yielding albino chlorophyll-deficient wild-type leaves devoid of functional chloroplasts, as illustrated in FIG. 13A (see, e.g., Roelfsema et al., 2006). The absence of functional chloroplasts in the Nf-treated plants was confirmed by visualizing, as illustrated in FIG. 13B, and quantifying, as illustrated in FIG. 13C, chlorophyll fluorescence with confocal microscopy As illustrated in FIG. 13D, the stomatal $CO_2$ response to both high and low $[CO_2]$ in intact leaves was not affected by the absence of functional chloroplasts (albino 0 ppm. $[CO_2]$ compared to albino 800 ppm. $[CO_2]$, P=8.9E-21, n=6). Thus, our data demonstrate that photosynthetic activities are not disrupted in ca mutant plants which display impaired $CO_2$ perception and are not required for a functional stomatal $CO_2$ response in *Arabidopsis* (as illustrated in FIGS. 12 and 13) as previously reported in *Vicia faba* (see, e.g., Roelfsema et al., 2006). However, noting that this invention is not limited by any particular mechanism of action, these findings do not exclude additional CA-independent mechanisms by which photosynthesis may be linked to stomatal movements (see, e.g. Messinger et al., 2006).

In summary, in FIGS. 12 and 13: photosynthesis-related activities are not directly linked to CA-mediated $CO_2$-induced stomatal response. FIG. 12A, FIG. 1B and FIG. 12C graphically illustrate chlorophyll fluorescence analysis that revealed no differences between WT and ca1ca4ca6 mutant plants with respect to the maximum efficiency of photosystem II (PSII)-Fv/Fm, in dark-adapted leaves (n=10) (FIG. 12A) or to the quantum yield of PSII-$\Phi p_{SSII}$ in leaves (n=6) pre-adapted at 50 µmol $m^{-2}s^{-1}$ (FIG. 12B) or 2000 mmol $m^{-2}s^{-1}$ (FIG. 12C) photosynthetically active radiation. FIG. 12D illustrates red light-induced photosynthetic activity of intact leaves was not impaired in ca1ca4ca6 (n=6).

FIG. 13A illustrates an image of chlorophyll-deficient albino wild-type leaves devoid of functional chloroplasts were generated by application of the carotenoid biosynthesis inhibitor norflurazon. The absence of chlorophyll in albino guard cells compared to wild-type was visualized by confocal microscopy (FIG. 13B graphically illustrates data) and quantified by image analysis of the chlorophyll fluorescence intensity (FIG. 13C graphically illustrates data) (n=3, 12 stomata/sample.). FIG. 13D graphically illustrates data showing $CO_2$-induced stomatal movements in albino versus control plant leaves (n=7, 50 stomata/sample). Error bars depict means±s.e.m.

CA1 and CA4 are expressed in both guard cells and mesophyll cells (see FIG. 9A) and knock-out mutant plants show impaired $CO_2$ responses. We next analyzed whether CA1 or CA4 expression targeted to guard cells is sufficient to complement the $CO_2$ response phenotypes of the ca1ca4 mutant.

Figure 27:
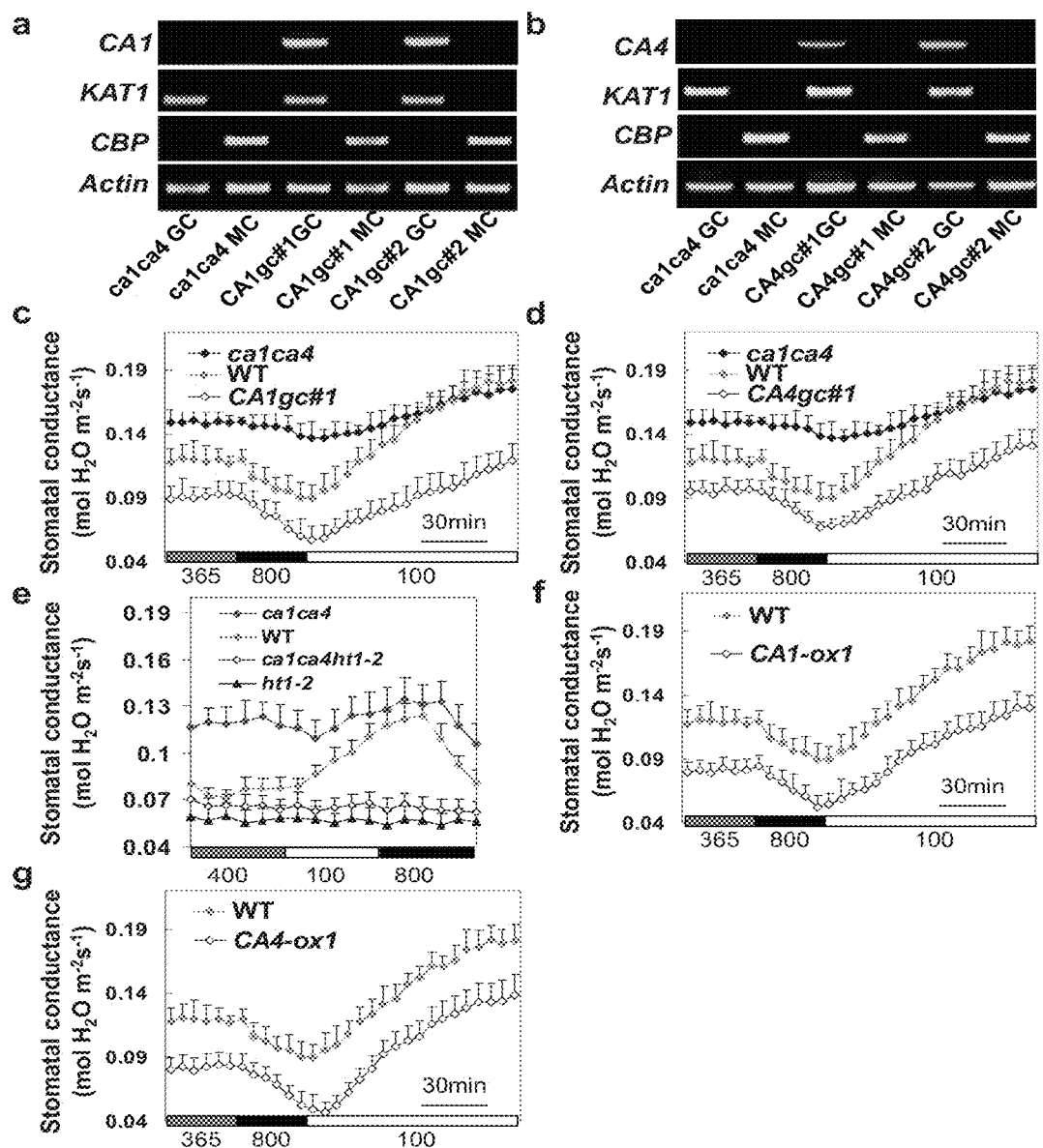
FIG. 27A to G, graphically illustrate data showing that guard cell preferential driven expression of CA1 or CA4 cDNAs restores $CO_2$ perception in ca1ca4 and CA over-expressing plants exhibit improved water use efficiency.
Figure 28:
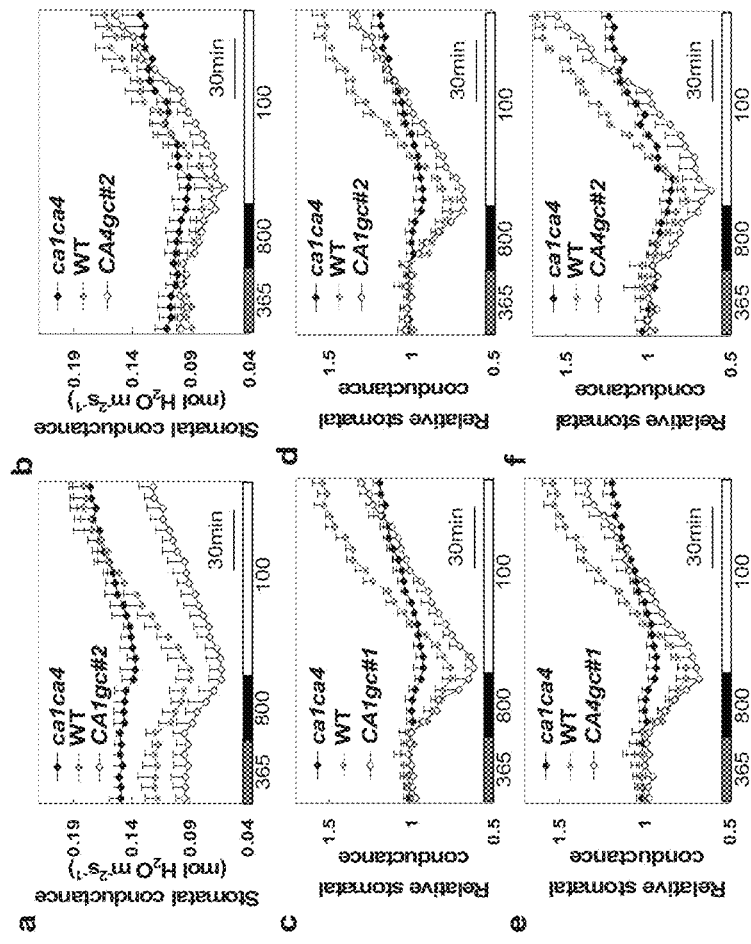
FIGS. 28A to F graphically illustrate guard-cell specific complementation of either CA1 or CA4 restores stomatal $CO_2$ responses in ca1ca4: $CO_2$ response data of an additional line complemented with CA1 or CA4 guard cell-targeted expression, as graphically illustrated in FIG. 28A and FIG. 28B and relative stomatal conductance $CO_2$ response of the guard cell-targeted 4 independent complemented lines analyzed; two in FIG. 27C and FIG. 27D; two in FIG. 28A and FIG. 28B.

The cDNAs of CA1 or CA4 driven by a strong guard cell promoter of this invention, as described in Example 3, above, were transformed into ca1ca4 double mutant plants and their preferential guard cell expression was confirmed by RT-PCR in several independent transgenic lines, as illustrated in FIG. 27A and FIG. 27B, using the guard cell specific marker KAT1 (see, e.g., Nakamira et al., 1998) and the mesophyll cell marker CBP (see, e.g., Mori et al., 2006). Transgenic ca1ca4 plants expressing CA1 or CA4 preferentially in guard cells showed stronger stomatal conductance changes in response to [$CO_2$] shifts, as illustrated in FIG. 27C, FIG. 27D; and FIG. 28; four total independent transgenic lines were analyzed. These results demonstrate that generating expression of $CO_2$ sensor genes of this invention, including CA1 or CA4 expression, in guard cells is sufficient to complement the impaired $CO_2$ response of ca1ca4 double mutant, and that these carbonic anhydrases (CAs) function in $CO_2$ perception primarily in guard cells. Thus, these results demonstrate that expressing $CO_2$ sensor genes of this invention, including CA1 or CA4 expression, in guard cells can manipulate plant $CO_2$ responses.

The earliest component of $CO_2$ signaling identified thus far in guard cells is the HT1 kinase, a negative regulator of the pathway (see, e.g., Hashimoto et al., 2006). The strong ht1-2 allele exhibits a constitutive high-[$CO_2$] response. To investigate whether the carbonic anhydrases (CAs) function upstream or downstream of HT1, the ca1ca4ht1-2 triple mutant was generated and its stomatal conductance was analyzed in response to [$CO_2$] changes. As clearly depicted in FIG. 27E, and in clear contrast with ca1ca4 double mutant or wild-type, ca1ca4ht1-2 plants exhibited a phenotype indistinguishable from the single ht1-2 mutant. These data provide genetic evidence that CA1 and CA4 act upstream of the earliest $CO_2$ signaling component known to date, consistent with a $CO_2$ sensor function for these carbonic anhydrases (CAs).

In summary, FIG. 27A to G, and FIG. 14C, graphically illustrate data showing that guard cell preferential driven expression of CA1 or CA4 cDNAs restores $CO_2$ perception in ca1ca4 and CA over-expressing plants exhibit improved water use efficiency. FIG. 27A and FIG. 27B graphically illustrate a RT-PCR analysis of CA1 and CA4 expression in guard cell protoplasts and mesophyll cells of complementation plants with CA1 or CA4 driven by the guard cell-targeted promoter of this invention pGC1 (see Example 3, above). GC, guard cell; MC, mesophyll cell. CA1gc#n, complementation line n with CA1 cDNA driven by the guard cell promoter. KAT1, At5g46240, guard cell marker (Nakamura et al., 1998); CBP, At4g33050, mesophyll cell marker (Mori et al., 2006).'

FIG. 27C and FIG. 27D graphically illustrate $CO_2$-induced stomatal conductance change of guard cell-targeted lines, ca1ca4 double mutant and wild-type (WT) plants in response to the indicated [$CO_2$] shifts (in ppm, n=4, ±s.e.m.). CA1 or CA4 expression in guard cells is sufficient for restoration of the $CO_2$ response. FIG. 27E graphically illustrates stomatal conductance of ca1ca4 (n=4), wild-type (n=4), ht1-2 (n=7) and triple ca1ca4ht1-2 mutant (n=7) leaves in response to the indicated [$CO_2$] changes (in ppm, ±s.e.m.). FIG. 27F and FIG. 27G graphically illustrate stomatal conductance of CA over-expressing lines and wild-type (WT) plants in response to the indicated [$CO_2$] changes (in ppm, n=4, ±s.e.m.).

FIG. 14A and FIG. 14B graphically illustrate CA1 (FIG. 14A) and CA4 (FIG. 14B) over-expressing plants show improved water use efficiency (WUE, µmol $CO_2$ mmol $H_2O^{-1}$) (n=5, ±s.e.m.). FIG. 14C illustrates photographs of wild-type, ca1ca4 and CA over-expressing lines grown under standard conditions.

In summary, FIGS. 28A to F graphically illustrate guard-cell specific complementation of either CA1 or CA4 restores stomatal $CO_2$ responses in ca1ca4. $CO_2$ response data of an additional line complemented with CA1 or CA4 guard cell-targeted expression, as graphically illustrated in FIG. 28A and FIG. 28B (n=4) and relative stomatal conductance $CO_2$ response of the guard cell-targeted 4 independent complemented lines analyzed (two in FIG. 27C and FIG. 27D; two in FIG. 28A and FIG. 28B). FIGS. 28C to F graphically illustrate relative stomatal conductance values were normalized to the last data point prior to the 365-800 ppm $CO_2$ switch. Error bars depict means±s.e.m.

We also analyzed whether over-expression of CA1 or CA4 in guard cells of wild-type plants could be a good strategy to enhance plant response to atmospheric [$CO_2$] changes. Transgenic plants over-expressing CA1 or CA4 under control of a strong guard cell promoter of this invention (as described in Example 3, above) were generated in the wild-type background and confirmed by RT-PCR, as illustrated in FIG. 14A and FIG. 14B. Four independent CA1- and CA4-overexpressing lines displayed a reduced stomatal conductance at all $CO_2$ concentrations tested, consistent with an enhanced $CO_2$ response, as illustrated in FIG. 27F and FIG. 27G. Interestingly, a significant difference in water use efficiency (WUE) among the double ca1ca4 mutant, CA over-expressing and wild-type plants was consistently noticed. Over-expression of either the CA1 or CA4 gene in wild-type substantially improved water use efficiency by 50% at ambient [$CO_2$], as illustrated in FIG. 14C, where $p<0.01$. Under the imposed standard condition, no other phenotypic growth differences were observed among wild-type and CA over-expressing plants, as in the photo illustrated in FIG. 14C. These data demonstrate that guard cell targeted over-expression of carbonic anhydrases (CAs), including the CA genes of this invention, provide an efficient and effective approach for improving the water use efficiency of plants. These data demonstrate that the compositions and methods of this invention can be used to address and ameliorate the increase in atmospheric $CO_2$ concentrations.

Figure 29:
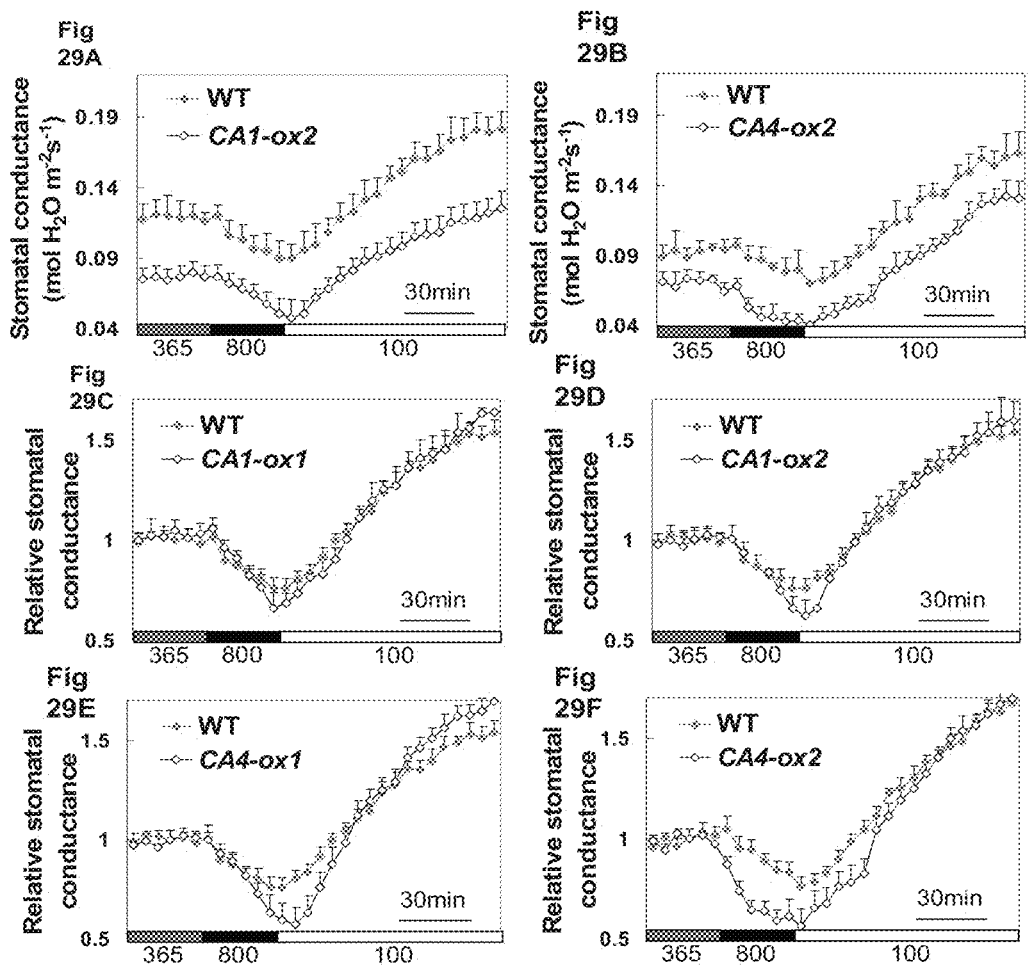
FIG. 29 graphically illustrates data showing that the over-expression of either CA1 or CA4 in wild-type guard cells decreases the overall stomatal conductance and slightly increases the magnitude of the stomatal $CO_2$ response.

In summary, in FIG. 29 graphically illustrates data showing that the over-expression of either CA1 or CA4 in wild-type guard cells decreases the overall stomatal conductance and slightly increases the magnitude of the stomatal $CO_2$ response. FIG. 29C and FIG. 29D graphically illustrate RT-PCR analysis of CA1 or CA4 in leaves of over-expressing lines driven by the preferential guard cell promoter pGC1. Stomatal conductance measurements of an additional line over-expressing the CA1 gene, as illustrated in FIG. 29A, and additional line over-expressing the CA4 gene, as illustrated in FIG. 29B. Relative stomatal conductance values, as illustrated in FIG. 29C, FIG. 29D, FIG. 29E, and FIG. 29F, were normalized to the last data point prior to the 365-800 ppm $CO_2$ switch. Error bars depict means±s.e.m. FIG. 29A, FIG. 29C, FIG. 29D, and FIG. 29E, n=4; FIG. 29B, FIG. 29F, n=3.

REFERENCES CITED

1. Becker, H.M. & Deitmer, J.W. Carbonic anhydrase II increases the activity of the human electrogenic Na+/HCO3-cotransporter. *Journal of Biological Chemistry* 282, 13508-13521 (2007).
2. Delucia, E.H. et al. Net primary production of a forest ecosystem with experimental CO2 enrichment. *Science* 284, 1177-1179 (1999).
3. Fabre, N., Reiter, I.M., Becuwe-Linka, N., Genty, B. & Rumeau, D. Characterization and expression analysis of genes encoding alpha and beta carbonic anhydrases in *Arabidopsis*. *Plant Cell and Environment* 30, 617-629 (2007).
4. Hashimoto, M. et al. *Arabidopsis* HT1 kinase controls stomatal movements in response to CO2. *Nature Cell Biology* 8, 391-U52 (2006).
5. Hetherington, A.M. & Woodward, F.I. The role of stomata in sensing and driving environmental change. *Nature* 424, 901-908 (2003).
6. Hu, J. et al. Detection of near-atmospheric concentrations of CO2 by an olfactory subsystem in the mouse. *Science* 317, 953-957 (2007).
7. Hungate, B.A. et al. The fate of carbon in grasslands under carbon dioxide enrichment. *Nature* 388, 576-579 (1997).
8. Jones, W.D., Cayirlioglu, P., Kadow, I.G. & Vosshall, L.B. Two chemosensory receptors together mediate carbon dioxide detection in *Drosophila*. *Nature* 445, 86-90 (2007).
9. Kinoshita, T. et al. phot1 and phot2 mediate blue light regulation of stomatal opening. *Nature* 414, 656-660 (2001).
10. Kwak, J.M. et al. Dominant negative guard cell K+ channel mutants reduce inward-rectifying K+ currents and light-induced stomatal opening in *Arabidopsis*. *Plant Physiology* 127, 473-485 (2001).
11. Ladeau, S.L. & Clark, J.S. Rising CO2 levels and the fecundity of forest trees. *Science* 292, 95-98 (2001).
12. Leonhardt, N. et al. Microarray expression analyses of *Arabidopsis* guard cells and isolation of a recessive abscisic acid hypersensitive protein phosphatase 2C mutant. *Plant Cell* 16, 596-615 (2004).
13. Medlyn, B.E. et al. Stomatal conductance of forest species after long-term exposure to elevated CO2 concentration: a synthesis. *New Phytologist* 149, 247-264 (2001).
14. Messinger, S.M., Buckley, T.N. & Mott, K.A. Evidence for involvement of photosynthetic processes in the stomatal response to CO2. *Plant Physiology* 140, 771-778 (2006).
15. Mori, I.C. et al. CDPKs CPK6 and CPK3 function in ABA regulation of guard cell S-type anion- and Ca2+-permeable channels and stomatal closure. *Plos Biology* 4, 1749-1762 (2006).
16. Nakamura, R.L. & Gaber, R.F. Studying ion channels using yeast genetics. *Ion Channels, Pt B* 293, 89-104 (1998).
17. Nakamura, R.L. et al. Expression of an *Arabidopsis* Potassium Channel Gene in Guard-Cells. *Plant Physiology* 109, 371-374 (1995).
18. Negi, J. et al. CO2 regulator SLAC1 and its homologues are essential for anion homeostasis in plant cells. *Nature* 452, 483-U13 (2008).
19. Robatzek, S., Chinchilla, D. & Boller, T. Ligand-induced endocytosis of the pattern recognition receptor FLS2 in *Arabidopsis*. *Genes & Development* 20, 537-542 (2006).
20. Roelfsema, M.R.G. et al. Guard cells in albino leaf patches do not respond to photosynthetically active radiation, but are sensitive to blue light, CO2 and abscisic acid. *Plant Cell and Environment* 29, 1595-1605 (2006).
21. Sellers, P.J. et al. Modeling the exchanges of energy, water, and carbon between continents and the atmosphere. *Science* 275, 502-509 (1997).
22. Vahisalu, T. et al. SLAC1 is required for plant guard cell S-type anion channel function in stomatal signalling. *Nature* 452, 487-U15 (2008).
23. von Caemmerer, S. et al. Stomatal conductance does not correlate with photosynthetic capacity in transgenic tobacco with reduced amounts of Rubisco. *Journal of Experimental Botany* 55, 1157-1166 (2004).
24. Webb, A.A.R. & Hetherington, A.M. Convergence of the abscisic acid, CO2, and extracellular calcium signal transduction pathways in stomatal guard cells. *Plant Physiology* 114, 1557-1560 (1997).
20. Yang, Y., Costa, A., Leonhardt, N., Siegel, R.S. & Schroeder, J.I. Isolation of a strong *Arabidopsis* guard cell promoter and its potential role as a research tool. *Plant Methods* 4, (2008).
26. Young, J.J. et al. CO2 signaling in guard cells: Calcium sensitivity response modulation, a Ca2+-independent phase, and CO2 insensitivity of the gca2 mutant. *Proceedings of the National Academy of Sciences of the United States of America* 103, 7506-7511 (2006).

Example 5

Exemplary PEPC and Rubisco Enzymes to Control Plant $CO_2$ Uptake and Water Use Efficiency The invention provides compositions and methods for regulating carbon dioxide ($CO_2$) exchange and $CO_2$ use and uptake in a plant or plant part, e.g., a leaf, by manipulating expression of a $CO_2$ binding protein "Phosphoenolpyruvate (PEP) Carboxylase" (or PEP carboxylase, or PEPC) and/or a ribulose-1,5-bisphosphate carboxylase/oxygenase, or "Rubisco" enzyme; thus, the invention also provides compositions and methods for manipulating $CO_2$ signal transduction and regulation of gas exchange in a plant or plant part, e.g., a plant organ, leaf and the like. For example, in one aspect, the invention provides compositions and methods for engineering an increased amount of PEPC (to facilitate stomatal opening) and/or engineering the amount of "Rubisco" enzyme.

In alternative aspects of this invention, PEPCs and Rubisco nucleic acids are expressed in plant cells, e.g., in plant guard cells and mesophyll cells; and in one aspect, they are expressed at high levels (higher than wild type levels); or, PEPCs and Rubisco nucleic acids expression is inhibited, decreased or repressed in plant cells, e.g., in plant guard cells and mesophyll cells; and in one aspect, they are expressed at lower levels (lower than wild type levels). Plant cells engineered in these alternative embodiments include isolated, cultured or transgenic plants and plant cells of this invention.

The following exemplary PEPCs and Rubisco nucleic acids and subsequences thereof, including sense coding, and antisense sequences (such as siRNA, miRNA, and the like) can be used to practice the compositions and methods and methods of this invention:

| Name - activity | SEQ ID NO: and Genbank No. | sequence |
|---|---|---|
| PPC1 | SEQ ID NO: 12 At1g53310 | gttatgtatctctgaaatctgaatctgactgacttcaaaggacacagcttttacttct ataactgagcgaagcaggtgaaaaaatggcgaatcggaagttagagaagatg gcatcgattgatgttcatcttcgtcaactggttcctggcaaagttagtgaagacga caagcttgttgagtatgatgctttgcttctagatcggtttctcgatatcctccaggat ttgcacggtgaagatctccgtgaaactgttcaagagctttatgagcattctgcag aatacgaagggaagcatgaacctaagaagctagaggagctagggagtgtgct aacgagtttagatccaggagattccattgttatcgctaaagcttctctcatatgctt aacttagccaatttggctgaggaagtgcagattgcttatcgccgtaggatcaag aagctgaagaaaggtgattttgttgatgagagctctgctactactgaatctgatct tgaagaaacttttcaagaagcttgttggagatctgaacaagtctcctgaagagatc tttgatgctctcaagaatcagactgtggatttggttttgactgctcatcctactcagt ctgtgagaagatcattgcttcagaaacatggaggataagagactgtctggctc aactatatgctaaggatattactcctgatgacaagcaagagctcgatgaggctct tcagagagagattcaagctgcattccgaacagatgaaatcaaaagaacaccac ctactcctcaagatgagatgagagcgggaatgagttatttccatgaaactatctg gaaaggtgttcctaagtttctgcgccgtgttgacacggctttgaaaaacatagg atcgaagaacgtgttccatataatgctccattgattcagttctcttcttggatgggt ggtgatcgtgacggtaacccaagggttacacctgaagtcaccagagatgtttgc ttgttagctagaatgatggctgctactatgtactttaaccaaatcgaagatcttatgt ttgagatgtctatgtggcgttgcaatgacgagctgcgtgcgcgagctgatgaag ttcatgcaaattcgaggaaagatgctgcaaaacattacatagaattctggaagtc aattcctacaactgagccataccgtgtgattcttggcgatgtaagggacaagctt tatcacacacgtgaacgcgctcatcaactgctcagcaatggacactctgatgtc cctgtagaggctactttcattaacttggaacagttcttggaacctcttgagctctgt taccgatctctgtgttcatgtggtgatcgtccaatagcagatggaagccttcttga tttcttgaggcaagtctcaacctttgggctctctcttgtgagacttgacataaggca agaatctgaccgccacactgatgtattggatgctatcaccacgcatttagatatc ggatcctacagagagtggtctgaagaacgccgccaagaatggcttttatctgag ctaagtggcaaacgtccgcttttcggttctgatcttcctaaaaccgaagaaatag ctgatgttctggacacgtttcatgtcatagccgagctaccagcagatagctttggt gcttacattatctctatggcaactgcaccttctgatgtattagctgttgagctttttac agcgtgaatgccgagtgaaacagccttttgagagttgttccgctctttgagaagct agcagatctggaagcagctcctgctgcagttgctaggctcttttctgttgattggt acaaaaaccgaattaacggtaagcaagaggttatgattggttattcggattcagg aaaagatgctggacggttatctgctgcttggcagttatacaaagctcaagaaga gcttgtgaaggttgctaaagagtacggtgtgaagctaacaatgtttcacggtcgt ggtggcacggtcggaagaggaggtggaccaacccatcttgctatattgtctca gcctccggatactattaacggttccctccgtgtcacagttcaaggtgaagtcatc gagcaatcgtttggtgaagagcacttatgctttagaacacttcagcgtttcacag ctgctacactcgagcacggtatgcgtcctccaatttcgcctaaaccagaatggc gcgctttgctggatgaaatggcggttgttgcaaccgaggagtatcgctcagttgt gttccaagaacctcggtttgtcgagtacttccgcctcgctacaccggaactgga gtatggacgtatgaatatcggaagcagaccttcgaagcgtaaaccaagcggtg gcattgaatctctccgtgcaattccatggatcttcgcttggactcaaacaagattc catcttcctgtatggcttggattcggatcagcaattagacatgtgatcgaaaaag acgtcaggaacctccatatgctccaagatatgtaccaacactggcctttctttaga gtcaccattgatctaatcgaaatggtgttcgctaaaggagatcctggtattgctgc tttgtacgataagcttcttgtttcagaggaactctggcctttggtgagaaactcag agctaacttcgaagaaaccaagaaactcatcctccagaccgctggacacaaag atcttcttgaaggtgatccttacttgaaacagagactgagacttcgtgattcttaca ttacaactctcaatgtctgtcaagatacacattgaagagaatccgtgatccgagt taccatgtgactctgcgaccacacattttctaaggagatgcggaatcgagcaaa ccagcaaaagaactcatcgagcttaacccgactagcgaatacgcgccaggac ttgaagatacactcatcttgacgatgaagggtattgctgctggtctacaaaacac cggttaagctacaaagagatggttaaacaaactttgaatctctctttctctctcaag tctctccttttttttaactacagatttggaaaataaggttggattctggtttattttatgta tccaccgtcaaaatgttgattttcgtgtacgagtacttcgagatcattgaacacat gctctgttttttttctcaagtttaataaaacagaacaagagaatctttcttgtttatttc ttatct |

| Name - activity | SEQ ID NO: and Genbank No. | sequence |
|---|---|---|
| PPC2 | SEQ ID NO: 13 At2g42600 | gtctcgtttaaattttttataaactccataattttttatcttaaagtgaatcttttttgttttttttt<br>gttccagattatcggatatatttccttgattttctccgattgtggtcaatctgaaaaa<br>ttattgagaatctctccctcacttaaccaaaagcgttttttaatcagatagagagag<br>aggaaaaagcatcaaccaaaccatggctgcgagaaatttggagaagatggctt<br>ctattgatgctcagctcaggcttcttgctcctggcaaggtttctgaagacgacaa<br>gcttatcgagtacgatgctctgttactggatcgatttctcgatattcttcaggatttg<br>catggcgaggatgtcagagaattcgttcaagaatgctacgaagttgcagctgat<br>tacgatggaaaccgcaacactgagaagcttgaggagcttggaaatatgctgac<br>gagtttggatccaggggattcaattgttgtcactaaatcattctccaacatgcttag<br>cttggctaatctggctgaggaagtccagattgcttaccggcgtaggattaagaa<br>actcaagaaaggtgatttcgctgatgaggcctctgcaacaacggaatctgacat<br>tgaagagactctcaagaggcttttgcagcttaacaagactcctgaagaggtcttt<br>gatgctcttaagaatcagactgttgacttggttttaactgctcatcccactcaatct<br>gttcgtcggtctttgctccaaaagtttggaaggattcgtgattgtttgacgcagtta<br>tatgcaaaggacattactcctgatgacaaacaagaactcgatgaagctctgcaa<br>cgagagattcaagctgcttttcgcacagatgaaatccgaagaactcctcctaca<br>ccgcaagatgaaatgagagcagggatgagctacttccatgagacaatctggaa<br>aggagttccaaagttcttaagacgtgttgacacagctttaaagaacattggaatc<br>aacgagcgtgttccttacaatgcgcctctcattcagttctcttcttggatgggcgg<br>agaccgtgatggaaacccgcgagtaactcctgaagttacaagagatgtatgat<br>attagctagaatgatggctgctaatctctacttctcccagatagaagatcttatgttt<br>gagatgtctatgtggcgttgcaatgaggaacttcgggttcgtgcagaacgtcaa<br>agatgtgcgaagagggatgcaaaaacactatatagaattctggaaacaaatccct<br>gcgaatgagccataccgagctattatggagatgtgagggacaagctgtacaa<br>cacacgtgagcgtgcacgtcagttattgtcaagcggagtttcggacgttcccga<br>agacgcggttttcacaagtgtggatcagttttttggagccacttgagctttgttaca<br>ggtcgctctctgttgattgcggtgacagacctattgctgatggaagcctgcttgatttc<br>ttacgccaagtgtcaacatttggccttgctcttgtgaaacttgatatccgtcaaga<br>atctgaaagacactctgatgtatggatgccatcacgacgcacttaggtattggtt<br>cttacaaagaatggtcggaggataaaagacaggaatggctgttatctgagctaa<br>gcgggaaacgccctctctttggaccggatcttcccaaaaccgaagaggttgca<br>gatgtgttggacacttttcaaagtcattttctgagcttccttcggatagttttggtgctt<br>atattatctcaatggccactgctccatcagacgtgctcgctgttgagcttttgcaa<br>cgcgaatgcgggatcactgatcctctgagagttgtcccgttgttcgagaagcta<br>gcggatttagaatccgcacctgctgcagttgcccgtctcttctccatagaatggt<br>acagaaacaggatcaatggaaagcaagaagtcatgatcgggtactctgactcg<br>ggcaaagatgctggtcgtttatcagcggcttggcagttatacaagactcaagaa<br>gagctcgtgaaggtggcaaaagaatacggagtcaagctgacaatgttccacg<br>gaagaggtgggaccgttggacgaggaggtggacctacccatcttgctattttgt<br>ctcagcctccggataccattcatgggcaattgagggtaacggttcaaggtgaag<br>ttattgaacagtcttcggagaagagcacttatgctttaggactcttcagcgtttca<br>cagctgcaacacttgagcatggaatgcatccaccggtttcccctaagcctgagt<br>ggcgtgtcctcatggatgaaatggctataattgccactgaagaataccgttctgtt<br>gtcttcaaggagcccgttttgttgagtacttccgtctggcaacaccagagctcg<br>agtatggaaggatgaacataggaagccgaccatcaaaacgtaaaccaagcgg<br>aggaatcgagtcgctgcgtgcaatcccgtggatctttgcgtggactcagacga<br>ggttcacttacccgtgtggcttggctttggaggagcattcaaacgcgtgatacag<br>aaggacagtaagaatctcaacatgctcaaagagatgtacaaccaatggccattc<br>ttccgtgtcacaattgatctagtcgaaatggttttcgccaaaggagatcccggaa<br>ttgcggtctctgtatgaccgcctcctcgtctctgaagaacttcaaccattcggtgaa<br>caacttcgagttaactaccaagagaccagacgcctcctcctccaggttgcaggt<br>cacaaagacattttagaaggtgaccatacttgaggcaaaggctgcagatcgt<br>gacccatacatcacgacattgaacgtgtgtcaagcctatacactcaagcagatc<br>cgtgacccaagcttccacgtcaaagtccggcacatctctctaaggactacatg<br>gagtctagtccagcggctgagctcgtgaaactgaatccaaagagtgaatacgc<br>accgggacttgaagatacggttatcctcaccatgaagggtatcgctgctggtat<br>gcaaaacaccggttaaggcagtttaaaacgttcttgtaccattccctaaatctacg<br>ctatgtaatgtattatgttctatgatgtgatgaaatctctccaactcctatcccgtac<br>gcttttttaatgagtatgataatttcttgtgttattctattgttgttatgttaccatatctag<br>gaaatatatttctgaaagaaacaagaaaagaaatcttttctttttcgttctaagatgtt |
| PPC3 | SEQ ID NO: 14 At3g14940 | ataaatacttcactctgctttcctcaatcacatccatctctgaatctgattccaacatct<br>taaaccccttattccctaaacatcgaatttggttccttctcccacaatccgcagagat<br>ttcttcttttcagaagaagtaagagggtggcgaagaagatttgattgatcggcga<br>taatggcgggtcggaacatagagaagatggcatctattgatgctcagcttcggc<br>aactcgttcctgctaaagtcgaagacgataagctgttgagtacgatgctctt<br>ctccttgatcgcttctcgacattctccaggatttacacggcgaggatctccgtga<br>aacggttcaagagttatacgagctttctgctgagtatgaagggaagcgtgagcc<br>tagcaagcttgaggagctagggagtgtcctaacgagtttggatcctggtgactc<br>aattgttatctccaaggctttctctcacatgcttaacttagccaatttggctgagga<br>ggtgcagattgctcaccgtcgcaggatcaagaagctgaagaaaggtgatttcg<br>ttgatgagagttctgcaactactgacatattgaagagactttttaagaggctc<br>gtttcggatcttggtaagtctcctgaagagatctttgatgccttgaagaatcagac<br>tgtggatctggttttgactgctcatcctactcagtctgtgcgtagatcattgcttcag<br>aagcatggaggataagggactgtcttgctcaactctatgcaaaggacattact<br>cctgatgacaagcaggagctagatgagtctctgcaaagagagattcaagctgc<br>attccgaacagatgagattagaagaacacctccaaccccacaagatgaaatga |

-continued

| Name - activity | SEQ ID NO: and Genbank No. | sequence |
|---|---|---|
| | | gagctggaatgagttatttccacgagacaatctggaaaggtgtcccaagttctt gcgccgtgtggacacagctctgaaaaacattgggattgatgaacgtgttcctta caatgccccattgattcaattctcttcgtggatgggcggtgatcgtgatggtaatc cgagggtcacacctgaggtcactagagatgtgtgatgttggctagaatgatgg ctgccaatctctactataaccaaatcgagaatctgatgtttgagttatctatgtggc gttgcactgatgaattccgtgtgcgggcggatgaactgcacaggaactcaagg aaagatgctgcaaaacattacatagaattctggaagacaattcctccaactgag ccataccgtgtgattcttggtgatgtgagggataagctgtatcacacacgtgagc gttcccgccaattgctgagtaatggaatctcggatattcctgaagaagctaccttc actaatgtggaacagttcttggagcctcttgagctctgttaccgatcactatgttca tgtggtgacagcccgatagctgatgaagccttcttgatttcttgaggcaagtct ctaccttggactctccttgtgagacttgacatcaggcaagagtctgaacgcca cacagatgtcttggatgctatcaccaagcacttggacatcggttcctcctataga gactggtctgaagaaggccgacaggaatggcttcttgctgaactaagcggcaa acgtccacttttcggacctgatcttcccaaaaccgaagaaatttctgatgtcctgg acacattcaaagtcatatctgagctgccttcagattgttttggagcttatattatctct atggcaacttcacctagtgatgtgcttgcggttgagcttttacagcgcgaatgcc atgtgaaaaatccacttagagttgttccactctttgagaagctagctgatcttgaa gcagctcctgccgctgttgcagactcttttctatagactggtacaaaaaccgtat taacggtaaacaagaggttatgattggttactcagattcagggaaagatgcagg gcgtctctcagctgcttgggagctatacaaagctcaagaagagcttgtgaaggt tgctaagaaatatggagtgaagctaactatgttccatggccgtggtggcacagt cggaagaggaggtggtcctactcatcttgctatattgtctcagccaccagataca gttaatggctctcttcgagtcacggttcagggtgaagtcattgagcaatcatttgg ggaggcacacttatgctttagaacacttcaacgtttcacagcagctactctagag cacggaatgaaccctccgatttcaccaaaacccgagtggcgtgctttgcttgat gaaatggcggttgttgcaactgaggaataccgatctgtcgttttccaagaacctc gattcgtcgagtatttccgcctcgctactccggagctggagtatggacgtatgaa tattggaagtagaccttcaaagcgaaaaccaagcggtgggatcgaatctctcc gtgcaatcccatggatctttgcttggacgcaaacaagattccatcttcctgtatgg ttaggtttcggagcagcatttaggtatgcgatcaagaaggatgtgagaaaccttc acatgctgcaagatatgtataaacaatggcccttttccgagtcaccatcgatcta attgaaatggtgttcgccaagggagaccccgggatcgctgattgtacgacaaa cttcttgtctcagaagatttatgggcttttggagagaaactcagagccaactttgat gaaaccaagaacctcgtcctccagactgctggacataaagaccttcttgaagg agatccttacttgaaacagagactaaggctacgtgactcttacattacgacccctc aacgtttgccaagcctacacattgaagaggatccgtgatgcaaactacaatgtg actctgcgaccacacatttctaaagagatcatgcaatcaagcaaatcagcacaa gagctcgtcaagcttaaccccacgagtgaatacgcgcctggacttgaggacac acttatcttaaccatgaagggtattgctgcaggattgcaaaacaccggttaagtg agtcagtgaaagaaaacaaaacttcgaatctctcttttttatctaccctttttaataat ctcttttttttctagaatccaaaataattacggttggattacagtttactttatgtatcca ccgttgaaatcttaatcttccattgtcaaacgtcactgactctgtttctggaagtg taaacaagaacagagacagtgaatcttaatgttatcttcttttgtctttttcttt |
| PPC4 | SEQ ID NO: 15 At1g68750 | acaatgacggacacaacagacgatatcgcagaggaaatctcattccaaagctt cgaagatgactgcaaattgctcggtagtctcttccatgatgtgttacaaagggaa gttggcaacccattcatgaaaaagtcgaacgcattcggattcttgctcagagtg cgttaaatttgcgtatggctggtattgaggataccgcaaaccttttggagaagca attgactagtgaaatatccaaaatgccactagaagaagcttaacgttggctcgt acattcactcattctcttaacttaatgggcattgcagacactcatcacagaatgca caaagtccataacgttacacaacttgcaagatcttgtgatgatatattcagccagc tattgcaaagtggaatctctccagacgaactttataaaactgtttgcaaacagga ggtcgaaattgttcttactgctcatcctacccaaataaatcgaagaaccttgcagt acaagcatattagaattgctcatcttctagaatataacactagatcagatctaagc gttgaagatcgcgaaacgctcattgaagatttggttagagagattacttcactgtg gcaaactgatgagcttagacgtcagaaacctactccagttgatgaagctagagc tggtctaaacatagtggagcaatcccttttggaaagcagtaccacaatacctgcg tcgtgtcagcaattccttgaagaagtttacagggaagccacttccactaacatgc actcctatgaaatttggttcttggatgggaggtgatagagatggaaatccaaatg tcacggcaaaggtcacgaagaagtatctctcttgtctagatggatggctattga tttgtacataagagaggttgatagcttaagatttgaattatctacggatcgatgca gtgataggttttcaagattagctgataaaattcttgaaaaggattatgatagagga aaatcaaatttccaaaagcaacaaagttcatcatgcttgccaacacaacttccag ctagagctcaccttcctgcttgcattgactttggtgaatcacgacataccaaatttg aaattgcgacgacagattatatgccacccaatctccagaagcagaatgaacaa gacttttcggaaagcgactgggagaaaattgacaatggttcgcggtccggtctt acttctcgaggttcttttctcatctacttctcaacttcttctccagagaaaactatttga ggaatctcaggttgggaagactagtttccaaaagctactagaaccacctccactt aaacgagctggaagtgctccttatcgtattgttcttggagaagtaaaagaaaagc ttgtgaagacaagaagacttcttgaacttcttattgagggtcttccttgtgagtatg accctaaaaactcctatgaaacatcagatcagcttctcgaaccattgctcctctgtt acgaatctctgcaatcatcggtgctagggtactagctgatggacgacttgctg atctgattcgtagagtttctacctttggaatggttttggtgaaactcgacttacgcc aggaagctgcaagacattctgaagctttggatgcaattacaacatacttggatat gggtacttatagtgaatggatgaagagaagaaattagaattttttgacaagaga actaaaagggaaacgacctcttgttcctcaatgtattaaggttggtcctgacgtca |

| Name - activity | SEQ ID NO: and Genbank No. | sequence |
|---|---|---|
| | | aagaagtattggacacattccgagtcgctgctgaacttggaagtgaatcacttg gcgcttacgttatttctatggcttcaaatgcaagtgatgtcctcgctgtggaacttc ttcaaaaagatgctcgacttgctttaactagcgaacatggaaaaccatgtcctgg tggaacgctacgagtggtacctctcttttgaaacggtgaatgatttaagagccgct ggtccttcgataaggaaattgctctcaatcgattggtatagggaacacatccaaa agaaccacaacggtcaccaagaggtgatggttggatactctgattctggaaaa gatgctggacgttttactgcagcatgggaactctacaaagctcaagaaaatgttg ttgctgcttgtaatgaatttggaatcaaaataacattatttcatggacgaggagga agcattggtcgtggtggtggtccaacctatctcgctattcagtcccaaccaccag gctctgtaatgggctctttgcgttcaactgagcaaggtgagatggttcaagctaa gtttgggataccacaaacggctgttaggcaactagaggtatacacaaccgcgg ttctactcgctaccttaaagcctcctcagccaccctcgagaggaaaaatggcgaa acctaatggaagaaatctctggaatcagttgccaacactatagaagcacagtgt atgaaaacccagagtttctatcttattttcatgaggcaacaccgcaagcagaactt ggtttcctcaatataggaagccgaccaacacgaagaaagagctctagtggaat aggacatctccgagctatcccttgggtctttgcttggactcaaacaaggtttgttct tccagcttggcttggtgtaggggctggtttaaagggagtttctgagaagggtcat gcggatgatcttaaagagatgtacaaagaatggccatttttcagtccaccttga acttatagagatggtgttagctaaagcagacattccaatgaccaaacactacga cgaacaacttgtgtctgagaaaagaagaggacttggcactgagctaagaaaag aactaatgactactgagaagtacgttcttgtgataagtggtcacgagaaactctt gcaggacaataagagcttgaagaaactcattgatagtagacttccgtatctcaac gcaatgaacatgttacaagttgaaattcttaagaggctaagacgtgatgaagata acaataagctaagagatgcttgcttatcacaatcaatggtattgctgcaggaatg agaaataccggttaa |
| RBCS-1A | SEQ ID NO: 16 At1g67090 | tcagtcacacaaagagtaaagaagaacaatggcttcctctatgctctcttccgct actatggttgcctctccggctcaggccactatggtcgctcctttcaacggacttaa gtcctccgctgccttcccagccaccccgcaaggctaacaacgacattacttccat cacaagcaacggcggaagagttaactgcatgcaggtgtggcctccgattgga aagaagaagtttgagactctctcttaccttcctgaccttaccgattccgaattggct aaggaagttgactaccttatccgcaacaagtggattccttgtgttgaattcgagtt ggagcacggatttgtgtaccgtgagcacggtaactcaccggatactatgatg gacggtactggacaatgtggaagcttcccttgttcggttgcaccgactccgctc aagtgttgaaggaagtggaagagtgcaagaaggagtaccccaatgccttcatt aggatcatcggattcgacaacacccgtcaagtccagtgcatcagtttcattgcct acaagccaccaagcttcaccggttaatttccctttgcttttgtgtaaacctcaaaac tttatccccatctttgattttatccctgttttttctgctttttcttcttcttgggttttaat ttccggacttaacgtttgttttccggtttgcgagacatattctatcggattctcaact gtctgatgaaataaatatgtaatgttctataagtctttcaatttgatatgcatatcaac aaaaagaaaataggacaatgcggctacaaatatgaaatttacaagtttaagaac catgagtcgctaaagaaatcattaagaaaattagtttcac |
| RBCS-1B | SEQ ID NO: 17 At5g38430 | attaggcaaaagaagaagaagaagaagtaatggcttcctctatgctctcctctg ccgctgtggttacctcccccggctcaagccaccatggtcgctccattcactggttt gaagtcatccgcttctttcccggtcacccgcaaggccaacaacgacattacttc catcacaagcaatgggggaagagttagctgcatgaaggtgtggccaccaatc ggaaagaagaagtttgagactctatcttacctccctgaccttactgacgtcgaatt ggctaaggaagttgactaccttctccgcaacaaatggattccttgtgttgaattcg agttggagcacggatttgtgtaccgtgagcacggaaacactcccggatactac gatggacggtactggacaatgtggaagcttccattgttcggatgcaccgactcc gctcaagtgttgaaggaagttgaagaatgcaagaaggagtaccggggcgcctt cattaggatcatcggattcgacaacacccgtcaagtccaatgcatcagtttcatt gcctacaagccccaagcttcactgatgcttaaatccttttctggaatattcaatgt tgactatccggaacccaattttgtatggtcaatgtaaatttaagtaattattttgcca aagtgaaaaaactgaaggtttgttttctatcgtttcctctataaaaatctctattcat atcacttcatttctgctatatcacttttaactattttattcgttttatctcttttaactaac attttagttccttttaaatttctctccta |
| RBCS-2B | SEQ ID NO: 18 At5g38420 | caagtaagtaagagaaaaaccaaaagaagaagagaaacaacaagaagaagt aatggcttcctctatgttctcctccaccgctgtggttacctcccccggctcaagcca ccatggtcgctccattcaccggcttgaagtcatccgcttctttcccggtcacccg caaggccaacaacgacattacttccatcacaagcaacggaggaagagttagct gcatgaaggtgtggccaccaatcggaaagaagaagtttgagactctatcttacc tccctgaccttagtgacgttgaattggctaaggaagttgactaccttctccgcaac aagtggattccttgtgttgaattcgagttggagcacggatttgtgtaccgtgagca cggaaacactcccggatactatgatggacgatactggacaatgtggaagcttc cattgttcggatgcaccgactccgctcaagtgttgaaggaagttgaagaatgca agaaggagtaccctgcgcccttcattaggatcatcggttgcgacaacacccgtc aagtccaatgcatcagtttcattgcctacaagcccccaagcttcaccgaagctta atccccttctggaatattcagcgttgattattctggaacccatttctatgtggtcaa tgcaaatttaagaaattatttgccgacttaacagttgaggaactatgtttgaaagt gaaaatgttattcctatcagtttctctataattatagttatcatttcatttcattttgccc ttaaatctttgaaatcttattttcgtttagctccttaaacaacattgtggctccttaa attatcctcataattcttgct |

| Name - activity | SEQ ID NO: and Genbank No. | sequence |
|---|---|---|
| RBCS-3B | SEQ ID NO: 19 At5g38410 | gggcttttcgcctttaggggggttctcattatataaagatgacaacaccagtagga<br>aaacaagtcagtaagtaaacgagcaaaagaagaagagaaacaacaagaagt<br>agtaatggcttcctctatgctctcctccgccgctgtggttacatccccggctcag<br>gccaccatggtcgctccattcaccggcttgaagtcatccgctgcattcccggtc<br>acccgcaagaccaacaaggacatcacttccatcgcaagcaacgggggaaga<br>gttagctgcatgaaggtgtggccaccaattggaaagaagaagtttgagactcta<br>tcttacctccctgaccttagtgacgtcgaattggctaaggaagttgactaccttct<br>ccgcaacaagtggattccttgtgttgaattcgagttagagcacggaaacactcc<br>cggatactacgatggacggtactggacaatgtggaagcttccattgttcggatg<br>caccgactccgctcaagtgttgaaggaagttgaagaatgcaagaaggagtacc<br>cgggcgccttcattaggatcatcggattcgacaacacccgtcaagtccaatgca<br>tcagtttcattgcctacaagcccccaagcttaccgaagcttaatttcttttctaaa<br>acattcttatgaattatctctgctcatttcatttcctattgtctgtgttcttttttctcttat<br>gagacaatttctatcggattgtcaaatgtctgatttatgaatatgtaatttatatatcc<br>gtgcgtcttgattttttccgatggttaactagtttgaaaatttccgatgagataagac<br>aacatacaaaaaatcgaataaattgtgtaaatatagataatagtgacatatggatt<br>tgtattcatatttgtccattgttttaagaggaaaaaagttacaaaatcttattttcttaa<br>taataagtaaatttactttt |

Example 6

Exemplary Carbonic Anhydrase Enzymes to Control Plant CO$_2$ Uptake and Water Use Efficiency The invention provides compositions and methods for down-regulating or decreasing carbon dioxide (CO$_2$) and/or water exchange in a guard cell of a plant, plant cell, plant leaf, plant organ or plant part comprising inter alia use of a polypeptide having carbonic anhydrase activity. Carbonic anhydrase-encoding nucleic acids from any carbonic anhydrase gene, e.g., including plant and bacterial genes, can be used to practice this invention; for example, a nucleic acid from any carbonic anhydrase gene of any plant can be used, including any carbonic anhydrase-encoding nucleic acid sequence from any gene family of *Arabidopsis*, e.g., any carbonic anhydrase-encoding nucleic acid sequence from an *Arabidopsis* family, e.g., from *Arabidopsis thaliana*, can be used to practice the compositions and methods of this invention, such as the exemplary carbonic anhydrase-encoding nucleic acid sequences:

| Name - activity | SEQ ID NO: and Genbank No. | sequence |
|---|---|---|
| CA2 Full length AtβCA2 cDNA | SEQ ID NO: 20 At5g14740 | aaatagagaagctcttcaagtatccgatgttttttgtttaatcaacaagaggcggagat<br>acgggagaaattgcatgtgtaatcataaaatgtagatgttagcttcgtcgttttttactat<br>agtttagttctatatatatttttcgtcattacaatctattataatttacttatatgata<br>gtataattaagttgtttgtaataatctgtacaaagatgttgtgttctcataaaaaattcaa<br>ttttgtaaagaagctctacatgttccttgctctgtaaacatggtccccttttggactaca<br>gtttctcgaaatggctcatcagactcagagacgactctccaatctgcttcaaaagcc<br>acaaaacagtataaatatccttctcttcgtccctctcatcgcctgtctctcctcttcctct<br>tcccgttccatttatccgcaaacggagcttgttttcggtgcacctgcttcagccacttc<br>aaacttgaactgagaaggatgggaaacgaatcatatgaagacgccatcgaagctc<br>tcaagaagcttctcattgagaaggatgatctgaaggatgtagctgcggccaaggtg<br>aagaagatcacggcggagcttcaggcagcctcgtcatcggacagcaaatctttg<br>atcccgtcgaacgaattaaggaaggcttcgtcaccttcaagaaggagaaatacga<br>gaccaatcctgctttgtatggtgagctcgccaaaggtcaaagcccaaagtacatgg<br>tgtttgcttgttcggactcacgagtgtgcccatcacacgtactagacttccatcctgg<br>agatgccttcgtggtcgtaatatcgccaatatggttcctccttttgacaaggtcaaat<br>atgcaggagttggagccgccattgaatacgctgtcttgcaccttaaggtggaaaac<br>attgtggtgataggggcacagtgcatgtggtggcatcaaggggcttatgtcatttcctc<br>ttgacggaaacaactctactgacttcatagaggattgggtcaaaatctgtttaccagc<br>aaagtcaaaagttttggcagaaagtgaaagttcagcatttgaagaccaatgtggcc<br>gatgcgaaagggaggcagtgaatgtgtcactagcaaacctattgacatatccatttg<br>tgagagaaggagttgtgaaaggaacacttgctttgaagggaggctactatgactttt<br>gttaatggctcctttgagctttgggagctccagtttggaatttccccgttcattctatat<br>gaactaacacatcaccatcaccatcgctaccaccaccatcacaaacatcatcatcgt<br>cgtcatcatcatgatcagcatcttcatatataaatgttttactcttatttaattgctacttgt<br>aatggtatacatttacttgcgatgagcttcttttccttcattatccagttataaaataaata<br>aataaatcatgtttacttttcacagatatcgtttttgctgaagttgctttgattt |
| Full length AtαCA1 cDNA | SEQ ID NO: 21 AtαCA1 (At3g52720) | ATGCAGTAATCTGATAAAACCCTCCACAGAGATTTCCA<br>ACAAAACAGGAACTAAAACACAAGATGAAGATTATGA<br>TGATGATTAAGCTCTGCTTCTTCTCCATGTCCCTCATCT<br>GCATTGCACCTGCAGATGCTCAGACAGAAGGAGTAGT<br>GTTTGGATATAAAGGCAAAAATGGACCAAACCAATGG<br>GGACACTTAAACCCTCACTTCACCACATGCGCGGTCGG<br>TAAATTGCAATCTCCAATTGATATTCAAAGGAGGCAAA<br>TATTTTACAACCACAAATTGAATTCAATACACCGTGAA<br>TACTACTTCACAAACGCAACACTAGTGAACCACGTCTG<br>TAATGTTGCCATGTTCTTCGGGGAGGGAGCAGGAGAT |

| Name - activity | SEQ ID NO: and Genbank No. | sequence |
|---|---|---|
| | | GTGATAATAGAAAACAAGAACTATACCTTACTGCAAA
TGCATTGGCACACTCCTTCTGAACATCACCTCCATGGA
GTCCAATATGCAGCTGAGCTGCACATGGTACACCAAG
CAAAAGATGGAAGCTTTGCTGTGGTGGCAAGTCTCTTC
AAAATCGGCACTGAAGAGCCTTTCCTCTCTCAGATGAA
GGAGAAATTGGTGAAGCTAAAGGAAGAGAGACTCAAA
GGGAACCACACAGCACAAGTGGAAGTAGGAAGAATCG
ACACAAGACACATTGAACGTAAGACTCGAAAGTACTA
CAGATACATTGGTTCACTCACTACTCCTCCTTGCTCCG
AGAACGTTTCTTGGACCATCCTTGGCAAGGTGAGGTCA
ATGTCAAAGGAACAAGTAGAACTACTCAGATCTCCATT
GGACACTTCTTTCAAGAACAATTCAAGACCGTGTCAAC
CCCTCAACGGCCGGAGAGTTGAGATGTTCCACGACCA
CGAGCGTGTCGATAAAAAAGAAACCGGTAACAAAAAG
AAAAAACCCAATTAAAATAGTTTTACATTGTCTATTGG
TTTGTTTAGAACCCTAATTAGCTTTGTAAAACTAATAA
TCTCTTATGTAGTACTGTGTTGTTGTTTACGACTTGATA
TACGATTTCCAAAT |
| Full length AtαCA2 cDNA | SEQ ID NO: 22 AtαCA2 (At2g28210) | ATGGATGAATATGTAGAGGATGAACACGAATTCAGCT
ACGAATGGAACCAAGAGAACGGGCCAGCGAAATGGG
GAAAGCTAAGACCGGAATGGAAAATGTGCGGAAAAG
GAGAAATGCAATCGCCTATTGATCTTATGAACAAAAG
AGTTAGACTTGTTACTCATCTTAAAAAGCTTACTAGAC
ACTACAAACCTTGTAACGCCACTCTCAAAAATAGAGG
CCATGATATGATGCTGAAATTTGGAGAAGAAGGGTCA
GGGAGTATTACGGTCAATGGAACTGAGTATAAACTCTT
ACAGCTTCATTGGCATTCTCCCTCTGAACATACTATGA
ATGGAAGAAGGTTTGCTCTCGAGCTACACATGGTTCAC
GAAAACATTAACGGAAGTTTGGCTGTAGTCACAGTCCT
CTACAAAATCGGAAGGCCAGATTCTTTTCTCGGATTGC
TGGAAAATAAATTGTCGGCAATTACAGATCAAAATGA
GGCGGAGAAATATGTAGATGTGATTGACCCAAGGGAT
ATTAAGATTGGGAGCAGAAAATTTTATAGATACATTGG
ATCACTTACTACTCCTCCTTGTACGCAAAATGTTATTTG
GACCGTCGTTAAAAAGGTAAATACTCATCGTTATTTTC
TTCTCTTTTTTACTTAATCAAACATAGCATTAATAGATC
ATTACAAGGTACTAATAGTGTGAATATCCATATCCAAA
AGGTTTATCCATCTACATGTTA |
| Full length AtαCA3 cDNA | SEQ ID NO: 23 AtαCA3 (At5g04180) | AAAACACATTCTGAAGAAGAAGAAGAAAATA
AGAAAAAACAAAAGATGAAAACCATTATCCTTTT
TGTAACATTTCTTGCTCTTTCTTCTTCATCTCTAGC
CGATGAGACAGAGACTGAATTTCATTACAAACCC
GGTGAGATAGCCGATCCCTCGAAATGGAGCAGTA
TCAAGGCTGAATGGAAAATTTGCGGGACAGGGAA
GAGGCAATCGCCAATCAATCTTACTCCAAAAATA
GCTCGCATTGTTCACAATTCTACAGAGATTCTTCA
GACATATTACAAACCTGTAGAGGCTATTCTTAAGA
ACCGTGGATTCGACATGAAGGTTAAGTGGGAAGA
CGATGCAGGGAAGATCGTGATCAATGATACCGAC
TATAAATTGGTTCAAAGCCACTGGCACGCACCTTC
AGAGCATTTTCTCGATGGACAGAGGTTGGCAATG
GAACTTCACATGGTACACAAAAGTGTAGAAGGGC
ACTTGGCAGTGATTGGAGTTCTCTTCAGAGAAGG
AGAACCAAATGCTTTCATTTCGCGGATCATGGACA
AGATCCATAAGATCGCAGACGTACAAGATGGAGA
GGTCAGCATCGGAAAGATAGATCCAAGAGAATTT
GGATGGGATCTTACAAAGTTTTATGAATACAGAG
GTTCTCTCACGACTCCTCCTTGCACGGAAGATGTC
ATGTGGACCATCATCAACAAGGTGGGGACTGTTT
CACGTGAGCAAATTGATGTATTGACAGATGCTCGT
CGCGGTGGTTATGAGAAGAACGCGAGACCAGCTC
AACCTCTGAACGGACGTCTGGTTTATTTAAACGAG
CAGTCCAGTCCAAGTCCAACTCCACGGCTAAGAA
TACCACGAGTTGGTCCGGTCAAGACAGTCTTATA
GGACAAGGCAACTCCGAGCCCTAATTTCCATACA
AAGAAAATTCGGAAAAGAATTTTGAAGATGTATG
AAAATTGGGAGCCATAACTATTTTTTTTTAACTAT
TCTTTTGATTAAAAGATAAAACTACGCAATATTAT
ATGCATAAAGTTTTCTTTTATACATGTATTCCAAT
AAACAAGATGTAATAATATCCAACCATAATGAGT
TGTTTGATTATTTTATAACACAAGATCTCTCAC |

| Name - activity | SEQ ID NO: and Genbank No. | sequence |
|---|---|---|
| Full length AtαCA4 cDNA | SEQ ID NO: 24 AtαCA4 (At4g20990) | ATGGATACCAACGCAAAAACAATTTTCTTCATGGC TATGTGTTTCATCTATCTATCTTTCCCTAATATTTC ACACGCTCATTCTGAAGTCGACGACGAAACTCCA TTTACTTACGAACAAAAAACGGAAAAGGGACCAG AGGGATGGGGCAAAATAAATCCGCACTGGAAAGT TTGTAACACCGGAAGATATCAATCCCCGATCGATC TTACTAACGAAAGAGTCAGTCTTATTCATGATCAA GCATGGACAAGACAATATAAACCAGCTCCGGCTG TAATTACAAACAGAGGCCATGACATTATGGTATC ATGGAAAGGAGATGCTGGGAAGATGACAATACGG AAAACGGATTTTAATTTGGTGCAATGCCATTGGCA TTCACCTTCTGAGCATACCGTTAACGGAACTAGGT ACGACCTAGAGCTTCACATGGTTCACACGAGTGC ACGAGGCAGAACTGCGGTTATCGGAGTTCTTTAC AAATTAGGCGAACCTAATGAATTCCTCACCAAGC TACTAAATGGAATAAAAGCAGTGGGAAATAAAGA GATAAATCTAGGGATGATTGATCCACGAGAGATT AGGTTTCAAACAAGAAAATTCTATAGATACATTG GCTCTCTCACTGTTCCTCCTTGCACTGAAGGCGTC ATTTGGACTGTCGTCAAAAGGGTGAACACAATAT CAATGGAGCAAATTACAGCTCTTAGGCAAGCCGT TGACGATGGATTTGAGACAAATTCAAGACCGGTT CAAGACTCAAAGGGAAGATCAGTTTGGTTCTATG ATCCAAATGTTTGA |
| Full length AtαCA5 cDNA | SEQ ID NO: 25 AtαCA5 (At1g08065) | GATCAACATCTCCTTGAAGTTGTTTCATAAGAATA AGAGCTATAAAAGAGGATAAAACCAAAATTTGAA TTTTTTTCTTCTATCTCTCTCCCCAAGATATATAGC ACAAGAAAATGAAGATACCATCAATTGGCTATGT CTTTTTCCTTATCTTCATCTCTATTACAATTGTTTC GAGTTCACCAGATCATGGAGAAGTTGAGGACGAA ACGCAGTTTAACTACGAGAAGAAAGGAGAGAAG GGGCCAGAGAACTGGGGAAGACTAAAGCCAGAG TGGGCAATGTGTGGAAAAGGCAACATGCAGTCTC CGATTGATCTTACGGACAAAAGAGTCTTGATTGAT CATAATCTTGGATACCTTCGTAGCCAGTATTTACC TTCAAATGCCACCATTAAGAACAGAGGCCATGAT ATCATGATGAAATTTGAAGGAGGAAATGCAGGTT TAGGTATCACTATTAATGGTACTGAATATAAACTT CAACAGATTCATTGGCACTCTCCTTCCGAACACAC ACTCAATGGCAAAAGGTTTGTTCTTGAGGAACAC ATGGTTCATCAGAGCAAAGATGGACGCAACGCTG TTGTCGCTTTCTTTTACAAATTGGGAAAACCTGAC TATTTTCTCCTCACGTTGGAAAGATACTTGAAGAGGA TAACTGATACACACGAATCCCAGGAATTTGTCGAGATG GTTCATCCTAGAACATTCGGTTTTGAATCAAAACACTA TTATAGATTTATCGGATCACTTACAACTCCACCGTGTT CTGAAAATGTGATTTGGACGATTTCCAAAGAGATGAG GACTGTGACATTAAAACAATTGATCATGCTTCAGTGA CTGTACACGATCAATCTAACTCAAATGCTAGACCGCTT CAGCGTAAAAATGAGCGTCCGGTGGCACTTTACATACC AACATGGCATAGTAAACTATATTAAATATTTAAGTTTG GTTTATATTCTTTCTAGTAATCTTTGAAATATTGTAAGA GATAATGCTTCTAATAAATAACATTGGATTTATTGGAA TTAATGTATTGAAAAAACTATGCAAATACTACAGTGTA TTTTGGAACGACC |
| Full length AtαCA6 cDNA | SEQ ID NO: 26 AtαCA6 (At4g21000) | ATGGATGCCAACACAAAAACAATTTTATTTTTGTAGT GTTCTTCATCGATTTATTTTCCCTAATATTTTATTCGTT TATGCTCGTGAAATCGGCAACAAACCGCTATTTACATA CAAACAAAAAACAGAGAAAGGACCAGCGGAATGGGG CAAATTAGACCCTCAATGGAAAGTTTGTAGCACCGGA AAAATTCAATCTCCGATTGATCTCACTGACGAAAGAGT CAGTCTTATTCATGATCAAGCCTTGAGTAAACATTACA AACCAGCTTCGGCTGTAATTCAAAGTAGAGGACATGA CGTTATGGTATCGTGGAAGGAGATGGTGGGAAAATA ACAATACATCAAACGGATTATAAATTGGTGCAGTGCC ATTGGCATTCACCGTCTGAGCATACCATTAACGGAACT AGCTATGACCTAGAGCTTCACATGGTTCACACGAGTGC TAGTGGCAAAACCACTGTGGTTGGAGTTCTTTATAAAT TAGGTGAACCTGATGAATTCCTCACAAAGATACTAAAT GGAATAAAAGGAGTAGGGAAAAAGAGATAGATCTA GGAATCGTGGATCCTCGAGATATTGATTTGAAACCAA CAATTTCTATAGATACATTGGCTCTCTCACTATTCCTCC ATGCACCGAAGGCGTTATTTGGACCGTTCCAGAAAAGG |

| Name - activity | SEQ ID NO: and Genbank No. | sequence |
|---|---|---|
| | | GTATTATATTTTTTTGTTTCTGTTATAGATTAATTATCT<br>TCGTTACACCTTACATAAACATTTTTTGGATTTTTGTTT<br>TTGTATTTTGGTGTATGCTAATGTAA |
| Full length AtαCA7 cDNA | SEQ ID NO: 27 AtαCA7 (At1g08080) | ATGGTGAACTACTCATCAATCAGTTGCATCTTCTTTGT<br>GGCTCTGTTTAGTATTTTCACAATTGTTTCGATTTCGAG<br>TGCTGCTTCAAGTCACGGAGAAGTTGAGGACGAACGC<br>GAGTTTAACTACAAGAAGAACGATGAGAAGGGGCCAG<br>AGAGATGGGGAGAACTTAAACCGGAATGGGAAATGTG<br>TGGAAAAGGAGAGATGCAATCTCCCATAGATCTTATG<br>AACGAGAGAGTTAACATTGTTTCTCATCTTGGAAGGCT<br>TAATAGAGACTATAATCCTTCAAATGCAACTCTTAAGA<br>ACAGAGGCCATGACATCATGTTAAAATTTGAAGATGG<br>AGCAGGAACTATTAAGATCAATGGTTTTGAATATGAAC<br>TTCAACAGCTTCACTGGCACTCTCCGTCTGAACATACT<br>ATTAATGGAAGAAGGTTTGCACTTGAGCTGCATATGGT<br>TCACGAAGGCAGGAATAGAAGAATGGCTGTTGTGACT<br>GTGTTGTACAAGATCGGAAGAGCAGATACTTTTATCAG<br>ATCGTTGGAGAAAGAATTAGAGGGCATTGCTGAAATG<br>GAGGAGGCTGAGAAAAATGTAGGAATGATTGATCCCA<br>CCAAAATTAAGATCGGAAGCAGAAAATATTACAGATA<br>CACTGGTTCACTTACCACTCCTCCTTGCACTCAAAACG<br>TTACTTGGAGCGTCGTTAGAAAGGTTAGGACCGTGACA<br>AGAAAACAAGTGAAGCTCCTCCGCGTGGCAGTGCACG<br>ATGATGCTAATTCGAATGCGAGGCCGGTTCAACCAACC<br>AACAAGCGCATAGTGCACTTATACAGACCAATAGTTTA<br>ATATATGAAGATACTGAAAGCTTTTACTAATC |
| Full length AtαCA8 cDNA | SEQ ID NO: 28 AtαCA8 (At5g56330) | ATGAAGATATCATCACTAGGATGGGTCTTAGTCCTTAT<br>CTTCATCTCTATTACCATTGTTTCGAGTGCACCAGCACC<br>TAAACCTCCTAAACCTAAGCCTGCACCAGCACCTACAC<br>CTCCTAAACCTAAGCCCACACCAGCACCTACACCTCCT<br>AAACCTAAGCCCAAACCAGCACCTACACCTCCTAAAC<br>CTAAGCCTGCACCAGCACCTACACCTCCTAAACCTAAG<br>CCCGCACCAGCACCTACACCTCCTAAACCTAAGCCCAA<br>ACCAGCACCTACACCTCCTAATCCTAAGCCCACACCAG<br>CACCTACACCTCCTAAACCTAAGCCTGCACCAGCACCA<br>GCACCAACACCAGCACCGAAACCTAAACCTGCACCTA<br>AACCAGCACCAGGTGGAGAAGTTGAGGACGAAACCGA<br>GTTTAGCTACGAGACGAAAGGAAACAAGGGGCCAGCG<br>AAATGGGGAACACTAGATGCAGAGTGGAAAATGTGTG<br>GAATAGGCAAAATGCAATCTCCTATTGATCTTCGGGAC<br>AAAAATGTGGTAGTTAGTAATAAATTTGGATTGCTTCG<br>TAGCCAGTATCTGCCTTCTAATACCACCATTAAGAACA<br>GAGGTCATGATATCATGTTGAAATTCAAAGGAGGAAA<br>TAAAGGTATTGGTGTCACTATCCGTGGTACTAGATATC<br>AACTTCAACAACTTCATTGGCACTCTCCTTCCGAACAT<br>ACAATCAATGGCAAAAGGTTTGCGCTAGAGGAACACT<br>TGGTTCATGAGAGCAAAGATAAACGCTACGCTGTTGTC<br>GCATTCTTATACAATCTCGGAGCATCTGACCCTTTTCTC<br>TTTTCGTTGGAAAAACAATTGAAGAAGATAACTGATAC<br>ACATGCGTCCGAGGAACATATTCGCACTGTGTCAAGTA<br>AACAAGTGAAGCTTCTCCGTGTGGCTGTACACGATGCT<br>TCAGATTCAAATGCCAGGCCGCTTCAAGCAGTCAATAA<br>GCGCAAGGTATATTTATACAAACCAAAGGTTAAGTTA<br>ATGAAGAAATACTGTAATATAAGTTCTTACTAG |
| Full length AtβCA1 cDNA | SEQ ID NO: 7 AtβCA1 (At3g01500) | ATGAAGATATCATCACTAGGATGGGTCTTAGTCCTTAT<br>CTTCATCTCTATTACCATTGTTTCGAGTGCACCAGCACC<br>TAAACCTCCTAAACCTAAGCCTGCACCAGCACCTACAC<br>CTCCTAAACCTAAGCCCACACCAGCACCTACACCTCCT<br>AAACCTAAGCCCAAACCAGCACCTACACCTCCTAAAC<br>CTAAGCCTGCACCAGCACCTACACCTCCTAAACCTAAG<br>CCCGCACCAGCACCTACACCTCCTAAACCTAAGCCCAA<br>ACCAGCACCTACACCTCCTAATCCTAAGCCCACACCAG<br>CACCTACACCTCCTAAACCTAAGCCTGCACCAGCACCA<br>GCACCAACACCAGCACCGAAACCTAAACCTGCACCTA<br>AACCAGCACCAGGTGGAGAAGTTGAGGACGAAACCGA<br>GTTTAGCTACGAGACGAAAGGAAACAAGGGGCCAGCG<br>AAATGGGGAACACTAGATGCAGAGTGGAAAATGTGTG<br>GAATAGGCAAAATGCAATCTCCTATTGATCTTCGGGAC<br>AAAAATGTGGTAGTTAGTAATAAATTTGGATTGCTTCG<br>TAGCCAGTATCTGCCTTCTAATACCACCATTAAGAACA<br>GAGGTCATGATATCATGTTGAAATTCAAAGGAGGAAA<br>TAAAGGTATTGGTGTCACTATCCGTGGTACTAGATATC<br>AACTTCAACAACTTCATTGGCACTCTCCTTCCGAACAT<br>ACAATCAATGGCAAAAGGTTTGCGCTAGAGGAACACT<br>TGGTTCATGAGAGCAAAGATAAACGCTACGCTGTTGTC |

| Name - activity | SEQ ID NO: and Genbank No. | sequence |
|---|---|---|
| | | GCATTCTTATACAATCTCGGAGCATCTGACCCTTTTCTC<br>TTTTCGTTGGAAAAACAATTGAAGAAGATAACTGATAC<br>ACATGCGTCCGAGGAACATATTCGCACTGTGTCAAGTA<br>AACAAGTGAAGCTTCTCCGTGTGGCTGTACACGATGCT<br>TCAGATTCAAATGCCAGGCCGCTTCAAGCAGTCAATAA<br>GCGCAAGGTATATTTATACAAACCAAAGGTTAAGTTA<br>ATGAAGAAATACTGTAATATAAGTTCTTACTAG |
| Full length AtβCA3 cDNA | SEQ ID NO: 29 AtβCA3 (At1g23730) | CTAGAGAGCATCTTCTTATATCAACTAAACTTTGTATT<br>CATTTCCAAGTATCACTCTAAATCATCTTTTTCGAATTC<br>GCCTCCCAAGATATGTCGACAGAGTCGTACGAAGACG<br>CCATTAAAAGACTCGGAGAGCTTCTCAGTAAGAAATC<br>GGATCTCGGGAACGTGGCAGCCGCAAAGATCAAGAAG<br>TTAACGGATGAGTTAGAGGAACTTGATTCCAACAAGTT<br>AGATGCCGTAGAACGAATCAAATCCGGATTTCTCCATT<br>TCAAGACTAATAATTATGAGAAGAATCCTACTTTGTAC<br>AATTCACTTGCCAAGAGCCAGACCCCCAAGTTTTTGGT<br>GTTTGCTTGTGCGGATTCACGAGTTAGTCCATCTCACA<br>TCTTGAATTTCCAACTTGGGAAGCCTTCATCGTTAGA<br>AACATTGCAAACATGGTGCCACCTTATGACAAGACAA<br>AGCACTCTAATGTTGGTGCGGCCCTTGAATATCCAATT<br>ACAGTCCTCAACGTGGAGAACATTCTTGTTATTGGACA<br>CAGCTGTTGTGGTGGAATAAAGGGACTCATGGCCATTG<br>AAGATAATACAGCTCCCACTAAGACCGAGTTCATAGA<br>AAACTGGATCCAGATCTGTGCACCGGCCAAGAACAGG<br>ATCAAGCAGGATTGTAAAGACCTAAGCTTTGAAGATC<br>AGTGCACCAACTGTGAGAAGGAAGCCGTGAACGTGTC<br>CTTGGGGAATCTTTTGTCTTACCCATTCGTGAGAGAAA<br>GAGTGGTGAAGAACAAGCTTGCCATAAGAGGAGCTCA<br>CTATGATTTCGTAAAAGGAACGTTTGATCTTTGGGAAC<br>TTGACTTCAAGACTACCCCTGCCTTTGCCTTGTCTTAAA<br>AGATTCCTCCTACTCAAATATTTTCTCTATGTTGTTTCT<br>AATTATGTTCTTATAATCTTCTTCTGTTGCTTCTGTAAT<br>GTCATCTTTGCTACTTCTATTCCAATAGAAATGAATAA<br>AGCTTTAAAGAGC |
| Full length AtβCA5 cDNA | SEQ ID NO: 30 AtβCA5 (At4g33580) | TTGTTGTGTAAAACTCTTGTTCCTCTTCCTCTTCAACGT<br>GAACACTTCTATTTCTCAGAGAACATTCACCTATATGT<br>CTTTCTTCAAGGAGAAGTCTTCCTCTTTCCAGATTTAGA<br>TGAACACTCTTCAGATGCTTGTGCCTTATTGATCCAG<br>ATTCGAAGTACCCAACTTTACTCTCTAGACCTTTTTCAT<br>GGCAGCCACTCCCACACACTTCTCTGTCTCCCATGATC<br>CTTTTTCTTCCACGTCTCTCCTTAATCTCCAAACTCAAG<br>CGATCTTTGGTCCCAATCACAGTTTAAAGACAACCCAG<br>TTGAGAATTCCAGCTTCTTTCAGAAGAAAAGCTACAAA<br>CTTGCAAGTGATGGCTTCAGGAAAGACACCTGGACTG<br>ACTCAGGAAGCTAATGGGGTTGCAATTGATAGACAAA<br>ACAACACTGATGTATTTGACGACATGAAACAGCGGTTC<br>CTGGCCTTCAAGAAGCTTAAGTACATCAGGGATGACTT<br>TGAACACTACAAAATCTGGCAGATGCTCAAGCTCCA<br>AAGTTTCTGGTGATTGCTTGTGCAGACTCTAGAGTTTG<br>TCCTTCTGCTGTCCTGGGATTCCAACCGGGTGACGCAT<br>TCACTGTTCGTAACATTGCAAATTTAGTACCTCCATAT<br>GAGTCTGGACCTACTGAAACCAAAGCTGCTCTAGAGTT<br>CTCTGTGAATACTCTTAATGTGGAAAACATCTTAGTCA<br>TTGGTCATAGCCGGTGTGGAGGAATTCAAGCTTTAATG<br>AAAATGGAAGACGAAGGAGATTCCAGAAGTTTCATAC<br>ACAACTGGGTAGTTGTGGGAAAGAAGGCAAAGGAAAG<br>CACAAAAGCTGTTGCTTCAAACCTCCATTTTGATCATC<br>AGTGCCAACATTGTGAAAAGGCATCGATAAATCATTC<br>ATTAGAAAGGCTGCTTGGGTACCCGTGGATAGAAGAG<br>AAAGTGCGGCAAGGTTCACTGTCTCTCCATGGTGGATA<br>CTATAATTTTGTTGATTGTACGTTCGAGAAATGGACAG<br>TGGATTATGCAGCAAGCAGAGGTAAGAAGAAGGAAGG<br>CAGTGGAATCGCTGTTAAAGACCGGTCAGTTTGGTCTT<br>GACTTACGACTATCTCAATCTTCATAGAGTTTTTTTTCA<br>TAATTTATAGAGAAACATCAAACCCCTTTTGGTTGGGA<br>TTATCATGTGTTTGTTCCACTTGTGTGTTGAAGTCATTT<br>TCCTTCTTCTGTCTTATTGAGGCAGGGACTAATGTTTGT<br>TTTATCTTTCAGTTGTTTCGTTTAAATTCCACATTTGTG<br>CAATGAACTGGTTGGTGTTTCTTTAAGATATAATCATT<br>TTGCCACTGTAGTGAGATCGGAGGCATGCAT |

| Name - activity | SEQ ID NO: and Genbank No. | sequence |
|---|---|---|
| Full length AtγCA1 cDNA | SEQ ID NO: 31 AtγCA1 (At1g19580) | ATATTAAACCACTGTAACTGTAATTTATTGTTTCGCCGT CCCGGAATGTTCCTGTTGAAATCCATTTTCGCTGATTTT TTTTCTTCCGTCTCTTCTTCAGCTTCGACCATTTTCGTCT TCTTCATTCAGTGTTGAGTCCTCGTTTACCTGTGAGCTC GAAGAAAGTGACGATCAATGGGAACCCTAGGCAGAGC ATTTTACTCGGTCGGTTTTTGGATCCGTGAGACTGGTC AAGCTCTTGATCGCCTCGGTTGTCGCCTTCAAGGCAAA AATTACTTCCGAGAACAACTGTCAAGGCATCGGACACT GATGAATGTATTTGATAAGGCTCCGATTGTGGACAAGG AAGCTTTTGTGGCACCAAGCGCCTCAGTTATTGGGGAC GTTCACATTGGAAGAGGATCGTCCATTTGGTATGGATG CGTATTACGAGGCGATGTGAACACCGTAAGTGTTGGGT CAGGAACTAATATTCAGGACAACTCACTTGTGCATGTG GCAAAATCAAACTTAAGCGGGAAGGTGCACCCAACCA TAATTGGAGACAATGTAACCATTGGTCATAGTGCTGTT TTACATGGATGTACTGTTGAGGATGAGACCTTTATTGG GATGGGTGCGACACTTCTTGATGGGGTCGTTGTTGAAA AGCATGGGATGGTTGCTGCTGGTGCACTTGTACGACAA AACACCAGAATTCCTTCTGGAGAGGTATGGGGAGGAA ACCCAGCAAGGTTCCTCAGGAAGCTCACTGATGAGGA AATTGCTTTTATCTCAGTCAGCAACAAACTACTCAA ACCTCGCACAGGCTCACGCTGCAGAGAATGCAAAGCC ATTAAATGTGATTGAGTTCGAGAAGGTTCTACGCAAGA AGCATGCTCTAAAGGACGAGGAGTATGACTCAATGCT CGGAATAGTGAGAGAAACTCCACCAGAGCTTAACCTC CCTAACAACATACTGCCTGATAAAGAAACCAAGCGTC CTTCTAATGTGAACTGATTTTTCAGGGGTATGTTTTCTG GCCGAAGCCCTACAGGGTGAGATACTCAAGGGGATTA TGTTTCGGTCTCTGGTTTGAATATGGCAGGTAGAGTAC ATTAGGGTAGACGGATTTACAGCTTTTGAAGAAGCTAT GTTCAACATTTTTTCATGGTTTCTTAGGGAGTATTATTG TCTAATCAAACTTTGTATGTTATCACTTCGGTCTTTTGA ACGTAAGAATCAAGTTCATGAAACATGAGTGAATATT AGTCTGATGCATGTGCGTATGCAAAAATCCATGTGCGC CTATGTTGCTAGGCAAGCATGAAGAATAAAGATCCAA ACTGGATATATCATATATTTATCTTTTTATAATTACTGC |
| Full length AtγCA2 cDNA | SEQ ID NO: 32 AtγCA2 (At1g47260) | CGAACTCACTCGAGTTAAAAAAAAAAATCCTCCCATC AATACGCCTCCATAAACCTCTCTCTATCTGGTGGAGCG ACACCAAAAACAACAAAGCCTTCTCATTTTCACACTTT GGGTAATCGGAGAATCACAAAAAAATGGGAACCCTAG GACGAGCAATTTACACTGTGGGTAACTGGATTCGTGGA ACTGGTCAAGCTCTTGATCGCGTTGGTTCTCTTCTTCAA GGAAGTCACCGTATCGAGGAACATCTGTCGAGGCATC GGACGTTGATGAATGTGTTTGATAAATCACCATTGGTG GATAAAGATGTGTTTGTGGCTCCGAGTGCTTCTGTTAT TGGTGATGTTCAGATCGGAAAAGGCTCGTCGATTTGGT ATGGCTGTGTTCTTCGAGGTGATGTGAATAACATCAGT GTTGGATCTGGGACGAATATCCAAGATAATACGCTTGT ACATGTTGCAAAGACCAACATAAGTGGCAAGGTTCTA CCTACTCTGATTGGGGACAATGTAACAGTAGGTCACAG TGCTGTCATTCATGGGTGTACTGTTGAGGATGATGCTT TTGTTGGTATGGGAGCAACACTACTTGATGGTGTGGTG GTTGAGAAACATGCCATGGTTGCTGCTGGTTCTCTTGT GAAACAGAACACGCGAATCCCTTCTGGAGAGGTGTGG GGAGGAAATCCAGCAAGTTCATGAGAAAGTTAACAG ATGAAGAGATAGTATACATCTCACAGTCAGCAAAGAA TTACATCAATCTCGCACAGATTCACGCCTCAGAGAATT CAAAGTCATTTGAGCAGATCGAGGTTGAGAGAGCGCT TAGGAAGAAGTATGCACGCAAGGACGAGGATTACGAT TCAATGCTTGGGATTACCCGTGAAACTCCACCGGAGTT GATTCTTCCCGACAATGTCTTACCAGGTGGTAAACCCG TCGCCAAGGTTCCGTCTACTCAGTACTTCTAATTCCAA TCTCAGGTTGTTTTGTGTGTTGAAATCATTTCAAGACA GGATTGATTCTCTGGAAGGTCAAGAGAGATATTATTT GGTTTTAACTTTTCTTCCGAGCAAGCAGGAGATTTATC ATCCTTGCTCAATAATGTATGGTTGCATTATGAAGTCA TTTCTTCGAGGAACAATTTGCAGAAAGAGAAACAAAG TTGGATTAATCTTTC |
| Full length AtγCA3 cDNA | SEQ ID NO: 33 AtγCA3 (At5g66510) | CAAAGACTGCACTCTCTCCTCTTCCTCTGGCTCCGGCG AAAAACCCCTTTTCGATTTCATTGATAAAACGCAAATC GATCTCTCGTGTGGAAGAAGAAGAAGAACACGATGGG AACAATGGGTAAAGCATTCTACAGCGTAGGATTCTGG ATCCGTGAAACTGGTCAAGCACTTGATCGGCTCGGTTG TCGCCTCCAAGGGAAAAATCATTTCCGAGAACAGCTAT CAAGGCACCGCACACTCATGAATGTTTTTGACAAAACC |

| Name - activity | SEQ ID NO: and Genbank No. | sequence |
|---|---|---|
| | | CCTAATGTGGATAAGGGGCTTTTGTGGCTCCTAACGC TTCTCTCTCTGGTGATGTCCATGTGGGAAGAGGTTCTT CCATTTGGTATGGATGTGTCTTGAGAGACATACCCTTT GATTTAATGACCGACTCTGCAGGAGATGCTAACAGCAT TAGTGTTGGAGCTGGGACCAATATTCAGGACAACGCTC TTGTCCACGTTGCTAAGACCAACTTAAGTGGGAAGGTC TTACCTACTGTCATTGGAGACAATGTCACCATTGGTCA TAGTGCTGTTTTACATGGCTGCACTGTCGAGGATGAGG CCTATATTGGTACAAGTGCAACTGTCTTGGATGGAGCT CATGTTGAAAAACATGCCATGGTTGCTTCAGGAGCTCT TGTTAGGCAGAACACTAGAATTCCCTCTGGCGAGGTTT GGGGAGGCAACCCAGCTAAATTTCTGAGGAAGGTGAC AGAAGAAGAAAGAGTCTTCTTCTCCAGTTCGGCTGTGG AGTACTCCAACTTAGCTCAAGCTCACGCCACAGAGAA CGCAAAGAACTTGGACGAGGCTGAGTTCAAGAAGCTT CTAAACAAGAAGAACGCTCGCGATACAGAATATGATT CAGTACTCGATGATCTCACGCTCCCTGAGAATGTACCA AAAGCAGCTTGAGGCGTTTAACCTGTGCCGCCTTGCGA ATCTTGATTTGTTTGGATTTGAAAAGTAAAAACAAAGA ACTTGATTTCCTGCTTCTCCAATAAAGTTTTCTTGGGCG TAAAATCCATTGGCCAGTGCTCACTGGGAAAGTTTTCG GCTTAAAGGCATTCATTTCTCTGTTAAAGATTGTGAGG GGTTTTGTTCTCTTGTAACTTGAGAAAGAAAAGTTGTA ACCTTTTCTTCCTTTTTATGTCGTCTAATAAATTGTTGA TCAGACAGACATTTAGGTTGACCTTTGCCCATAAAAAG ATAGCTCTGCTTCAATAA |
| Full length AtγCAL1 cDNA | SEQ ID NO: 34 AtγCAL1 (At5g63510) | ACTCTCTCTCTTTTCCTCTTTGCAAATCCTTGAAGAAAT CCAAAATCCATAGCAATGGCGACTTCGATAGCTCGATT GTCTCGGAGAGGAGTCACTTCTAACCTGATCCGTCGTT GCTTCGCTGCGGAAGCGGCGTTGGCGAGGAAGACAGA GTTACCTAAACCGCAATTCACGGTGTCGCCGTCGACGG ATCGTGTGAAATGGGACTACAGAGGCCAACGACAGAT CATTCCTTTGGGACAGTGGCTTCCGAAGGTAGCCGTTG ATGCTTACGTGGCACCCAACGTTGTGCTGGCTGGTCAG GTCACAGTCTGGACGGCTCGTCTGTTTGGAACGGTGC CGTTTTGCGCGGCGATCTCAACAAAATCACTGTTGGAT TCTGCTCGAATGTACAGGAACGGTGTGTTGTTCATGCC GCCTGGTCTTCCCCAACAGGATTACCAGCAGCGACAAT AATCGACAGGTATGTGACAGTAGGTGCCTACAGTCTTC TGAGATCATGTACCATCGAACCAGAGTGCATCATCGGT CAACACTCAATACTAATGGAAGGCTCACTGGTTGAGA CCCGGTCAATCTTGGAAGCGGGTTCAGTTGTGCCGCCA GGAAGAAGGATCCCATCAGGTGAACTATGGGGAGGCA ATCCAGCAAGATTCATTAGAACCCTAACCAACGAAGA AACCCTAGAGATCCCAAAACTCGCTGTAGCCATCAACC ACTTAAGCGGAGATTACTTCTCTGAGTTCCTACCTTAC TCAACTGTCTACTTAGAGGGTAGAGAAGTTCAAGAAGTC CCTTGGGATCGCCGTTTAGAAGCTTCATCTTTTTCGTGA TTCACTTTCATGTGTTTATCTATCATATGAGGTCTTTCT CTCTGCATATTGCAATAAGTAGCTGATGAACATCAAAA CAAGTCCGGCTCTCTTTTTTGGTTCTAAAACGTTTTGTCA TTTCGTTTTTTGGGTTCTTTGTAAAATTCCATTTAAAAC TGATTTTGGCTGAATATTGTCTGAATGATAATGGCGAC GACTTCTGGTTTTGTT |
| Full length AtγCAL2 cDNA | SEQ ID NO: 35 AtγCAL2 (At3g48680) | CTCCCGACGACTCCTCTCTGTCTCCTCCTCCGGGAAGC TTTCTGTCTCTCTCTCTCTCTCTACACAAGACCTTGA AGAATCCGATTCCATAACAATGGCGACTTCGTTAGCAC GAATCTCTAAAAGAAGCATAACATCGGCTGTTTCATCG AATCTGATTCGGCGTTACTTCGCCGCGAAGCAGTAGC GGTGGCGACGACGGAAACACCTAAACCGAAATCGCAG GTGACGCCGTCGCCGGATCGGGTAAAATGGACTACA GAGGCCAGAGACAGATAATTCCTCTGGGACAGTGGCT ACCGAAGGTAGCTGTAGATGCTTACGTGGCACCCTAAC GTTGTGTTGGCTGGTCAGGTCACCGTCTGGGACGGCTC GTCTGTATGGAACGGTGCCGTTTTGAGAGGAGATCTTA ATAAGATCACCGTTGGATTCTGCTCAAATGTCCAGGAA CGGTGTGTTGTTCATGCTGCGTGGTCGTCGCCTACAGG ATTACCAGCACAAACATTGATCGATAGGTACGTGACA GTTGGTGCATACAGTCTTTTAAGATCATGCACTATCGA ACCAGAATGCATCATCGGGCAACACTCAATCCTAATG GAAGGTTCACTGGTCGAAACCCGCTCAATCCTAGAAG CTGGTTCTGTTTTACCACCTGGCAGAAGAATCCCATCT GGTGAACTATGGGAGGCAATCCAGCAAGGTTTATTC GAACACTCACCAATGAAGAAACCTTAGAGATCCCGAA ACTTGCTGTTGCCATTAACCACCTAAGTGGAGATTACT |

| Name - activity | SEQ ID NO: and Genbank No. | sequence |
|---|---|---|
| | | TCTCAGAGTTCTTGCCTTACTCAACTATCTATCTAGAG<br>GTTGAGAAGTTCAAGAAATCCCTTGGAATCGCCATCTA<br>GAAAGCTTCTTCCAGGTTTCTGGCTACTTCCCTCATTAA<br>GAAAGCTTCTTCGTTTTCGGAATTTGATCTGAATAAGT<br>AGCTGCGGAACAAGAAAAAGAGCAGAGCTGTGTTTCA<br>AATGTTGTCTTCTCTGTTTGTTTTGTTTAAGTTCATATC<br>CTTGTGTTCAAACTTTCTATGAAGATGATAATGGTGAA<br>AACTGGAAAGTGTAAAACTTCTTTCGTCTCCCCTCACA<br>ATTGGAAAAGCTAATAATCTCGTAGTGTTATAGAA |

A number of aspects of the invention have been described. Nevertheless, it will be understood that various modifications may be made without departing from the spirit and scope of the invention. Accordingly, other aspects are within the scope of the following claims.

What is claimed is:

1. A method for down-regulating or decreasing carbon dioxide ($CO_2$) and/or water exchange in a guard cell of a plant, a plant cell, a plant leaf, or a plant part comprising:
   (a) transgenically providing to the guard cell of the plant, plant cell, plant leaf, or plant part a nucleic acid or gene comprising:
      (i) a nucleic acid encoding a $CO_2Sen$ ($CO_2$ sensor) protein; or
      (ii) a nucleic acid encoding a polypeptide having a carbonic anhydrase (CA) activity, or a β-carbonic anhydrase activity;
   wherein the nucleic acid or gene has at least about 95% sequence identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene, or
   the protein or polypeptide is encoded by a nucleic acid or a gene having at least about 95% sequence identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene,
   wherein the nucleic acid encodes:
      (1) a $CO_2Sen$ ($CO_2$ sensor) protein that has a $CO_2Sen$ ($CO_2$ sensor) protein activity, and/or
      (2) a polypeptide having a carbonic anhydrase or a carbonate dehydratase activity, or a β-carbonic anhydrase activity,
   wherein the sequence identity is calculated using a sequence comparison algorithm consisting of a BLAST version 2.2.2 algorithm where a filtering setting is set to blastall -p blastp -d "nr pataa" -F F, and all other options are set to default; and
   (b) inserting into the guard cell and expressing, or overexpressing, the nucleic acid or gene of (a), thereby down-regulating or decreasing carbon dioxide ($CO_2$) and/or water exchange in the guard cell.

2. A method for regulating water exchange in a guard cell of a plant, a plant cell, a plant leaf, or a plant part comprising:
   transgenically inserting into and overexpressing in the guard cell of the plant, plant cell, plant leaf, or plant part a nucleic acid or gene encoding:
      (i) a $CO_2Sen$ ($CO_2$ sensor) protein, or
      (ii) a polypeptide having a carbonic anhydrase (CA) activity, or a 13-carbonic anhydrase activity,
   wherein the nucleic acid or gene has at least about 95% sequence identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene, or
   the protein or polypeptide is encoded by a nucleic acid or a gene having at least about 95% sequence identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene, thereby down-regulating or decreasing water exchange in the guard cell.

3. A method for regulating water uptake or water loss in a guard cell of a plant, a plant cell, a plant leaf, or a plant part, comprising transgenically inserting into and overexpressing in the guard cell of the plant, plant cell, plant leaf, or plant part a nucleic acid or gene encoding:
(i) a $CO_2Sen$ ($CO_2$ sensor) protein, or
(ii) a polypeptide having a carbonic anhydrase (CA) activity, or a β-carbonic anhydrase activity,
thereby regulating water uptake or water loss,
wherein the nucleic acid or gene has at least about 95% sequence identity to SEQ ID NO:1, or the protein or polypeptide is encoded by a nucleic acid or a gene having at least about 95% sequence identity to SEQ ID NO:1,
wherein overexpressing a $CO_2Sen$ ($CO_2$ sensor) or carbonic anhydrase protein in the guard cell decreases water loss.

4. A method for making an enhanced water use efficiency (WUE), or drought-resistant, plant comprising:
transgenically inserting into in a guard cell of the plant and overexpressing or increasing expression of a nucleic acid or a gene encoding:
(i) a $CO_2Sen$ ($CO_2$ sensor) protein, or
(ii) a polypeptide having a carbonic anhydrase (CA) activity, or a β-carbonic anhydrase activity;
wherein the nucleic acid or gene has at least about 95% sequence identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene, or
the protein or polypeptide is encoded by a nucleic acid or a gene having at least about 95% sequence identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene,
thereby making an enhanced water use efficiency (WUE), or drought-resistant plant.

5. A plant, a plant part, or a leaf thereof made by the method of claim 4 and comprising said nucleic acid or gene, wherein the plant is:
(i) a dicotyledonous or monocotyledonous plant;
(ii) wheat, oat, rye, barley, rice, sorghum, maize or corn, tobacco, a legume, a lupins, potato, sugar beet, pea, bean, soybean or soy, a cruciferous plant, a cauliflower, rape or rapa or canola, cane or sugarcane, flax, cotton, palm, sugar beet, peanut, a tree, a poplar, a lupin, a silk cotton tree, desert willow, creosote bush, winterfat, balsa, ramie, kenaf, hemp, roselle, jute, or sisal abaca; or,
(iii) a specie from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea*.

6. A method for closing a stomatal pore on a guard cell in the epidermis of a plant, a guard cell in a plant leaf, or a plant guard cell, comprising transgenically inserting into and overexpressing a nucleic acid or gene encoding:
(a)
(i) a $CO_2Sen$ ($CO_2$ sensor) protein, or
(ii) a polypeptide having a carbonic anhydrase (CA) activity, or a 13-carbonic anhydrase activity,
wherein the nucleic acid or gene has at least about 95% sequence identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene, or
the protein or polypeptide is encoded by a nucleic acid or a gene having at least about 95% sequence identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene,
thereby causing overexpression and/or increase in expression of the $CO_2Sen$ protein and/or the carbonic anhydrase (CA), and causing the stomatal pore to close.

7. The method of claim 1, wherein:
(a) the plant is:
(i) a dicotyledonous or monocotyledonous plant;
(ii) wheat, oat, rye, barley, rice, sorghum, maize or corn, tobacco, a legume, a lupins, potato, sugar beet, pea, bean, soybean or soy, a cruciferous plant, a cauliflower, rape or rapa or canola, cane or sugarcane, flax, cotton, palm, sugar beet, peanut, a tree, a poplar, a lupin, a silk cotton tree, desert willow, creosote bush, winterfat, balsa, ramie, kenaf, hemp, roselle, jute, or sisal abaca; or,
(iii) a specie from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea*;
(b) the plant is characterized by controlled $CO_2$ exchange under ambient 365 ppm $CO_2$, elevated ppm $CO_2$ or reduced ppm $CO_2$, or the plant is characterized by controlled water exchange under ambient 365 ppm $CO_2$, elevated ppm $CO_2$ or reduced ppm $CO_2$; or (c) the nucleic acid is operably linked to a constitutive or an inducible promoter, a tissue or cell specific promoter, or a promoter responsive to an environmental, a hormonal, a chemical or a developmental signal, or the nucleic acid is operably linked to a plant guard cell-specific promoter.

8. The method of claim 4, wherein:
(a) the overexpression or increased expression is in a plant guard cell;
(b) the nucleic acid is operably linked to a constitutive or an inducible promoter, a tissue or cell specific promoter, or a promoter responsive to an environmental, a hormonal, a chemical or a developmental signal, or the nucleic acid is operably linked to a plant guard cell-specific promoter;
wherein the sequence identity is calculated using a sequence comparison algorithm consisting of a BLAST version 2.2.2 algorithm where a filtering setting is set to blastall -p blastp -d "nr pataa" -F F, and all other options are set to default.

9. The method of claim 7, wherein:
(a) the plant guard cell-specific promoter comprises a sequence as set forth in SEQ ID NO:10 or SEQ ID NO:11, or functional transcriptional regulatory subsequences thereof, or
(b) the functional or transcriptional regulatory subsequence comprises:
−1140 bp/+23 bp of SEQ ID NO: 10 (pGC1(D1)), −861 bp/+23 bp of SEQ ID NO: 10 (pGC1(D2)) or −443 bp/+23 bp of SEQ ID NO: 10 (pGB1D3)).

10. The method of claim 1, wherein the sequence identity has at least about 98% identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene.

11. The method of claim 10, wherein the sequence identity is 100%.

12. The method of claim 8, wherein the sequence identity has at least about 98% identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene.

13. The method of claim 12, wherein the sequence identity is 100%.

14. The method of claim 1, wherein the sequence identity has at least about 98% identity to SEQ ID NO:1, SEQ ID NO:2, SEQ ID NO:4, SEQ ID NO:5, SEQ ID NO:7, SEQ ID NO:8, SEQ ID NO:20, SEQ ID NO:21, SEQ ID NO:22, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:32, SEQ ID NO:33, SEQ ID NO:34 and/or SEQ ID NO:35, over the full length of a protein coding sequence or gene.

15. The method of claim 14, wherein the sequence identity is 100%.

16. The method of claim 8, wherein the plant guard cell-specific promoter comprises a sequence as set forth in SEQ ID NO:10 or SEQ ID NO:11, or functional transcriptional regulatory subsequences thereof, or a functional transcriptional regulatory subsequence comprising: −1140 bp/+23 bp of SEQ ID NO: 10 (pGC1(D1)), −861 bp/+23 bp of SEQ ID NO: 10 (pGC1(D2)) or −443 bp/+23 bp of SEQ ID NO: 10 (pGB1D3)).

17. A method for down-regulating or decreasing carbon dioxide ($CO_2$) and/or water exchange in a guard cell of a plant, a plant cell, a plant leaf, or a plant part comprising:
(a) providing to the plant, plant cell, plant leaf, or plant part a nucleic acid comprising:
(i) a nucleotide sequence as set forth in SEQ ID NO:1, or
(ii) a nucleotide sequence encoding a polypeptide comprising a sequence as set forth in SEQ ID NO:3;
(b) inserting into the guard cell, plant cell, plant leaf, or plant part, and expressing, or overexpressing, the nucleic acid of (a),
thereby down-regulating or decreasing carbon dioxide ($CO_2$) and/or water exchange in the guard cell, plant cell, plant leaf, or plant part.

18. A seed derived from the plant of claim 5, wherein the seed comprises said nucleic acid or gene.

19. The seed of claim 18, wherein the nucleic acid encoding:
(i) the $CO_2$Sen ($CO_2$ sensor) protein, or
(ii) the polypeptide having a carbonic anhydrase (CA) activity, or β-carbonic anhydrase activity,
is operatively linked to a heterologous promoter.

20. The seed of claim 19, wherein the heterologous promoter comprises a constitutive or an inducible promoter, a tissue or cell specific promoter, or a promoter responsive to an environmental, a hormonal, a chemical or a developmental signal, a plant guard cell-specific promoter.

21. The seed of claim 20, wherein the plant guard cell-specific promoter comprises:
(a) a sequence as set forth in SEQ ID NO:10 or SEQ ID NO:11, or functional transcriptional regulatory subsequences thereof, or
(b) the sequence of (a), wherein the functional transcriptional regulatory subsequence comprises:
−1140 bp/+23 bp of SEQ ID NO: 10 (pGC1(D1)), −861 bp/+23 bp of SEQ ID NO: 10 (pGC1(D2)) or −443 bp/+23 bp of SEQ ID NO: 10 (pGB1D3)).

* * * * *

SEQUENCE LISTING

<160> NUMBER OF SEQ ID NOS: 46

<210> SEQ ID NO 1
<211> LENGTH: 1336
<212> TYPE: DNA
<213> ORGANISM: Arabidopsis thaliana

<400> SEQUENCE: 1

```
cgaacggtcg tcataattcc ttgaaacctc gaaaatccaa aaacccatat ccaatcttct      60
tcccatataa attaagattt ttatttattt atttgtttac ttatttcaat tcccaaaatc     120
ctctgcctca tcatcttcaa actgttacca cgtccatagg gttgtcgaag agctaggaag     180
agccttacca agagcttctt cttcccctaa catttaggtt ggtaggagaa gcaaggaag      240 agatcattta taatggctcc tgcattcgga aaatgtttca tgttctgctg cgctaaaacc     300
tccccggaaa aagacgaaat ggcaacggaa tcgtacgaag ccgccattaa aggactcaat     360
gatcttctca gtacgaaagc ggatctcgga aacgtcgccg ccgcgaagat caaagcgttg     420
acggcggagc taaggagct tgactcaagc aattcagacg caattgaacg aatcaagacc      480
ggttttactc aattcaaaac cgagaaatat ttgaagaata gtactttgtt caatcatctt     540
gccaagactc agaccccaaa gtttctggtg tttgcttgct ctgattctcg agtttgtcca     600
tctcacatct tgaatttcca acctggtgag gcttttgttg tcagaaacat agccaatatg     660 gttccaccctt ttgaccagaa gagacactct ggagttggcg ccgccgttga atacgcagtt    720
gtacatctca aggtggagaa cattttggtg ataggccata gctgctgtgg tggtattaag     780
ggactcatgt ccattgaaga tgatgctgcc ccaactcaaa gtgacttcat tgaaaattgg     840
gtgaagatag gcgcatcagc gaggaacaag atcaaggagg aacataaaga cttgagctac     900
gatgatcaat gcaacaagtg tgagaaggaa gctgtgaacg tatcgcttgg aaacttgctt     960
tcgtacccat tcgtgagagc tgaggtggtg aagaacacac ttgcaataag aggaggtcac    1020
tacaatttcg tcaaaggaac gtttgatctc tgggagctcg atttcaagac cactcctgct    1080
tttgccttct cttaagaaag aaagctaccg gaacatataa aactcttttg agataaaaaa    1140
agacactttg actcatcttt cttcattctc tcatgttgat gattcctctc caacttcttt    1200
gatttctttt tgttaattca aaacttcaac tttgctgctt ctatttcaaa agctcaaaca    1260
```

```
ataaagctgt aaccaacgtt tgaaacttct atatttgtct aattgatgtt tgaacgaaga   1320
tttgaacttt ccttct                                                   1336

<210> SEQ ID NO 2
<211> LENGTH: 843
<212> TYPE: DNA
<213> ORGANISM: Arabidopsis thaliana
<220> FEATURE:
<221> NAME/KEY: CDS
<222> LOCATION: (1)..(843)

<400> SEQUENCE: 2 atg gct cct gca ttc gga aaa tgt ttc atg ttc tgc tgc gct aaa acc    48
Met Ala Pro Ala Phe Gly Lys Cys Phe Met Phe Cys Cys Ala Lys Thr
1               5                   10                  15 tcc ccg gaa aaa gac gaa atg gca acg gaa tcg tac gaa gcc gcc att    96
Ser Pro Glu Lys Asp Glu Met Ala Thr Glu Ser Tyr Glu Ala Ala Ile
            20                  25                  30 aaa gga ctc aat gat ctt ctc agt acg aaa gcg gat ctc gga aac gtc   144
Lys Gly Leu Asn Asp Leu Leu Ser Thr Lys Ala Asp Leu Gly Asn Val
        35                  40                  45 gcc gcc gcg aag atc aaa gcg ttg acg gcg gag cta aag gag ctt gac   192
Ala Ala Ala Lys Ile Lys Ala Leu Thr Ala Glu Leu Lys Glu Leu Asp
    50                  55                  60 tca agc aat tca gac gca att gaa cga atc aag acc ggt ttt act caa   240
Ser Ser Asn Ser Asp Ala Ile Glu Arg Ile Lys Thr Gly Phe Thr Gln
65                  70                  75                  80 ttc aaa acc gag aaa tat ttg aag aat agt act ttg ttc aat cat ctt   288
Phe Lys Thr Glu Lys Tyr Leu Lys Asn Ser Thr Leu Phe Asn His Leu
                85                  90                  95 gcc aag act cag acc cca aag ttt ctg gtg ttt gct tgc tct gat tct   336
Ala Lys Thr Gln Thr Pro Lys Phe Leu Val Phe Ala Cys Ser Asp Ser
            100                 105                 110 cga gtt tgt cca tct cac atc ttg aat ttc caa cct ggt gag gct ttt   384
Arg Val Cys Pro Ser His Ile Leu Asn Phe Gln Pro Gly Glu Ala Phe
        115                 120                 125 gtt gtc aga aac ata gcc aat atg gtt cca cct ttt gac cag aag aga   432
Val Val Arg Asn Ile Ala Asn Met Val Pro Pro Phe Asp Gln Lys Arg
    130                 135                 140 cac tct gga gtt ggc gcc gcc gtt gaa tac gca gtt gta cat ctc aag   480
His Ser Gly Val Gly Ala Ala Val Glu Tyr Ala Val Val His Leu Lys
145                 150                 155                 160 gtg gag aac att ttg gtg ata ggc cat agc tgc tgt ggt ggt att aag   528
Val Glu Asn Ile Leu Val Ile Gly His Ser Cys Cys Gly Gly Ile Lys
                165                 170                 175 gga ctc atg tcc att gaa gat gat gct gcc cca act caa agt gac ttc   576
Gly Leu Met Ser Ile Glu Asp Asp Ala Ala Pro Thr Gln Ser Asp Phe
            180                 185                 190 att gaa aat tgg gtg aag ata ggc gca tca gcg agg aac aag atc aag   624
Ile Glu Asn Trp Val Lys Ile Gly Ala Ser Ala Arg Asn Lys Ile Lys
        195                 200                 205 gag gaa cat aaa gac ttg agc tac gat gat caa tgc aac aag tgt gag   672
Glu Glu His Lys Asp Leu Ser Tyr Asp Asp Gln Cys Asn Lys Cys Glu
    210                 215                 220 aag gaa gct gtg aac gta tcg ctt gga aac ttg ctt tcg tac cca ttc   720
Lys Glu Ala Val Asn Val Ser Leu Gly Asn Leu Leu Ser Tyr Pro Phe
225                 230                 235                 240 gtg aga gct gag gtg gtg aag aac aca ctt gca ata aga gga ggt cac   768
Val Arg Ala Glu Val Val Lys Asn Thr Leu Ala Ile Arg Gly Gly His
                245                 250                 255
```

```
tac aat ttc gtc aaa gga acg ttt gat ctc tgg gag ctc gat ttc aag      816
Tyr Asn Phe Val Lys Gly Thr Phe Asp Leu Trp Glu Leu Asp Phe Lys
        260                 265                 270 acc act cct gct ttt gcc ttc tct taa                                   843
Thr Thr Pro Ala Phe Ala Phe Ser
        275             280
```

<210> SEQ ID NO 3
<211> LENGTH: 280
<212> TYPE: PRT
<213> ORGANISM: Arabidopsis thaliana

<400> SEQUENCE: 3

```
Met Ala Pro Ala Phe Gly Lys Cys Phe Met Phe Cys Cys Ala Lys Thr
1               5                   10                  15

Ser Pro Glu Lys Asp Glu Met Ala Thr Glu Ser Tyr Glu Ala Ala Ile
            20                  25                  30

Lys Gly Leu Asn Asp Leu Leu Ser Thr Lys Ala Asp Leu Gly Asn Val
        35                  40                  45

Ala Ala Ala Lys Ile Lys Ala Leu Thr Ala Glu Leu Lys Glu Leu Asp
    50                  55                  60

Ser Ser Asn Ser Asp Ala Ile Glu Arg Ile Lys Thr Gly Phe Thr Gln
65                  70                  75                  80

Phe Lys Thr Glu Lys Tyr Leu Lys Asn Ser Thr Leu Phe Asn His Leu
                85                  90                  95

Ala Lys Thr Gln Thr Pro Lys Phe Leu Val Phe Ala Cys Ser Asp Ser
            100                 105                 110

Arg Val Cys Pro Ser His Ile Leu Asn Phe Gln Pro Gly Glu Ala Phe
        115                 120                 125

Val Val Arg Asn Ile Ala Asn Met Val Pro Pro Phe Asp Gln Lys Arg
    130                 135                 140

His Ser Gly Val Gly Ala Ala Val Glu Tyr Ala Val His Leu Lys
145                 150                 155                 160

Val Glu Asn Ile Leu Val Ile Gly His Ser Cys Cys Gly Gly Ile Lys
                165                 170                 175

Gly Leu Met Ser Ile Glu Asp Ala Ala Pro Thr Gln Ser Asp Phe
            180                 185                 190

Ile Glu Asn Trp Val Lys Ile Gly Ala Ser Ala Arg Asn Lys Ile Lys
        195                 200                 205

Glu Glu His Lys Asp Leu Ser Tyr Asp Asp Gln Cys Asn Lys Cys Glu
    210                 215                 220

Lys Glu Ala Val Asn Val Ser Leu Gly Asn Leu Leu Ser Tyr Pro Phe
225                 230                 235                 240

Val Arg Ala Glu Val Val Lys Asn Thr Leu Ala Ile Arg Gly Gly His
                245                 250                 255

Tyr Asn Phe Val Lys Gly Thr Phe Asp Leu Trp Glu Leu Asp Phe Lys
            260                 265                 270

Thr Thr Pro Ala Phe Ala Phe Ser
        275             280
```

<210> SEQ ID NO 4
<211> LENGTH: 1151
<212> TYPE: DNA
<213> ORGANISM: Arabidopsis thaliana

<400> SEQUENCE: 4

-continued

| | |
|---|---|
| caaaattcat gtgttagttc ttcttctttta caaaattgag tttaaactgt tttattacta | 60 |
| atccaaatga ggaatcactt tgcactatta atagaaaata atacacaacc aaacatctaa | 120 |
| aagatactat aatagtagag atcaaagacc tgagcaaaaa ctgaaagaaa aaaaaaaaaa | 180 |
| aaaaaaaaga cttctcctca aaaatggcgt ttacactagg tggaagagct cgtcgtctag | 240 |
| tctctgcaac atcagttcat caaaatggtt gcttacacaa actgcaacaa attggatcgg | 300 |
| atcggtttca gcttggtgaa gcaaaagcaa taagattact acccaggaga acaaacatgg | 360 |
| ttcaagaatt aggaatcagg gaagaattta tggatctaaa cagagaaaca gagacaagtt | 420 |
| atgatttttct ggatgaaatg agacacagat ttctgaaatt caagacaa aagtatctac | 480 |
| cggagataga aaagttaaa gctttggcca tagctcaatc accaaaggta atggtgatag | 540 |
| gatgtgcaga ttcaagggta tgtccatctt atgtactagg atttcaacct ggtgaagctt | 600 |
| ttactatccg aaatgtcgcc aatctcgtta ccccggttca gaatggacca acagaaacca | 660 |
| actcggctct tgagtttgcg gtcaccactc ttcaggttga gaacattata gttatgggtc | 720 |
| atagcaattg tggaggaatt gcagcactta tgagtcatca aaaccaccaa gggcaacact | 780 |
| ctagtttagt agaaaggtgg gttatgaatg ggaaagccgc taagttaaga acacaattag | 840 |
| cttcatcaca tttatccttt gatgaacaat gcagaaactg tgagaaggaa tctataaagg | 900 |
| attctgtgat gaatttgata acttattcat ggataagaga tagagtaaag agaggtgaag | 960 |
| tcaagattca tggatgttat tacaatttgt cagattgtag tcttgagaag tggagattaa | 1020 |
| gttcagacaa gactaactat ggattctata tttcagacag agagatatgg agttgagtaa | 1080 |
| atattgaaca atcctcagtt ctaatattca gatgtatctt tgtacatacg aaatgatatt | 1140 |
| tacacaattg g | 1151 |

<210> SEQ ID NO 5
<211> LENGTH: 873
<212> TYPE: DNA
<213> ORGANISM: Arabidopsis thaliana
<220> FEATURE:
<221> NAME/KEY: CDS
<222> LOCATION: (1)..(873)

<400> SEQUENCE: 5

| | |
|---|---|
| atg gcg ttt aca cta ggt gga aga gct cgt cgt cta gtc tct gca aca<br>Met Ala Phe Thr Leu Gly Gly Arg Ala Arg Arg Leu Val Ser Ala Thr<br>1               5                    10               15 | 48 |
| tca gtt cat caa aat ggt tgc tta cac aaa ctg caa caa att gga tcg<br>Ser Val His Gln Asn Gly Cys Leu His Lys Leu Gln Gln Ile Gly Ser<br>            20                    25                    30 | 96 |
| gat cgg ttt cag ctt ggt gaa gca aaa gca ata aga tta cta ccc agg<br>Asp Arg Phe Gln Leu Gly Glu Ala Lys Ala Ile Arg Leu Leu Pro Arg<br>        35                    40                    45 | 144 |
| aga aca aac atg gtt caa gaa tta gga atc agg gaa gaa ttt atg gat<br>Arg Thr Asn Met Val Gln Glu Leu Gly Ile Arg Glu Glu Phe Met Asp<br>50                      55                    60 | 192 |
| cta aac aga gaa aca gag aca agt tat gat ttt ctg gat gaa atg aga<br>Leu Asn Arg Glu Thr Glu Thr Ser Tyr Asp Phe Leu Asp Glu Met Arg<br>65                         70                    75               80 | 240 |
| cac aga ttt ctg aaa ttc aag aga caa aag tat cta ccg gag ata gaa<br>His Arg Phe Leu Lys Phe Lys Arg Gln Lys Tyr Leu Pro Glu Ile Glu<br>                    85                    90                    95 | 288 |
| aag ttt aaa gct ttg gcc ata gct caa tca cca aag gta atg gtg ata<br>Lys Phe Lys Ala Leu Ala Ile Ala Gln Ser Pro Lys Val Met Val Ile<br>            100                  105               110 | 336 |

```
gga tgt gca gat tca agg gta tgt cca tct tat gta cta gga ttt caa      384
Gly Cys Ala Asp Ser Arg Val Cys Pro Ser Tyr Val Leu Gly Phe Gln
            115                 120                 125 cct ggt gaa gct ttt act atc cga aat gtc gcc aat ctc gtt acc ccg      432
Pro Gly Glu Ala Phe Thr Ile Arg Asn Val Ala Asn Leu Val Thr Pro
130                 135                 140 gtt cag aat gga cca aca gaa acc aac tcg gct ctt gag ttt gcg gtc      480
Val Gln Asn Gly Pro Thr Glu Thr Asn Ser Ala Leu Glu Phe Ala Val
145                 150                 155                 160 acc act ctt cag gtt gag aac att ata gtt atg ggt cat agc aat tgt      528
Thr Thr Leu Gln Val Glu Asn Ile Ile Val Met Gly His Ser Asn Cys
                165                 170                 175 gga gga att gca gca ctt atg agt cat caa aac cac caa ggg caa cac      576
Gly Gly Ile Ala Ala Leu Met Ser His Gln Asn His Gln Gly Gln His
            180                 185                 190 tct agt tta gta gaa agg tgg gtt atg aat ggg aaa gcc gct aag tta      624
Ser Ser Leu Val Glu Arg Trp Val Met Asn Gly Lys Ala Ala Lys Leu
        195                 200                 205 aga aca caa tta gct tca tca cat tta tcc ttt gat gaa caa tgc aga      672
Arg Thr Gln Leu Ala Ser Ser His Leu Ser Phe Asp Glu Gln Cys Arg
210                 215                 220 aac tgt gag aag gaa tct ata aag gat tct gtg atg aat ttg ata act      720
Asn Cys Glu Lys Glu Ser Ile Lys Asp Ser Val Met Asn Leu Ile Thr
225                 230                 235                 240 tat tca tgg ata aga gat aga gta aag aga ggt gaa gtc aag att cat      768
Tyr Ser Trp Ile Arg Asp Arg Val Lys Arg Gly Glu Val Lys Ile His
                245                 250                 255 gga tgt tat tac aat ttg tca gat tgt agt ctt gag aag tgg aga tta      816
Gly Cys Tyr Tyr Asn Leu Ser Asp Cys Ser Leu Glu Lys Trp Arg Leu
            260                 265                 270 agt tca gac aag act aac tat gga ttc tat att tca gac aga gag ata      864
Ser Ser Asp Lys Thr Asn Tyr Gly Phe Tyr Ile Ser Asp Arg Glu Ile
        275                 280                 285 tgg agt tga                                                          873
Trp Ser
    290

<210> SEQ ID NO 6
<211> LENGTH: 290
<212> TYPE: PRT
<213> ORGANISM: Arabidopsis thaliana

<400> SEQUENCE: 6

Met Ala Phe Thr Leu Gly Gly Arg Ala Arg Arg Leu Val Ser Ala Thr
1               5                   10                  15

Ser Val His Gln Asn Gly Cys Leu His Lys Leu Gln Gln Ile Gly Ser
            20                  25                  30

Asp Arg Phe Gln Leu Gly Glu Ala Lys Ala Ile Arg Leu Leu Pro Arg
        35                  40                  45

Arg Thr Asn Met Val Gln Glu Leu Gly Ile Arg Glu Glu Phe Met Asp
    50                  55                  60

Leu Asn Arg Glu Thr Glu Thr Ser Tyr Asp Phe Leu Asp Glu Met Arg
65                  70                  75                  80

His Arg Phe Leu Lys Phe Lys Arg Gln Lys Tyr Leu Pro Glu Ile Glu
                85                  90                  95

Lys Phe Lys Ala Leu Ala Ile Ala Gln Ser Pro Lys Val Met Val Ile
            100                 105                 110

Gly Cys Ala Asp Ser Arg Val Cys Pro Ser Tyr Val Leu Gly Phe Gln
        115                 120                 125
```

```
Pro Gly Glu Ala Phe Thr Ile Arg Asn Val Ala Asn Leu Val Thr Pro
    130                 135                 140

Val Gln Asn Gly Pro Thr Glu Thr Asn Ser Ala Leu Glu Phe Ala Val
145                 150                 155                 160

Thr Thr Leu Gln Val Glu Asn Ile Ile Val Met Gly His Ser Asn Cys
            165                 170                 175

Gly Gly Ile Ala Ala Leu Met Ser His Gln Asn His Gln Gly Gln His
                180                 185                 190

Ser Ser Leu Val Glu Arg Trp Val Met Asn Gly Lys Ala Ala Lys Leu
        195                 200                 205

Arg Thr Gln Leu Ala Ser Ser His Leu Ser Phe Asp Glu Gln Cys Arg
    210                 215                 220

Asn Cys Glu Lys Glu Ser Ile Lys Asp Ser Val Met Asn Leu Ile Thr
225                 230                 235                 240

Tyr Ser Trp Ile Arg Asp Arg Val Lys Arg Gly Glu Val Lys Ile His
            245                 250                 255

Gly Cys Tyr Tyr Asn Leu Ser Asp Cys Ser Leu Glu Lys Trp Arg Leu
                260                 265                 270

Ser Ser Asp Lys Thr Asn Tyr Gly Phe Tyr Ile Ser Asp Arg Glu Ile
        275                 280                 285

Trp Ser
    290

<210> SEQ ID NO 7
<211> LENGTH: 1319
<212> TYPE: DNA
<213> ORGANISM: Arabidopsis thaliana

<400> SEQUENCE: 7
atgagactcc gttcttttaa actcccaaat ctttcaacca atcccattat tcacttaagt      60
atatagtagc ttccataaga gtcttagttc taactataaa tacacatatc tcactctctc     120
tgatctccgc ttctcttcgc caacaaatgt cgaccgctcc tctctccggc ttctttctca     180
cttcactttc tccttctcaa tcttctctcc agaaactctc tcttcgtact tcttccaccg     240
tcgcttgcct cccacccgcc tcttcttctt cctcatcttc ctcctcctcg tcttccgtt      300 ccgttccaac gcttatccgt aacgagccag ttttgccgc cctgctcct atcattgccc      360 cttattggag tgaagagatg ggaaccgaag catacgacga ggctattgaa gctctcaaga     420
agcttctcat cgagaaggaa gagctaaaga cggttcagc ggcaaaggtg gagcagatca      480
cagcggctct tcagacaggt acttcatccg acaagaaagc tttcgacccc gtcgaaacca     540
ttaagcaggg cttcatcaaa ttcaagaagg agaaatacga accaacccct gctttgtacg     600
gtgagctcgc aaagggtcaa agtcctaagt acatggtgtt tgcttgttca gactcacgtg     660
tgtgtccatc acacgttctg gactttcagc aggagatgc cttcgtggtc cgtaacatag      720
ccaacatggt tcctccttc gacaaggtca aatacggtgg cgttggagca gccattgaat     780
acgcggtctt acaccttaag gtggagaaca ttgtggtgat aggacacagt gcatgtggtg     840
ggatcaaagg gctatgtct ttccccttag atggaaacaa ctccactgac ttcatagagg      900
actgggtcaa atctgtttta ccagccaagt caaaggttat atcagaactt ggagattcag     960
cctttgaaga tcaatgtggc cgatgtgaaa gggaggcggt gaatgtttca ctagcaaacc    1020
tattgacata tccatttgtg agagaaggac ttgtgaaggg aacacttgct ttgaagggag    1080
gctactatga cttcgtcaag ggtgcttttg agctttgggg acttgaattt ggcctctccg    1140
```

-continued

```
aaactagctc tgttaaagat gtggctacca tactacattg gaagctgtag gaaactcttt    1200
gaagccttac ccgatttcac attgtcaatt caataacacc aagttgttgt ttacatgcag    1260
atcttgatga aactggtttt tgattttaca gaattaaaat cttgggggac agaaatttg     1319
```

<210> SEQ ID NO 8
<211> LENGTH: 1044
<212> TYPE: PRT
<213> ORGANISM: Arabidopsis thaliana

<400> SEQUENCE: 8

```
Ala Thr Gly Thr Cys Gly Ala Cys Cys Gly Cys Thr Cys Cys
1               5                   10                  15

Thr Cys Thr Cys Cys Gly Gly Cys Thr Thr Cys Thr Thr Cys Thr
                20                  25                  30

Cys Ala Cys Thr Thr Cys Ala Cys Thr Thr Cys Thr Cys Cys Thr
                35                  40                  45

Thr Cys Thr Cys Ala Ala Thr Cys Thr Thr Cys Thr Thr Cys Cys
        50                  55                  60

Ala Gly Ala Ala Ala Cys Thr Cys Thr Cys Thr Thr Cys Gly
65                  70                  75                  80

Thr Ala Cys Thr Thr Cys Thr Thr Cys Cys Ala Cys Cys Gly Thr Cys
                85                  90                  95

Gly Cys Thr Thr Gly Cys Cys Thr Cys Cys Ala Cys Cys Gly
                100                 105                 110

Cys Cys Thr Cys Thr Thr Cys Thr Thr Cys Thr Thr Cys Cys Thr Cys
                115                 120                 125

Ala Thr Cys Thr Thr Cys Cys Thr Cys Cys Thr Cys Thr Cys Gly
        130                 135                 140

Thr Cys Thr Thr Cys Cys Cys Gly Thr Thr Cys Cys Gly Thr Thr Cys
145                 150                 155                 160

Cys Ala Ala Cys Gly Cys Thr Thr Ala Thr Cys Cys Gly Thr Ala Ala
                165                 170                 175

Cys Gly Ala Gly Cys Cys Ala Gly Thr Thr Thr Thr Gly Cys Cys
                180                 185                 190

Gly Cys Thr Cys Cys Thr Gly Cys Thr Cys Cys Thr Ala Thr Cys Ala
                195                 200                 205

Thr Thr Gly Cys Cys Cys Thr Ala Thr Thr Gly Gly Ala Gly
        210                 215                 220

Thr Gly Ala Ala Gly Ala Gly Ala Thr Gly Gly Gly Ala Ala Cys Cys
225                 230                 235                 240

Gly Ala Ala Gly Cys Ala Thr Ala Cys Gly Ala Cys Gly Ala Gly Gly
                245                 250                 255

Cys Thr Ala Thr Thr Gly Ala Ala Gly Cys Thr Cys Thr Cys Ala Ala
                260                 265                 270

Gly Ala Ala Gly Cys Thr Thr Cys Thr Cys Ala Thr Cys Gly Ala Gly
                275                 280                 285

Ala Ala Gly Gly Ala Ala Gly Ala Gly Cys Thr Ala Ala Gly Ala
        290                 295                 300

Cys Gly Gly Thr Thr Gly Cys Ala Gly Cys Gly Gly Cys Ala Ala Ala
305                 310                 315                 320

Gly Gly Thr Gly Gly Ala Gly Cys Ala Gly Ala Thr Cys Ala Cys Ala
                325                 330                 335

Gly Cys Gly Gly Cys Thr Cys Thr Thr Cys Ala Gly Ala Cys Ala Gly
```

-continued

```
            340                 345                 350

Gly Thr Ala Cys Thr Thr Cys Ala Thr Cys Cys Gly Ala Cys Ala Ala
        355                 360                 365

Gly Ala Ala Ala Gly Cys Thr Thr Thr Cys Gly Ala Cys Cys Cys Cys
    370                 375                 380

Gly Thr Cys Gly Ala Ala Ala Cys Cys Ala Thr Thr Ala Ala Gly Cys
385                 390                 395                 400

Ala Gly Gly Gly Cys Thr Thr Cys Ala Thr Cys Ala Ala Ala Thr Thr
                405                 410                 415

Cys Ala Ala Gly Ala Ala Gly Gly Ala Gly Ala Ala Ala Thr Ala Cys
            420                 425                 430

Gly Ala Ala Ala Cys Cys Ala Ala Cys Cys Cys Thr Gly Cys Thr Thr
        435                 440                 445

Thr Gly Thr Ala Cys Gly Gly Thr Gly Ala Gly Cys Thr Cys Gly Cys
    450                 455                 460

Ala Ala Ala Gly Gly Gly Thr Cys Ala Ala Ala Gly Thr Cys Cys Thr
465                 470                 475                 480

Ala Ala Gly Thr Ala Cys Ala Thr Gly Gly Thr Gly Thr Thr Thr Gly
                485                 490                 495

Cys Thr Thr Gly Thr Thr Cys Ala Gly Ala Cys Thr Cys Ala Cys Gly
            500                 505                 510

Thr Gly Thr Gly Thr Gly Thr Cys Cys Ala Thr Cys Ala Cys Ala Cys
        515                 520                 525

Gly Thr Thr Cys Thr Gly Gly Ala Cys Thr Thr Thr Cys Ala Gly Cys
    530                 535                 540

Cys Ala Gly Gly Ala Gly Ala Thr Gly Cys Cys Thr Thr Cys Gly Thr
545                 550                 555                 560

Gly Gly Thr Cys Cys Gly Thr Ala Ala Cys Ala Thr Ala Gly Cys Cys
                565                 570                 575

Ala Ala Cys Ala Thr Gly Gly Thr Thr Cys Cys Thr Cys Cys Thr Thr
            580                 585                 590

Thr Cys Gly Ala Cys Ala Ala Gly Gly Thr Cys Ala Ala Ala Thr Ala
        595                 600                 605

Cys Gly Gly Thr Gly Gly Cys Gly Thr Thr Gly Gly Ala Gly Cys Ala
    610                 615                 620

Gly Cys Cys Ala Thr Thr Gly Ala Ala Thr Ala Cys Gly Cys Gly Gly
625                 630                 635                 640

Thr Cys Thr Thr Ala Cys Ala Cys Cys Thr Thr Ala Ala Gly Gly Thr
                645                 650                 655

Gly Gly Ala Gly Ala Ala Cys Ala Thr Thr Gly Thr Gly Gly Thr Gly
            660                 665                 670

Ala Thr Ala Gly Gly Ala Cys Ala Cys Ala Gly Thr Gly Cys Ala Thr
        675                 680                 685

Gly Thr Gly Gly Thr Gly Gly Gly Ala Thr Cys Ala Ala Ala Gly Gly
    690                 695                 700

Gly Cys Thr Thr Ala Thr Gly Thr Cys Thr Thr Thr Cys Cys Cys Cys
705                 710                 715                 720

Thr Thr Ala Gly Ala Thr Gly Gly Ala Ala Ala Cys Ala Ala Cys Thr
                725                 730                 735

Cys Cys Ala Cys Thr Gly Ala Cys Thr Thr Cys Ala Thr Ala Gly Ala
            740                 745                 750

Gly Gly Ala Cys Thr Gly Gly Gly Thr Cys Ala Ala Ala Ala Thr Cys
        755                 760                 765
```

```
Thr Gly Thr Thr Thr Ala Cys Cys Ala Gly Cys Cys Ala Ala Gly Thr
        770                 775                 780

Cys Ala Ala Ala Gly Gly Thr Thr Ala Thr Ala Thr Cys Ala Gly Ala
785                 790                 795                 800

Ala Cys Thr Thr Gly Gly Ala Gly Ala Thr Thr Cys Ala Gly Cys Cys
                805                 810                 815

Thr Thr Thr Gly Ala Ala Gly Ala Thr Cys Ala Ala Thr Gly Thr Gly
                820                 825                 830

Gly Cys Cys Gly Ala Thr Gly Thr Gly Ala Ala Gly Gly Gly Gly Ala
                835                 840                 845

Gly Gly Cys Gly Gly Thr Gly Ala Ala Thr Gly Thr Thr Cys Ala
            850                 855                 860

Cys Thr Ala Gly Cys Ala Ala Ala Cys Cys Thr Ala Thr Thr Gly Ala
865                 870                 875                 880

Cys Ala Thr Ala Thr Cys Cys Ala Thr Thr Gly Thr Gly Ala Gly
                885                 890                 895

Ala Gly Ala Ala Gly Gly Ala Cys Thr Thr Gly Thr Gly Ala Ala Gly
                900                 905                 910

Gly Gly Ala Ala Cys Ala Cys Thr Thr Gly Cys Thr Thr Gly Thr Ala
            915                 920                 925

Ala Gly Gly Gly Ala Gly Gly Cys Thr Ala Cys Thr Ala Thr Gly Ala
            930                 935                 940

Cys Thr Thr Cys Gly Thr Cys Ala Ala Gly Gly Gly Thr Gly Cys Thr
945                 950                 955                 960

Thr Thr Thr Gly Ala Gly Gly Cys Thr Thr Thr Gly Gly Gly Ala Cys
                965                 970                 975

Thr Thr Gly Ala Ala Thr Thr Thr Gly Gly Cys Cys Thr Cys Thr Cys
                980                 985                 990

Cys Gly Ala Ala Ala Cys Thr Ala Gly Cys Thr Cys Thr Gly Thr Thr
                995                 1000                1005

Ala Ala Ala Gly Ala Thr Gly Thr Gly Gly Cys Thr Ala Cys Cys
            1010                 1015                1020

Ala Thr Ala Cys Thr Ala Cys Ala Thr Thr Gly Gly Ala Ala Gly
1025                1030                1035

Cys Thr Gly Thr Ala Gly
            1040

<210> SEQ ID NO 9
<211> LENGTH: 346
<212> TYPE: PRT
<213> ORGANISM: Arabidopsis thaliana

<400> SEQUENCE: 9

Ser Thr Ala Pro Leu Ser Gly Phe Phe Leu Thr Ser Leu Ser Pro Ser
1               5                   10                  15

Gln Ser Ser Leu Gln Lys Leu Ser Leu Arg Thr Ser Ser Thr Val Ala
                20                  25                  30

Cys Leu Pro Pro Ala Ser Ser Ser Ser Ser Ser Ser Ser Ser Ser Ser
            35                  40                  45

Ser Arg Ser Val Pro Thr Leu Ile Arg Asn Glu Pro Val Phe Ala Ala
        50                  55                  60

Pro Ala Pro Ile Ile Ala Pro Tyr Trp Ser Glu Glu Met Gly Thr Glu
65                  70                  75                  80

Ala Tyr Asp Glu Ala Ile Glu Ala Leu Lys Lys Leu Leu Ile Glu Lys
```

```
                    85                  90                  95
Glu Glu Leu Lys Thr Val Ala Ala Ala Lys Val Glu Gln Ile Thr Ala
                100                 105                 110

Ala Leu Gln Thr Gly Thr Ser Ser Asp Lys Lys Ala Phe Asp Pro Val
            115                 120                 125

Glu Thr Ile Lys Gln Gly Phe Ile Lys Phe Lys Lys Glu Lys Tyr Glu
        130                 135                 140

Thr Asn Pro Ala Leu Tyr Gly Glu Leu Ala Lys Gly Gln Ser Pro Lys
145                 150                 155                 160

Tyr Met Val Phe Ala Cys Ser Asp Ser Arg Val Cys Pro Ser His Val
                165                 170                 175

Leu Asp Phe Gln Pro Gly Asp Ala Phe Val Val Arg Asn Ile Ala Asn
            180                 185                 190

Met Val Pro Pro Phe Asp Lys Val Lys Tyr Gly Gly Val Gly Ala Ala
        195                 200                 205

Ile Glu Tyr Ala Val Leu His Leu Lys Val Glu Asn Ile Val Val Ile
    210                 215                 220

Gly His Ser Ala Cys Gly Gly Ile Lys Gly Leu Met Ser Phe Pro Leu
225                 230                 235                 240

Asp Gly Asn Asn Ser Thr Asp Phe Ile Glu Asp Trp Val Lys Ile Cys
                245                 250                 255

Leu Pro Ala Lys Ser Lys Val Ile Ser Glu Leu Gly Asp Ser Ala Phe
            260                 265                 270

Glu Asp Gln Cys Gly Arg Cys Glu Arg Glu Ala Val Asn Val Ser Leu
        275                 280                 285

Ala Asn Leu Leu Thr Tyr Pro Phe Val Arg Glu Gly Leu Val Lys Gly
    290                 295                 300

Thr Leu Ala Leu Lys Gly Gly Tyr Tyr Asp Phe Val Lys Gly Ala Phe
305                 310                 315                 320

Glu Leu Trp Gly Leu Glu Phe Gly Leu Ser Glu Thr Ser Ser Val Lys
                325                 330                 335

Asp Val Ala Thr Ile Leu His Trp Lys Leu
            340                 345

<210> SEQ ID NO 10
<211> LENGTH: 1716
<212> TYPE: DNA
<213> ORGANISM: Arabidopsis thaliana

<400> SEQUENCE: 10
gagtaaagat tcagtaaccc gatgctcctg ctcttcctca agaccttcct tgattcgccg    60
ccggtatgtt ctccgtctgt ggtagcgcct ttggaacact ctaccaacgc cgccatgaaa   120
ggatctctca tggccgcagg ggacgtgttc ttcttacatc tggtgttagg gctatggtta   180
ctccagtgag gagggagagg caagaggttg cttaatgatt cgttttccg gtgatacgag    240 aactctttag gtttaccggg aagctttttcc catgaaaatg ggatgccaag tggatggaga   300
ggagttgccg gagagttgcc ggagaatagg agggaattgg aggaggagga agagagtgat    360 cgccggggttg aaatgttaac cgtcgaggag aatttgaccg agttggatcg tctagtaggt   420
acaattcggg tccttggcga agtatccatt caaaatagtg tttagttttg acttgagaa    480 cttgttgtct ctttgatctc ttttatataa aactttggac gtgtaggaca aacttgtcaa   540
cataagaaac aaaatggttg caacagagag gatgaattta taagttttca acaccgcttt   600
tcttattaga cggacaacaa tctatagtgg agtaaatttt tatttttggt aaaatggtta   660
```

```
gtgaattcaa atatctaaat tttgtgactc actaacatta acaaatatgc ataagacata      720
aaaaaaagaa agaataattc ttatgaaaca agaaaaaaaa cctatacaat caatctttag      780
gaattgacga tgtagaattg tagatgataa attttctcaa atatagatgg gcctaatgaa      840
gggtgccgct tattggatct gacccatttt gaggacatta atattttcat tggttataag      900
ccttttaatc aaaattgtca ttaaattgat gtctccctct cgggtcattt tcctttctcc      960
ctcacaatta atgtagactt tagcaatttg cacgctgtgc tttgtcttta tatttagtaa     1020
cacaaacatt ttgacttgtc ttgtagagtt tttctctttt attttctat ccaatatgaa      1080 aactaaaagt gttctcgtat acatatatta aaattaaaga aacctatgaa acaccaata      1140 caaatgcgat attgttttca gttcgacgtt tcatgtttgt tagaaaattt ctaatgacgt     1200
ttgtataaaa tagacaatta aacgccaaac actacatctg tgttttcgaa caatattgcg     1260
tctgcgtttc cttcatctat ctctctcagt gtcacaatgt ctgaactaag agacagctgt     1320
aaactatcat taagacataa actaccaaag tatcaagcta atgtaaaaat tactctcatt     1380
tccacgtaac aaattgagtt agcttaagat attagtgaaa ctaggtttga attttcttct     1440
tcttcttcca tgcatcctcc gaaaaaaggg aaccaatcaa aactgtttgc atatcaaact     1500
ccaacacttt acagcaaatg caatctataa tctgtgattt atccaataaa aacctgtgat     1560
ttatgtttgg ctccagcgat gaaagtctat gcatgtgatc tctatccaac atgagtaatt     1620
gttcagaaaa taaaaagtag ctgaaatgta tctatataaa gaatcatcca caagtactat     1680
tttcacacac tacttcaaaa tcactactca agaaat                                1716

<210> SEQ ID NO 11
<211> LENGTH: 1163
<212> TYPE: DNA
<213> ORGANISM: Arabidopsis thaliana

<400> SEQUENCE: 11
atggttgcaa cagagaggat gaatttataa gttttcaaca ccgctttct tattagacgg       60 acaacaatct atagtggagt aaatttttat ttttggtaaa atggttagtg aattcaaata     120
tctaaatttt gtgactcact aacattaaca aatatgcata agacataaaa aaaagaaaga     180
ataattctta tgaaacaaga aaaaaaacct atacaatcaa tctttaggaa ttgacgatgt     240
agaattgtag atgataaatt ttctcaaata tagatgggcc taatgaaggg tgccgcttat     300
tggatctgac ccattttgag gacattaata ttttcattgg ttataagcct tttaatcaaa     360
attgtcatta aattgatgtc tccctctcgg tcattttcc tttctccctc acaattaatg      420
tagactttag caatttgcac gctgtgcttt gtctttatat ttagtaacac aaacattttg     480
acttgtcttg tagagttttt ctcttttatt ttctatcca atatgaaaac taaaagtgtt      540
ctcgtataca tatattaaaa ttaaagaaac ctatgaaaac accaatacaa atgcgatatt     600
gttttcagtt cgacgtttca tgtttgttag aaaattcta atgacgttg tataaaatag       660 acaattaaac gccaaacact acatctgtgt tttcgaacaa tattgcgtct gcgtttcctt     720
catctatctc tctcagtgtc acaatgtctg aactaagaga cagctgtaaa ctatcattaa     780
gacataaact accaaagtat caagctaatg taaaaattac tctcatttcc acgtaacaaa     840
ttgagttagc ttaagatatt agtgaaacta ggtttgaatt ttcttcttct tcttccatgc     900
atcctccgaa aaagggaac caatcaaaac tgtttgcata tcaaactcca acactttaca      960
gcaaatgcaa tctataatct gtgatttatc caataaaaac ctgtgattta tgtttggctc    1020
```

| | |
|---|---|
| cagcgatgaa agtctatgca tgtgatctct atccaacatg agtaattgtt cagaaaataa | 1080 |
| aaagtagctg aaatgtatct atataaagaa tcatccacaa gtactatttt cacacactac | 1140 |
| ttcaaaatca ctactcaaga aat | 1163 |

<210> SEQ ID NO 12
<211> LENGTH: 3221
<212> TYPE: DNA
<213> ORGANISM: Arabidopsis thaliana

<400> SEQUENCE: 12

| | |
|---|---|
| gttatgtatc tctgaaatct gaatctgact gacttcaaag gacacagctt ttacttctat | 60 |
| aactgagcga agcaggtgaa aaaatggcga atcggaagtt agagaagatg gcatcgattg | 120 |
| atgttcatct tcgtcaactg gttcctggca agttagtga agacgacaag cttgttgagt | 180 |
| atgatgcttt gcttctagat cggtttctcg atatcctcca ggatttgcac ggtgaagatc | 240 |
| tccgtgaaac tgttcaagag ctttatgagc attctgcaga atacgaaggg aagcatgaac | 300 |
| ctaagaagct agaggagcta gggagtgtgc taacgagttt agatccagga gattccattg | 360 |
| ttatcgctaa agctttctct catatgctta acttagccaa tttggctgag gaagtgcaga | 420 |
| ttgcttatcg ccgtaggatc aagaagctga agaaggtga ttttgttgat gagagctctg | 480 |
| ctactactga atctgatctt gaagaaactt caagaagct tgttggagat ctgaacaagt | 540 |
| ctcctgaaga gatctttgat gctctcaaga atcagactgt ggatttggtt ttgactgctc | 600 |
| atcctactca gtctgtgaga agatcattgc ttcagaaaca tgggaggata agagactgtc | 660 |
| tggctcaact atatgctaag gatattactc ctgatgacaa gcaagagctc gatgaggctc | 720 |
| ttcagagaga gattcaagct gcattccgaa cagatgaaat caaaagaaca ccacctactc | 780 |
| ctcaagatga gatgagagcg ggaatgagtt atttccatga aactatctgg aaaggtgttc | 840 |
| ctaagtttct gcgccgtgtt gacacggctt tgaaaaacat agggatcgaa gaacgtgttc | 900 |
| catataatgc tccattgatt cagttctctc ttggatggg tggtgatcgt gacggtaacc | 960 |
| caagggttac acctgaagtc accagagatg tttgcttgtt agctagaatg atggctgcta | 1020 |
| ctatgtactt taaccaaatc gaagatctta tgtttgagat gtctatgtgg cgttgcaatg | 1080 |
| acgagctgcg tgcgcgagct gatgaagttc atgcaaattc gaggaaagat gctgcaaaac | 1140 |
| attacataga attctggaag tcaattccta caactgagcc ataccgtgtg attcttggcg | 1200 |
| atgtaaggga caagctttat cacacacgtg aacgcgctca tcaactgctc agcaatggac | 1260 |
| actctgatgt ccctgtagag gctactttca ttaacttgga acagttcttg gaacctcttg | 1320 |
| agctctgtta ccgatctctg tgttcatgtg gtgatcgtcc aatagcagat ggaagccttc | 1380 |
| ttgatttctt gaggcaagtc tcaaccttg ggctctctct tgtgagactt gacataaggc | 1440 |
| aagaatctga ccgccacact gatgtattgg atgctatcac cacgcattta gatatcggat | 1500 |
| cctacagaga gtggtctgaa gaacgccgcc aagaatggct tttatctgag ctaagtggca | 1560 |
| aacgtccgct tttcggttct gatcttccta aaaccgaaga aatagctgat gttctggaca | 1620 |
| cgtttcatgt catagccgag ctaccagcag atagctttgg tgcttacatt atctctatgg | 1680 |
| caactgcacc ttctgatgta ttagctgttg agcttttaca gcgtgaatgc cgagtgaaac | 1740 |
| agcctttgag agttgttccg ctctttgaga agctagcaga tctggaagca gctcctgctg | 1800 |
| cagttgctag gctctttttct gttgattggt acaaaaaccg aattaacggt aagcaagagg | 1860 |
| ttatgattgg ttattcggat tcaggaaaag atgctggacg ttatctgct gcttggcagt | 1920 |
| tatacaaagc tcaagaagag cttgtgaagg ttgctaaaga gtacggtgtg aagctaacaa | 1980 |

```
tgtttcacgg tcgtggtggc acggtcggaa gaggaggtgg accaacccat cttgctatat    2040
tgtctcagcc tccggatact attaacggtt ccctccgtgt cacagttcaa ggtgaagtca    2100
tcgagcaatc gtttggtgaa gagcacttat gctttagaac acttcagcgt ttcacagctg    2160
ctacactcga gcacggtatg cgtcctccaa tttcgcctaa accagaatgg cgcgctttgc    2220
tggatgaaat ggcggttgtt gcaaccgagg agtatcgctc agttgtgttc caagaacctc    2280
ggtttgtcga gtacttccgc ctcgctacac cggaactgga gtatggacgt atgaatatcg    2340
gaagcagacc ttcgaagcgt aaaccaagcg gtggcattga atctctccgt gcaattccat    2400
ggatcttcgc ttggactcaa acaagattcc atcttcctgt atggcttgga ttcggatcag    2460
caattagaca tgtgatcgaa aaagacgtca ggaacctcca tatgctccaa gatatgtacc    2520
aacactggcc tttctttaga gtcaccattg atctaatcga aatggtgttc gctaaaggag    2580
atcctggtat tgctgctttg tacgataagc ttcttgtttc agaggaactc tggccttttg    2640
gtgagaaact cagagctaac ttcgaagaaa ccaagaaact catcctccag accgctggac    2700
acaaagatct tcttgaaggt gatccttact tgaaacagag actgagactt cgtgattctt    2760
acattacaac tctcaatgtc tgtcaagctt acacattgaa gagaatccgt gatccgagtt    2820
accatgtgac tctgcgacca cacatttcta aggagatagc ggaatcgagc aaaccagcaa    2880
aagaactcat cgagcttaac ccgactagcg aatacgcgcc aggacttgaa gatacactca    2940
tcttgacgat gaagggtatt gctgctggtc tacaaaacac cggttaagct acaaagagat    3000
ggttaaacaa actttgaatc tctctttctc tctcaagtct ctcctttttt taactacaga    3060
tttggaaaat aaggttggat tctggtttat tttatgtatc caccgtcaaa atgttgattt    3120
tcgtgtacga gtacttcgag atcattgaac acatgctctg ttttttctc aagtttaata    3180 aaacagaaca agagaatctt ttcttgttta ttttcttatc t                      3221
```

<210> SEQ ID NO 13
<211> LENGTH: 3309
<212> TYPE: DNA
<213> ORGANISM: Arabidopsis thaliana

<400> SEQUENCE: 13

```
gtctcgttta aatttttata aactccataa ttttatctta aagtgaatct ttttgtttt     60 ttttgttcca gctttatcgg atatatttcc ttgattttct ccgattgtgg tcaatctgga    120
aaattattga gaatctctcc ctcacttaac caaaagcgtt tttaatcaga tagagagaga    180
ggaaaaagca tcaaccaaac catggctgcg agaaatttgg agaagatggc ttctattgat    240
gctcagctca ggcttcttgc tcctggcaag gtttctgaag cgacaagct tatcgagtac    300 gatgctctgt tactggatcg atttctcgat attcttcagg atttgcatgg cgaggatgtc    360
agagaattcg ttcaagaatg ctacgaagtt gcagctgatt acgatggaaa ccgcaacact    420
gagaagcttg aggagcttgg aaatatgctg acgagtttgg atccagggga ttcaattgtt    480
gtcactaaat cattctccaa catgcttagc ttggctaatc tggctgagga agtccagatt    540
gcttaccggc gtaggattaa gaaactcaag aaaggtgatt tcgctgatga ggcctctgca    600
acaacggaat ctgacattga agagactctc aagaggcttt tgcagcttaa caagactcct    660
gaagaggtct tgatgctct  aagaatcag actgttgact tggttttaac tgctcatccc    720
actcaatctg ttcgtcggtc tttgctccaa aagtttggaa ggattcgtga ttgtttgacg    780
cagttatatg caaaggacat tactcctgat gacaaacaag aactcgatga agctctgcaa    840
```

```
cgagagattc aagctgcttt tcgcacagat gaaatccgaa gaactcctcc tacaccgcaa    900
gatgaaatga gagcagggat gagctacttc catgagacaa tctggaaagg agttccaaag    960
ttcttaagac gtgttgacac agctttaaag aacattggaa tcaacgagcg tgttccttac   1020
aatgcgcctc tcattcagtt ctcttcttgg atgggcggag accgtgatgg aaacccgcga   1080
gtaactcctg aagttacaag agatgtatgc ttattagcta gaatgatggc tgctaatctc   1140
tacttctccc agatagaaga tcttatgttt gagatgtcta tgtggcgttg caatgaggaa   1200
cttcgggttc gtgcagaacg tcaaagatgt gcgaagaggg atgcaaaaca ctatatagaa   1260
ttctggaaac aaatccctgc gaatgagcca taccgagcta tcttggaga tgtgagggac    1320
aagctgtaca acacacgtga gcgtgcacgt cagttattgt caagcggagt ttcggacgtt   1380
cccgaagacg cggttttcac aagtgtggat cagttttttgg agccacttga gctttgttac   1440
aggtcgctct gtgattgcgg tgacagacct attgctgatg aagcctgct tgatttctta    1500
cgccaagtgt caacatttgg ccttgctctt gtgaaacttg atatccgtca agaatctgaa   1560
agacactctg atgtcttgga tgccatcacg acgcacttag gtattggttc ttacaaagaa   1620
tggtcggagg ataaaagaca ggaatggctg ttatctgagc taagcgggaa acgccctctc   1680
tttgaccgga tcttcccaa aaccgaagag gttgcagatg tgttggacac tttcaaagtc    1740
atttctgagc ttccttcgga tagttttggt gcttatatta tctcaatggc cactgctcca   1800
tcagacgtgc tcgctgttga gcttttgcaa cgcgaatgcg ggatcactga tcctctgaga   1860
gttgtcccgt tgttcgagaa gctagcggat ttagaatccg cacctgctgc agttgcccgt   1920
ctcttctcca tagaatggta cagaaacagg atcaatggaa agcaagaagt catgatcggg   1980
tactctgact cgggcaaaga tgctggtcgt ttatcagcgg cttggcagtt atacaagact   2040
caagaagagc tcgtgaaggt ggcaaaagaa tacggagtca agctgacaat gttccacgga   2100
agaggtggga ccgttggacg aggaggtgga cctacccatc ttgctatttt gtctcagcct   2160
ccggatacca ttcatgggca attgagggta acggttcaag gtgaagttat tgaacagtct   2220
ttcggagaag agcacttatg ctttaggact cttcagcgtt tcacagctgc aacacttgag   2280
catgaaatgc atccaccggt ttcccctaag cctgagtggc gtgtcctcat ggatgaaatg   2340
gctataattg ccactgaaga ataccgttct gttgtcttca aggagccccg ttttgttgag   2400
tacttccgtc tggcaacacc agagctcgag tatggaagga tgaacatagg aagccgacca   2460
tcaaaacgta aaccaagcgg aggaatcgag tcgctgcgtg caatcccgtg gatctttgcg   2520
tggactcaga cgaggttcac ttacccgtgt ggcttggctt tggaggagca ttcaaacgcg   2580
tgatacagaa ggacagtaag aatctcaaca tgctcaaaga gatgtacaac caatggccat   2640
tcttccgtgt cacaattgat ctagtcgaaa tggttttcgc caaggagat cccggaattg     2700
cggctctgta tgaccgcctc ctcgtctctg aagaacttca accattcggt gaacaacttc   2760
gagttaacta ccaagagacc agacgcctcc tcctccaggt tgcaggtcac aaagacattt   2820
tagaaggtga cccttacttg aggcaaaggc tgcagcttcg tgacccatac atcacgacat   2880
tgaacgtgtg tcaagcctat acactcaagc agatccgtga cccaagcttc cacgtcaaag   2940
tccggccaca tctctctaag gactacatgg agtctagtcc agcggctgag ctcgtgaaac   3000
tgaatccaaa gagtgaatac gcaccgggac ttgaagatac ggttatcctc accatgaagg   3060
gtatcgctgc tggtatgcaa aacaccggtt aaggcagttt aaaacgttct tgtaccattc   3120
cctaaatcta cgctatgtaa tgtattatgt tctatgatgt gatgaaatct ctccaactcc   3180
tatcccgtac gctttttaat gagtatgata atttcttgtg ttattctatt gttgttatgt   3240
```

```
taccatatct aggaaatata tttctgaaag aaacaagaaa agaaatcttt cttttcgttc    3300
taagatgtt                                                            3309

<210> SEQ ID NO 14
<211> LENGTH: 3313
<212> TYPE: DNA
<213> ORGANISM: Arabidopsis thaliana

<400> SEQUENCE: 14
ataaatactt cactctgctt tcctcaatca catccatctc tgaatctgat tccacatctt      60
aaacccttat tccctaaaca tcgaatttgg ttccttctcc cacaatccgc agagatttct     120
tcttttcaga agaagtaaga gggtggcgaa gaagatttga ttgatcggcg ataatggcgg     180
gtcggaacat agagaagatg gcatctattg atgctcagct tcggcaactc gttcctgcta     240
aagtcagtga agacgataag cttgttgagt acgatgctct tctccttgat cgctttctcg     300
acattctcca ggatttacac ggcgaggatc tccgtgaaac ggttcaagag ttatacgagc     360
tttctgctga gtatgaaggg aagcgtgagc ctagcaagct tgaggagcta gggagtgtcc     420
taacgagttt ggatcctggt gactcaattg ttatctccaa ggctttctct cacatgctta     480
acttagccaa tttggctgag gaggtgcaga ttgctcaccg tcgcaggatc aagaagctga     540
agaaaggtga tttcgttgat gagagttctg caactactga atccgatatt gaagagactt     600
ttaagaggct cgtttcggat cttggtaagt ctcctgaaga gatctttgat gccttgaaga     660
atcagactgt ggatctggtt ttgactgctc atcctactca gtctgtgcgt agatcattgc     720
ttcagaagca tgggaggata agggactgtc ttgctcaact ctatgcaaag gacattactc     780
ctgatgacaa gcaggagcta gatgagtctc tgcaaagaga gattcaagct gcattccgaa     840
cagatgagat tagaagaaca cctccaaccc cacaagatga aatgagagct ggaatgagtt     900
atttccacga gacaatctgg aaaggtgtcc ccaagttctt gcgccgtgtg gacacagctc     960
tgaaaaacat tgggattgat gaacgtgttc cttacaatgc cccattgatt caattctctt    1020
cgtggatggg cggtgatcgt gatggtaatc cgagggtcac acctgaggtc actagagatg    1080
tgtgcttgtt ggctagaatg atggctgcca atctctacta taaccaaatc gagaatctga    1140
tgtttgagtt atctatgtgg cgttgcactg atgaattccg tgtgcgggcg gatgaactgc    1200
acaggaactc aaggaaagat gctgcaaaac attacataga attctggaag acaattcctc    1260
caactgagcc ataccgtgtg attcttggtg atgtgaggga taagctgtat cacacacgtg    1320
agcgttcccg ccaattgctg agtaatggaa tctcggatat tcctgaagaa gctaccttca    1380
ctaatgtgga acagttcttg gagcctcttg agctctgtta ccgatcacta tgttcatgtg    1440
gtgacagccc gatagctgat ggaagccttc ttgatttctt gaggcaagtc tctacctttg    1500
gactctccct tgtgagactt gacatcaggc aagagtctga acgccacaca gatgtcttgg    1560
atgctatcac caagcacttg gacatcggtt cctcctatag agactggtct gaagaaggcc    1620
gacaggaatg gcttcttgct gaactaagcg gcaaacgtcc acttttcgga cctgatcttc    1680
ccaaaaccga agaaatttct gatgtcctgg acacattcaa agtcatatct gagctgcctt    1740
cagattgttt tggagcttat attatctcta tggcaacttc acctagtgat gtgcttgcgg    1800
ttgagctttt acagcgcgaa tgccatgtga aaaatccact tagagttgtt ccactctttg    1860
agaagctagc tgatcttgaa gcagctcctg ccgctgttgc aagactcttt tctatagact    1920
ggtacaaaaa ccgtattaac ggtaaacaag aggttatgat tggttactca gattcaggga    1980
```

```
aagatgcagg gcgtctctca gctgcttggg agctatacaa agctcaagaa gagcttgtga    2040
aggttgctaa gaaatatgga gtgaagctaa ctatgttcca tggccgtggt ggcacagtcg    2100
gaagaggagg tggtcctact catcttgcta tattgtctca gccaccagat acagttaatg    2160
gctctcttcg agtcacggtt cagggtgaag tcattgagca atcatttggg gaggcacact    2220
tatgctttag aacacttcaa cgtttcacag cagctactct agagcacgga atgaaccctc    2280
cgatttcacc aaaacccgag tggcgtgctt gcttgatga aatggcggtt gttgcaactg     2340
aggaataccg atctgtcgtt ttccaagaac ctcgattcgt cgagtatttc cgcctcgcta    2400
ctccggagct ggagtatgga cgtatgaata ttggaagtag accttcaaag cgaaaaccaa    2460
gcggtgggat cgaatctctc cgtgcaatcc catggatctt tgcttggacg caaacaagat    2520
tccatcttcc tgtatggtta ggtttcggag cagcatttag gtatgcgatc aagaaggatg    2580
tgagaaacct tcacatgctg caagatatgt ataaacaatg gccctttttc cgagtcacca    2640
tcgatctaat tgaaatggtg ttcgccaagg gagaccccgg gatcgctgct ttgtacgaca    2700
aacttcttgt ctcagaagat ttatgggctt ttggagagaa actcagagcc aactttgatg    2760
aaaccaagaa cctcgtcctc cagactgctg gacataaaga ccttcttgaa ggagatcctt    2820
acttgaaaca gagactaagg ctacgtgact cttacattac gaccctcaac gtttgccaag    2880
cctacacatt gaagaggatc cgtgatgcaa actacaatgt gactctgcga ccacacattt    2940
ctaaagagat catgcaatca agcaaatcag cacaagagct cgtcaagctt aaccccacga    3000
gtgaatacgc gcctggactt gaggacacac ttatcttaac catgaagggt attgctgcag    3060
gattgcaaaa caccggttaa gtgagtcagt gaaagaaaac aaaacttcga atctctcttt    3120
tttatctacc cttttaata atctcttttt ttctagaatc caaataatt acggttggat      3180 tacagtttac tttatgtatc caccgttgaa atcttaatct tccattgtat caaacgtcac    3240
tgactctgtt tctggaagtg taaacaagaa cagagacagt gaatcttaat gttatcttct    3300
ttgtcttttt ctt                                                       3313

<210> SEQ ID NO 15
<211> LENGTH: 3102
<212> TYPE: DNA
<213> ORGANISM: Arabidopsis thaliana

<400> SEQUENCE: 15
acaatgacgg acacaacaga cgatatcgca gaggaaatct cattccaaag cttcgaagat     60
gactgcaaat tgctcggtag tctcttccat gatgtgttac aaagggaagt tggcaaccca    120
ttcatggaaa aagtcgaacg cattcggatt cttgctcaga gtgcgttaaa tttgcgtatg    180
gctggtattg aggataccgc aaaccttttg gagaagcaat tgactagtga aatatccaaa    240
atgccactag aagaagcctt aacgttggct cgtacattca ctcattctct taacttaatg    300
ggcattgcag acactcatca cagaatgcac aaagtcccata acgttacaca acttgcaaga    360
tcttgtgatg atatattcag ccagctattg caaagtggaa tctctccaga cgaactttat    420
aaaactgttt gcaaacagga ggtcgaaatt gttcttactg ctcatcctac ccaaataaat    480
cgaagaacct tgcagtacaa gcatattaga attgctcatc ttctagaata taacactaga    540
tcagatctaa gcgttgaaga tcgcgaaacg ctcattgaag atttggttag agagattact    600
tcactgtggc aaactgatga gcttagacgt cagaaaccta ctccagttga tgaagctaga    660
gctggtctaa acatagtgga gcaatccctt tggaaagcag taccacaata cctgcgtcgt    720
gtcagcaatt ccttgaagaa gtttacaggg aagccacttc cactaacatg cactcctatg    780
```

```
aaatttggtt cttggatggg aggtgataga gatggaaatc caaatgtcac ggcaaaggtc     840
acgaaagaag tatctctctt gtctagatgg atggctattg atttgtacat aagagaggtt     900
gatagcttaa gatttgaatt atctacggat cgatgcagtg ataggttttc aagattagct     960
gataaaattc ttgaaaagga ttatgataga ggaaaatcaa atttccaaaa gcaacaaagt    1020
tcatcatgct tgccaacaca acttccagct agagctcacc ttcctgcttg cattgacttt    1080
ggtgaatcac gacataccaa atttgaaatt gcgacgacag attatatgcc acccaatctc    1140
cagaagcaga atgaacaaga cttttcggaa agcgactggg agaaaattga caatggttcg    1200
cggtccggtc ttacttctcg aggttctttc tcatctactt ctcaacttct tctccagaga    1260
aaactatttg aggaatctca ggttgggaag actagtttcc aaaagctact agaaccacct    1320
ccacttaaac gagctggaag tgctccttat cgtattgttc ttggagaagt aaaagaaaag    1380
cttgtgaaga caagaagact tcttgaactt cttattgagg gtcttccttg tgagtatgac    1440
cctaaaaact cctatgaaac atcagatcag cttcttgaac cattgctcct ctgttacgaa    1500
tctctgcaat catcgggtgc tagggtacta gctgatggac gacttgctga tctgattcgt    1560
agagtttcta cctttggaat ggttttggtg aaactcgact tacgccagga agctgcaaga    1620
cattctgaag ctttggatgc aattacaaca tacttggata tgggtactta tagtgaatgg    1680
gatgaagaga agaaattaga atttttgaca agagaactaa aagggaaacg acctcttgtt    1740
cctcaatgta ttaaggttgg tcctgacgtc aaagaagtat tggacacatt ccgagtcgct    1800
gctgaacttg gaagtgaatc acttggcgct tacgttattt ctatggcttc aaatgcaagt    1860
gatgtcctcg ctgtggaact tcttcaaaaa gatgctcgac ttgctttaac tagcgaacat    1920
ggaaaaccat gtcctggtgg aacgctacga gtggtacctc tttttgaaac ggtgaatgat    1980
ttaagagccg ctggtccttc gataaggaaa ttgctctcaa tcgattggta tagggaacac    2040
atccaaaaga accacaacgg tcaccaagag gtgatggttg atactctgat tctggaaaa     2100 gatgctggac gttttactgc agcatgggaa ctctacaaag ctcaagaaaa tgttgttgct    2160
gcttgtaatg aatttggaat caaaataaca ttatttcatg gacgaggagg aagcattggt    2220
cgtggtggtg gtccaaccta tctcgctatt cagtcccaac caccaggctc tgtaatgggc    2280
tctttgcgtt caactgagca aggtgagatg gttcaagcta agtttgggat accacaaacg    2340
gctgttaggc aactagaggt atacacaacc gcggttctac tcgctacctt aaagcctcct    2400
cagccacctc gagaggaaaa atggcgaaac ctaatggaag aaatctctgg aatcagttgc    2460
caacactata gaagcacagt gtatgaaaac ccagagtttc tatcttattt tcatgaggca    2520
acaccgcaag cagaacttgg tttcctcaat ataggaagcc gaccaacacg aagaaagagc    2580
tctagtggaa taggacatct ccgagctatc ccttgggtct ttgcttggac tcaaacaagg    2640
tttgttcttc cagcttggct tggtgtaggg gctggtttaa agggagtttc tgagaagggt    2700
catgcggatg atcttaaaga gatgtacaaa gaatggccat tttttcagtc caccccttgaa   2760 cttatagaga tggtgttagc taaagcagac attccaatga ccaaacacta cgacgaacaa    2820
cttgtgtctg agaaaagaag aggacttggc actgagctaa gaaaagaact aatgactact    2880
gagaagtacg ttcttgtgat aagtggtcac gagaaactct gcaggacaa taagagcttg     2940 aagaaactca ttgatagtag acttccgtat ctcaacgcaa tgaacatgtt acaagttgaa    3000
attcttaaga ggctaagacg tgatgaagat aacaataagc taagagatgc tttgcttatc    3060
acaatcaatg gtattgctgc aggaatgaga aataccggtt aa                       3102
```

<210> SEQ ID NO 16
<211> LENGTH: 878
<212> TYPE: DNA
<213> ORGANISM: Arabidopsis thaliana

<400> SEQUENCE: 16

| | | | | | |
|---|---|---|---|---|---|
| tcagtcacac | aaagagtaaa | gaagaacaat | ggcttcctct | atgctctctt | ccgctactat | 60 |
| ggttgcctct | ccggctcagg | ccactatggt | cgctcctttc | aacggactta | agtcctccgc | 120 |
| tgccttccca | gccacccgca | aggctaacaa | cgacattact | tccatcacaa | gcaacggcgg | 180 |
| aagagttaac | tgcatgcagg | tgtggcctcc | gattggaaag | aagaagtttg | agactctctc | 240 |
| ttaccttcct | gaccttaccg | attccgaatt | ggctaaggaa | gttgactacc | ttatccgcaa | 300 |
| caagtggatt | ccttgtgttg | aattcgagtt | ggagcacgga | tttgtgtacc | gtgagcacgg | 360 |
| taactcaccc | ggatactatg | atggacggta | ctggacaatg | tggaagcttc | ccttgttcgg | 420 |
| ttgcaccgac | tccgctcaag | tgttgaagga | agtggaagag | tgcaagaagg | agtaccccaa | 480 |
| tgccttcatt | aggatcatcg | gattcgacaa | cacccgtcaa | gtccagtgca | tcagtttcat | 540 |
| tgcctacaag | ccaccaagct | tcaccggtta | atttcccttt | gcttttgtgt | aaacctcaaa | 600 |
| actttatccc | ccatctttga | ttttatccct | tgttttctg | ctttttcett | ctttcttggg | 660 |
| ttttaatttc | cggacttaac | gtttgttttc | cggtttgcga | gacatattct | atcggattct | 720 |
| caactgtctg | atgaaataaa | tatgtaatgt | tctataagtc | tttcaatttg | atatgcatat | 780 |
| caacaaaaag | aaaataggac | aatgcggcta | caaatatgaa | atttacaagt | ttaagaacca | 840 |
| tgagtcgcta | aagaaatcat | taagaaaatt | agtttcac | | | 878 |

<210> SEQ ID NO 17
<211> LENGTH: 808
<212> TYPE: DNA
<213> ORGANISM: Arabidopsis thaliana

<400> SEQUENCE: 17

| | | | | | |
|---|---|---|---|---|---|
| attaggcaaa | agaagaagaa | gaagaagtaa | tggcttcctc | tatgctctcc | tctgccgctg | 60 |
| tggttacctc | cccggctcaa | gccaccatgg | tcgctccatt | cactggtttg | aagtcatccg | 120 |
| cttctttccc | ggtcacccgc | aaggccaaca | acgacattac | ttccatcaca | agcaatgggg | 180 |
| gaagagttag | ctgcatgaag | gtgtggccac | caatcggaaa | gaagaagttt | gagactctat | 240 |
| cttacctccc | tgaccttact | gacgtcgaat | tggctaagga | agttgactac | cttctccgca | 300 |
| acaaatggat | tccttgtgtt | gaattcgagt | tggagcacgg | atttgtgtac | cgtgagcacg | 360 |
| gaaacactcc | cggatactac | gatggacggt | actggacaat | gtggaagctt | ccattgttcg | 420 |
| gatgcaccga | ctccgctcaa | gtgttgaagg | aagttgaaga | atgcaagaag | gagtaccgg | 480 |
| gcgccttcat | taggatcatc | ggattcgaca | acacccgtca | agtccaatgc | atcagtttca | 540 |
| ttgcctacaa | gccccaagc | ttcactgatg | cttaaatcct | tttctggaat | attcaatgtt | 600 |
| gactatccgg | aacccaattt | tgtatggtca | atgtaaattt | aagtaattat | tttgccaaag | 660 |
| tgaaaaaact | gaaggtttgt | ttttctatcg | tttcctctat | aaaaatctct | attcatatca | 720 |
| cttcatttct | gctcttatca | cttttaactc | tttttattcg | ttttatctct | tttaactaac | 780 |
| attttagttc | ctttaaattt | ctctccta | | | | 808 |

<210> SEQ ID NO 18
<211> LENGTH: 856
<212> TYPE: DNA
<213> ORGANISM: Arabidopsis thaliana

<400> SEQUENCE: 18

```
caagtaagta agagaaaaac caaaagaaga agagaaacaa caagaagaag taatggcttc    60
ctctatgttc tcctccaccg ctgtggttac ctccccggct caagccacca tggtcgctcc   120
attcaccggc ttgaagtcat ccgcttcttt cccggtcacc cgcaaggcca acaacgacat   180
tacttccatc acaagcaacg gaggaagagt tagctgcatg aaggtgtggc accaatcgg    240
aaagaagaag tttgagactc tatcttacct ccctgacctt agtgacgttg aattggctaa   300
ggaagttgac taccttctcc gcaacaagtg gattccttgt gttgaattcg agttggagca   360
cggatttgtg taccgtgagc acggaaacac tcccggatac tatgatggac gatactggac   420
aatgtggaag cttccattgt tcggatgcac cgactccgct caagtgttga aggaagttga   480
agaatgcaag aaggagtacc ctggcgcctt cattaggatc atcggattcg acaacacccg   540
tcaagtccaa tgcatcagtt tcattgccta caagcccca agcttcaccg aagcttaatc   600
cccttctgg aatattcagc gttgattatt ctggaaccca tttctatgtg gtcaatgcaa   660
atttaagaaa ttatttgccg acttaacagt tgaggaacta ttgttgaaa gtgaaaatgt   720
tattcctatc agtttctcta taattatagt tatcatttca tttcattttt gcccttaaat   780
ctttgaaatc ttattttcg tttagctcct ttaaacaaca ttgtggctcc tttaaattat   840
cctcataatt cttgct                                                  856
```

<210> SEQ ID NO 19
<211> LENGTH: 963
<212> TYPE: DNA
<213> ORGANISM: Arabidopsis thaliana

<400> SEQUENCE: 19

```
gggcttttcg cctttagggg gttctcatta tataaagatg acaacaccag taggaaaaca    60
agtcagtaag taaacgagca aagaagaag agaaacaaca agaagtagta atggcttcct   120
ctatgctctc ctccgccgct gtggttacat ccccggctca ggccaccatg gtcgctccat   180
tcaccggctt gaagtcatcc gctgcattcc cggtcacccg caagaccaac aaggacatca   240
cttccatcgc aagcaacggg ggaagagtta gctgcatgaa ggtgtggcca ccaattggaa   300
agaagaagtt tgagactcta tcttacctcc ctgaccttag tgacgtcgaa ttggctaagg   360
aagttgacta ccttctccgc aacaagtgga ttccttgtgt tgaattcgag ttagagcacg   420
gaaacactcc cggatactac gatggacggt actggacaat gtggaagctt ccattgttcg   480
gatgcaccga ctccgctcaa gtgttgaagg aagttgaaga atgcaagaag gagtacccgg   540
gcgccttcat taggatcatc ggattcgaca cacccgtca agtccaatgc atcagtttca   600
ttgcctacaa gcccccaagc ttcaccgaag cttaatttct ttctaaaac attcttatga   660
attatctctg ctcatttcat ttcctattgt ctgtgttctt tttctcttta tgagacaatt   720
tctatcggat tgtcaaatgt ctgatttatg aaatatgtaat ttatatatcc gtgcgtcttg   780
attttttccg atggttaact agtttgaaaa tttccgatga gataagacaa catacaaaaa   840
atcgaataaa ttgtgtaaat atagataata gtgacatatg gatttgtatt catatttgtc   900
cattgtttta agaggaaaaa agttacaaaa tcttattttc ttaataataa gtaaatttac   960
ttt                                                                963
```

<210> SEQ ID NO 20
<211> LENGTH: 1514
<212> TYPE: DNA

<213> ORGANISM: Arabidopsis thaliana

<400> SEQUENCE: 20

```
aaatagagaa gctcttcaag tatccgatgt ttttgtttaa tcaacaagag gcggagatac      60
gggagaaatt gcatgtgtaa tcataaaatg tagatgttag cttcgtcgtt tttactatag     120
tttagttctc ttcttcttct tttttcgtca ttacaatctc tttcttaatt tacttcttct     180
tgatagtata attaagttgt ttgtaataat ctgtacaaag atgttgtgtt ctcataaaaa     240
attcaatttt gtaaagaagc tctacatgtt ccttgctctg taaacatggt cccctttttgg    300
actacagttt ctcgaaatgg ctcatcagac tcagagacga ctctccaatc tgcttcaaaa     360
gccacaaaac agtataaata tccttctctt cgtccctctc atcgcctgtc tctcctcttc     420
ctcttcccgt tccatttatc cgcaaacgga gcttgttttc ggtgcacctg cttcagccac     480
ttcaaacttg aactgagaag gatgggaaac gaatcatatg aagacgccat cgaagctctc     540
aagaagcttc tcattgagaa ggatgatctg aaggatgtag ctgcggccaa ggtgaagaag     600
atcacggcgg agcttcaggc agcctcgtca tcggacagca aatcttttga tcccgtcgaa     660
cgaattaagg aaggcttcgt caccttcaag aaggagaaat acgagaccaa tcctgctttg     720
tatggtgagc tcgccaaagg tcaaagccca agtacatgtg tgtttgcttg ttcggactca     780
cgagtgtgcc catcacacgt actagacttc catcctggag atgccttcgt ggttcgtaat     840
atcgccaata tggttcctcc ttttgacaag gtcaaatatg caggagttgg agccgccatt     900
gaatacgctg tcttgcacct taaggtggaa acattgtggt gatagggca cagtgcatgt      960
ggtggcatca agggggcttat gtcatttcct cttgacggaa acaactctac tgacttcata    1020
gaggattggg tcaaaatctg tttaccagca aagtcaaaag ttttggcaga aagtgaaagt    1080
tcagcatttg aagaccaatg tggccgatgc gaaaggagg cagtgaatgt gtcactagca     1140
aacctattga catatccatt tgtgagagaa ggagttgtga aggaacact tgctttgaag     1200
ggaggctact atgactttgt taatggctcc tttgagcttt gggagctcca gtttggaatt    1260
tcccccgttc attctatatg aactaacaca tcaccatcac catcgctacc accaccatca    1320
caaacatcat catcgtcgtc atcatcatga tcagcatctt catatataaa tgttttactc    1380
ttatttaatt gctacttgta atggtataca tttacttgcg atgagcttct tttccttcat    1440
tatccagtta taaataaat aaataaatca tgtttacttt cacagatatc gttttgctga    1500
agttgctttg atttt                                                    1514
```

<210> SEQ ID NO 21
<211> LENGTH: 1031
<212> TYPE: DNA
<213> ORGANISM: Arabidopsis thaliana

<400> SEQUENCE: 21

```
atgcagtaat ctgataaaac cctccacaga gatttccaac aaaacaggaa ctaaaacaca      60
agatgaagat tatgatgatg attaagctct gcttcttctc catgtccctc atctgcattg     120
cacctgcaga tgctcagaca gaaggagtag tgtttggata taaaggcaaa aatggaccaa     180
accaatgggg acacttaaac cctcacttca ccacatgcgc ggtcggtaaa ttgcaatctc     240
caattgatat tcaaaggagg caaatatttt acaaccacaa attgaattca atacaccgtg     300
aatactactt cacaaacgca acactagtga accacgtctg taatgttgcc atgttcttcg     360
gggagggagc aggagatgtg ataatagaaa acaagaacta taccttactg caaatgcatt     420
ggcacactcc ttctgaacat cacctccatg gagtccaata tgcagctgag ctgcacatgg     480
```

```
tacaccaagc aaaagatgga agctttgctg tggtggcaag tctcttcaaa atcggcactg    540
aagagccttt cctctctcag atgaaggaga aattggtgaa gctaaaggaa gagagactca    600
aagggaacca cacagcacaa gtggaagtag gaagaatcga cacaagacac attgaacgta    660
agactcgaaa gtactacaga tacattggtt cactcactac tcctccttgc tccgagaacg    720
tttcttggac catccttggc aaggtgaggt caatgtcaaa ggaacaagta gaactactca    780
gatctccatt ggacacttct ttcaagaaca attcaagacc gtgtcaaccc ctcaacggcc    840
ggagagttga gatgttccac gaccacgagc gtgtcgataa aaagaaaccc ggtaacaaaa    900
agaaaaaacc caattaaaat agttttacat tgtctattgg tttgtttaga accctaatta    960
gctttgtaaa actaataatc tcttatgtag tactgtgttg ttgtttacga cttgatatac   1020
gatttccaaa t                                                        1031

<210> SEQ ID NO 22
<211> LENGTH: 736
<212> TYPE: DNA
<213> ORGANISM: Arabidopsis thaliana

<400> SEQUENCE: 22
atggatgaat atgtagagga tgaacacgaa ttcagctacg aatggaacca agagaacggg     60
ccagcgaaat ggggaaagct aagaccggaa tggaaaatgt gcggaaaagg agaaatgcaa    120
tcgcctattg atcttatgaa caaagagtt agacttgtta ctcatcttaa aaagcttact    180
agacactaca aaccttgtaa cgccactctc aaaaatagag gccatgatat gatgctgaaa    240
tttggagaag aagggtcagg gagtattacg gtcaatggaa ctgagtataa actcttacag    300
cttcattggc attctccctc tgaacatact atgaatggaa gaaggtttgc tctcgagcta    360
cacatggttc acgaaaacat taacggaagt ttggctgtag tcacagtcct ctacaaaatc    420
ggaaggccag attcttttct cggattgctg gaaaataaat tgtcggcaat tacagatcaa    480
aatgaggcgg agaaatatgt agatgtgatt gacccaaggg atattaagat tgggagcaga    540 aaatttttata gatacattgg atcacttact actcctcctt gtacgcaaaa tgttatttgg    600
accgtcgtta aaaaggtaaa tactcatcgt tattttcttc tcttttttac ttaatcaaac    660
atagcattaa tagatcatta caaggtacta atagtgtgaa tatccatatc caaaaggttt    720
atccatctac atgtta                                                    736

<210> SEQ ID NO 23
<211> LENGTH: 1134
<212> TYPE: DNA
<213> ORGANISM: Arabidopsis thaliana

<400> SEQUENCE: 23
aaaacacatt ctgagaagaa gaagaagaaa ataagaaaaa acaaaagatg aaaaccatta     60 tccttttttgt aacatttctt gctctttctt cttcatctct agccgatgag acagagactg    120
aatttcatta caaacccggt gagatagccg atccctcgaa atggagcagt atcaaggctg    180
aatggaaaat ttgcgggaca gggaagaggc aatcgccaat caatcttact ccaaaaatag    240
ctcgcattgt tcacaattct acagagattc ttcagacata ttacaaacct gtagaggcta    300
ttcttaagaa ccgtggattc gacatgaagg ttaagtggga agacgatgca gggaagatcg    360
tgatcaatga taccgactat aaattggttc aaagccactg gcacgcacct tcagagcatt    420
ttctcgatgg acagaggttg gcaatggaac ttcacatggt acacaaaagt gtagaagggc    480
```

```
acttggcagt gattggagtt ctcttcagag aaggagaacc aaatgctttc atttcgcgga      540
tcatggacaa gatccataag atcgcagacg tacaagatgg agaggtcagc atcggaaaga      600
tagatccaag agaatttgga tgggatctta caaagtttta tgaatacaga ggttctctca      660
cgactcctcc ttgcacggaa gatgtcatgt ggaccatcat caacaaggtg gggactgttt      720
cacgtgagca aattgatgta ttgacagatg ctcgtcgcgg tggttatgag aagaacgcga      780
gaccagctca acctctgaac ggacgtctgg tttatttaaa cgagcagtcc agtccaagtc      840
caactccacg gctaagaata ccacgagttg gtccggtcta agacagtctt ataggacaag      900
gcaactccga gccctaattt ccatacaaag aaaattcgga aaagaatttt gaagatgtat      960
gaaaattggg agccataact attttttttt aactattctt ttgattaaaa gataaaacta     1020
cgcaatatta tatgcataaa gttttctttt tatacatgta ttccaataaa caagatgtaa     1080
taatatccaa ccataatgag ttgtttgatt attttataac acaagatctc tcac           1134

<210> SEQ ID NO 24
<211> LENGTH: 804
<212> TYPE: DNA
<213> ORGANISM: Arabidopsis thaliana

<400> SEQUENCE: 24
atggatacca acgcaaaaac aatttttcttc atggctatgt gtttcatcta tctatctttc       60
cctaatattt cacacgctca ttctgaagtc gacgacgaaa ctccatttac ttacgaacaa      120
aaaacggaaa agggaccaga gggatggggc aaaataaatc cgcactggaa agtttgtaac      180
accggaagat atcaatcccc gatcgatctt actaacgaaa gagtcagtct tattcatgat      240
caagcatgga caagacaata taaaccagct ccggctgtaa ttacaaacag aggccatgac      300
attatggtat catggaaagg agatgctggg aagatgacaa tacggaaaac ggattttaat      360
ttggtgcaat gccattggca ttcaccttct gagcataccg ttaacggaac taggtacgac      420
ctagagcttc acatggttca cacgagtgca cgaggcagaa ctgcggttat cggagttctt      480
tacaaattag gcgaacctaa tgaattcctc accaagctac taaatggaat aaaagcagtg      540
ggaaataaag agataaatct agggatgatt gatccacgag agattaggtt tcaaacaaga      600
aaattctata gatacattgg ctctctcact gttcctcctt gcactgaagg cgtcatttgg      660
actgtcgtca aagggtgaa cacaaatatca atggagcaaa ttacagctct taggcaagcc      720
gttgacgatg gatttgagac aaaattcaaga ccggttcaag actcaagggg aagatcagtt      780
tggttctatg atccaaatgt ttga                                              804

<210> SEQ ID NO 25
<211> LENGTH: 1088
<212> TYPE: DNA
<213> ORGANISM: Arabidopsis thaliana

<400> SEQUENCE: 25
gatcaacatc tccttgaagt tgtttcataa gaataagagc tataaagag gataaaacca        60 aaatttgaat ttttttcttc tatctctctc cccaagatat atagcacaag aaaatgaaga      120
taccatcaat tggctatgtc ttttttcctta tcttcatctc tattacaatt gtttcgagtt      180
caccagatca tggagaagtt gaggacgaaa cgcagtttaa ctacgagaag aaaggagaga      240
aggggccaga gaactgggga agactaaagc cagagtgggc aatgtgtgga aaaggcaaca      300
tgcagtctcc gattgatctt acggacaaaa gagtcttgat tgatcataat cttggatacc      360
ttcgtagcca gtatttacct tcaaatgcca ccattaagaa cagaggccat gatatcatga      420
```

-continued

```
tgaaatttga aggaggaaat gcaggtttag gtatcactat taatggtact gaatataaac      480
ttcaacagat tcattggcac tctccttccg aacacacact caatggcaaa aggtttgttc      540
ttgaggaaca catggttcat cagagcaaag atggacgcaa cgctgttgtc gctttctttt      600
acaaattggg aaaacctgac tatttctcc tcacgttgga agatacttg aagaggataa        660 ctgatacaca cgaatcccag gaatttgtcg agatggttca tcctagaaca ttcggttttg      720
aatcaaaaca ctattataga tttatcggat cacttacaac tccaccgtgt tctgaaaatg      780
tgatttggac gatttccaaa gagatgagga ctgtgacatt aaaacaattg atcatgcttc      840
gagtgactgt acacgatcaa tctaactcaa atgctagacc gcttcagcgt aaaaatgagc      900
gtccggtggc actttacata ccaacatggc atagtaaact atattaaata tttaagtttg      960
gtttatattc tttctagtaa tctttgaaat attgtaagag ataatgcttc taataaataa     1020
cattggattt attggaatta atgtattgaa aaaactatgc aaatactaca gtgtattttg     1080
gaacgacc                                                              1088

<210> SEQ ID NO 26
<211> LENGTH: 783
<212> TYPE: DNA
<213> ORGANISM: Arabidopsis thaliana

<400> SEQUENCE: 26
atggatgcca acacaaaaac aatttttattt tttgtagtgt tcttcatcga tttatttcc       60 cctaatattt tattcgttta tgctcgtgaa atcggcaaca aaccgctatt tacatacaaa      120
caaaaaacag agaaaggacc agcggaatgg ggcaaattag ccctcaatg gaaagtttgt       180 agcaccggaa aaattcaatc tccgattgat ctcactgacg aaagagtcag tcttattcat      240
gatcaagcct tgagtaaaca ttacaaacca gcttcggctg taattcaaag tagaggacat      300
gacgttatgg tatcgtggaa aggagatggt gggaaaataa caatacatca aacggattat      360
aaattggtgc agtgccattg gcattcaccg tctgagcata ccattaacgg aactagctat      420
gacctagagc ttcacatggt tcacacgagt gctagtggca aaaccactgt ggttggagtt      480
ctttataaat taggtgaacc tgatgaattc ctcacaaaga tactaaatgg aataaaagga      540
gtagggaaaa aagagataga tctaggaatc gtggatcctc gagatattag atttgaaacc      600
aacaatttct atagatacat tggctctctc actattcctc catgcaccga aggcgttatt      660
tggaccgtcc agaaaagggt attatatttt ttttgtttct gttatagatt aattatcttc      720
gttacacctt acataaacat tttttggatt tttgttttg tatttggtg tatgctaatg        780 taa                                                                   783

<210> SEQ ID NO 27
<211> LENGTH: 859
<212> TYPE: DNA
<213> ORGANISM: Arabidopsis thaliana

<400> SEQUENCE: 27
atggtgaact actcatcaat cagttgcatc ttctttgtgg ctctgtttag tattttcaca       60 attgttcga tttcgagtgc tgcttcaagt cacgagaag ttgaggacga acgcgagttt         120
aactacaaga agaacgatga gaaggggcca gagagatggg gagaacttaa accggaatgg      180
gaaatgtgtg aaaaggaga gatgcaatct cccatagatc ttatgaacga gagagttaac      240
attgtttctc atcttggaag gcttaataga gactataatc cttcaaatgc aactcttaag      300
```

```
aacagaggcc atgacatcat gttaaaattt gaagatggag caggaactat taagatcaat      360
ggttttgaat atgaacttca acagcttcac tggcactctc cgtctgaaca tactattaat      420
ggaagaaggt ttgcacttga gctgcatatg gttcacgaag gcaggaatag aagaatggct      480
gttgtgactg tgttgtacaa gatcggaaga gcagatactt ttatcagatc gttggagaaa      540
gaattagagg gcattgctga atggaggag gctgagaaaa atgtaggaat gattgatccc       600
accaaaatta agatcggaag cagaaaatat tacagataca ctggttcact taccactcct      660
ccttgcactc aaaacgttac ttggagcgtc gttagaaagg ttaggaccgt gacaagaaaa      720
caagtgaagc tcctccgcgt ggcagtgcac gatgatgcta attcgaatgc gaggccggtt      780
caaccaacca acaagcgcat agtgcactta tacagaccaa tagtttaata tatgaagata      840
ctgaaagctt ttactaatc                                                  859
```

```
<210> SEQ ID NO 28
<211> LENGTH: 1028
<212> TYPE: DNA
<213> ORGANISM: Arabidopsis thaliana

<400> SEQUENCE: 28
atgaagatat catcactagg atgggtctta gtccttatct tcatctctat taccattgtt       60
tcgagtgcac cagcacctaa acctcctaaa cctaagcctg caccagcacc tacacctcct      120
aaacctaagc ccacaccagc acctacacct cctaaaccta gcccaaaacc agcacctaca      180
cctcctaaac ctaagcctgc accagcacct acacctccta aacctaagcc cgcaccagca      240
cctacacctc ctaaacctaa gcccaaacca gcacctacac ctcctaatcc taagcccaca      300
ccagcaccta cacctcctaa acctaagcct gcaccagcac cagcaccaac accagcaccg      360
aaacctaaac ctgcacctaa accagcacca ggtggagaag ttgaggacga aaccgagttt      420
agctacgaga cgaaaggaaa caaggggcca gcgaaatggg gaacactaga tgcagagtgg      480
aaaatgtgtg gaataggcaa aatgcaatct cctattgatc ttcgggacaa aaatgtggta      540
gttagtaata aatttggatt gcttcgtagc cagtatctgc cttctaatac caccattaag      600
aacagaggtc atgatatcat gttgaaattc aaaggaggaa ataaaggtat tggtgtcact      660
atccgtggta ctagatatca acttcaacaa cttcattggc actctccttc cgaacataca      720
atcaatggca aaaggtttgc gctagaggaa cacttggttc atgagagcaa agataaacgc      780
tacgctgttg tcgcattctt atacaatctc ggagcatctg acaattgaag aagataactg      840
atacacatgc gtccgaggaa catattcgca ctgtgtcaag taaacaagtg aagcttctcc      900
gtgtggctgt acacgatgct tcagattcaa atgccaggcc gcttcaagca gtcaataagc      960
gcaaggtata tttatacaaa ccaaaggtta agttaatgaa gaaatactgt aatataagtt     1020
cttactag                                                              1028
```

```
<210> SEQ ID NO 29
<211> LENGTH: 996
<212> TYPE: DNA
<213> ORGANISM: Arabidopsis thaliana

<400> SEQUENCE: 29
ctagagagca tcttcttata tcaactaaac tttgtattca tttccaagta tcactctaaa       60
tcatcttttt cgaattcgcc tcccaagata tgtcgacaga gtcgtacgaa gacgccatta      120
aaagactcgg agagcttctc agtaagaaat cggatctcgg gaacgtggca gccgcaaaga      180
tcaagaagtt aacggatgag ttagaggaac ttgattccaa caagttagat gccgtagaac      240
```

```
gaatcaaatc cggatttctc catttcaaga ctaataatta tgagaagaat cctactttgt    300
acaattcact tgccaagagc cagaccccca agttttggt gtttgcttgt gcggattcac    360
gagttagtcc atctcacatc ttgaatttcc aacttgggga agccttcatc gttagaaaca    420
ttgcaaacat ggtgccacct tatgacaaga caaagcactc taatgttggt gcggcccttg    480
aatatccaat tacagtcctc aacgtggaga acattcttgt tattggacac agctgttgtg    540
gtggaataaa gggactcatg gccattgaag ataatacagc tcccactaag accgagttca    600
tagaaaactg gatccagatc tgtgcaccgg ccaagaacag gatcaagcag gattgtaaag    660
acctaagctt gaagatcag tgcaccaact gtgagaagga agccgtgaac gtgtccttgg    720
ggaatctttt gtcttaccca ttcgtgagag aaagagtggt gaagaacaag cttgccataa    780
gaggagctca ctatgatttc gtaaaaggaa cgtttgatct ttgggaactt gacttcaaga    840 ctaccctgc ctttgccttg tcttaaaaga ttcctcctac tcaaatattt tctctatgtt    900
gtttctaatt atgttcttat aatcttcttc tgttgcttct gtaatgtcat ctttgctact    960
tctattccaa tagaaatgaa taaagcttta aagagc                              996
```

<210> SEQ ID NO 30
<211> LENGTH: 1361
<212> TYPE: DNA
<213> ORGANISM: Arabidopsis thaliana

<400> SEQUENCE: 30

```
ttgttgtgta aaactcttgt tcctcttcct cttcaacgtg aacacttcta tttctcagag     60
aacattcacc tatatgtctt tcttcaagga gaagtcttcc tctttccaga tttagatgaa    120
cactcttcag atgccttgtg ccttattgat ccagattcga agtacccaac tttactctct    180
agaccttttt catggcagcc actcccacac acttctctgt ctcccatgat cctttttctt    240
ccacgtctct ccttaatctc caaactcaag cgatctttgg tcccaatcac agtttaaaga    300
caacccagtt gagaattcca gcttctttca gaagaaaagc tacaaacttg caagtgatgg    360
cttcaggaaa gacacctgga ctgactcagg aagctaatgg ggttgcaatt gatagacaaa    420
acaacactga tgtatttgac gacatgaaac agcggttcct ggccttcaag aagcttaagt    480
acatcaggga tgactttgaa cactacaaaa atctggcaga tgctcaagct ccaaagtttc    540
tggtgattgc ttgtgcagac tctagagttt gtccttctgc tgtcctggga ttccaaccgg    600
gtgacgcatt cactgttcgt aacattgcaa atttagtacc tccatatgag tctggaccta    660
ctgaaaccaa agctgctcta gagttctctg tgaatactct taatgtggaa aacatcttag    720
tcattggtca tagccggtgt ggaggaattc aagctttaat gaaaatggaa gacgaaggag    780
attccagaag tttcatacac aactgggtag ttgtgggaaa gaaggcaaag gaaagcacaa    840
aagctgttgc ttcaaaccct cattttgatc atcagtgcca acattgtgaa aaggcatcga    900
taaatcattc attagaaagg ctgcttgggt acccgtggat agaagagaaa gtgcggcaag    960
gttcactgtc tctccatggt ggatactata attttgttga ttgtacgttc gagaaatgga   1020
cagtggatta tgcagcaagc agaggtaaga agaaggaagg cagtggaatc gctgttaaag   1080
accggtcagt ttggtcttga cttacgacta tctcaatctt catagagttt ttttcataa    1140 tttatagaga aacatcaaac cccttttggt tgggattatc atgtgtttgt tccacttgtg   1200
tgttgaagtc attttccttc ttctgtctta ttgaggcagg gactaatgtt tgttttatct   1260
ttcagttgtt tcgtttaaat tccacatttg tgcaatgaac tggttggtgt ttctttaaga   1320
```

| | |
|---|---|
| tataatcatt ttgccactgt agtgagatcg gaggcatgca t | 1361 |

<210> SEQ ID NO 31
<211> LENGTH: 1366
<212> TYPE: DNA
<213> ORGANISM: Arabidopsis thaliana

<400> SEQUENCE: 31

| | |
|---|---|
| atattaaacc actgtaactg taatttattg tttcgccgtc ccggaatgtt cctgttgaaa | 60 |
| tccattttcg ctgattttt ttcttccgtc tcttcttcag cttcgaccat tttcgtcttc | 120 |
| ttcattcagt gttgagtcct cgtttacctg tgagctcgaa gaaagtgacg atcaatggga | 180 |
| accctaggca gagcattta ctcggtcggt ttttggatcc gtgagactgg tcaagctctt | 240 |
| gatcgcctcg gttgtcgcct tcaaggcaaa aattacttcc gagaacaact gtcaaggcat | 300 |
| cggacactga tgaatgtatt tgataaggct ccgattgtgg acaaggaagc ttttgtggca | 360 |
| ccaagcgcct cagttattgg ggacgttcac attggaagag gatcgtccat ttggtatgga | 420 |
| tgcgtattac gaggcgatgt gaacaccgta agtgttgggt caggaactaa tattcaggac | 480 |
| aactcacttg tgcatgtggc aaaatcaaac ttaagcggga aggtgcaccc aaccataatt | 540 |
| ggagacaatg taaccattgg tcatagtgct gttttacatg gatgtactgt tgaggatgag | 600 |
| acctttattg ggatgggtgc gacacttctt gatgggtcg ttgttgaaaa gcatgggatg | 660 |
| gttgctgctg tgcacttgt acgacaaaac accagaattc cttctggaga ggtatgggga | 720 |
| ggaaacccag caaggttcct caggaagctc actgatgagg aaattgcttt tatctctcag | 780 |
| tcagcaacaa actactcaaa cctcgcacag gctcacgctg cagagaatgc aaagccatta | 840 |
| aatgtgattg agttcgagaa ggttctacgc aagaagcatg ctctaaagga cgaggagtat | 900 |
| gactcaatgc tcggaatagt gagagaaact ccaccagagc ttaacctccc taacaacata | 960 |
| ctgcctgata agaaaccaa gcgtccttct aatgtgaact gattttttcag gggtatgttt | 1020 |
| tctggccgaa gccctacagg gtgagatact caaggggatt atgtttcggt ctctggtttg | 1080 |
| aatatggcag gtagagtaca ttagggtaga cggatttaca gcttttgaag aagctatgtt | 1140 |
| caacatttt tcatggttc ttagggagta ttattgtcta atcaaacttt gtatgttatc | 1200 |
| acttcggtct tttgaacgta agaatcaagt tcatgaaaca tgagtgaata ttagtctgat | 1260 |
| gcatgtgcgt atgcaaaaat ccatgtgcgc ctatgttgct aggcaagcat gaagaataaa | 1320 |
| gatccaaact ggatatatca tatatttatc tttttataat tactgc | 1366 |

<210> SEQ ID NO 32
<211> LENGTH: 1185
<212> TYPE: DNA
<213> ORGANISM: Arabidopsis thaliana

<400> SEQUENCE: 32

| | |
|---|---|
| cgaactcact cgagttaaaa aaaaaaatcc tcccatcaat acgcctccat aaacctctct | 60 |
| ctatctggtg gagcgacacc aaaaacaaca aagccttctc attttcacac tttgggtaat | 120 |
| cggagaatca caaaaaaatg gaaccctag acgagcaat ttacactgtg ggtaactgga | 180 |
| ttcgtggaac tggtcaagct cttgatcgcg ttggttctct tcttcaagga agtcaccgta | 240 |
| tcgaggaaca tctgtcgagg catcggacgt tgatgaatgt gtttgataaa tcaccattgg | 300 |
| tggataaaga tgtgttgtg gctccgagtg cttctgttat tggtgatgtt cagatcggaa | 360 |
| aaggctcgtc gatttggtat ggctgtgttc ttcgaggtga tgtgaataac atcagtgttg | 420 |
| gatctgggac gaatatccaa gataatacgc ttgtacatgt tgcaaagacc aacataagtg | 480 |

-continued

```
gcaaggttct acctactctg attggggaca atgtaacagt aggtcacagt gctgtcattc    540
atgggtgtac tgttgaggat gatgcttttg ttggtatggg agcaacacta cttgatggtg    600
tggtggttga gaaacatgcc atggttgctg ctggttctct tgtgaaacag aacacgcgaa    660
tcccttctgg agaggtgtgg ggaggaaatc cagcaaagtt catgagaaag ttaacagatg    720
aagagatagt atacatctca cagtcagcaa agaattacat caatctcgca cagattcacg    780
cctcagagaa ttcaaagtca tttgagcaga tcgaggttga gagagcgctt aggaagaagt    840
atgcacgcaa ggacgaggat tacgattcaa tgcttgggat tacccgtgaa actccaccgg    900
agttgattct tcccgacaat gtcttaccag gtggtaaacc cgtcgccaag gttccgtcta    960
ctcagtactt ctaattccaa tctcaggttg tttttgtgtg ttgaaatcat ttcaagacag   1020
gattgattct ctggaaggtc aagagagata ttatttggt tttaactttt cttccgagca    1080
agcaggagat ttatcatcct tgctcaataa tgtatggttg cattatgaag tcatttcttc   1140
gaggaacaat ttgcagaaag agaaacaaag ttggattaat ctttc                  1185
```

<210> SEQ ID NO 33
<211> LENGTH: 1230
<212> TYPE: DNA
<213> ORGANISM: Arabidopsis thaliana

<400> SEQUENCE: 33

```
caaagactgc actctctcct cttcctctgg ctccggcgaa aaacccctttt tcgatttcat     60 tgataaaacg caaatcgatc tctcgtgtgg aagaagaaga agaacacgat gggaacaatg    120
ggtaaagcat tctacagcgt aggattctgg atccgtgaaa ctggtcaagc acttgatcgg    180
ctcggttgtc gcctccaagg gaaaaatcat ttccgagaac agctatcaag caccgcaca     240 ctcatgaatg ttttttgacaa aaccctaat gtggataagg gggcttttgt ggctcctaac    300
gcttctctct ctggtgatgt ccatgtggga agaggttctt ccatttggta tggatgtgtc    360
ttgagagaca tacccttga tttaatgacc gactctgcag gagatgctaa cagcattagt    420
gttggagctg ggaccaatat tcaggacaac gctcttgtcc acgttgctaa gaccaactta    480
agtgggaagg tcttacctac tgtcattgga gacaatgtca ccattggtca tagtgctgtt    540
ttacatggct gcactgtcga ggatgaggcc tatattggta caagtgcaac tgtcttggat    600
ggagctcatg ttgaaaaaca tgccatggtt gcttcaggag ctcttgttag gcagaacact    660
agaattccct ctggcgaggt ttggggaggc aacccagcta aatttctgag gaaggtgaca    720
gaagaagaaa gagtcttctt ctccagttcg gctgtggagt actccaactt agctcaagct    780
cacgccacag agaacgcaaa gaacttggac gaggctgagt tcaagaagct tctaaacaag    840
aagaacgctc gcgatacaga atatgattca gtactcgatg atctcacgct ccctgagaat    900
gtaccaaaag cagcttgagg cgtttaacct gtgccgcctt gcgaatcttg atttgtttgg    960
atttgaaaag taaaaacaaa gaacttgatt tcctgcttct ccaataaagt tttcttgggc   1020
gtaaaatcca ttggccagtg ctcactggga aagttttcgg cttaaaggca ttcatttctc   1080
tgttaaagat tgtgaggggt tttgttctct tgtaacttga gaaagaaaag ttgtaacctt   1140
ttcttccttt ttatgtcgtc taataaattg ttgatcagac agacatttag gttgacctttt  1200 gcccataaaa agatagctct gcttcaataa                                    1230
```

<210> SEQ ID NO 34
<211> LENGTH: 1042
<212> TYPE: DNA

<213> ORGANISM: Arabidopsis thaliana

<400> SEQUENCE: 34

```
actctctctc ttttcctctt tgcaaatcct tgaagaaatc caaaatccat agcaatggcg      60
acttcgatag ctcgattgtc tcggagagga gtcacttcta acctgatccg tcgttgcttc    120
gctgcggaag cggcgttggc gaggaagaca gagttaccta aaccgcaatt cacggtgtcg    180
ccgtcgacgg atcgtgtgaa atgggactac agaggccaac gacagatcat tccttttggga   240
cagtggcttc cgaaggtagc cgttgatgct tacgtggcac ccaacgttgt gctggctggt    300
caggtcacag tctgggacgg ctcgtctgtt tggaacggtg ccgttttgcg cggcgatctc    360
aacaaaatca ctgttggatt ctgctcgaat gtacaggaac ggtgtgttgt tcatgccgcc    420
tggtcttccc caacaggatt accagcagcg acaataatcg acaggtatgt gacagtaggt    480
gcctacagtc ttctgagatc atgtaccatc gaaccagagt gcatcatcgg tcaacactca    540
atactaatgg aaggctcact ggttgagacc cggtcaatct ggaagcgggt tcagttgtg    600
ccgccaggaa gaaggatccc atcaggtgaa ctatggggag gcaatccagc aagattcatt    660
agaaccctaa ccaacgaaga aaccctagag atcccaaaac tcgctgtagc catcaaccac    720
ttaagcggag attacttctc tgagttccta ccttactcaa ctgtctactt agaggtagag    780
aagttcaaga gtcccttgg gatcgccgtt tagaagcttc atctttttcg tgattcactt    840
tcatgtgttt atctatcata tgaggtcttt ctctctgcat attgcaataa gtagctgatg    900
aacatcaaaa caagtccggc tctctttttt ggttctaaaa cgtttgtcat ttcgtttttt    960
gggttctttg taaaattcca tttaaaactg attttggctg aatattgtct gaatgataat   1020
ggcgacgact tctggttttg tt                                            1042
```

<210> SEQ ID NO 35
<211> LENGTH: 1130
<212> TYPE: DNA
<213> ORGANISM: Arabidopsis thaliana

<400> SEQUENCE: 35

```
ctcccgacga ctcctctctg tctcctcctc cgggaagctt tctgtctctc tctctctctc      60
tctacacaag accttgaaga atccgattcc ataacaatgg cgacttcgtt agcacgaatc    120
tctaaaagaa gcataacatc ggctgtttca tcgaatctga ttcggcgtta cttcgccgcg    180
gaagcagtag cggtggcgac gacggaaaca cctaaaccga aatcgcaggt gacgccgtcg    240
ccggatcggg taaaatggga ctacagaggc cagagacaga taattcctct gggacagtgg    300
ctaccgaagg tagctgtaga tgcttacgtg gcacctaacg ttgtgttggc tggtcaggtc    360
accgtctggg acggctcgtc tgtatggaac ggtgccgttt tgagaggaga tcttaataag    420
atcaccgttg gattctgctc aaatgtccag gaacggtgtg ttgttcatgc tgcgtggtcg    480
tcgcctacag gattaccagc acaaacattg atcgataggt acgtgacagt tggtgcatac    540
agtctttttaa gatcatgcac tatcgaacca gaatgcatca tcgggcaaca ctcaatccta    600
atggaaggtt cactggtcga aacccgctca atcctagaag ctggttctgt tttaccacct    660
ggcagaagaa tccatctgg tgaactatgg ggaggcaatc cagcaaggtt tattcgaaca    720
ctcaccaatg aagaaacctt agagatcccg aaacttgctg ttgccattaa ccacctaagt    780
ggagattact tctcagagtt cttgccttac tcaactatct atctagaggt tgagaagttc    840
aagaaatccc ttggaatcgc catctagaaa gcttcttcca ggtttctggc tacttccctc    900
attaagaaag cttcttcgtt ttcggaattt gatctgaata agtagctgcg gaacaagaaa    960
```

-continued

| | |
|---|---|
| aagagcagag ctgtgtttca aatgttgtct tctctgtttg ttttgtttaa gttcatatcc | 1020 |
| ttgtgttcaa actttctatg aagatgataa tggtgaaaac tggaaagtgt aaaacttctt | 1080 |
| tcgtctcccc tcacaattgg aaaagctaat aatctcgtag tgttatagaa | 1130 |

<210> SEQ ID NO 36
<211> LENGTH: 1719
<212> TYPE: DNA
<213> ORGANISM: Arabidopsis thaliana

<400> SEQUENCE: 36

| | |
|---|---|
| gagtaaagat tcagtaaccc gatgctcctg ctcttcctca agaccttcct tgattcgccg | 60 |
| ccggtatgtt ctccgtctgt ggtagcgcct ttggaacact ctaccaacgc cgccatgaaa | 120 |
| ggatctctca tggccgcagg ggacgtgttc ttcttacatc tggtgttagg gctatggtta | 180 |
| ctccagtgag gagggagagg caagaggttg cttaatgatt cgttttccg gtgatacgag | 240 |
| aactctttag gttaccgggg aagcttttcc catgaaaatg ggatgccaag tggatggaga | 300 |
| ggagttgccg gagagttgcc ggagaatagg agggaattgg aggaggagga agagagtgat | 360 |
| cgccgggttg aaatgttaac cgtcgaggag aatttgaccg agttggatcg tctagtaggt | 420 |
| acaattcggg tccttggcga agtatccatt caaaatagtg tttagttttg gacttgagaa | 480 |
| cttgttgtct ctttgatctc ttttatataa aactttggac gtgtaggaca aacttgtcaa | 540 |
| cataagaaac aaaatggttg caacagagag gatgaattta taagttttca acaccgcttt | 600 |
| tcttattaga cggacaacaa tctatagtgg agtaaatttt tattttggt aaaatggtta | 660 |
| gtgaattcaa atatctaaat tttgtgactc actaacatta acaaatatgc ataagacata | 720 |
| aaaaaaagaa agaataattc ttatgaaaca agaaaaaaaa cctatacaat caatctttag | 780 |
| gaattgacga tgtagaattg tagatgataa atttttctcaa atatagatgg gcctaatgaa | 840 |
| gggtgccgct tattggatct gacccatttt gaggacatta atattttcat tggttataag | 900 |
| cctttaatc aaaattgtca ttaaattgat gtctccctct cgggtcattt tccttctcc | 960 |
| ctcacaatta atgtagactt tagcaatttg cacgctgtgc tttgtcttta tatttagtaa | 1020 |
| cacaaacatt ttgacttgtc ttgtagagtt tttctctttt attttctat ccaatatgaa | 1080 |
| aactaaaagt gttctcgtat acatatatta aaattaaaga aacctatgaa aacaccaata | 1140 |
| caaatgcgat attgttttca gttcgacgtt tcatgtttgt tagaaaattt ctaatgacgt | 1200 |
| ttgtataaaa tagacaatta aacgccaaac actacatctg tgttttcgaa caatattgcg | 1260 |
| tctgcgtttc cttcatctat ctctctcagt gtcacaatgt ctgaactaag agacagctgt | 1320 |
| aaactatcat taagacataa actaccaaag tatcaagcta atgtaaaaat tactctcatt | 1380 |
| tccacgtaac aaattgagtt agcttaagat attagtgaaa ctaggtttga attttcttct | 1440 |
| tcttcttcca tgcatcctcc gaaaaaggg aaccaatcaa aactgtttgc atatcaaact | 1500 |
| ccaacacttt acagcaaatg caatctataa tctgtgattt atccaataaa aacctgtgat | 1560 |
| ttatgtttgg ctccagcgat gaaagtctat gcatgtgatc tctatccaac atgagtaatt | 1620 |
| gttcagaaaa taaaaagtag ctgaaatgta tctatataaa gaatcatcca caagtactat | 1680 |
| tttcacacac tacttcaaaa tcactactca agaaatatg | 1719 |

<210> SEQ ID NO 37
<211> LENGTH: 34
<212> TYPE: DNA
<213> ORGANISM: artificial sequence
<220> FEATURE:

<223> OTHER INFORMATION: synthetic polynucleotide

<400> SEQUENCE: 37
catgccatgg atttcttgag tagtgatttt gaag                                    34

<210> SEQ ID NO 38
<211> LENGTH: 31
<212> TYPE: DNA
<213> ORGANISM: artificial sequence
<220> FEATURE:
<223> OTHER INFORMATION: synthetic polynucleotide

<400> SEQUENCE: 38
acgcgtcgac gagtaaagat tcagtaaccc g                                       31

<210> SEQ ID NO 39
<211> LENGTH: 30
<212> TYPE: DNA
<213> ORGANISM: artificial sequence
<220> FEATURE:
<223> OTHER INFORMATION: synthetic polynucleotide

<400> SEQUENCE: 39
gcgtcgacat ggttgcaaca gagaggatga                                         30

<210> SEQ ID NO 40
<211> LENGTH: 31
<212> TYPE: DNA
<213> ORGANISM: artificial sequence
<220> FEATURE:
<223> OTHER INFORMATION: synthetic polynucleotide

<400> SEQUENCE: 40
gcgtcgacct aatgaagggt gccgcttatt g                                       31

<210> SEQ ID NO 41
<211> LENGTH: 30
<212> TYPE: DNA
<213> ORGANISM: artificial sequence
<220> FEATURE:
<223> OTHER INFORMATION: synthetic polynucleotide

<400> SEQUENCE: 41
gcgtcgacca atattgcgtc tgcgtttcct                                         30

<210> SEQ ID NO 42
<211> LENGTH: 32
<212> TYPE: DNA
<213> ORGANISM: artificial sequence
<220> FEATURE:
<223> OTHER INFORMATION: synthetic polynucleotide

<400> SEQUENCE: 42
gcgtcgacga accaatcaaa actgtttgca ta                                      32

<210> SEQ ID NO 43
<211> LENGTH: 24
<212> TYPE: DNA
<213> ORGANISM: artificial sequence
<220> FEATURE:
<223> OTHER INFORMATION: synthetic polynucleotide

<400> SEQUENCE: 43
aagagatcta tctagagtcc gcaa                                               24

```
<210> SEQ ID NO 44
<211> LENGTH: 36
<212> TYPE: DNA
<213> ORGANISM: artificial sequence
<220> FEATURE:
<223> OTHER INFORMATION: synthetic polynucleotide

<400> SEQUENCE: 44
gcacgctcga gctcgtcact ggattttggt tttagg                              36

<210> SEQ ID NO 45
<211> LENGTH: 35
<212> TYPE: DNA
<213> ORGANISM: artificial sequence
<220> FEATURE:
<223> OTHER INFORMATION: synthetic polynucleotide

<400> SEQUENCE: 45
acatgccatg gttacttgta cagctcgtcc atgcc                               35

<210> SEQ ID NO 46
<211> LENGTH: 29
<212> TYPE: DNA
<213> ORGANISM: artificial sequence
<220> FEATURE:
<223> OTHER INFORMATION: synthetic polynucleotide

<400> SEQUENCE: 46
ctagtctaga atggtgagca agggcgagg                                      29
```